United States Patent
Kim et al.

(10) Patent No.: US 6,376,674 B1
(45) Date of Patent: Apr. 23, 2002

(54) PIPERIDINE COMPOUNDS

(75) Inventors: Choung U. Kim, San Carlos; Matthew A. Williams, Foster City, both of CA (US)

(73) Assignee: Gilead Sciences, Inc., Foster City, CA (US)

(*) Notice: Subject to any disclaimer, the term of this patent is extended or adjusted under 35 U.S.C. 154(b) by 0 days.

(21) Appl. No.: 09/376,995

(22) Filed: Aug. 18, 1999

Related U.S. Application Data

(60) Division of application No. 08/955,564, filed on Oct. 17, 1997, now Pat. No. 5,994,377, which is a continuation-in-part of application No. 08/735,285, filed on Oct. 21, 1996, now abandoned
(60) Provisional application No. 60/028,901, filed on Oct. 21, 1996.

(51) Int. Cl.$^7$ ............................................. C07D 211/56
(52) U.S. Cl. ..................................... 546/244; 546/192
(58) Field of Search ................................. 546/192, 244

(56) References Cited

U.S. PATENT DOCUMENTS

| | | | |
|---|---|---|---|
| 4,968,788 A | 11/1990 | Farquhar | 536/27 |
| 5,175,273 A | 12/1992 | Bischofberger et al. | 536/126.13 |
| 5,206,400 A | 4/1993 | Witiak et al. | 556/137 |
| 5,292,938 A | 3/1994 | Mease et al. | 562/507 |
| 5,360,817 A | 11/1994 | von Izstein et al. | 514/459 |
| 5,428,073 A | 6/1995 | Kunisch et al. | 562/507 |
| 5,512,596 A | 4/1996 | Kim et al. | 514/568 |
| 5,514,798 A | 5/1996 | Bischofberger et al. | 514/561 |
| 5,536,734 A | 7/1996 | Mueller et al. | 514/336 |
| 5,556,963 A | 9/1996 | Liav et al. | 536/55.3 |
| 5,597,933 A | 1/1997 | Searle et al. | 549/424 |
| 5,602,277 A | 2/1997 | Babu et al. | 562/439 |
| 5,622,916 A | 4/1997 | Kunisch et al. | 536/22.1 |
| 5,633,360 A | 5/1997 | Bischofberger et al. | 536/22.1 |
| 5,639,786 A | 6/1997 | Von Itzstein et al. | 514/459 |
| 5,714,509 A | 2/1998 | Luo et al. | 514/459 |
| 5,763,483 A | 6/1998 | Bischofberger et al. | 514/529 |
| 5,859,284 A | 1/1999 | Kent et al. | 560/125 |
| 5,866,601 A | 2/1999 | Lew et al. | 514/459 |
| 5,886,213 A | 3/1999 | Kent et al. | 560/156 |
| 5,919,819 A | 7/1999 | Andrews et al. | 514/459 |
| 5,948,816 A | 9/1999 | Ohira | 514/459 |
| 5,952,375 A | 9/1999 | Bischofberger et al. | 514/459 |
| 5,990,156 A | 11/1999 | Cherry et al. | 514/459 |
| 6,111,132 A | 8/2000 | Kim et al. | 560/125 |

FOREIGN PATENT DOCUMENTS

| | | |
|---|---|---|
| AU | PK 2896 | 11/1991 |
| AU | PK 4537 | 11/1991 |
| AU | PJ 9800 | 11/1991 |
| AU | 654815 | 11/1994 |
| EP | 0 534 216 A1 | 9/1992 |
| EP | 0 539 204 A1 | 10/1992 |
| GB | 9510141.6 | 5/1995 |
| GB | 9516276.4 | 8/1995 |
| GB | 9525389.4 | 12/1995 |
| WO | WO 91/16320 | 10/1991 |
| WO | WO 92/06691 | 4/1992 |
| WO | WO 93/12105 | 6/1993 |
| WO | WO 93/16049 | 8/1993 |
| WO | WO 94/07885 | 4/1994 |
| WO | WO 94/07886 | 4/1994 |
| WO | WO 94/28956 | 12/1994 |
| WO | WO 94/29476 | 12/1994 |
| WO | WO 95/00503 | 1/1995 |
| WO | WO 95/16680 | 6/1995 |
| WO | WO 95/18800 | 7/1995 |
| WO | WO 95/20583 | 8/1995 |
| WO | WO 95/32712 | 12/1995 |
| WO | WO 96/04265 | 2/1996 |
| WO | WO 96/14314 | 5/1996 |
| WO | WO 96/26933 | 9/1996 |
| WO | WO 96/30329 | 10/1996 |
| WO | WO 96/34603 | 11/1996 |
| WO | WO 96/36628 | 11/1996 |
| WO | WO 96/39838 | 12/1996 |
| WO | WO 98/07685 | 2/1998 |

OTHER PUBLICATIONS

Mair, Hans–Jurgen, "Process for the preparation of shikimic acid and its derivatives", CA131:336883, , 1999.

Nagai et al., "Preparation of quinic acid derivatives, shikimic acid precursors, and shikimic acid", CA132:35988, , 1999.

Bamford et al., "Synthesis of 6–, 7– and 8–carbon sugar analogues of potent anti–influenza 2,3–didehydro–2, 3–dideoxy–N–acetylneuraminic acid derivatives", pp. 1181–1187, J Chem Soc Perkin Trans I, 1995.

Bamford, Mark J., "Neuraminidase Inhibitors as Potential Anti–Influence Drugs", 10:1–16, J Enzyme Inhibition, 1995.

Baumberger et al., "Synthesis of New Sialidase Inhibitors, 6–Amino–6–deoxysialic Acids", 71:429–445, Helvetica Chimica Acta, 1988.

Burger, Alfred, "Relation of Chemical Structure and Biological Activity", Third edition, part 1, pp. 73–75, Medicinal Chemistry, 1979.

(List continued on next page.)

*Primary Examiner*—Zinna Northington Davis
(74) *Attorney, Agent, or Firm*—Mark L. Bosse

(57) ABSTRACT

Novel compounds are described. The compounds generally comprise an acidic group, a basic group, a substituted amino or N-acyl and a group having an optionally hydroxylated alkane moiety. Pharmaceutical compositions comprising the inhibitors of the invention are also described. Methods of inhibiting neuraminidase in samples suspected of containing neuraminidase are also described. Antigenic materials, polymers, antibodies, conjugates of the compounds of the invention with labels, and assay methods for detecting neuraminidaseactivity are also described.

2 Claims, No Drawings

OTHER PUBLICATIONS

Campbell et al., "The Biosynthesis and Synthesis of Shikimic Acid, Chorismic Acid, and Related Compounds", pp. 179–193, Synthesis, Feb. 1993.

Carless et al., "Synthesis of Pseudo–alpha–L–fucopyranose from Toluene", pp. 2447–2448, J Chem Soc (C), 1995.

Chahoua et al., "Synthesis of (–)–Shikimate and (–)–Quinate 3–Phosphates by Differentiation of the Hydroxyl Functions of (–)–Shikimic and (–)–Quinic Acids", 57:5798–5801, J Org Chem, 1992.

Chandler et al., "Synthesis of the potent influenza neuraminidase inhibitor 4–guanidino Neu5Ac2en. X–Ray molecular structure of 5–acetamido–4–amino–2,6–anhydro–3,4,5–trideoxy–D–erythrol–L–gluco–nononic acid", pp. 1173–1180, J Chem Soc Perkin Trans I, 1995.

Chandler et al., "Approaches to carbocyclic analgues of the potent neuraminidase inhibitor 4–guanidino–Neu5Ac2en. X–Ray molecular structure of N–[(1S,2S,6R)–2–azido–6–benzyloxymethyl–4–formylcyclohex–3–enyl]acetamide", pp. 1189–1197, J Chem Soc Perkin Trans I, 1995.

Ciccotosto et al., "Synthesis of Methyl 5–Acetamido–3,4,5–trideoxy–4–Guanidinyl–D–glycero–D–galacto–2–nonul opyranosidonic acid (4–deoxy–4–guanidono–Neu5Acalpha2Me)", 36(30):5405–5408, Tet Lett, 1995.

Colman, P.M., "Influenza virus neuraminidase: Structure, antibodies, and inhibitors", 3:1687–1696, Protein Science, 1994.

Dernick, Rudolf, "Sterical Requirements for Inhibitors of Viral Neuraminidases", 96:256, Chem AB, 1982.

Douglas, R. Gordon, Jr., "Prophylaxis and Treatment of Influenza", 322(7):443–450, N Engl J Med, Feb. 15, 1990.

Fernandez et al., "New and Efficient Enantiospecific Synthesis of (–)–Methyl 5–epi–Skikimate and Methyl 5–epi–Quinate from (–)–Quinic Acid", 38(29):5225–5228, Tet Lett, 1997.

Fleet et al., "An Entry to Chiral Cyclohexenes from Carbohydrates: A Short, Efficient, and Enantiospecific Synthesis of (–) Shikimic Acid from D–Mannose", pp. 849–850, J. Chem. Soc. Chem. Commun., 1983.

Fleet et al., "Enantiospecific Synthesis of Shikimic Acid from D–Mannose: Formation of a Chiral Cyclohexene by Intramolecular Olefination of a Carbohydrate–derived Intermediate", pp. 905–908, J Chem Soc Perkin Trans I, 1984.

Funded Research Agreement, "Agreement between Gilead Sciences, Inc. and the University of California, Berkeley", 2 pages,, Dec. 7, 1995.

Ganem, Bruce, "Tetrahedron Report No. 59. From Glucose to Aromatics: Recent Developments in Natural Products of the Shikimic Acid Pathway", 34:3353–3383, Tetrahedron, 1978.

Grewe et al, "Eine einfache Synthese der Shikimisaure", 100:2546–2553, Chem Ber, 1967.

Grewe et al, "Synthese der Homochinasaure und des beta–Chino–athylamins", 575:1–17, Liebigs Ann Chem, 1952.

Grewe et al, "Darstellung und Eigenschaften des Chinaaldehyds", 658:113–119, Liebigs Ann Chem, 1962.

Grewe et al, "Uberfuhrung der Chinasaure in ungesattigte Verbingunden vom Type der Shikimisaure", 69:61, Angew Chem Int Ed, 1957.

Grewe et al, "Die Uberfuhrung der Shikimisaure in Chinasaure", 86:928–938, Chem Ber, 1953.

Grewe et al, "Die Totalsynthese der Chinasaure", 87:793–802, Chem Ber, 1954.

Grewe et al, "Eine neue Synthese der Shikimisaure", 97:443–448, Chem Ber, 1964.

Grewe et al, "Abbau der Chinasaure nach Hunsdiecker", 98:104–110, Chem Ber, 1965.

Hanessian et al., "Anomeric Deoxygenation of 2–Ulosonic Acids Using SmI2: Rapid Access to 2–Deoxy–KDO and 2–Deoxy–NANA", pp. 863–864, Synlett, Oct.–1994.

Hayden et al., "Safety and Efficacy of the Neuraminidase Inhibitor GG167 in Experimental Human Influenza", 275(4):295–299, JAMA, Jan.–1996.

Janakiraman et al., "Structure of Influenza Virus Neuraminidase B/Lee/40 Complexed with Sialic Acid and a Dehydro Analog at 1.8–Angstrom Resolution: Implications for the Catalytic Mechanism", 33:8172–8179, Biochem, 1994.

Kiefel et al., "Synthesis and Biological Evaluation of N–Acetylneuraminic Acid–Based Rotavirus Inhibitors", 39:1314–1320, J Med Chem, 1996.

Kim et al., "Influenza Neuraminidase Inhibitors Possessing a Novel Hydrophobic Interaction in the Enzyme Active Site: Design, Synthesis, and Structural Analysis of Carbocyclic Sialic Acid Analogues with Potent Anti–Influenza Activity", 119:681–690, J Am Chem Soc, 1997.

Kong et al., "The First Synthesis of a C–7 Nitrogen–containing Sialic Acid Analogue, 5–Acetamido–7–azido–3,5,7–trideoxy–D–glycero–D–galacto–2–nonulopyranosonic acid (7–azido–7–deoxy–Neu5Ac)", 36(6):957–960, Tet Lett, 1995.

Kudo et al., "Synthesis of the Potent Inhibitors of Neuraminidase, N–(1,2–Dihydoxypropyl) Derivatives of Siastatin B and its 4–Deoxy Analogs", 46(2):300–309, J Antibiot, Feb.–1993.

Kudo, et al., "Syntheses and Activities of N–Substituted Derivatives of Siastatin B", 45(10):1662–1668, The Journal of Antibiotics, Oct. 1992.

Lew et al., "C3–Thia and C3–Carba Isosteres of a Carbocyclic Influenza Neuraminidase Inhibitor, (3R, 4R, 5S)–4–Acetamido–5–Amino–3–Propoxy–1–Cyclohexene–1–Carboxylic Acid", 7(14):1843–1846, Bioorg Med Chem Lett, 1997.

Luo et al., "Abstract of Presentation C52: Designed Non–Carbohydrate Inhibitors or Influenza Virus Neuraminidase and Accompanying Notes",, International Antiviral Conference, Nice, France, Jun. 10, 1994.

Mack et al., "Synthesis of 6–Trhiosialic Acids and 6–Thio–N–Acetyl–D–Neuraminic Acid", 28(2):191–194, Tet Lett, 1987.

McCauley et al., "4–Guanidino–Neu5Ac2en fails to protect chickens from infection with highly pathogenic avian influenza virus", 27:179–186, Antiviral Res, 1995.

McKimm–Breschkin et al., "Generation and Characterization of Variants of NWS/G70C Influenza Virus after In Vitro Passage in 4–Amino–Neu5Ac2en and 4–Guanidiono–Neui5Ac2en", 40(1):40–46, Antimicro AG & Chemo, Jan.–1996.

Meindl et al., "2–Deoxy–2,3–dehydrosialic acids. 3. Inhibition of Vibrio cholerae[comma]neuraminidase by oxidation products of 2–deoxy–2,3–dehydro–N–acetylneuraminic acid", 73:42027b, Chem AB, 1970.

Microbial Chem Res Found, "Siastatin B Derivative as Novel Antiviral Substance and its Production", Publication No. 04089481, Patent Abstracts of Japan, Mar. 23, 1992.

Nishimura et al., "Design of Potential Neuraminidase Inhibitors By Dehydradion, Deoxygenation and Epimerization of Siastatin B", 1(1):39–44, Natural Product Letters, 1992.

Nishimura et al., "The First L–Iduronic Acid–Type 1–N–Iminosugars Having Inhibitory Activity of Experimental Metastasis", 118:3051–3052, J Am Chem Soc, 1996.

Nishimura et al., "Synthesis of 3–Episiastatin B Analogues Having Anti–Influenza Virus Activity", 46(12):1883–1889, J Antibiot, Dec.–1993.

Nishimura et al., "Totally Synthetic Analogues of Siastatin B. III. Trifluoroacetamide Analogues Having Inhibitory Activity for Tumor Metastasis", 47(1):101–107, The Journal of Antibiotics, Jan. 1994.

Nishimura, et al., "Potent Inhibition of Neuraminidase by N–(1,2–Dihydroxypropyl) Derivatives of Siastatin B and its Analogs", 1(1):33–38, Natural Product Letters, 1992.

Ogawa et al., "Synthesis of carbocyclic analogues of 3–deoxy–D–manno–2–octulosonic acid and N–acetylneuraminic acid", 269:53–78, Carb Res, 1995.

Ogawa et al., "Synthesis of a Carbocyclic Analogue of N–Acetylneuraminic Acid (Pseudo–N–acethylneuraminic Acid)", pp. 406–408, J Chem Soc (C), 1992.

Raner et al., 43:609–616, Aust J Chem, 1990.

Ryan et al., "Inhibition of Influenza Virus Replication in Mice by GG167 (4–Guanidino–2,4–Dideoxy–2,3–Dehydro–N–Acetylneuraminic Acid) Is Consistent with Extracellular Activity of Viral Neuraminidase (Sialidase)", 38(10):2270–2275, Antimicro & Chemo, Oct.–1994.

Saito et al., "Steps in Maturation of Influenza A Virus Neuraminidase", 69(8):5011–5017, J Virol, Aug.–1995.

Singh et al., "Structure–Based Inhibitors of Influenza Virus Sialidase. A Benzoic Acid Lead with Novel Interaction", 38:3217–3225, J Med Chem, 1995.

Smith et al., "Synthesis and influenza virus sialidase inhibitory activity of analogues of 4–guanidino–Neu5Ac2en (GG167) with modified 5–substituents", 31:143–150, Eur J Med Chem, Jun. 22, 1995.

Smith et al., "Novel Inhibitors of Influenza Sialidases Related to GG167", 6(24):2931–2936, Bioorg Med Chem Lett, 1996.

Sollis et al, "Novel Inhibitors of Influenza Sialidase Related to GG167", 6(15):1805–1808,Abstract, Table of Contents, Bioorg Med Chem Lett, 1996.

Starkey et al., "Synthesis and Influenza Virus Sialidase Inhibitory Activity of the 5–Desacetamido Analogue of 2,3–Didehydro–2, 4–dideoxy–4–guanidinyl–N–acetylneuraminic acid", 36(2):299–302, Tet Lett, 1995.

Staschke et al., "Molecular Basis for the Resistance of Influence Viruses to 4–Guanidino–Neu5Ac2en", 214:642–646, Virology, 1995.

Stevens, Ray, "Letter from Assistant Prof. Ray Stevens to Dr. Choung Kim", 1 page, Oct. 10, 1996.

Stevens, Ray, "Letter from Assistant Prof. Ray Stevens to Dr. Choung Kim", 2 pages,, Feb. 18, 1996.

Ulibarri et al., "Construction of the Bicyclic Core Structure of the Enediyne Antibiotic Esperamicin–A1 in Either Enantiomeric Form from (–)–Quinic Acid", 60:2753–2761, J Org Chem, 1995.

Ulmer et al., "Heterologous Protection Against Influenza by Injection of DNA Encoding a Viral Protein", 259:1745–1749, Science, Mar. 19, 1993.

Williams et al, "Structure–Activity Relationships of Carbocyclic Influenza Neuraminidase Inhibitors", 7(14):1837–1842, Bioorg Med Chem Lett, 1997.

Wu et al., "Non–Sialate Inhibitor of Influenza A/WSN/33 Neuraminidase", 34:7154–7160, Biochem, 1995.

Zhang et al., "Synthesis and Activity of C2–Substituted Analogs of Influenza Neuraminidase Inhibitor GS 4071", 7(14):1847–1850, Bioorg Med Chem Lett, 1997.

von Itzsten et al, "Rational design of potent sialidase–based inhibitors of influenza virus replication", 363:418–423, Nature, 1993.

von Itzstein et al., "A Study of the Active Site of Influenza Virus Sialidase: An Approach to the Rational Design of Novel Anti–influenza Drugs", 39:388–391, J Med Chem, 1996.

PIPERIDINE COMPOUNDS

CROSS REFERENCE TO RELATED APPLICATIONS

This is a divisional application of Ser. No. 08/955,564 filed Oct. 17, 1997, now U.S. Pat. No. 5,994,377, which is a continuation-in-part of Ser. No. 08/735,285 filed Oct. 21, 1996, now abandoned which claims the benefit to provisional application Ser. No. 60/028,901 filed Oct. 21, 1996. The entire disclosure of which is hereby incorporated by reference.

BACKGROUND OF THE INVENTION

1. Field of the Invention

Neuraminidase (also known as sialidase, acylneuraminyl hydrolase, and EC 3.2.1.18) is an enzyme common among animals and a number of microorganisms. It is a glycohydrolase that cleaves terminal alphaketosidically linked sialic acids from glycoproteins, glycolipids and oligiosaccharides. Many of the microorganisms containing neuraminidase are pathogenic to man and other animals including fowl, horses, swine and seals. Organisms having N-acetylneuraminidases include bacteria such as *Vibrio cholerae, C. perfringens* and *Streptococcus* sp. and viruses such as influenza virus, and parainfluenza virus.

Influenza neuraminidase has been implicated in the pathogenicity of influenza viruses. It is thought to help the elution of newly synthesized virons from infected cells and assist in the movement of the virus (through its hydrolase activity) through the mucus of the respiratory tract.

2. Brief Description of Related Art

Von Itzstein, L. M. et al., "Nature", 363(6428):418–423 (1993), discloses the rational design of sialidase-based inhibitors of influenza virus replication.

Colman, P. M. et al. International Patent Publication No. WO 92/06691 (Int. App. No. PCT/AU90/00501, publication date Apr. 30, 1992), von Itzstein, L. M. et al., European Patent Publication No. 0 539 204 A1 (EP App. No. 92309684.6, publication date Apr. 28, 1993), and von Itzstein, L. M. et al. International Publication No. WO 91/16320 (Int. App. No. PCT/AU91/00161, publication date Oct. 31, 1991) disclose compounds that bind neuraminidase and are asserted to exhibited antiviral activity in vivo.

Umezawa, H. et al., "J. Antibiotics" 27:963–969 (1974), discloses the isolation of Siastatin B. Nishimura, Y. et al., "J. Am. Chem. Soc." 110:7249–7250 (1988), and "Bull. Chem. Soc. Jpn." 65:978–986 (1992), disclose the total synthesis of Siastatin B. Nishimura, Y. et al. "J. Antibiotics" 45(10):1662–1668 (1992); 46(2): 300–309 (1993); 46(12):1883–1889 (1993); 47(1):101–107 (1994); and "Nat. prod. Lett." 1(1): 39–44 (1992); as well as Japanese Patent Applications 92-287381 (Oct. 26, 1992); 90-201437 (Jul. 31, 1990); 88-125020 (May 24, 1988) and 50046895 (Apr. 25, 1975) disclose synthetic transformations of Siastatin B including certain dehydrosiastatin B analogs. Zbiral, E. et al., "Liebigs Ann. Chem." 129–134 (1991), and von Itzstein, L. M. et al., "Carbohydrate Res." 244:181–185 (1993), disclose synthetic transformation of the hydroxy group at C4 of sialic acid to an amino group.

OBJECTS OF THE INVENTION

Selected embodiments of the invention satisfy one or more of the following objects:

A principal object of the invention is inhibition of bacteria and viruses, in particular influenza viruses. In particular, an object is inhibition of glycolytic enzymes such as neuraminidase, in particular the selective inhibition of viral or bacterial neuraminidases.

An additional object of the invention is to provide neuraminidase inhibitors that have a retarded rate of urinary excretion, that enter into nasal or pulmonary secretions from the systemic circulation, that have sufficient oral bioavailability to be therapeutically effective, that possess elevated potency, that exhibit clinically acceptable toxicity profiles and have other desirable pharmacologic properties.

Another object is to provide improved and less costly methods for synthesis of neuraminidase inhibitors.

A still further object is to provide improved methods for administration of known and novel neuraminidase inhibitors.

An additional object is to provide compositions useful in preparing polymers, surfactants or immunogens and for use in other industrial processes and articles.

These and other objects will be readily apparent to the ordinary artisan from consideration of the invention as a whole.

SUMMARY OF THE INVENTION

Compounds, or compositions having formula (IX) are provided herein:

$$(IX)$$

[Structural formula showing piperidine ring with substituents $W_6$, N, $T_1$, $J_2$, $G_1$, $J_{2a}$, $J_{1a}$, $E_1$, and $J_2$]

wherein $E_1$ is $-(CR_1R_1)_{m1}W_1$;

$G_1$ is $N_3$, $-CN$, $-OH$, $-OR_{6a}$, $-NO_2$, or $-(CR_1R_1)_{m1}W_2$;

$T_1$ is $-NR_1W_3$, or a heterocycle;

$J_{1a}$ are independently $R_1$, Br, Cl, F, I, CN, $NO_2$ or $N_3$;

$J_2$ and $J_{2a}$ are independently H or $R_1$;

$R_1$ is independently H or alkyl of 1 to 12 carbon atoms;

$R_2$ is independently $R_3$ or $R_4$ wherein each $R_4$ is independently substituted with 0 to 3 $R_3$ groups;

$R_3$ is independently F, Cl, Br, I, $-CN$, $N_3$, $-NO_2$, $OR_{6a}$, $-OR_1$, $-N(R_1)_2$, $-N(R_1)(R_{6b})$, $-N(R_{6b})_2$, $-SR_1$, $-SR_{6a}$, $-S(O)R_1$, $-S(O)_2R_1$, $-S(O)OR_1$, $-S(O)OR_{6a}$, $-S(O)_2OR_1$, $-S(O)_2OR_{6a}$, $-C(O)OR_1$, $-C(O)R_{6c}$, $-C(O)OR_{6a}$, $-OC(O)R_1$, $-N(R_1)(C(O)R_1)$, $-N(R_{6b})(C(O)R_1)$, $-N(R_1)(C(O)OR_1)$, $-N(R_{6b})(C(O)OR_1)$, $-C(O)N(R_1)_2$, $-C(O)N(R_{6b})(R_1)$, $-C(O)N(R_{6b})_2$, $-C(NR_1)(N(R_1)_2)$, $-C(N(R_{6b}))(N(R_1)_2)$, $-C(N(R_1))(N(R_1)(R_{6b}))$, $-C(N(R_{6b}))(N(R_1)(R_{6b}))$, $-C(N(R_1))(N(R_{6b})_2)$, $-C(N(R_{6b}))(N(R_{6b})_2)$, $-N(R_1)C(N(R_1))(N(R_1)_2)$, $-N(R_1)C(N(R_1))(N(R_1)(R_{6b}))$, $-N(R_1)C(N(R_{6b}))(N(R_1)_2)$, $-N(R_{6b})C(N(R_1))(N(R_1)_2)$, $-N(R_{6b})C(N(R_{6b}))(N(R_1)_2)$, $-N(R_{6b})C(N(R_1))(N(R_1)(R_{6b}))$, $-N(R_1)C(N(R_{6b}))(N(R_1)(R_{6b}))$, $-N(R_1)C(N(R_1))(N(R_{6b})_2)$, $-N(R_{6b})C(N(R_{6b}))(N(R_1)(R_{6b}))$, $-N(R_{6b})C(N(R_1))(N(R_{6b})_2)$, $-N(R_1)C(N(R_{6b}))(N(R_{6b})_2)$, $-N(R_{6b})C(N(R_{6b}))(N(R_{6b})_2)$, $=O$, $=S$, $=N(R_1)$ or $=N(R_{6b})$;

$R_4$ is independently alkyl of 1 to 12 carbon atoms, alkenyl of 2 to 12 carbon atoms, or alkynyl of 2 to 12 carbon atoms;

$R_5$ is independently $R_4$ wherein each $R_4$ is substituted with 0 to 3 $R_3$ groups;

$R_{5a}$ is independently alkylene of 1 to 12 carbon atoms, alkenylene of 2 to 12 carbon atoms, or alkynylene of 2–12 carbon atoms any one of which alkylene, alkenylene or alkynylene is substituted with 0–3 $R_3$ groups;

$R_{6a}$ is independently H or an ether- or ester-forming group;

$R_{6b}$ is independently H, a protecting group for amino or the residue of a carboxyl-containing compound;

$R_{6c}$ is independently H or the residue of an amino-containing compound;

$W_1$ is a group comprising an acidic hydrogen, a protected acidic group, or an $R_{6c}$ amide of the group comprising an acidic hydrogen;

$W_2$ is a group comprising a basic heteroatom or a protected basic heteroatom, or an $R_{6b}$ amide of the basic heteroatom;

$W_3$ is $W_4$ or $W_5$;

$W_4$ is $R_5$ or $-C(O)R_5$, $-C(O)W_5$, $-SO_2R_5$, or $-SO_2W_5$;

$W_5$ is carbocycle or heterocycle wherein $W_5$ is independently substituted with 0 to 3 $R_2$ groups;

$W_6$ is $-R_5$, $-W_5$, $-R_{5a}W_5$, $-C(O)OR_{6a}$, $-C(O)R_{6c}$, $-C(O)N(R_{6b})_2$, $-C(NR_{6b})(N(R_{6b})_2)$, $-C(NR_{6b})(N(H)(R_{6b}))$, $-C(N(H)(N(R_{6b})_2)$, $-C(S)N(R_{6b})_2$, or $-C(O)R_2$; and each $m_1$ is independently an integer from 0 to 2; provided, however, that compounds are excluded wherein $J_{1a}$ is H, each $J_2$ is H, $J_{2a}$ is H and $T_1$ is $-N(H)(Ac)$ and:

$E_1$ is $-CO_2H$ or $-CO_2CH_3$,
$G_1$ is $-OBoc$, and
$W_6$ is Boc;

$E_1$ is $-CO_2H$ or $-CO_2CH_3$,
$G_1$ is $-OH$, and
$W_6$ is H;

$E_1$ is $-CO_2H$, $-CO_2CH_3$ or $-CO_2Bn$
$G_1$ is $-OH$, and
$W_6$ is Boc;

$E_1$ is $-CONH_2$,
$G_1$ is $-OH$, and
$W_6$ is Boc or H;

$E_1$ is $-CO_2H$ or $-CO_2CH_3$,
$G_1$ is OH, and
$W_6$ is Bn; or $E_1$ is $-CO_2H$ or $-CO_2CH_3$,
$G_1$ is $-OH$, and
$W_6$ is $-CH_2CH(OH)CH_2(OH)$;

wherein Bn is benzyl and Boc is $-CO_2C(CH_3)_3$; and the salts, solvates, resolved enantiomers and purified diastereomers thereof.

In another embodiment, compounds, or compositions having formula (X) are provided herein:

(X)

wherein
one $Z_1$ is $W_6$ and the other $Z_1$ is $G_1$;
$Z_2$ is H or $W_6$;
$E_1$ is $-(CR_1R_1)_{m1}W_1$;
$G_1$ is $-OH$, $-OR_{6a}$, or $-(CR_1R_1)_{m1}W_2$;
$T_1$ is $-NR_1W_3$ or a heterocycle;
$J_1$ and $J_{1a}$ are independently $R_1$, Br, Cl, F, I, CN, $NO_2$ or $N_3$;
$J_2$ is H or $R_1$;
$R_1$ is independently H or alkyl of 1 to 12 carbon atoms;
$R_2$ is independently $R_3$ or $R_4$ wherein each $R_4$ is independently substituted with 0 to 3 $R_3$ groups;
$R_3$ is independently F, Cl, Br, I, $-CN$, $N_3$, $-NO_2$, $-OR_{6a}$, $-OR_1$, $-N(R_1)_2$, $-N(R_1)(R_{6b})$, $-N(R_{6b})_2$, $-SR_1$, $SR_{6a}$, $-S(O)R_1$, $-S(O)_2R_1$, $-S(O)OR_1$, $-S(O)OR_{6a}$, $-S(O)_2OR_1$, $-S(O)_2OR_{6a}$, $-C(O)OR_1$, $-C(O)R_{6c}$, $-C(O)OR_{6a}$, $-OC(O)R_1$, $-N(R_1)(C(O)R_1)$, $-N(R_{6b})(C(O)R_1)$, $-N(R_1)(C(O)OR_1)$, $-N(R_{6b})(C(O)OR_1)$, $-C(O)N(R_1)_2$, $-C(O)N(R_{6b})(R_1)$, $-C(O)N(R_{6b})_2$, $-C(NR_1)(N(R_1)_2)$, $-C(N(R_{6b}))(N(R_1)_2)$, $-C(N(R_1))(N(R_1)(R_{6b}))$, $-C(N(R_{6b}))(N(R_1)(R_{6b}))$, $-C(N(R_1))(N(R_{6b})_2)$, $-C(N(R_{6b}))(N(R_{6b})_2)$, $-N(R_1)C(N(R_1))(N(R_1)_2)$, $-N(R_1)C(N(R_1))(N(R_1)(R_{6b}))$, $-N(R_1)C(N(R_{6b}))(N(R_1)_2)$, $-N(R_{6b})C(N(R_1))(N(R_1)_2)$, $-N(R_{6b})C(N(R_{6b}))(N(R_1)_2)$, $-N(R_{6b})C(N(R_1))(N(R_1)(R_{6b}))$, $-N(R_1)C(N(R_{6b}))(N(R_1)(R_{6b}))$, $-N(R_1)C(N(R_1))(N(R_{6b})_2)$, $-N(R_{6b})C(N(R_{6b}))(N(R_1)(R_{6b}))$, $-N(R_{6b})C(N(R_1))(N(R_{6b})_2)$, $-N(R_1)C(N(R_{6b}))(N(R_{6b})_2)$, $-N(R_{6b})C(N(R_{6b}))(N(R_{6b})_2)$, $=O$, $=S$, $=N(R_1)$ or $=N(R_{6b})$;

$R_4$ is independently alkyl of 1 to 12 carbon atoms, alkenyl of 2 to 12 carbon atoms, or alkynyl of 2 to 12 carbon atoms;

$R_5$ is independently $R_4$ wherein each $R_4$ is substituted with 0 to 3 $R_3$ groups;

$R_{5a}$ is independently alkylene of 1 to 12 carbon atoms, alkenylene of 2 to 12 carbon atoms, or alkynylene of 2–12 carbon atoms any one of which alkylene, alkenylene or alkynylene is substituted with 0–3 $R_3$ groups;

$R_{6a}$ is independently H or an ether- or ester-forming group;

$R_{6b}$ is independently H, a protecting group for amino or the residue of a carboxyl-containing compound;

$R_{6c}$ is independently H or the residue of an amino-containing compound;

$W_1$ is a group comprising an acidic hydrogen, a protected acidic group, or an $R_{6c}$ amide of the group comprising an acidic hydrogen;

$W_2$ is H or a group comprising a basic heteroatom or a protected basic heteroatom, or an $R_{6b}$ amide of the basic heteroatom;

$W_3$ is $W_4$ or $W_5$;

$W_4$ is $R_5$ or —C(O)$R_5$, —C(O)$W_5$, —SO$_2R_5$, or —SO$_2W_5$;

$W_5$ is carbocycle or heterocycle wherein $W_5$ is independently substituted with 0 to 3 $R_2$ groups;

$W_6$ is —$R_5$, —$W_5$, —$R_{5a}W_5$, —C(O)O$R_{6a}$, —C(O)$R_{6c}$, —C(O)N($R_{6b}$)$_2$, —C(N$R_{6b}$)(N($R_{6b}$)$_2$), —C(N$R_{6b}$)(N(H)($R_{6b}$)), —C(N(H)(N($R_{6b}$)$_2$), —C(S)N($R_{6b}$)$_2$, or —C(O)$R_2$;

each $m_1$ is independently an integer from 0 to 2;

and the salts, solvates, resolved enantiomers and purified diastereomers thereof.

In another embodiment of the invention a compound or composition of the invention is provided that further comprises a pharmaceutically-acceptable carrier.

In another embodiment of the invention the activity of neuraminidase is inhibited by a method comprising the step of treating a sample suspected of containing neuraminidase with a compound or composition of the invention.

Another embodiment of the invention provides a method for inhibiting the activity of neuraminidase comprising the step of contacting a sample suspected of containing neuraminidase with the composition embodiments of the invention.

DETAILED DESCRIPTION

Compositions of the Invention

The compounds of this invention exclude compounds heretofore known. However, as will be further apparent below, in other embodiments, it is within the invention to use for antiviral purposes known compounds heretofore only produced and used as intermediates in the preparation of antiviral compounds. With respect to the United States, the compounds or compositions herein exclude compounds that are anticipated under 35 USC §102 or obvious under 35 USC §103. In particular, the claims herein shall be construed as excluding the compounds which are anticipated by or not possessing novelty over WO 96/26933 (Sep. 6, 1996); Nishimura, Y. et al., "J. Am. Chem. Soc." 110:7249–7250 (1988); and "Bull. Chem. Soc. Jpn." 65:978–986 (1992), disclose the total synthesis of Siastatin B. Nishimura, Y. et al., "J. Antibiotics" 45(10):1662–1668 (1992); 46(2): 300–309 (1993); 46(12):1883–1889 (1993); 47(1):101–107 (1994); "Nat. Prod. Lett." 1(1):39–44 (1992); and Japanese Patent Applications 92-287381 (Oct. 26, 1992); 90-201437 (Jul. 31, 1990); 88-125020 (May 24, 1988) and 50046895 (Apr. 25, 1975).

In a further embodiment, the compounds of this invention are those in which $W_6$ is not —CH$_2$OH, —CH$_2$OAc, or —CH$_2$OCH$_2$Ph.

In a further embodiment, the compounds of this invention are those in which $E_1$ is not —CH$_2$OH, —CH$_2$OTMS, or —CHO.

In a further embodiment, the compounds of this invention are those in which $W_6$ is not polyhydroxyalkane, especially —CH(OH)CH(OH)CH$_2$OH. In a further embodiment, $W_6$ is a branched chain group $R_5$ as described below or a carbocycle which is substituted with at least one group $R_5$.

Whenever a compound described herein is substituted with more than one of the same designated group, e.g., "$R_1$" or "$R_{6a}$", then it will be understood that the groups may be the same or different, i.e., each group is independently selected.

"Heterocycle" as used herein includes by way of example and not limitation these heterocycles described in Paquette, Leo A., "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and "J. Am. Chem. Soc.", 82:5566 (1960).

Examples of heterocycles include by way of example and not limitation pyridyl, thiazolyl, tetrahydrothiophenyl, sulfur oxidized tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxathiinyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, phthalazinyl, naphthyridinyl, quinoxalinyl, quinazolinyl, cinnolinyl, pteridinyl, 4aH-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, and isatinoyl.

By way of example and not limitation, carbon bonded heterocycles are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Still more typically, carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example and not limitation, nitrogen bonded heterocycles are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline. Still more typically, nitrogen bonded heterocycles include 1-aziridyl, 1-azetedyl, 1-pyrrolyl, 1-imidazolyl, 1-pyrazolyl, and 1-piperidinyl.

"Alkyl" as used herein, unless stated to the contrary, is $C_1$-$C_{12}$ hydrocarbon containing normal, secondary, tertiary or cyclic carbon atoms. Examples are methyl (Me, —CH$_3$), ethyl (Et, —CH$_2$CH$_3$), 1-propyl (n-Pr, n-propyl, —CH$_2$CH$_2$CH$_3$), 2-propyl (i-Pr, i-propyl, —CH(CH$_3$)$_2$), 1-butyl (n-Bu, n-butyl, —CH$_2$CH$_2$CH$_2$CH$_3$), 2-methyl-1-propyl (i-Bu, i-butyl, —CH$_2$CH(CH$_3$)$_2$), 2-butyl (s-Bu, s-butyl, —CH(CH$_3$)CH$_2$CH$_3$), 2-methyl-2-propyl (t-Bu, t-butyl, —C(CH$_3$)$_3$), 1-pentyl (n-pentyl, —CH$_2$CH$_2$CH$_2$CH$_2$CH$_3$), 2-pentyl (—CH(CH$_3$)

CH$_2$CH$_2$CH$_3$), 3-pentyl (—CH(CH$_2$CH$_3$)$_2$), 2-methyl-2-butyl (—C(CH$_3$)$_2$CH$_2$CH$_3$), 3-methyl-2-butyl (—CH(CH$_3$)CH(CH$_3$)$_2$), 3-methyl-1-butyl (—CH$_2$CH$_2$CH(CH$_3$)$_2$), 2-methyl-1-butyl (—CH$_2$CH(CH$_3$)CH$_2$CH$_3$), 1-hexyl (—CH$_2$CH$_2$CH$_2$CH$_2$CH$_2$CH$_3$), 2-hexyl (—CH(CH$_3$)CH$_2$CH$_2$CH$_2$CH$_3$), 3-hexyl (—CH(CH$_2$CH$_3$)(CH$_2$CH$_2$CH$_3$)), 2-methyl-2-pentyl (—C(CH$_3$)$_2$CH$_2$CH$_2$CH$_3$), 3-methyl-2-pentyl (—CH(CH$_3$)CH(CH$_3$)CH$_2$CH$_3$), 4-methyl-2-pentyl (—CH(CH$_3$)CH$_2$CH(CH$_3$)$_2$), 3-methyl-3-pentyl (—C(CH$_3$)(CH$_2$CH$_3$)$_2$), 2-methyl-3-pentyl (—CH(CH$_2$CH$_3$)CH(CH$_3$)$_2$), 2,3-dimethyl-2-butyl (—C(CH$_3$)$_2$CH(CH$_3$)$_2$), 3,3-dimethyl-2-butyl (—CH(CH$_3$)C(CH$_3$)$_3$). Examples of alkyl groups appear in Table 2 as groups 2–5, 7, 9, and 100–399.

The compositions of the invention comprise compounds of either formula:

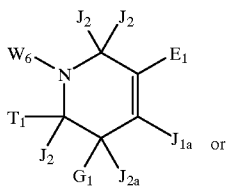

(IX)

or

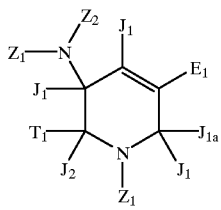

(X)

In the typical embodiment, the compounds of Formula IX are chosen.

$J_1$ and $J_{1a}$ are independently $R_1$, Br, Cl, F, I, CN, NO$_2$ or N$_3$, typically $R_1$ or F, more typically H or F, more typically yet H.

$J_2$ and $J_{2a}$ are independently H or $R_1$, typically H.

One $Z_1$ of Formula X is $W_6$ and the other is $G_1$.

$Z_2$ of Formula X is H or $W_6$, typically H.

$E_1$ is —(CR$_1$R$_1$)$_{m1}$W$_1$.

Typically, $R_1$ is H or alkyl of 1 to 12 carbon atoms, usually H or an alkyl of 1 to 4 or 5 to 10 carbon atoms, still more typically, H or an alkyl of 1, 2, 3, 4, 5, 6, 7, 8, 9, 10, 11, or 12 carbon atoms, more typically yet, H or an alkyl of 1 to 3 carbon atoms selected from methyl, ethyl, n-propyl, and i-propyl. Most typically $R_1$ is H.

m1 is an integer of 0 to 2, typically 0 or 1, most typically 0.

m2 is an integer of 0 to 1.

m3 is an integer of 1 to 3.

$W_1$ is a group comprising an acidic hydrogen, a protected acidic group or an R$_{6c}$ amide of the group comprising an acidic hydrogen which, within the context of the invention, means a group having a hydrogen atom that can be removed by a base yielding an anion or its corresponding salt or solvate. The general principles of acidity and basicity of organic materials are well understood and are to be understood as defining $W_1$. They will not be detailed here. However, a description appears in Streitwieser, A. and Heathcock, C. H. "Introduction to Organic Chemistry, Second Edition" (Macmillan, New York, 1981), pages 60–64. Generally, acidic groups of the invention have pK values less than that of water, usually less than pK=10, typically less than pK=8, and frequently less than pK=6. They include tetrazoles and the acids of carbon, sulfur, phosphorous and nitrogen, typically the carboxylic, sulfuric, sulfonic, sulfinic, phosphoric and phosphonic acids, together with the R$_{6c}$ amides and R$_{6b}$ esters of those acids (R$_{6c}$ and R$_{6b}$ are defined below). Exemplary $W_1$ are —CO$_2$H, —CO$_2$R$_{6a}$, —OSO$_3$H, —SO$_3$H, —SO$_2$H, —OPO$_3$H$_2$, —PO$_3$(R$_{6a}$)$_2$, —PO$_3$H$_2$, —PO$_3$(H)(R$_{6a}$), and —OPO$_3$(R$_{6a}$)$_2$. $E_1$ typically is $W_1$, and $W_1$ typically is —CO$_2$H, —CO$_2$R$_{6a}$, —CO$_2$R$_4$ or CO$_2$R$_1$, and most typically is CO$_2$R$_{14}$ wherein R$_{14}$ is normal or terminally secondary C$_1$–C$_6$ alkyl.

$W_1$ may also be a protected acidic group, which, within the context of the invention means an acidic group as described above that has been protected by one of the groups commonly used in the art for such groups and are described below under R$_{6a}$. More typically, protected $W_1$ is —CO$_2$R$_1$, —SO$_3$R$_1$, —S(O)OR$_1$, —P(O)(OR$_1$)$_2$, —C(O)NHSO$_2$R$_4$, or —SO$_2$NHC(O)—R$_4$, wherein $R_1$ and $R_4$ are defined above.

Most typically, $E_1$ is selected from —C(O)O(CH$_2$)$_b$CH((CH$_2$)$_c$CH$_3$)$_2$ where b=0 to 4, c=0 to 4, and b+c=1 to 4, or from the group of

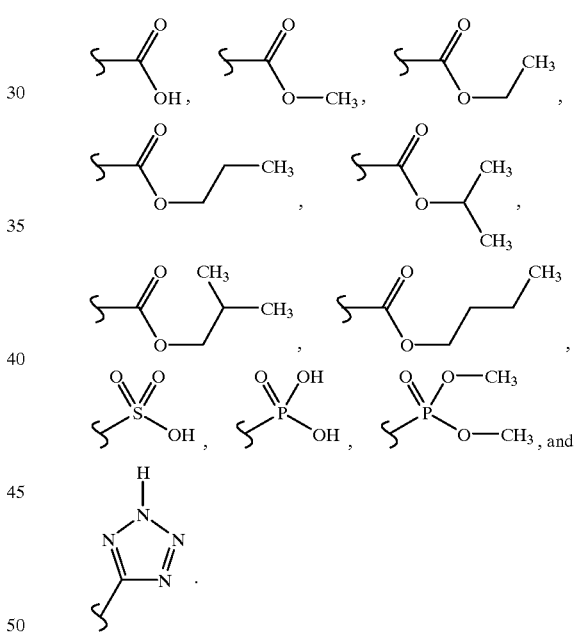

Exemplary $E_1$ groups are listed in Tables 3a through 3b.

$G_1$ of Formula X is —OH, OR$_{6a}$, or —(CR$_1$R$_1$)$_{m1}$W$_2$, $G_1$ of Formula IX is —N$_3$, —CN, —OH, OR$_{6a}$, —NO$_2$ or —(CR$_1$R$_1$)$_{m1}$W$_2$, wherein $R_1$ and m1 are defined above. Ordinarily, $G_1$ of Formula (IX) is —(CR$_1$R$_1$)$_{m1}$W$_2$ and $G_1$ of Formula (X) is H.

$W_2$ of Formula (X) is H or a group comprising a basic heteroatom, a protected basic heteroatom or an R$_{6b}$ amide of the basic heteroatom. $W_2$ of Formula (IX) is a group comprising a basic heteroatom, a protected basic heteroatom or an R$_{6b}$ amide of the basic heteroatom. $W_2$ generally comprises a basic heteroatom, which, within the context of the invention means an atom other than carbon which is capable of protonation, typically by an acidic hydrogen having an acidity in the range described above for $W_1$. The basic principles of basicity are described in Streitwieser and Heathcock (op. cit.) and provide meaning for the term basic heteroatom as will be understood by those ordinarily skilled in the art. Generally, the basic heteroatoms employed in the compounds of the invention have pK values for the corresponding protonated form that are in the range of values described above for $W_1$. Basic heteroatoms include the heteroatoms common in organic compounds which have an un-shared, non-bonding, n-type, or the like, electron pair. By way of example and not limitation, typical basic heteroatoms include the oxygen, nitrogen, and sulfur atoms of groups such as alcohols, amines, amidines, guanidines, sulfides, and the like, frequently, amines, amidines and guanidines. Ordinarily, $W_2$ is amino or an amino alkyl (generally lower alkyl $C_1$ to $C_6$) group such as aminomethyl, aminoethyl or aminopropyl; an amidinyl, or an amidinoalkyl group such as amidinomethyl, amidinoethyl, or amidinopropyl; or guanidinyl, or a guanidinoalkyl group such as guanidinomethyl, guanidinoethyl, or guanidinopropyl (in each instance wherein the alkyl group serves to bridge the basic substituent to the carbocyclic ring). More typically, $W_2$ is amino, amidino, guanidino, heterocycle, heterocycle substituted with 1 or 2 amino or guanidino groups (usually 1), or an alkyl of 2 to 3 carbon atoms substituted with amino or guanidino, or such alkyl substituted with an amino and a second group selected from the group consisting of hydroxy and amino. The heterocycles useful as $W_2$ include typically N or S-containing 5 or 6 membered rings, wherein the ring contains 1 or 2 heteroatoms. Such heterocycles generally are substituted at ring carbon atoms. They may be saturated or unsaturated and may be linked to the core cyclohexene by lower alkyl (m1=1 or 2) or by —$NR_1$—. Still more typically, $W_2$ is —$NHR_1$, —$C(NH)(NH_2)$, —$NR_1$—$C(NR_1)(NR_1R_3)$, —NH—$C(NH)(NHR_3)$, —NH—$C(NH)(NHR_1)$, —NH—$C(NH)NH_2$, —$CH(CH_2NHR_1)(CH_2OH)$, —$CH(CH_2NHR_1)(CH_2NHR_1)$, —$CH(NHR_1)$—$(CR_1R_1)_{m2}$—$CH(NHR_1)R_1$, —$CH(OH)$—$(CR_1R_1)_{m2}$—$CH(NHR_1)R_1$, or —$CH(NHR_1)$—$(CR_1R_1)_{m2}$—$CH(OH)R_1$, —$(CR_1R_1)_{m2}$—S—$C(NH)NH_2$, —$N$=$C(NHR_1)(R_3)$, —$N$=$C(SR_1)N(R_1)_2$, —$N(R_1)C(NH)N(R_1)C$=$N$, or —$N$=$C(NHR_1)(R_1)$; wherein each m2 is ordinarily 0, and ordinarily $R_1$ is H and $R_3$ is $C(O)N(R_1)_2$.

$W_2$ optionally is a protected basic heteroatom which within the context of the invention means a basic heteroatom as described above that has been protected by $R_{6b}$ such as one of the groups common in the art. Such groups are described in detail in Greene (op. cit.) as set forth below. Such groups include by way of example and not limitation, amides, carbamates, amino acetals, imines, enamines, N-alkyl or N-aryl phosphinyls, N-alkyl or N-aryl sulfenyls or sulfonyls, N-alkyl or N-aryl silyls, thioethers, thioesters, disulfides, sulfenyls, and the like. In some embodiments, the protecting group $R_{6b}$ will be cleavable under physiological conditions, typically it will be cleavable in vivo where, for example, the basic heteroatom forms an amide with an organic acid or an amino acid such as a naturally occurring amino acid or a polypeptide as described below for the $R_{6a}$ group.

Typically $G_1$ of Formula (X) is H and $G_1$ of Formula (IX) is selected from the group consisting of:

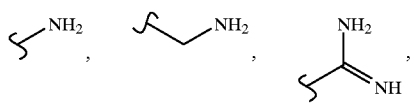

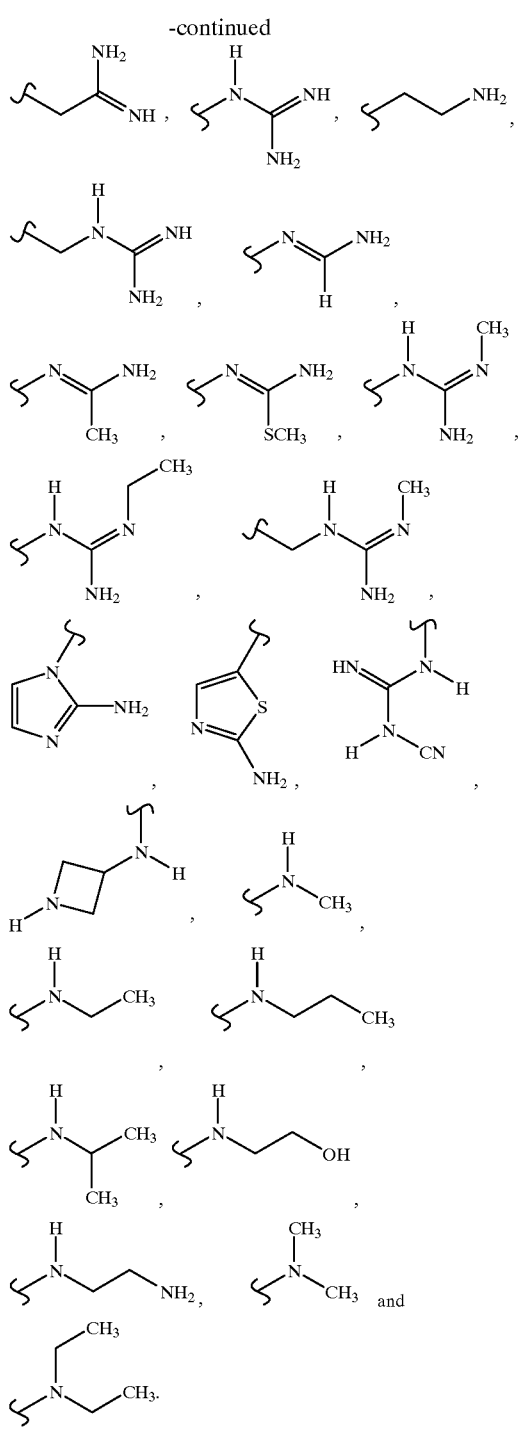

Further exemplary $G_1$ groups are listed in Table 4.

$T_1$ is —$NR_1W_3$, —$R_3$, —$R_5$ or heterocycle. Typically $T_1$ is —$NR_1W_3$ or heterocycle. Generally $T_1$ is selected from the group consisting of:

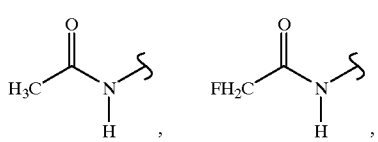

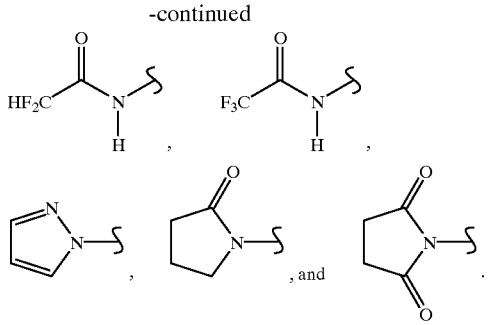

Exemplary $T_1$ groups are listed in Table 5.

$W_3$ is $W_4$ or $W_5$, wherein $W_4$ is $R_5$ or —C(O)$R_5$, —C(O)$W_5$, —SO$_2R_5$, or —SO$_2W_5$. Typically, $W_3$ is —C(O)$R_5$ or $W_5$.

$R_2$ is independently $R_3$ or $R_4$ as defined below, with the proviso that each $R_4$ is independently substituted with 0 to 3 $R_3$ groups;

$R_3$ is independently F, Cl, Br, I, —CN, $N_3$, —NO$_2$, —OR$_{6a}$, —OR$_1$, —N(R$_1$)$_2$, —N(R$_1$)(R$_{6b}$), —N(R$_{6b}$)$_2$, —SR$_1$, —SR$_{6a}$, —S(O)R$_1$, —S(O)$_2R_1$, —S(O)OR$_1$, —S(O)OR$_{6a}$, —S(O)$_2$OR$_1$, —S(O)$_2$OR$_{6a}$, —C(O)OR$_1$, —C(O)R$_{6c}$, —C(O)OR$_{6a}$, —OC(O)R$_1$, —N(R$_1$)(C(O)R$_1$), —N(R$_{6b}$)(C(O)R$_1$), —N(R$_1$)(C(O)OR$_1$), —N(R$_{6b}$)(C(O)OR$_1$), —C(O)N(R$_1$)$_2$, —C(O)N(R$_{6b}$)(R$_1$), —C(O)N(R$_{6b}$)$_2$, —C(NR$_1$)(N(R$_1$)$_2$), —C(N(R$_{6b}$))(N(R$_1$)$_2$), —C(N(R$_1$))(N(R$_1$)(R$_{6b}$)), —C(N(R$_{6b}$))(N(R$_1$)(R$_{6b}$)), —C(N(R$_1$))(N(R$_{6b}$)$_2$), —C(N(R$_{6b}$))(N(R$_{6b}$)$_2$), —N(R$_1$)C(N(R$_1$))(N(R$_1$)$_2$), —N(R$_1$)C(N(R$_1$))(N(R$_1$)(R$_{6b}$)), —N(R$_1$)C(N(R$_{6b}$))(N(R$_1$)$_2$), —N(R$_{6b}$)C(N(R$_1$))(N(R$_1$)$_2$), —N(R$_{6b}$)C(N(R$_{6b}$))(N(R$_1$)$_2$), —N(R$_{6b}$)C(N(R$_1$))(N(R$_1$)(R$_{6b}$)), —N(R$_1$)C(N(R$_{6b}$))(N(R$_1$)(R$_{6b}$)), —N(R$_1$)C(N(R$_1$))(N(R$_{6b}$)$_2$), —N(R$_{6b}$)C(N(R$_{6b}$))(N(R$_1$)(R$_{6b}$)), —N(R$_{6b}$)C(N(R$_1$))(N(R$_{6b}$)$_2$), —N(R$_1$)C(N(R$_{6b}$))(N(R$_{6b}$)$_2$), —N(R$_{6b}$)C(N(R$_{6b}$))(N(R$_{6b}$)$_2$), =O, =S, =N(R$_1$), =N(R$_{6b}$) or $W_5$. Typically $R_3$ is F, Cl, —CN, $N_3$, NO$_2$, —OR$_{6a}$—OR$_1$, —N(R$_1$)$_2$, —N(R$_1$)(R$_{6b}$), —N(R$_{6b}$)$_2$, —SR$_1$, —SR$_{6a}$, —C(O)OR$_1$, —C(O)R$_{6c}$, —C(O)OR$_{6a}$, —OC(O)R$_1$, —NR$_1$C(O)R$_1$, —N(R$_{6b}$)C(O)R$_1$, —C(O)N(R$_1$)$_2$, —C(O)N(R$_{6b}$)(R$_1$), —C(O)N(R$_{6b}$)$_2$, or =O. More typical $R_3$ groups comprising $R_{6b}$ include —C(O)N(R$_{6b}$)$_2$ or —C(O)N(R$_{6b}$)(R$_1$). More typically yet $R_3$ is F, Cl, —CN, $N_3$, —OR$_1$, —N(R$_1$)$_2$, —SR$_1$, —C(O)OR$_1$, —OC(O)R$_1$, or =O. More typically still, $R_3$ is F, —OR$_1$, —N(R$_1$)$_2$, or =O. In the context of the present application, "=O" denotes a double bonded oxygen atom (oxo), and "=S" =N(R$_{6b}$) and "=N(R$_1$)" denote the sulfur and nitrogen analogs.

$R_4$ is alkyl of 1 to 12 carbon atoms, and alkynyl or alkenyl of 2 to 12 carbon atoms. The alkyl $R_4$'s are typically of 1, 2, 3, 4, 5, 6, 7, 8, 9, 10, 11, or 12 carbon atoms and the alkenyl and alkynyl $R_4$'s are typically of 2, 3, 4, 5, 6, 7, 8, 9, 10, 11, or 12 carbon atoms. $R_4$ ordinarily is alkyl (as defined above). When $R_4$ is alkenyl it is typically ethenyl (—CH=CH$_2$), 1-prop-1-enyl (—CH=CHCH$_3$), 1-prop-2-enyl (—CH$_2$CH=CH$_2$), 2-prop-1-enyl (—C(=CH$_2$)(CH$_3$)), 1-but-1-enyl (—CH=CHCH$_2$CH$_3$), 1-but-2-enyl (—CH$_2$CH=CHCH$_3$), 1-but-3-enyl (—CH$_2$CH$_2$CH=CH$_2$), 2-methyl-1-prop-1-enyl (—CH=C(CH$_3$)$_2$), 2-methyl-1-prop-2-enyl (—CH$_2$C(=CH$_2$)(CH$_3$)), 2-but-1-enyl (—C(=CH$_2$)CH$_2$CH$_3$), 2-but-2-enyl (—C(CH$_3$)=CHCH$_3$), 2-but-3-enyl (—CH(CH$_3$)CH=CH$_2$), 1-pent-1-enyl (—C=CHCH$_2$CH$_2$CH$_3$), 1-pent-2-enyl (CHCH=CHCH$_2$CH$_3$), 1-pent-3-enyl (—CHCH$_2$CH=CHCH$_3$), 1-pent-4-enyl (—CHCH$_2$CH$_2$CH=CH$_2$), 2-pent-1-enyl (—C(=CH$_2$)CH$_2$CH$_2$CH$_3$), 2-pent-2-enyl (—C(CH$_3$)=CH$_2$CH$_2$CH$_3$), 2-pent-3-enyl (—CH(CH$_3$)CH=CHCH$_3$), 2-pent-4-enyl (—CH(CH$_3$)CH$_2$CH=CH$_2$) or 3-methyl-1-but-2-enyl (—CH$_2$CH=C(CH$_3$)$_2$). More typically, $R_4$ alkenyl groups are of 2,3 or 4 carbon atoms. When $R_4$ is alkynyl it is typically ethynyl (—C≡CH), 1-prop-1-ynyl (—C≡CCH$_3$), 1-prop-2-ynyl (—CH$_2$C≡CH), 1-but-1-ynyl (—C≡CCH$_2$CH$_3$), 1-but-2-ynyl (—CH$_2$C≡CCH$_3$), 1-but-3-ynyl (—CH$_2$CH$_2$C≡CH), 2-but-3-ynyl (CH(CH$_3$)C≡CH), 1-pent-1-ynyl (—C—CCH$_2$CH$_2$CH$_3$), 1-pent-2-ynyl (CH$_2$C≡CCH$_2$CH$_3$), 1-pent-3-ynyl (—CH$_2$CH$_2$C-=CCH$_3$) or 1-pent-4-ynyl (—CH$_2$CH$_2$CH$_2$C≡CH). More typically, $R_4$ alkynyl groups are of 2, 3 or 4 carbon atoms.

$R_5$ is $R_4$, as defined above, or $R_4$ substituted with 0 to 3 $R_3$ groups. Typically $R_5$ is an alkyl of 1 to 4 carbon atoms substituted with 0 to 3 fluorine atoms.

$R_{5a}$ is independently alkylene of 1 to 12 carbon atoms, alkenylene of 2 to 12 carbon atoms, or alkynylene of 2–12 carbon atoms any one of which alkylene, alkenylene or alkynylene is substituted with 0–3 $R_3$ groups. As defined above for $R_4$, $R_{5a}$'s are of 1, 2, 3, 4, 5, 6, 7, 8, 9, 10, 11, or 12 carbon atoms when alkylene and of 2, 3, 4, 5, 6, 7, 8, 9, 10, 11, or 12 carbon atoms when alkenylene or alkynylene. Each of the typical $R_4$ groups is a typical $R_{5a}$ group with the proviso that one of the hydrogen atoms of the described $R_4$ group is removed to form the open valence to a carbon atom through which the second bond to the $R_{5a}$ is attached.

$R_{14}$ is normal or terminally secondary $C_1$–$C_6$ alkyl.

$W_5$ is a carbocycle or heterocycle, with the proviso that each $W_5$ is independently substituted with 0 to 3 $R_2$ groups. $W_5$ carbocycles and $T_1$ and $W_5$ heterocycles are stable chemical structures. Such structures are isolatable in measurable yield, with measurable purity, from reaction mixtures at temperatures from −78° C. to 200° C. Each $W_5$ is independently substituted with 0 to 3 $R_2$ groups. Typically, $T_1$ and $W_5$ are a saturated, unsaturated or aromatic ring comprising a mono- or bicyclic carbocycle or heterocycle. More typically, $T_1$ or $W_5$ has 3 to 10 ring atoms, still more typically, 3 to 7 ring atoms, and ordinarily 3 to 6 ring atoms. The $T_1$ and $W_5$ rings are saturated when containing 3 ring atoms, saturated or monounsaturated when containing 4 ring atoms, saturated, or mono- or diunsaturated when containing 5 ring atoms, and saturated, mono- or diunsaturated, or aromatic when containing 6 ring atoms. Unsaturation of the $W_5$ rings include internal and external unsaturation wherein the external incorporates a ring atom.

When $W_5$ is carbocyclic, it is typically a 3 to 7 carbon monocycle or a 7 to 12 carbon atom bicycle. More typically, $W_5$ monocyclic carbocycles have 3 to 6 ring atoms, still more typically 5 or 6 ring atoms. $W_5$ bicyclic carbocycles typically have 7 to 12 ring atoms arranged as a bicyclo [4,5], [5,5], [5,6] or [6,6] system, still more typically, 9 or 10 ring atoms arranged as a bicyclo [5,6] or [6,6] system. Examples include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, phenyl, spiryl and naphthyl.

A $T_1$ or $W_5$ heterocycle is typically a monocycle having 3 to 7 ring members (2 to 6 carbon atoms and 1 to 3 heteroatoms selected from N, O, P, and S) or a bicycle having 7 to 10 ring members (4 to 9 carbon atoms and 1 to 3 heteroatoms selected from N, O, P, and S). More typically, $T_1$ and $W_5$ heterocyclic monocycles have 3 to 6 ring atoms (2 to 5 carbon atoms and 1 to 2 heteroatoms selected from N, O, and S), still more typically, 5 or 6 ring atoms (3 to 5 carbon atoms and 1 to 2 heteroatoms selected from N and S). $T_1$ and $W_5$ heterocyclic bicycles have 7 to 10 ring atoms (6 to 9 carbon atoms and 1 to 2 heteroatoms selected from N, O, and S) arranged as a bicyclo [4,5], [5,5], [5,6], or [6,6] system, still more typically, 9 to 10 ring atoms (8 to 9 carbon atoms and 1 to 2 hetero atoms selected from N and S) arranged as a bicyclo [5,6] or [6,6] system.

Typically $T_1$ and $W_5$ heterocycles are selected from pyridyl, pyridazinyl, pyrimidinyl, pyrazinyl, s-triazinyl, oxazolyl, imidazolyl, thiazolyl, isoxazolyl, pyrazolyl, isothiazolyl, furanyl, thiofuranyl, thienyl, or pyrrolyl.

More typically, the heterocycle of $T_1$ and $W_5$ is bonded through a carbon atom or nitrogen atom thereof. Still more typically $T_1$ heterocycles are bonded by a stable covalent bond through a nitrogen atom thereof to the cyclohexene ring of the compositions of the invention and $W_5$ heterocycles are bonded by a stable covalent bond through a carbon or nitrogen atom thereof to the cyclohexene ring of the compositions of the invention. Stable covalent bonds are chemically stable structures as described above.

$W_5$ optionally is selected from the group consisting of:

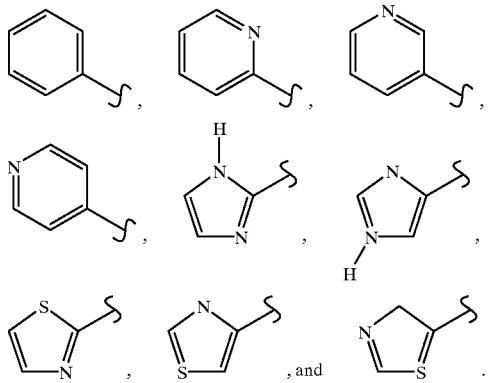

$W_6$ is $-R_5$, $-W_5$, $-R_{5a}W_5$, $-C(O)OR_{6a}$, $-C(O)R_{6c}$, $-C(O)N(R_{6b})_2$, $-C(NR_{6b})(N(R_{6b})_2)$, $-C(NR_{6b})(N(H)(R_{6b}))$, $-C(N(H))(N(R_{6b})_2)$, $-C(S)N(R_{6b})_2$, or $-C(O)R_2$, typically $W_6$ is $-R_5$, $-W_5$, or $-R_{5a}W_5$; in some embodiments, $W_6$ is $R_1$, $-C(O)-R_1$, $-CHR_1W_7$, $-CH(R_1)_aW_7$, $-CH(W_7)_2$, (where, $W_7$ is monovalent a is 0 or 1, but is 0 when $W_7$ is divalent) or $-C(O)W_7$. In some embodiments, $W_6$ is $-CHR_1W_7$ or $-C(O)W_7$, or $W_6$ is $-(CH_2)_{m1}CH((CH_2)_{m3}R_3)_2$; $-(CH_2)_{m1}C((CH_2)_{m3}R_3)_3$; $-(CH_2)_{m1}CH((CH_2)_{m3}R_{5a}W_5)_2$; $-(CH_2)_{m1}CH((CH_2)_{m3}R_3)((CH_2)_{m3}R_{5a}W_5)$; $-(CH_2)_{m1}C((CH_2)_{m3}R_3)_2(CH_2)_{m3}R_{5a}W_5)$; $-(CH_2)_{m1}C((CH_2)_{m3}R_{5a}W_5)_3$ or $-(CH_2)_{m1}C((CH_2)_{m3}R_3)((CH_2)_{m3}R_{5a}W_5)_2$; and wherein $m_3$ is an integer from 1 to 3.

$W_7$ is $R_3$ or $R_5$, but typically is alkyl of 1 to 12 carbons substituted with 0 to 3 $R_3$ groups, the latter typically selected from the group consisting of $-NR_1(R_{6b})$, $-N(R_{6b})_2$, $-OR_{6a}$, or $SR_{6a}$. More typically, $W_7$ is $-OR_1$ or an alkyl of 3 to 12 carbon atoms substituted with $OR_1$.

In general, $W_6$ is $R_1-$, $-CHR_1W_7$,

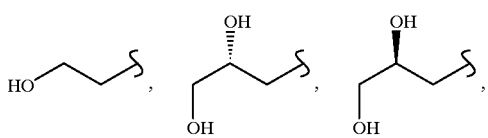

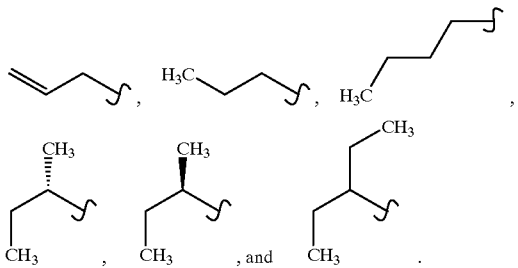

Exemplary $W_6$ groups are listed in Table 2.

An embodiment of the invention comprises a compound of the formula:

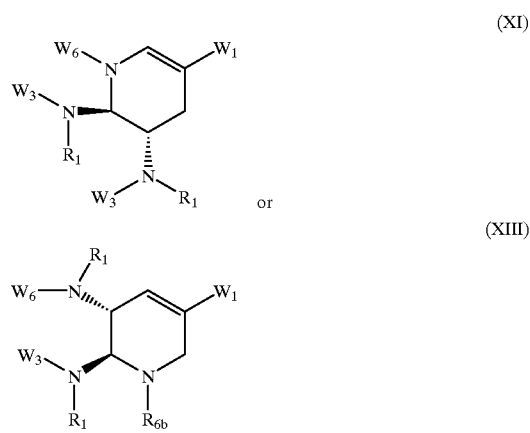

wherein each $R_1$ and $R_{6b}$ are typically H, and $W_2$ is typically selected from the group consisting of:

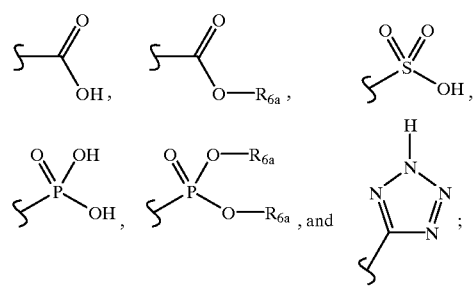

and $W_6$ is one of:

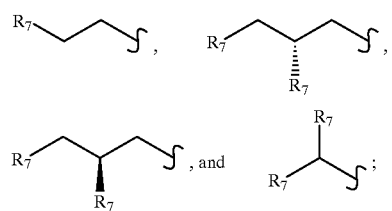

wherein $R_7$ is H, $-CH_3$, $-CH_2CH_3$, $-CH_2CH_2CH_3$, $-OCH_3$, $-OAc$ ($-O-C(O)CH_3$), $-OH$, $-NH_2$, or $-SH$, typically H, $-CH_3$ or $-CH_2CH_3$.

Another embodiment of the invention is directed toward compounds of formula (XX) or (XXa):

(XX)

(XXa)

wherein
- $A_3$ is N, N(O) or N(S);
- $Z_3$ is H, $W_6$, $G_1$ or $R_{3a}$;
- $E_1$ is $-(CR_1R_1)_{m1}W_1$;
- $G_1$ is $N_3$, $-CN$, $-OH$, $-OR_{6a}$, $-NO_2$ or $-(CR_1R_1)_{m1}W_2$;
- $G_2$ is $G_1$ or $-X_1W_6$;
- $T_1$ is $-NR_1W_3$ or a heterocycle;
- $J_1$ is $R_1$, Br, Cl, F, I, CN, $NO_2$ or $N_3$;
- $J_2$ is H or $R_1$;
- $J_3$ is $J_1$ if $X_1$ is a bond; and $J_3$ is $J_2$ if $X_1$ is $-O-$, $-N(H)-$, $-N(W_6)-$, $-N(OH)-$, $-N(OW_6)-$, $-N(NH_2)-$, $-N(N(H)(W_6))-$, $-N(N(W_6)_2)-$, $-N(H)N(W_6)-$, $-S-$, $-SO-$, or $-SO_2-$;
- $R_1$ is independently H or alkyl of 1 to 12 carbon atoms;
- $R_2$ is independently $R_3$ or $R_4$ wherein each $R_4$ is independently substituted with 0 to 3 $R_3$ groups;
- $R_3$ is independently F, Cl, Br, I, $-CN$, $N_3$, $-NO_2$, $OR_{6a}$, $-OR_1$, $-N(R_1)_2$, $-N(R_1)(R_{6b})$, $-N(R_{6b})_2$, $-SR_1$, $-SR_{6a}$, $-S(O)R_1$, $-S(O)_2R_1$, $-S(O)OR_1$, $-S(O)OR_{6a}$, $-S(O)_2OR_1$, $-S(O)_2OR_{6a}$, $-C(O)OR_1$, $-C(O)R_{6c}$, $-C(O)OR_{6a}$, $-OC(O)R_1$, $-N(R_1)(C(O)R_1)$, $-N(R_{6b})(C(O)R_1)$, $-N(R_1)(C(O)OR_1)$, $-N(R_{6b})(C(O)OR_1)$, $-C(O)N(R_1)_2$, $-C(O)N(R_{6b})(R_1)$, $-C(O)N(R_{6b})_2$, $-C(NR_1)(N(R_1)_2)$, $-C(N(R_{6b}))(N(R_1)_2)$, $-C(N(R_1))(N(R_1)(R_{6b}))$, $-C(N(R_{6b}))(N(R_1)(R_{6b}))$, $-C(N(R_1))(N(R_{6b})_2)$, $-C(N(R_{6b}))(N(R_{6b})_2)$, $-N(R_1)C(N(R_1))(N(R_1)_2)$, $-N(R_1)C(N(R_1))(N(R_1)(R_{6b}))$, $-N(R_1)C(N(R_{6b}))(N(R_1)_2)$, $-N(R_{6b})C(N(R_1))(N(R_1)_2)$, $-N(R_{6b})C(N(R_{6b}))(N(R_1)_2)$, $-N(R_{6b})C(N(R_1))(N(R_1)(R_{6b}))$, $-N(R_1)C(N(R_{6b}))(N(R_1)(R_{6b}))$, $-N(R_1)C(N(R_1))(N(R_{6b})_2)$, $-N(R_{6b})C(N(R_{6b}))(N(R_1)(R_{6b}))$, $-N(R_{6b})C(N(R_1))(N(R_{6b})_2)$, $-N(R_1)C(N(R_{6b}))(N(R_{6b})_2)$ or $-N(R_{6b})C(N(R_{6b}))(N(R_{6b})_2)$, $=O$, $=S$, $=N(R_1)$, $=N(R_{6b})$ or $W_5$;
- $R_{3a}$ is independently $-CN$, $N_3$, $-NO$, $-NO_2$, $-OR_{6a}$, $-OR_1$, $-N(R_1)_2$, $-N(R_1)(R_{6b})$, $-N(Rb)_2$, $-SR_1$, $SR_{6a}$, $-S(O)R_1$, $-S(O)_2R_1$, $-S(O)OR_1$, $-S(O)OR_{6a}$, $-S(O)_2OR_1$, $-S(O)_2OR_{6a}$, $-C(O)R_1$, $-C(O)R_{6c}$, $-C(O)OR_{6a}$, $-OC(O)R_1$, $-N(R_1)(C(O)R_1)$, $-N(R_{6b})(C(O)R_1)$, $-N(R_1)(C(O)OR_1)$, $-N(R_{6b})(C(O)OR_1)$, $-C(O)N(R_1)_2$, $-C(O)N(R_{6b})(R_1)$, $-C(O)N(R_{6b})_2$, $-C(NR_1)(N(R_1)_2)$, $-C(N(R_{6b}))(N(R_1)_2)$, $-C(N(R_1))(N(R_1)(R_{6b}))$, $-C(N(R_{6b}))(N(R_1)(R_{6b}))$, $-C(N(R_1))(N(R_{6b})_2)$, $-C(N(R_{6b}))(N(R_{6b})_2)$, $-N(R_1)C(N(R_1))(N(R_1)_2)$, $-N(R_1)C(N(R_1))(N(R_1)(R_{6b}))$, $-N(R_1)C(N(R_{6b}))(N(R_1)_2)$, $-N(R_{6b})C(N(R_1))(N(R_1)_2)$, $-N(R_{6b})C(N(R_{6b}))(N(R_1)_2)$, $-N(R_{6b})C(N(R_1))(N(R_1)(R_{6b}))$, $-N(R_1)C(N(R_{6b}))(N(R_1)(R_{6b}))$, $-N(R_1)C(N(R_1))(N(R_{6b})_2)$, $-N(R_{6b})C(N(R_{6b}))(N(R_1)(R_{6b}))$, $-N(R_{6b})C(N(R_1))(N(R_{6b})_2)$, $-N(R_1)C(N(R_{6b}))(N(R_{6b})_2)$ or $-N(R_{6b})C(N(R_{6b}))(N(R_{6b})_2)$;
- $R_4$ is independently alkyl of 1 to 12 carbon atoms, alkenyl of 2 to 12 carbon atoms, or alkynyl of 2 to 12 carbon atoms;
- $R_5$ is independently $R_4$ wherein each $R_4$ is substituted with 0 to 3 $R_3$ groups;
- $R_{5a}$ is independently alkylene of 1 to 12 carbon atoms, alkenylene of 2 to 12 carbon atoms, or alkynylene of 2–12 carbon atoms any one of which alkylene, alkenylene or alkynylene is substituted with 0–3 $R_3$ groups;
- $R_{6a}$ is independently H or an ether- or ester-forming group;
- $R_{6b}$ is independently H, a protecting group for amino or the residue of a carboxyl-containing compound;
- $R_{6c}$ is independently H or the residue of an amino-containing compound;
- $W_1$ is a group comprising an acidic hydrogen, a protected acidic group, or an $R_{6c}$ amide of the group comprising an acidic hydrogen;
- $W_2$ is a group comprising a basic heteroatom or a protected basic heteroatom, or an $R_{6b}$ amide of the basic heteroatom;
- $W_3$ is $W_4$ or $W_5$;
- $W_4$ is $R_5$ or $-C(O)R_5$, $-C(O)W_5$, $-SO_2R_5$, or $-SO_2W_5$;
- $W_5$ is carbocycle or heterocycle wherein $W_5$ is independently substituted with 0 to 3 $R_2$ groups;
- $W_6$ is $-R_5$, $-W_5$, $-R_{5a}W_5$, $-C(O)OR_{6a}$, $-C(O)R_{6c}$, $-C(O)N(R_{6b})_2$, $-C(N_{6b})(N_{6b})_2)$, $-C(N_{6b})(N(H)(R_{6b}))$, $-C(N(H)(N_{6b})_2)$, $-C(S)N_{6b})_2$, or $-C(O)R_2$;
- $X_1$ is a bond, $-O-$, $-N(H)-$, $-N(W_6)-$, $-N(OH)-$, $-N(OW_6)-$, $-N(NH_2)-$, $-N(N(H)(W_6))-$, $-N(N(W_6)_2)-$, $-N(H)N(W_6)-$, $-S-$, $-SO-$, or $-SO_2-$; and each $m_1$ is independently an integer from 0 to 2; provided, however, that compounds of formula (XX) are excluded wherein $A_3$ is N, each $J_1$, $J_2$, $J_{2a}$ and $J_3$ is H and $T_1$ is $-N(H)(Ac)$ and:
- $E_1$ is $-CO_2H$ or $-CO_2CH_3$,
- $G_2$ is $-OBoc$, and
- $Z_3$ is Boc;
- $E_1$ is $-CO_2H$ or $-CO_2CH_3$,
- $G_2$ is $-OH$, and
- $Z_3$ is H;
- $E_1$ is $-CO_2H$, $-OCH_3$ or $-CO_2Bn$
- $G_2$ is $-OH$, and
- $Z_3$ is Boc;
- $E_1$ is $-CONH_2$,
- $G_2$ is $-OH$, and
- $Z_3$ is Boc or H;
- $E_1$ is $-CO_2H$ or $-CO_2CH_3$,
- $G_2$ is OH, and
- $Z_3$ is Bn; or
- $E_1$ is $-CO_2H$ or $-CO_2CH_3$, G$_2$ is —OH, and Z$_3$ is —CH$_2$CH(OH)CH$_2$(OH);

wherein Bn is benzyl and Boc is —CO$_2$C(CH$_3$)$_3$; further excluded are compounds of the formula: (VII) or (VIII):

(VII)

(VIII)

wherein

E$_1$ is —(CR$_1$R$_1$)$_{m1}$W$_1$;

G$_1$ is N$_3$, —CN, —OH, —OR$_{6a}$, —NO$_2$, or —(CR$_1$R$_1$)$_{m1}$W$_2$;

T$_1$ is —NR$_1$W$_3$, a heterocycle, or is taken together with G$_1$ to form a group having the structure U$_1$ is —X$_1$W$_6$;

J$_1$ and J$_{1a}$ are independently R$_1$, Br, Cl, F, I, CN, NO$_2$ or N$_3$;

J$_2$ and J$_{2a}$ are independently H or R$_1$;

R$_1$ is independently H or alkyl of 1 to 12 carbon atoms;

R$_2$ is independently R$_3$ or R$_4$ wherein each R$_4$ is independently substituted with 0 to 3 R$_3$ groups;

R$_3$ is independently F, Cl, Br, I, —CN, N$_3$, —NO$_2$, OR$_{6a}$, —OR$_1$, —N(R$_1$)$_2$, —N(R$_1$)(R$_{6b}$), —N(R$_{6b}$)$_2$, —SR$_1$, SR$_{6a}$, —S(O)R$_1$, —S(O)$_2$R$_1$, —S(O)OR$_1$, S(O)OR$_{6a}$, —S(O)$_2$OR$_1$, —S(O)$_2$OR$_{6a}$, —C(O)OR$_1$, —C(O)R$_{6c}$, —C(O)OR$_{6a}$, —OC(O)R$_1$, —N(R$_1$)(C(O)R$_1$), —N(R$_{6b}$)(C(O)R$_1$), —N(R$_1$)(C(O)OR$_1$), —N(R$_{6b}$)(C(O)OR$_1$), —C(O)N(R$_1$)$_2$, —C(O)N(R$_{6b}$)(R$_1$), —C(O)N(R$_{6b}$)$_2$, —C(NR$_1$)(N(R$_1$)$_2$), —C(N(R$_{6b}$))(N(R$_1$)$_2$), —C(N(R$_1$))(N(R$_1$)(R$_{6b}$)), —C(N(R$_{6b}$))(N(R$_1$)(R$_{6b}$)), —C(N(R$_1$))(N(R$_{6b}$)$_2$), —C(N(R$_{6b}$))(N(R$_{6b}$)$_2$), —N(R$_1$)C(N(R$_1$))(N(R$_1$)$_2$), —N(R$_1$)C(N(R$_1$))(N(R$_1$)(R$_{6b}$)), —N(R$_1$)C(N(R$_{6b}$))(N(R$_1$)$_2$), —N(R$_{6b}$)C(N(R$_1$))(N(R$_1$)$_2$), —N(R$_{6b}$)C(N(R$_{6b}$))(N(R$_1$)$_2$), —N(R$_{6b}$)C(N(R$_1$))(N(R$_1$)(R$_{6b}$)), —N(R$_1$)C(N(R$_{6b}$))(N(R$_1$)(R$_{6b}$)), —N(R$_1$)C(N(R$_1$))(N(R$_{6b}$)$_2$), —N(R$_{6b}$)C(N(R$_{6b}$))(N(R$_1$)(R$_{6b}$)), —N(R$_{6b}$)C(N(R$_1$))(N(R$_{6b}$)$_2$), —N(R$_1$)C(N(R$_{6b}$))(N(R$_{6b}$)$_2$), —N(R$_{6b}$)C(N(R$_{6b}$))(N(R$_{6b}$)$_2$), =O, =S, =N(R$_1$) or =N(R$_{6b}$);

R$_4$ is independently alkyl of 1 to 12 carbon atoms, alkenyl of 2 to 12 carbon atoms, or alkynyl of 2 to 12 carbon atoms;

R$_5$ is independently R$_4$ wherein each R$_4$ is substituted with 0 to 3 R$_3$ groups;

R$_{5a}$ is independently alkylene of 1 to 12 carbon atoms, alkenylene of 2 to 12 carbon atoms, or alkynylene of 2–12 carbon atoms any one of which alkylene, alkenylene or alkynylene is substituted with 0–3 R$_3$ groups;

R$_{6a}$ is independently H or an ether- or ester-forming group;

R$_{6b}$ is independently H, a protecting group for amino or the residue of a carboxyl-containing compound;

R$_{6c}$ is independently H or the residue of an amino-containing compound;

W$_1$ is a group comprising an acidic hydrogen, a protected acidic group, or an R$_{6c}$ amide of the group comprising an acidic hydrogen;

W$_2$ is a group comprising a basic heteroatom or a protected basic heteroatom, or an R$_{6b}$ amide of the basic heteroatom;

W$_3$ is W$_4$ or W$_5$;

W$_4$ is R$_5$ or —C(O)R$_5$, —C(O)W$_5$, —SO$_2$R$_5$, or —SO$_2$W$_5$;

W$_5$ is carbocycle or heterocycle wherein W$_5$ is independently substituted with 0 to 3 R$_2$ groups;

W$_6$ is —R$_5$, —W$_5$, —R$_{5a}$W$_5$, —C(O)OR$_{6a}$, —C(O)R$_{6c}$, —C(O)N(R$_{6b}$)$_2$, —C(NR$_{6b}$)(N(R$_{6b}$)$_2$), —C(NR$_{6b}$)(N(H)(R$_{6b}$)), —C(N(H)(N(R$_{6b}$)$_2$), —C(S)N(R$_{6b}$)$_2$, or —C(O)R$_2$;

X$_1$ is a bond, —O—, —N(H)—, —N(W$_6$)—, —S—, —SO—, or —SO$_2$—; and each m$_1$ is independently an integer from 0 to 2; and the salts, solvates, resolved enantiomers and purified diastereomers thereof.

Typically A$_3$ is N or N(O), more typically A$_3$ is N.

In typical embodiments, one of Z$_3$ and G$_2$ is G$_1$ or R$_{3a}$ and the other is W$_6$ or —X$_1$W$_6$. More typically, Z$_3$ is W$_6$ or R$_{3a}$ and G$_2$ is G$_1$ or —X$_1$W$_6$. More typically yet, Z$_3$ is W$_6$ and G$_2$ is G$_1$; or Z$_3$ is R$_{3a}$ and G$_2$ is —X$_1$W$_6$.

J$_3$ is J$_1$ if X$_1$ is a bond; and J$_3$ is J$_2$ if X$_1$ is —O—, —N(H)—, —N(W$_6$)—, —N(OH)—, —N(OW$_6$)—, —N(NH$_2$)—, —N(N(H)(W$_6$))—, —N(N(W$_6$)$_2$)—, —N(H)N(W$_6$)—, —S—, —SO—, or —SO$_2$—. The typical embodiments of J$_1$ and J$_2$, described above, are typical embodiments of J$_3$.

An embodiment of the invention comprises a compound of the formula (XXI) or (XXIa):

(XXI)

(XXIa)

An embodiment of the invention comprises a compound of the formula (XXII) or (XXIIa):

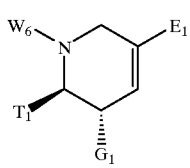
(XXII)

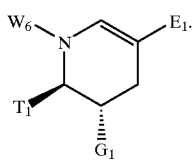
(XXIIa)

An embodiment of the invention comprises a compound of the formula (XXIII) or (XXIIIa):

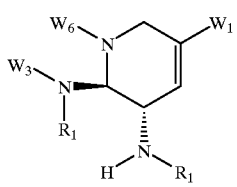
(XXIII)

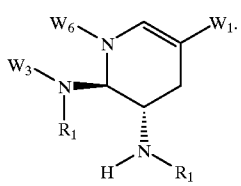
(XXIIIa)

An embodiment of the invention comprises a compound of the formula (XXIV) or (XXIVa):

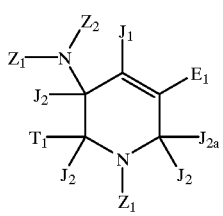
(XXIV)

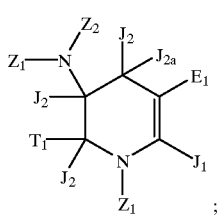
(XXIVa)

wherein one $Z_1$ is $W_6$ and the other $Z_1$ is $G_1$; and $Z_2$ is H or $W_6$. Typically, $Z_2$ is H.

An embodiment of the invention comprises a compound of the formula (XXV) or (XXVa):

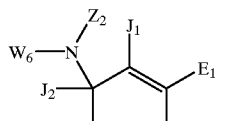
(XXV)

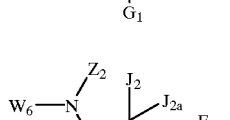
(XXVa)

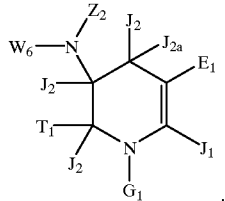

An embodiment of the invention comprises a compound of the formula (XXVI) or (XXVIa):

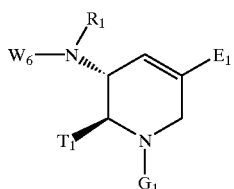
(XXVI)

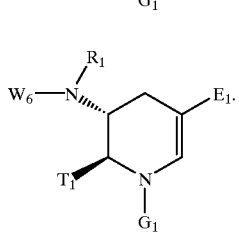
(XXVIa)

An embodiment of the invention comprises a compound of the formula (XXVII) or (XXVIIa):

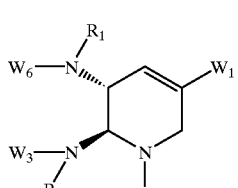
(XXVII)

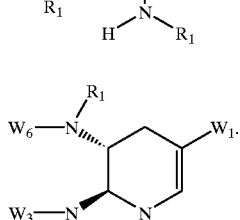
(XXVIIa)

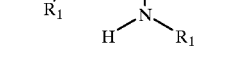

An embodiment of the invention comprises a compound of the formula (XXVIII) or (XXVIIIa):

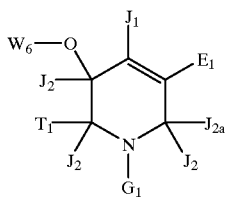

(XXVIII)

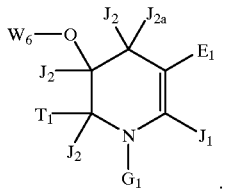

(XXVIIIa)

An embodiment of the invention comprises a compound of the formula (XXIX) or (XXIXa):

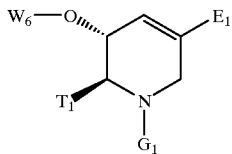

(XXIX)

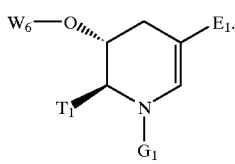

(XXIXa)

An embodiment of the invention comprises a compound of the formula (XXX) or (XXXa):

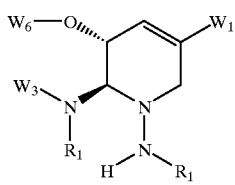

(XXX)

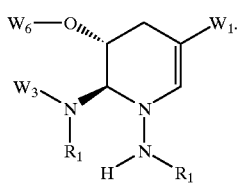

(XXXa)

It is important to appreciate that each of the typical embodiments of formula (XXX) and (XXXa), set forth above and in the appended claims, are also embodiments of formulas (XXI)–(XXX) and (XXIa)–(XXXa), set forth immediately above.

Groups $R_{6a}$ and $R_{6b}$ are not critical functionalities and may vary widely. When not H, their function is to serve as intermediates for the parental drug substance. This does not mean that they are biologically inactive. On the contrary, a principal function of these groups is to convert the parental drug into a prodrug, whereby the parental drug is released upon conversion of the prodrug in vivo. Because active prodrugs are absorbed more effectively than the parental drug they in fact often possess greater potency in vivo than the parental drug. When not hydrogen, $R_{6a}$ and $R_{6b}$ are removed either in vitro, in the instance of chemical intermediates, or in vivo, in the case of prodrugs. With chemical intermediates, it is not particularly important that the resulting pro-functionality products, e.g. alcohols, be physiologically acceptable, although in general it is more desirable if the products are pharmacologically innocuous.

$R_{6a}$ is H or an ether- or ester-forming group. "Ether-forming group" means a group which is capable of forming a stable, covalent bond between the parental molecule and a group having the formula:

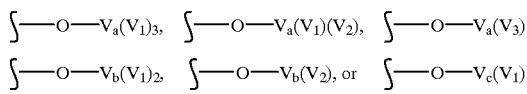

Wherein $V_a$ is a tetravalent atom typically selected from C and Si; $V_b$ is a trivalent atom typically selected from B, Al, N, and P, more typically N and P; $V_c$ is a divalent atom typically selected from O, S, and Se, more typically S; $V_1$ is a group bonded to Va, $V_b$ or $V_c$ by a stable, single covalent bond, typically $V_1$ is $W_6$ groups, more typically $V_1$ is H, $R_2$, $W_5$, or —$R_{5a}W_5$, still more typically H or $R_2$; $V_2$ is a group bonded to $V_a$ or $V_b$ by a stable, double covalent bond, provided that $V_2$ is not =O, =S or =N—, typically $V_2$ is =C($V_1$)$_2$ wherein $V_1$ is as described above; and $V_3$ is a group bonded to $V_a$ by a stable, triple covalent bond, typically $V_3$ is ≡C($V_1$) wherein $V_1$ is as described above.

"Ester-forming group" means a group which is capable of forming a stable, covalent bond between the parental molecule and a group having the formula:

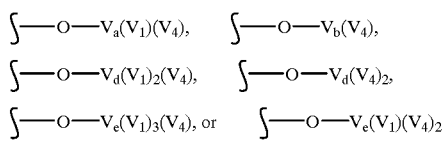

Wherein $V_a$, $V_b$, and $V_1$, are as described above; $V_d$ is a pentavalent atom typically selected from P and N; $V_e$ is a hexavalent atom typically S; and $V_4$ is a group bonded to $V_a$, $V_b$, $V_d$ or $V_e$ by a stable, double covalent bond, provided that at least one $V_4$ is =O, =S or =N—$V_1$, typically $V_4$, when other than =O, =S or =N—, is =C($V_1$)$_2$ wherein $V_1$ is as described above.

Protecting groups for —OH functions (whether hydroxy, acid or other functions) are embodiments of "ether- or ester-forming groups".

Particularly of interest are ether- or ester-forming groups that are capable of functioning as protecting groups in the synthetic schemes set forth herein. However, some hydroxyl and thio protecting groups are neither ether- nor ester-forming groups, as will be understood by those skilled in the art, and are included with amides, discussed under $R_{6c}$ below. $R_{6c}$ is capable of protecting hydroxyl or thio groups such that hydrolysis from the parental molecule yields hydroxyl or thio.

In its ester-forming role, $R_{6a}$ typically is bound to any acidic group such as, by way of example and not limitation, a —CO$_2$H or —C(S)OH group, thereby resulting in —$CO_2R_{6a}$. $R_{6a}$ for example is deduced from the enumerated ester groups of WO 95/07920.

Examples of $R_{6a}$ include $C_3$–$C_{12}$ heterocycle (described above) or $C_6$–$C_{12}$ aryl. These aromatic groups optionally are polycyclic or monocyclic. Examples include phenyl, spiryl, 2- and 3-pyrrolyl, 2- and 3-thienyl, 2- and 4-imidazolyl, 2-, 4- and 5-oxazolyl, 3- and 4-isoxazolyl, 2-, 4- and 5-thiazolyl, 3-, 4- and 5-isothiazolyl, 3- and 4-pyrazolyl, 1-, 2-, 3- and 4-pyridinyl, and 1-, 2-, 4- and 5-pyrimidinyl, $C_3$–$C_{12}$ heterocycle or $C_6$–$C_{12}$ aryl substituted with halo, $R_1$, $R_1$—O—$C_1$–$C_{12}$ alkylene, $C_1$–$C_{12}$ alkoxy, CN, $NO_2$, OH, carboxy, carboxyester, thiol, thioester, $C_1$–$C_{12}$ haloalkyl (1–6 halogen atoms), $C_2$–$C_{12}$ alkenyl or $C_2$–$C_{12}$ alkynyl. Such groups include 2-, 3- and 4-alkoxyphenyl ($C_1$–$C_{12}$ alkyl), 2-, 3- and 4-methoxyphenyl, 2-, 3- and 4-ethoxyphenyl, 2,3-, 2,4-, 2,5-, 2,6-, 3,4- and 3,5-diethoxyphenyl, 2- and 3-carboethoxy-4hydroxyphenyl, 2- and 3-ethoxy-4-hydroxyphenyl, 2- and 3-ethoxy-5-hydroxyphenyl, 2- and 3-ethoxy-6-hydroxyphenyl, 2-, 3- and 4-O-acetylphenyl, 2-, 3- and 4-dimethylaminophenyl, 2-, 3- and 4-methylmercaptophenyl, 2-, 3- and 4-halophenyl (including 2-, 3- and 4-fluorophenyl and 2-, 3- and 4-chlorophenyl), 2,3-, 2,4-, 2,5-, 2,6-, 3,4- and 3,5-dimethylphenyl, 2,3-, 2,4-, 2,5-, 2,6-, 3,4- and 3,5-biscarboxyethylphenyl, 2,3-, 2,4-, 2,5-, 2,6, 3,4- and 3,5-dimethoxyphenyl, 2,3-, 2,4-, 2,5-, 2,6-, 3,4- and 3,5-dihalophenyl (including 2,4-difluorophenyl and 3,5-difluorophenyl), 2-, 3- and 4-haloalkylphenyl (1 to 5 halogen atoms, $C_1$–$C_{12}$ alkyl including 4-trifluoromethylphenyl), 2-, 3- and 4-cyanophenyl, 2-, 3- and 4-nitrophenyl, 2-, 3- and 4-haloalkylbenzyl (1 to 5 halogen atoms, $C_1$–$C_{12}$ alkyl including 4-trifluoromethylbenzyl and 2-, 3- and 4-trichloromethylphenyl and 2-, 3- and 4-trichloromethylphenyl), 4-N-methylpiperidinyl, 3-N-methylpiperidinyl, 1-ethylpiperazinyl, benzyl, alkylsalicylphenyl ($C_1$–$C_4$ alkyl, including 2-, 3- and 4-ethylsalicylphenyl), 2-,3- and 4-acetylphenyl, 1,8-dihydroxynaphthyl (—$C_{10}H_6$—OH) and aryloxy ethyl [$C_6$–$C_9$ aryl (including phenoxy ethyl)], 2,2'-dihydroxybiphenyl, 2-, 3- and 4-N,N-dialkylaminophenol, —$C_6H_4CH_2$—$N(CH_3)_2$, trimethoxybenzyl, triethoxybenzyl, 2-alkyl pyridinyl ($C_{1-4}$ alkyl); $R_1O(O)C$

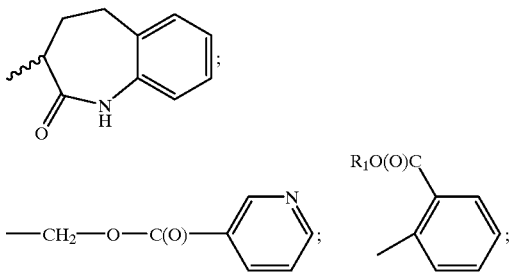

$C_4$–$C_8$ esters of 2-carboxyphenyl; and $C_1$–$C_4$ alkylene—$C_3$–$C_6$ aryl (including benzyl, —$CH_2$-pyrrolyl, —$CH_2$-thienyl, —$CH_2$-imidazolyl, —$CH_2$-oxazolyl, —$CH_2$-isoxazolyl, —$CH_2$-thiazolyl, —$CH_2$-isothiazolyl, —$CH_2$-pyrazolyl, —$CH_2$-pyridinyl and —$CH_2$-pyrimidinyl) substituted in the aryl moiety by 3 to 5 halogen atoms or 1 to 2 atoms or groups selected from halogen, $C_1$–$C_{12}$ alkoxy (including methoxy and ethoxy), cyano, nitro, OH, $C_1$–$C_{12}$ haloalkyl (1 to 6 halogen atoms; including —$CH_2$—$CCl_3$), $C_1$–$C_{12}$ alkyl (including methyl and ethyl), $C_2$–$C_{12}$ alkenyl or $C_2$–$C_{12}$ alkynyl;

alkoxy ethyl [$C_1$–$C_6$ alkyl including —$CH_2$—$CH_2$—O—$CH_3$ (methoxy ethyl)];

alkyl substituted by any of the groups set forth above for aryl, in particular OH or by 1 to 3 halo atoms (including —$CH_3$, —$CH(CH_3)_2$, —$C(CH_3)_3$, —$CH_2CH_3$, —$(CH_2)_2CH_3$, —$(CH_2)_3CH_3$, —$(CH_2)_4CH_3$, —$(CH_2)_5$ $CH_3$, —$CH_2CH_2F$, —$CH_2CH_2Cl$, —$CH_2CF_3$, and —$CH_2CCl_3$);

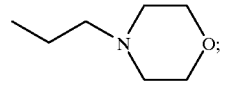

—N-2-propylmorpholino, 2,3-dihydro-6-hydroxyindene, sesamol, catechol monoester, —$CH_2$—$C(O)$—$N(R^1)_2$, —$CH_2$—$S(O)(R^1)$, —$CH_2$—$S(O)_2(R^1)$, —$CH_2$—CH$(OC(O)CH_2R^1)$—$CH_2(OC(O)CH_2R^1)$, cholesteryl, enolpyruvate (HOOC—C(=$CH_2$)—), glycerol;

a 5 or 6 carbon monosaccharide, disaccharide or oligosaccharide (3 to 9 monosaccharide residues);

triglycerides such as α-D-β-diglycerides (wherein the fatty acids composing glyceride lipids generally are naturally occurring saturated or unsaturated $C_{6-26}$, $C_{6-18}$ or $C_{6-10}$ fatty acids such as linoleic, lauric, myristic, palmitic, stearic, oleic, palmitoleic, linolenic and the like fatty acids) linked to acyl of the parental compounds herein through a glyceryl oxygen of the triglyceride;

phospholipids linked to the carboxyl group through the phosphate of the phospholipid;

phthalidyl (shown in FIG. 1 of Clayton et al., "Antimicrob. Agents Chemo." 5(6):670–671 [1974]);

cyclic carbonates such as (5-$R_d$-2-oxo-1,3-dioxolen-4-yl) methyl esters (Sakamoto et al., "Chem. Pharm. Bull." 32(6):2241–2248 [1984]) where $R_d$ is $R_1$, $R_4$ or aryl; and

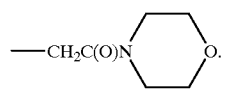

The hydroxyl groups of the compounds of this invention optionally are substituted with one of groups III, IV or V disclosed in WO 94/21604, or with isopropyl.

As further embodiments, Table A lists examples of $R_{6a}$ ester moieties that for example can be bonded via oxygen to —C(O)O— and P(O)(O—)$_2$ groups. Several $R_{6c}$ amidates also are shown, which are bound directly to —C(O)— or —P(O)$_2$. Esters of structures 1–5, 8–10 and 16, 17, 19–22 are synthesized by reacting the compound herein having a free hydroxyl with the corresponding halide (chloride or acyl chloride and the like) and N,N-dicyclohexyl-N-morpholine carboxamidine (or another base such as DBU, triethylamine, $CsCO_3$, N,N-dimethylaniline and the like) in DMF (or other solvent such as acetonitrile or N-methylpyrrolidone). When $W_1$ is phosphonate, the esters of structures 5–7, 11, 12, 21, and 23–26 are synthesized by reaction of the alcohol or alkoxide salt (or the corresponding arnines in the case of compounds such as 13, 14 and 15) with the monochlorophosphonate or dichlorophosphonate (or another activated phosphonate).

TABLE A

| | |
|---|---|
| 1. | —$CH_2$—$C(O)$—$N(R_1)_2$ |
| 2. | —$CH_2$—$S(O)(R_1)$ |
| 3. | —$CH_2$—$S(O)_2(R_1)$ |
| 4. | —$CH_2$—O—$C(O)$—$CH_2$—$C_6H_5$ |
| 5. | 3-cholesteryl |
| 6. | 3-pyridyl |
| 7. | N-ethylmorpholino |
| 8. | —$CH_2$—O—$C(O)$—$C_6H_5$ |
| 9. | —$CH_2$—O—$C(O)$—$CH_2CH_3$ |
| 10. | —$CH_2$—O—$C(O)$—$C(CH_3)_3$ |
| 11. | —$CH_2$—$CCl_3$ |
| 12. | —$C_6H_5$ |
| 13. | —NH—$CH_2$—$C(O)O$—$CH_2CH_3$ |
| 14. | —$N(CH_3)$—$CH_2$—$C(O)O$—$CH_2CH_3$ |
| 15. | —$NHR_1$ |
| 16. | —$CH_2$—O—$C(O)$—$C_{10}H_{15}$ |
| 17. | —$CH_2$—O—$C(O)$—$CH(CH_3)_2$ |
| 18. | —$CH_2$—C#H($OC(O)CH_2R_1$)—$CH_2$—$(OC(O)CH_2R_1)$ |
| 19. | —$CH_2C(O)N$⟨morpholino⟩ |
| 20. | ⟨benzazepinone structure⟩ |
| 21. | ⟨sugar structure with HO, OH, HO, HO⟩ |
| 22. | —$CH_2$—O—$C(O)$—⟨3-pyridyl⟩ |
| 23. | —$CH_2CH_2$—⟨2-pyridyl⟩ |
| 24. | $CH_3O(O)C$—⟨o-tolyl⟩ |
| 25. | $CH_3CH_2O(O)C$—⟨o-tolyl⟩ |
| 26. | —$CH_2$—⟨2,3,4-trimethoxyphenyl: $OCH_3$, $OCH_3$, $OCH_3$⟩ |

-chiral center is (R), (S) or racemate.

Other esters that are suitable for use herein are described in EP 632,048.

$R_{6a}$ also includes "double ester" forming profunctionalities such as

—$CH_2OC(O)OCH_3$,

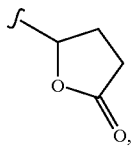

—$CH_2SCOCH_3$, —$CH_2OCON(CH_3)_2$, or alkyl- or arylacyloxyalkyl groups of the structure —$CH(R_1$ or $W_5)O((CO)R_{37})$ or —$CH(R_1$ or $W_5)((CO)OR_{38})$(linked to oxygen of the acidic group) wherein $R_{37}$ and $R_{38}$ are alkyl, aryl, or alkylaryl groups (see U.S. Pat. No. 4,968,788). Frequently $R_{37}$ and $R_{38}$ are bulky groups such as branched alkyl, ortho-substituted aryl, meta-substituted aryl, or combinations thereof, including normal, secondary, iso- and tertiary alkyls of 1–6 carbon atoms. An example is the pivaloyloxymethyl group. These are of particular use with prodrugs for oral administration. Examples of such useful $R_{6a}$ groups are alkylacyloxymethyl esters and their derivatives, including —$CH(CH_2CH_2OCH_3)OC(O)C(CH_3)_3$,

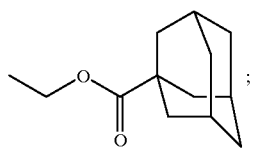

—$CH_2OC(O)C_{10}H_{15}$, —$CH_2OC(O)C(CH_3)_3$, —$CH(CH_2OCH_3)OC(O)C(CH_3)_3$, —$CH(CH(CH_3)_2)OC(O)C(CH_3)_3$, —$CH_2OC(O)CH_2CH(CH_3)_2$, —$CH_2OC(O)C_6H_{11}$, —$CH_2OC(O)C_6H_5$, —$CH_2OC(O)C_{10}H_{15}$, —$CH_2OC(O)CH_2CH_3$, —$CH_2OC(O)CH(CH_3)_2$, —$CH_2OC(O)C(CH_3)_3$ and —$CH_2OC(O)CH_2C_6H_5$.

For prodrug purposes, the ester typically chosen is one heretofore used for antibiotic drugs, in particular the cyclic carbonates, double esters, or the phthalidyl, aryl or alkyl esters.

As noted, $R_{6a}$, $R_{6c}$ and $R_{6b}$ groups optionally are used to prevent side reactions with the protected group during synthetic procedures, so they function as protecting groups (PRT) during synthesis. For the most part the decision as to which groups to protect, when to do so, and the nature of the PRT will be dependent upon the chemistry of the reaction to be protected against (e.g., acidic, basic, oxidative, reductive or other conditions) and the intended direction of the synthesis. The PRT groups do not need to be, and generally are not, the same if the compound is substituted with multiple PRT. In general, PRT will be used to protect carboxyl, hydroxyl or amino groups. The order of deprotection to yield free groups is dependent upon the intended direction of the synthesis and the reaction conditions to be encountered, and may occur in any order as determined by the artisan.

A very large number of $R_{6a}$ hydroxy protecting groups and $R_{6c}$ amide-forming groups and corresponding chemical cleavage reactions are described in "Protective Groups in Organic Chemistry", Theodora W. Greene (John Wiley & Sons, Inc., New York, 1991, ISBN 0-471-62301-6)

("Greene"). See also Kocienski, Philip J. "Protecting Groups" (Georg Thieme Verlag Stuttgart, New York, 1994), which is incorporated by reference in its entirety herein. In particular Chapter 1, Protecting Groups: An Overview, pages 1–20, Chapter 2, Hydroxyl Protecting Groups, pages 21–94, Chapter 3, Diol Protecting Groups, pages 95–117, Chapter 4, Carboxyl Protecting Groups, pages 118–154, Chapter 5, Carbonyl Protecting Groups, pages 155–184. For $R_{6a}$ carboxylic acid, phosphonic acid, phosphonate, sulfonic acid and other protecting groups for $W_1$ acids see Greene as set forth below. Such groups include by way of example and not limitation, esters, amides, hydrazides, and the like.

In some embodiments the $R_{6a}$ protected acidic group is an ester of the acidic group and $R_{6a}$ is the residue of a hydroxyl-containing functionality. In other embodiments, an $R_{6c}$ amino compound is used to protect the acid functionality. The residues of suitable hydroxyl or amino-containing functionalities are set forth above or are found in WO 95/07920. Of particular interest are the residues of amino acids, amino acid esters, polypeptides, or aryl alcohols. Typical amino acid, polypeptide and carboxyl-esterified amino acid residues are described on pages 11–18 and related text of WO 95/07920 as groups L1 or L2. WO 95/07920 expressly teaches the amidates of phosphonic acids, but it will be understood that such amidates are formed with any of the acid groups set forth herein and the amino acid residues set forth in WO 95/07920.

Typical $R_{6a}$ esters for protecting $W_1$ acidic functionalities are also described in WO 95/07920, again understanding that the same esters can be formed with the acidic groups herein as with the phosphonate of the '920 publication. Typical ester groups are defined at least on WO 95/07920 pages 89–93 (under $R^{31}$ or $R^{35}$), the table on page 105, and pages 21–23 (as R). Of particular interest are esters of unsubstituted aryl such as phenyl or arylalkyl such benzyl, or hydroxy-, halo-, alkoxy-, carboxy- and/or alkylestercarboxy-substituted aryl or alkylaryl, especially phenyl, ortho-ethoxyphenyl, or $C_1$–$C_4$ alkylestercarboxyphenyl (salicylate $C_1$–$C_{12}$ alkylesters).

The protected acidic groups $W_1$, particularly when using the esters or amides of WO 95/07920, are useful as prodrugs for oral administration. However, it is not essential that the $W_1$ acidic group be protected in order for the compounds of this invention to be effectively administered by the oral route. When the compounds of the invention having protected groups, in particular amino acid amidates or substituted and unsubstituted aryl esters are administered systemically or orally they are capable of hydrolytic cleavage in vivo to yield the free acid.

One or more of the acidic hydroxyls are protected. If more than one acidic hydroxyl is protected then the same or a different protecting group is employed, e.g., the esters may be different or the same, or a mixed amidate and ester may be used.

Typical $R_{6a}$ hydroxy protecting groups described in Greene (pages 14–118) include Ethers (Methyl); Substituted Methyl Ethers (Methoxymethyl, Methylthiomethyl, t-Butylthiomethyl, (Phenyldimethylsilyl)methoxymethyl, Benzyloxymethyl, p-Methoxybenzyloxymethyl, (4-Methoxyphenoxy)methyl, Guaiacolmethyl, t-Butoxymethyl, 4-Pentenyloxymethyl, Siloxymethyl, 2-Methoxyethoxymethyl, 2,2,2-Trichloroethoxymethyl, Bis(2-chloroethoxy)methyl, 2-(Trimethylsilyl)ethoxymethyl, Tetrahydropyranyl, 3-Bromotetrahydropyranyl, Tetrahydropthiopyranyl, 1-Methoxycyclohexyl, 4-Methoxytetrahydropyranyl, 4-Methoxytetrahydrothiopyranyl, 4-Methoxytetrahydropthiopyranyl S,S-Dioxido, 1-[(2-Chloro-4-methyl)phenyl]-4-methoxypiperidin-4-yl, 35, 1,4-Dioxan-2-yl, Tetrahydrofuranyl, Tetrahydrothiofuranyl, 2,3,3a,4,5,6,7,7a-Octahydro-7,8,8-trimethyl-4,7-methanobenzofuran-2-yl)); Substituted Ethyl Ethers (1-Ethoxyethyl, 1-(2-Chloroethoxy)ethyl, 1-Methyl-1-methoxyethyl, 1-Methyl-1-benzyloxyethyl, 1-Methyl-1-benzyloxy-2-fluoroethyl, 2,2,2-Trichloroethyl, 2-Trimethylsilylethyl, 2-(Phenylselenyl)ethyl, t-Butyl, Allyl, p-Chlorophenyl, p-Methoxyphenyl, 2,4-Dinitrophenyl, Benzyl); Substituted Benzyl Ethers (p-Methoxybenzyl, 3,4-Dimethoxybenzyl, o-Nitrobenzyl, p-Nitrobenzyl, p-Halobenzyl, 2,6-Dichlorobenzyl, p-Cyanobenzyl, p-Phenylbenzyl, 2- and 4-Picolyl, 3-Methyl-2-picolyl N-Oxido, Diphenylmethyl, p,p'-Dinitrobenzhydryl, 5-Dibenzosuberyl, Triphenylmethyl, α-Naphthyldiphenylmethyl, p-methoxyphenyldiphenylmethyl, Di(p-methoxyphenyl)phenylmethyl, Tri(p-methoxyphenyl)methyl, 4-(4'-Bromophenacyloxy)phenyldiphenylmethyl, 4,4',4"-Tris(4,5-dichlorophthalimidophenyl)methyl, 4,4',4"-Tris(levulinoyloxyphenyl)methyl, 4,4',4"-Tris(benzoyloxyphenyl)methyl, 3-(Imidazol-1-ylmethyl)bis(4',4"-dimethoxyphenyl)methyl, 1,1-Bis(4-methoxyphenyl)-1'-pyrenylmethyl, 9-Anthryl, 9-(9-Phenyl)xanthenyl, 9-(9-Phenyl-10-oxo)anthryl, 1,3-Benzodithiolan-2-yl, Benzisothiazolyl S,S-Dioxido); Silyl Ethers (Trimethylsilyl, Triethylsilyl, Triisopropylsilyl, Dimethylisopropylsilyl, Diethylisopropylsily, Dimethylthexylsilyl, t-Butyldimethylsilyl, t-Butyldiphenylsilyl, Tribenzylsilyl, Tri-p-xylylsilyl, Triphenylsilyl, Diphenylmethylsilyl, t-Butylmethoxyphenylsilyl); Esters (Formate, Benzoylformate, Acetate, Choroacetate, Dichloroacetate, Trichloroacetate, Trifluoroacetate, Methoxyacetate, Triphenylmethoxyacetate, Phenoxyacetate, p-Chlorophenoxyacetate, p-poly-Phenylacetate, 3-Phenylpropionate, 4-Oxopentanoate (Levulinate), 4,4-(Ethylenedithio)pentanoate, Pivaloate, Adamantoate, Crotonate, 4-Methoxycrotonate, Benzoate, p-Phenylbenzoate, 2,4,6-Trimethylbenzoate (Mesitoate)); Carbonates (Methyl, 9-Fluorenylmethyl, Ethyl, 2,2,2-Trichloroethyl, 2-(Trimethylsilyl)ethyl, 2-(Phenylsulfonyl)ethyl, 2-(Triphenylphosphonio)ethyl, Isobutyl, Vinyl, Allyl, p-Nitrophenyl, Benzyl, p-Methoxybenzyl, 3,4-Dimethoxybenzyl, o-Nitrobenzyl, p-Nitrobenzyl, S-Benzyl Thiocarbonate, 4-Ethoxy-1-naphthyl, Methyl Dithiocarbonate); Groups With Assisted Cleavage (2-Iodobenzoate, 4-Azidobutyrate, 4-Niotro-4-methylpentanoate, o-(Dibromomethyl)benzoate, 2-Formylbenzenesulfonate, 2-(Methylthiomethoxy)ethyl Carbonate, 4-(Methylthiomethoxy)butyrate, 2-(Methylthiomethoxymethyl)benzoate); Miscellaneous Esters (2,6-Dichloro-4-methylphenoxyacetate, 2,6-Dichloro-4-(1,1,3,3 tetramethylbutyl)phenoxyacetate, 2,4-Bis(1,1-dimethylpropyl)phenoxyacetate, Chorodiphenylacetate, Isobutyrate, Monosuccinoate, (E)-2-Methyl-2-butenoate (Tigloate), o-(Methoxycarbonyl)benzoate, p-poly-Benzoate, α-Naphthoate, Nitrate, Alkyl N,N,N',N'-Tetramethylphosphorodiamidate, N-Phenylcarbamate, Borate, Dimethylphosphinothioyl, 2,4-Dinitrophenylsulfenate); and Sulfonates (Sulfate, Methanesulfonate (Mesylate), Benzylsulfonate, Tosylate).

More typically, $R_{6a}$ hydroxy protecting groups include substituted methyl ethers, substituted benzyl ethers, silyl ethers, and esters induding sulfonic acid esters, still more typically, trialkylsilyl ethers, tosylates and acetates.

Typical 1,2-diol protecting groups (thus, generally where two OH groups are taken together with the $R_{6a}$ protecting functionality) are described in Greene at pages 118–142 and include Cyclic Acetals and Ketals (Methylene, Ethylidene, 1-t-Butylethylidene, 1-Phenylethylidene, (4-Methoxyphenyl)ethylidene, 2,2,2-Trichloroethylidene, Acetonide (Isopropylidene), Cyclopentylidene, Cyclohexylidene, Cycloheptylidene, Benzylidene, p-Methoxybenzylidene, 2,4-Dimethoxybenzylidene, 3,4-Dimethoxybenzylidene, 2-Nitrobenzylidene); Cyclic Ortho Esters (Methoxymethylene, Ethoxymethylene, Dimethoxymethylene, 1-Methoxyethylidene, 1-Ethoxyethylidine, 1,2-Dimethoxyethylidene, α-Methoxybenzylidene, 1-(N,N-Dimethylamino)ethylidene Derivative, α-(N,N-Dimethylamino)benzylidene Derivative, 2-Oxacyclopentylidene); Silyl Derivatives (Di-t-butylsilylene Group, 1,3-(1,1,3,3-Tetraisopropyldisiloxanylidene), and Tetra-t-butoxydisiloxane-1,3-diylidene), Cyclic Carbonates, Cyclic Boronates, Ethyl Boronate and Phenyl Boronate.

More typically, 1,2-diol protecting groups include those shown in Table B, still more typically, epoxides, acetonides, cyclic ketals and aryl acetals.

TABLE B

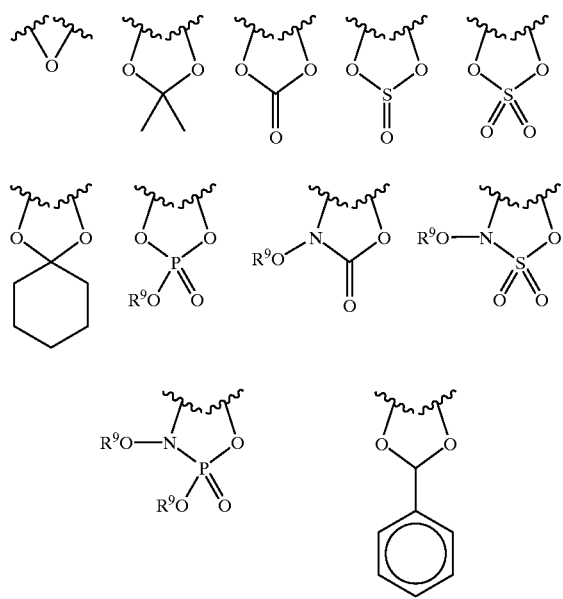

wherein $R^9$ is $C_1$–$C_6$ alkyl.

$R_{6b}$ is H, a protecting group for amino or the residue of a carboxyl-containing compound, in particular H, —C(O)$R_4$, an amino acid, a polypeptide or a protecting group not —C(O)$R_4$, amino acid or polypeptide. Amide-forming $R_{6b}$ are found for instance in group $G_1$. When $R_{6b}$ is an amino acid or polypeptide it has the structure $R_{15}$NHCH($R_{16}$)C(O)—, where $R_{15}$ is H, an amino acid or polypeptide residue, or $R_5$, and $R_{16}$ is defined below.

$R_{16}$ is lower alkyl or lower alkyl ($C_1$–$C_6$) substituted with amino, carboxyl, amide, carboxyl ester, hydroxyl, $C_6$–$C_7$ aryl, guanidinyl, imidazolyl, indolyl, sulfhydryl, sulfoxide, and/or alkylphosphate. $R_{16}$ also is taken together with the amino acid α N to form a proline residue ($R_{16}$=—CH$_2$)$_3$—). However, $R_{16}$ is generally the side group of a naturally-occurring amino acid such as H, —CH$_3$, —CH(CH$_3$)$_2$, —CH$_2$—CH(CH$_3$)$_2$, —CHCH$_3$—CH$_2$—CH$_3$, —CH$_2$—C$_6$H$_5$, —CH$_2$CH$_2$—S—CH$_3$, —CH$_2$OH, —CH(OH)—CH$_3$, —CH$_2$—SH, —CH$_2$—C$_6$H$_4$OH, —CH$_2$—CO—NH$_2$, —CH$_2$—CH$_2$—CO—NH$_2$, —CH$_2$—COOH, —CH$_2$—CH$_2$—COOH, —(CH$_2$)$_4$—NH$_2$ and —(CH$_2$)$_3$—NH—C(NH$_2$)—NH$_2$. $R_{16}$ also includes 1-guanidinoprop-3-yl, benzyl, 4-hydroxybenzyl, imidazol-4-yl, indol-3-yl, methoxyphenyl and ethoxyphenyl.

$R_{6b}$ are residues of carboxylic acids for the most part, but any of the typical amino protecting groups described by Greene at pages 315–385 are useful. They include Carbamates (methyl and ethyl, 9-fluorenylmethyl, 9(2-sulfo)fluoroenylmethyl, 9-(2,7-dibromo)fluorenylmethyl, 2,7-di-t-buthyl-[9-(10,10-dioxo-10,10,10,10-tetrahydrothioxanthyl)] methyl, 4-methoxyphenacyl); Substituted Ethyl (2,2,2-trichoroethyl, 2-trimethylsilylethyl, 2-phenylethyl, 1-(1-adamantyl)-1-methylethyl, 1,1-dimethyl-2-haloethyl, 1,1-dimethyl-2,2-dibromoethyl, 1,1-dimethyl-2,2,2-trichloroethyl, 1-methyl-1-(4-biphenylyl)ethyl, 1-(3,5-di-t-butylphenyl)-1-methylethyl, 2-(2'- and 4'-pyridyl)ethyl, 2-(N,N-dicyclohexylcarboxamido)ethyl, t-butyl, 1-adamantyl, vinyl, allyl, 1-isopropylallyl, cinnamyl, 4-nitrocinnamyl, 8-quinolyl, N-hydroxypiperidinyl, alkyldithio, benzyl, p-methoxybenzyl, p-nitrobenzyl, p-bromobenzyl, p-chorobenzyl, 2,4-dichlorobenzyl, 4-methylsulfinylbenzyl, 9-anthrylmethyl, diphenylmethyl); Groups With Assisted Cleavage (2-methylthioethyl, 2-methylsulfonylethyl, 2-(p-toluenesulfonyl)ethyl, [2-(1,3-dithianyl)]methyl, 4-methylthiophenyl, 2,4-dimethylthiophenyl, 2-phosphonioethyl, 2-triphenylphosphonioisopropyl, 1,1-dimethyl-2-cyanoethyl, m-choro-p-acyloxybenzyl, p-(dihydroxyboryl)benzyl, 5-benzisoxazolylmethyl, 2-(trifluoromethyl)-6-chromonylmethyl); Groups Capable of Photolytic Cleavage (m-nitrophenyl, 3,5-dimethoxybenzyl, o-nitrobenzyl, 3,4-dimethoxy-6-nitrobenzyl, phenyl(o-nitrophenyl)methyl); Urea-Type Derivatives (phenothiazinyl-(10)-carbonyl, N'-p-toluenesulfonylaminocarbonyl, N'-phenylaminothiocarbonyl); Miscellaneous Carbamates (t-amyl, S-benzyl thiocarbamate, p-cyanobenzyl, cyclobutyl, cyclohexyl, cyclopentyl, cydopropylmethyl, p-decyloxybenzyl, diisopropylmethyl, 2,2-dimethoxycarbonylvinyl, o-(N,N-dimethylcarboxamido)benzyl, 1,1-dimethyl-3-(N,N-dimethylcarboxamido)propyl, 1,1-dimethylpropynyl, di(2-pyridyl)methyl, 2-furanylmethyl, 2-Iodoethyl, Isobomyl, Isobutyl, Isonicotinyl, p-(p'-Methoxyphenylazo)benzyl, 1-methylcyclobutyl, 1-methylcyclohexyl, 1-methyl-1-cyclopropylmethyl, 1-methyl-1-(3,5-dimethoxyphenyl)ethyl, 1-methyl-1-(p-phenylazophenyl)ethyl, 1-methyl-1-phenylethyl, 1-methyl-1-(4-pyridyl)ethyl, phenyl, p-(phenylazo)benzyl, 2,4,6-tri-t-butylphenyl, 4-(trimethylammonium)benzyl, 2,4,6-trimethylbenzyl); Amides (N-formyl, N-acetyl, N-choroacetyl, N-trichoroacetyl, N-trifluoroacetyl, N-phenylacetyl, N-3-phenylpropionyl, N-picolinoyl, N-3-pyridylcarboxamide, N-benzoylphenylalanyl, N-benzoyl, N-p-phenylbenzoyl); Anides With Assisted Cleavage (N-o-nitrophenylacetyl, N-o-nitrophenoxyacetyl, N-acetoacetyl, (N'-dithiobenzyloxycarbonylamino)cetyl, N-3-(p-hydroxyphenyl)propionyl, N-3-(o-nitrophenyl)propionyl, N-2-methyl-2-(o-nitrophenoxy)propionyl, N-2-methyl-2-(o-phenylazophenoxy)propionyl, N-4-chlorobutyryl, N-3-methyl-3-nitrobutyryl, N-o-nitrocinnamoyl, N-acetylmethionine, N-o-nitrobenzoyl, N-o-(benzoyloxymethyl)benzoyl, 4,5-diphenyl-3-oxazolin-2-one); Cyclic Imide Derivatives (N-phthalimide, N-dithiasuccinoyl, N-2,3-diphenylmaleoyl, N-2,5-dimethylpyrrolyl, N-1,1,4,4-tetramethyldisilylazacyclopentane adduct, 5-substituted 1,3-dimethyl-1,3,5-triazacyclohexan-2-one, 5-substituted 1,3- dibenzyl-1,3,5-triazacyclohexan-2-one, 1-substituted 3,5-dinitro-4pyridonyl); N-Alkyl and N-Aryl Amines (N-methyl, N-allyl, N-[2-(trimethylsilyl)ethoxy]methyl, N-3-acetoxypropyl, N-(1-isopropyl-4-nitro-2-oxo-3-pyrrolin-3-yl), Quaternary Ammonium Salts, N-benzyl, N-di(4-methoxyphenyl)methyl, N-5-dibenzosuberyl, N-triphenylmethyl, N-(4-methoxyphenyl)diphenylmethyl, N-9-phenylfluorenyl, N-2,7-dichloro-9-fluorenylmethylene, N-ferrocenylmethyl, N-2-picolylamine N'-oxide), Imine Derivatives (N-1,1-dimethylthiomethylene, N-benzylidene, N-p-methoxybenylidene, N-diphenylmethylene, N-[(2-pyridyl)mesityl]methylene, N,(N',N'-dimethylaminomethylene, N,N'-isopropylidene, N-p-nitrobenzylidene, N-salicylidene, N-5-chlorosalicylidene, N-(5-chloro-2-hydroxyphenyl)phenylmethylene, N-cyclohexylidene); Enamine Derivatives (N-(5,5-dimethyl-3-oxo-1-cyclohexenyl)); N-Metal Derivatives (N-borane derivatives, N-diphenylborinic acid derivatives, N-[phenyl(pentacarbonylchromium- or -tungsten)]carbenyl, N-copper or N-zinc chelate); N-N Derivatives (N-nitro, N-nitroso, N-oxide); N-P Derivatives (N-diphenylphosphinyl, N-dimethylthiophosphinyl, N-diphenylthiophosphinyl, N-dialkyl phosphoryl, N-dibenzyl phosphoryl, N-diphenyl phosphoryl); N—Si Derivatives; N-S Derivatives; N-Sulfenyl Derivatives (N-benzenesulfenyl, N-o-nitrobenzenesulfenyl, N-2,4-dinitrobenzenesulfenyl, N-pentachlorobenzenesulfenyl, N-2-nitro-4-methoxybenzenesulfenyl, N-triphenylmethylsulfenyl, N-3-nitropyridinesulfenyl); and N-sulfonyl Derivatives (N-p-toluenesulfonyl, N-benzenesulfonyl, N-2,3,6-trimethyl-4-methoxybenzenesulfonyl, N-2,4,6-trimethoxybenzenesulfonyl, N-2,6-dimethyl-4-methoxybenzenesulfonyl, N-pentamethylbenzenesulfonyl, N-2,3,5,6,-tetramethyl-4-methoxybenzenesulfonyl, N-4-methoxybenzenesulfonyl, N-2,4,6-trimethylbenzenesulfonyl, N-2,6-dimethoxy-4-methylbenzenesulfonyl, N-2,2,5,7,8-pentamethylchroman-6-sulfonyl, N-methanesulfonyl, N-β-trimethylsilyethanesulfonyl, N-9-anthracenesulfonyl, N-4-(4',8'-dimethoxynaphthylmethyl)benzenesulfonyl, N-benzylsulfonyl, N-trifluoromethylsulfonyl, N-phenacylsulfonyl).

More typically, protected amino groups include carbamates and amides, still more typically, —NHC(O)R$_1$ or —N═CR$_1$N(R$_1$)$_2$. Another protecting group, also useful as a prodrug at the G$_1$ site, particularly for amino or —NH(R$_5$), is:

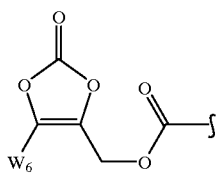

see for example Alexander, J. et al., "J. Med. Chem." 39:480–486 (1996).

R$_{6c}$ is H or the residue of an amino-containing compound, in particular an amino acid, a polypeptide, a protecting group, —NHSO$_2$R$_4$, NHC(O)R$_4$, —N(R$_4$)$_2$, NH$_2$ or —NH(R$_4$)(H), whereby for example the carboxyl or phosphonic acid groups of W$_1$ are reacted with the amine to form an amide, as in —C(O)R$_{6c}$, —P(O)(R$_{6c}$)$_2$ or —P(O)(OH)(R$_{6c}$). In general, R$_{6c}$ has the structure R$_{17}$C(O)CH(R$_{16}$)NH—, where R$_{17}$ is OH, OR$_{6a}$, OR$_5$, an amino acid or a polypeptide residue.

Amino acids are low molecular weight compounds, on the order of less than about 1,000 MW, that contain at least one amino or imino group and at least one carboxyl group. Generally the amino acids will be found in nature, i.e., can be detected in biological material such as bacteria or other microbes, plants, animals or man. Suitable amino acids typically are alpha amino acids, i.e. compounds characterized by one amino or imino nitrogen atom separated from the carbon atom of one carboxyl group by a single substituted or unsubstituted alpha carbon atom. Of particular interest are hydrophobic residues such as mono- or di-alkyl or aryl amino acids, cycloalkylamino acids and the like. These residues contribute to cell permeability by increasing the partition coefficient of the parental drug. Typically, the residue does not contain a sulfhydryl or guanidino substituent.

Naturally-occurring amino acid residues are those residues found naturally in plants, animals or microbes, especially proteins thereof. Polypeptides most typically will be substantially composed of such naturally-occurring amino acid residues. These amino acids are glycine, alanine, valine, leucine, isoleucine, serine, threonine, cysteine, methionine, glutamic acid, aspartic acid, lysine, hydroxylysine, arginine, histidine, phenylalanine, tyrosine, tryptophan, proline, asparagine, glutamine and hydroxyproline.

When R$_{6b}$ and R$_{6c}$ are single amino acid residues or polypeptides they usually are substituted at R$_3$, W$_6$, W$_1$ and/or W$_2$, but typically only W$_1$ or W$_2$. These conjugates are produced by forming an amide bond between a carboxyl group of the amino acid (or C-terminal amino acid of a polypeptide for example) and W$_2$. Similarly, conjugates are formed between W$_1$ and an amino group of an amino acid or polypeptide. Generally, only one of any site in the parental molecule is amidated with an amino acid as described herein, although it is within the scope of this invention to introduce amino acids at more than one permitted site. Usually, a carboxyl group of W$_1$ is amidated with an amino acid. In general, the α-amino or α-carboxyl group of the amino acid or the terminal amino or carboxyl group of a polypeptide are bonded to the parental functionalities, i.e., carboxyl or amino groups in the amino acid side chains generally are not used to form the amide bonds with the parental compound (although these groups may need to be protected during synthesis of the conjugates as described further below).

With respect to the carboxyl-containing side chains of amino adds or polypeptides it will be understood that the carboxyl group optionally will be blocked, e.g. by R$_{6a}$, esterified with R$_5$ or amidated with R$_{6c}$. Similarly, the amino side chains R$_{16}$ optionally will be blocked with R$_{6b}$ or substituted with R$_5$.

Such ester or amide bonds with side chain amino or carboxyl groups, like the esters or amides with the parental molecule, optionally are hydrolyzable in vivo or in vitro under acidic (pH<3) or basic (pH>10) conditions. Alternatively, they are substantially stable in the gastrointestinal tract of humans but are hydrolyzed enzymatically in blood or in intracellular environments. The esters or amino acid or polypeptide amidates also are useful as intermediates for the preparation of the parental molecule containing free amino or carboxyl groups. The free acid or base of the parental compound, for example, is readily formed from the esters or amino acid or polypeptide conjugates of this invention by conventional hydrolysis procedures.

When an amino acid residue contains one or more chiral centers, any of the D, L, meso, threo or erythro (as appropriate) racemates, scalemates or mixtures thereof may be used. In general, if the intermediates are to be hydrolyzed non-enzymatically (as would be the case where the amides are used as chemical intermediates for the free acids or free amines), D isomers are useful. On the other hand, L isomers are more versatile since they can be susceptible to both non-enzymatic and enzymatic hydrolysis, and are more efficiently transported by amino acid or dipeptidyl transport systems in the gastrointestinal tract.

Examples of suitable amino acids whose residues are represented by $R_{6b}$ and $R_{6c}$ include the following:

Glycine;

Aminopolycarboxylic acids, e.g., aspartic acid, β-hydroxyaspartic acid, glutamic acid, β-hydroxyglutamic acid, β-methylaspartic acid, β-methylglutamic acid, β,β-dimethylaspartic acid, γ-hydroxyglutamic acid, β,γ-dihydroxyglutamic acid, β-phenylglutamic acid, γ-methyleneglutamic acid, 3-aminoadipic acid, 2-aminopimelic acid, 2-aminosuberic acid and 2-aminosebacic acid;

Amino acid amides such as glutamine and asparagine;

Polyamino- or polybasic-monocarboxylic acids such as arginine, lysine, β-aminoalanine, γ-aminobutyrine, ornithine, citruline, homoarginine, homocitrulline, hydroxylysine, allohydroxylsine and diaminobutyric acid;

Other basic amino acid residues such as histidine;

Diaminodicarboxylic acids such as α,α'-diaminosuccinic acid, α,α'-diaminoglutaric acid, α,α'-diaminoadipic acid, α,α'-diaminopimelic acid, α,α'-diamino-β-hydroxypimelic acid, α,α'-diaminosuberic acid, α,α'-diaminoazelaic acid, and α,α'-diaminosebacic acid;

Imino acids such as proline, hydroxyproline, allohydroxyproline, γ-methylproline, pipecolic acid, 5-hydroxypipecolic acid, and azetidine-2-carboxylic acid;

A mono- or di-alkyl (typically $C_1$–$C_8$ branched or normal) amino acid such as alanine, valine, leucine, allylglycine, butyrine, norvaline, norleucine, heptyline, α-methylserine, α-amino-α-methyl-γ-hydroxyvaleric acid, α-amino-α-methyl-δ-hydroxyvaleric acid, α-amino-α-methyl-ε-hydroxycaproic acid, isovaline, α-methylglutamic acid, α-aminoisobutyric acid, α-aminodiethylacetic acid, α-aminodiisopropylacefic acid, α-aminodi-n-propylacetic acid, α-aminodiisobutylacetic acid, α-aminodi-n-butylacetic acid, α-aminoethylisopropylacetic acid, α-amino-n-propylacetic acid, α-aminodiisoamyacetic acid, α-methylaspartic acid, α-methylglutamic acid, 1-aminocyclopropane-1-carboxylic acid, isoleucine, alloisoleucine, tert-leucine, β-methyltryptophan and α-amino-β-ethyl-β-phenylpropionic acid;

β-phenylserinyl;

Aliphatic α-amino-β-hydroxy acids such as serine, β-hydroxyleucine, β-hydroxynorleucine, β-hydroxynorvaline, and α-amino-β-hydroxystearic acid;

α-Amino, α-, γ-, δ- or ε-hydroxy acids such as homoserine, γ-hydroxynorvaline, δ-hydroxynorvaline and epsilon-hydroxynorleucine residues; canavine and canaline; γ-hydroxyornithine;

2-hexosaminic acids such as D-glucosaminic acid or D-galactosaminic acid;

α-Amino-β-thiols such as penicillamine, β-thiolnorvaline or β-thiolbutyrine;

Other sulfur containing amino acid residues including cysteine; homocystine, β-phenylmethionine, methionine, S-allyl-L-cysteine sulfoxide, 2-thiolhistidine, cystathionine, and thiol ethers of cysteine or homocysteine;

Phenylalanine, tryptophan and ring-substituted α amino acids such as the phenyl- or cyclohexylamino acids α-aminophenylacetic acid, α-aminocyclohexylacetic acid and α-amino-β-cyclohexylpropionic acid; phenylalanine analogues and derivatives comprising aryl, lower alkyl, hydroxy, guanidino, oxyalkylether, nitro, sulfur or halo-substituted phenyl (e.g., tyrosine, methyltyrosine and o-chloro-, p-chloro-, 3,4dicloro, o-, m- or p-methyl-, 2,4,6-trimethyl-, 2-ethoxy-5-nitro-, 2-hydroxy-5-nitro- and p-nitro-phenylalanine); furyl-, thienyl-, pyridyl-, pyrimidinyl-, purinyl- or naphthyl-alanines; and tryptophan analogues and derivatives including kynurenine, 3-hydroxykynurenine, 2-hydroxytryptophan and 4-carboxytryptophan;

α-Amino substituted amino acids including sarcosine (N-methylglycine), N-benzylglycine, N-methylalanine, N-benzylalanine, N-methylphenylalanine, N-benzylphenylalanine, N-methylvaline and N-benzylvaline; and α-Hydroxy and substituted α-hydroxy amino acids including serine, threonine, allothreonine, phosphoserine and phosphothreonine.

Polypeptides are polymers of amino acids in which a carboxyl group of one amino acid monomer is bonded to an amino or imino group of the next amino acid monomer by an amide bond. Polypeptides include dipeptides, low molecular weight polypeptides (about 1500–5000MW) and proteins. Proteins optionally contain 3, 5, 10, 50, 75, 100 or more residues, and suitably are substantially sequence-homologous with human, animal, plant or microbial proteins. They include enzymes (e.g., hydrogen peroxidase) as well as immunogens such as KLH, or antibodies or proteins of any type against which one wishes to raise an immune response. The nature and identity of the polypeptide may vary widely.

The polypeptide amidates are useful as immunogens in raising antibodies against either the polypeptide (if it is not immunogenic in the animal to which it is administered) or against the epitopes on the remainder of the compound of this invention.

Antibodies capable of binding to the parental non-peptidyl compound are used to separate the parental compound from mixtures, for example in diagnosis or manufacturing of the parental compound. The conjugates of parental compound and polypeptide generally are more immunogenic than the polypeptides in closely homologous animals, and therefore make the polypeptide more immunogenic for facilitating raising antibodies against it. Accordingly, the polypeptide or protein may not need to be immunogenic in an animal typically used to raise antibodies, e.g., rabbit, mouse, horse, or rat, but the final product conjugate should be immunogenic in at least one of such animals. The polypeptide optionally contains a peptidolytic enzyme cleavage site at the peptide bond between the first and second residues adjacent to the acidic heteroatom. Such cleavage sites are flanked by enzymatic recognition structures, e.g. a particular sequence of residues recognized by a peptidolytic enzyme.

Peptidolytic enzymes for cleaving the polypeptide conjugates of this invention are well known, and in particular include carboxypeptidases. Carboxypeptidases digest polypeptides by removing C-terminal residues, and are specific in many instances for particular C-terminal sequences. Such enzymes and their substrate requirements in general are well known. For example, a dipeptide (having a given pair of residues and a free carboxyl terminus) is covalently bonded through its α-amino group to the phosphorus or carbon atoms of the compounds herein. In embodiments where $W_1$ is phosphonate it is expected that this peptide will be cleaved by the appropriate peptidolytic enzyme, leaving the carboxyl of the proximal amino acid residue to autocatalytically cleave the phosphonoamidate bond.

Suitable dipeptidyl groups (designated by their single letter code) are AA, AR, AN, AD, AC, AE, AQ, AG, AH, AI, AL, AK, AM, AF, AP, AS, AT, AW, AY, AV, RA, RR, RN, RD, RC, RE, RQ, RG, RH, RI, RL, RK, RM, RF, RP, RS, RT, RW, RY, RV, NA, NR, NN, ND, NC, NE, NQ, NG, NH, NI, NL, NK, NM, NF, NP, NS, NT, NW, NY, NV, DA, DR, DN, DD, DC, DE, DQ, DG, DH, DI, DL, DK, DM, DF, DP, DS, DT, DW, DY, DV, CA, CR, CN, CD, CC, CE, CQ, CG, CH, CI, CL, CK, CM, CF, CP, CS, CT, CW, CY, CV, EA, ER, EN, ED, EC, EE, EQ, EG, EH, EI, EL, EK, EM, EF, EP, ES, ET, EW, EY, EV, QA, QR, QN, QD, QC, QE, QQ, QG, QH, QI, QL, QK, QM, QF, QP, QS, QT, QW, QY, QV, GA, GR, GN, GD, GC, GE, GQ, GG, GH, GI, GL, GK, GM, GF, GP, GS, GT, GW, GY, GV, HA, HR, HN, HD, HC, HE, HQ, HG, HH, HI, HL, HK, HM, HF, HP, HS, HT, HW, HY, HV, IA, IR, IN, ID, IC, IE, IQ, IG, IH, II, IL, IK, IM, IF, IP, IS, IT, IW, IY, IV, LA, LR, LN, LD, LC, LE, LQ, LG, LH, LI, LL, LK, LM, LF, LP, LS, LT, LW, LY, LV, KA, KR, KN, KD, KC, KE, KQ, KG, KH, KI, KL, KK, KM, KF, KP, KS, KT, KW, KY, KV, MA, MR, MN, MD, MC, ME, MQ, MG, MH, MI, ML, MK, MM, MF, MP, MS, MT, MW, MY, MV, FA, FR, FN, FD, FC, FE, FQ, FG, FH, FI, FL, FK, FM, FF, FP, FS, FT, FW, FY, FV, PA, PR, PN, PD, PC, PE, PQ, PG, PH, PI, PL, PK, PM, PF, PP, PS, PT, PW, PY, PV, SA, SR, SN, SD, SC, SE, SQ, SG, SH, SI, SL, SK, SM, SF, SP, SS, ST, SW, SY, SV, TA, TR, TN, TD, TC, TE, TQ, TG, TH, TI, TL, TK, TM, TF, TP, TS, TT, TW, TY, TV, WA, WR, WN, WD, WC, WE, WQ, WG, WH, WI, WL, WK, WM, WF, WP, WS, WT, WW, WY, WV, YA, YR, YN, YD, YC, YE, YQ, YG, YH, YI, YL, YK, YM, YF, YP, YS, YT, YW, YY, YV, VA, VR, VN, VD, VC, VE, VQ, VG, VH, VI, VL, VK, VM, VF, VP, VS, VT, VW, VY and VV.

Tripeptide residues are also useful as $R_{6b}$ or $R_{6c}$. When $W_1$ is phosphonate, the sequence —X4-pro-X5— (where X4 is any amino acid residue and X5 is an amino acid residue, a carboxyl ester of proline, or hydrogen) will be cleaved by luminal carboxypeptidase to yield X4 with a free carboxyl, which in turn is expected to autocatalytically cleave the phosphonoamidate bond. The carboxy group of X5 optionally is esterified with benzyl.

Dipeptide or tripeptide species can be selected on the basis of known transport properties and/or susceptibility to peptidases that can affect transport to intestinal mucosal or other cell types. Dipeptides and tripeptides lacking an α-amino group are transport substrates for the peptide transporter found in brush border membrane of intestinal mucosal cells (Bai, J.P.F., "Pharm Res." 9:969–978 (1992). Transport competent peptides can thus be used to enhance bioavailability of the amidate compounds. Di- or tripeptides having one or more amino acids in the D configuration are also compatible with peptide transport and can be utilized in the amidate compounds of this invention. Amino acids in the D configuration can be used to reduce the susceptibility of a di- or tripeptide to hydrolysis by proteases common to the brush border such as aminopeptidase N (EC 3.4.11.2). In addition, di- or tripeptides alternatively are selected on the basis of their relative resistance to hydrolysis by proteases found in the lumen of the intestine. For example, tripeptides or polypeptides lacking asp and/or glu are poor substrates for aminopeptidase A (EC 3.4.11.7), di- or tripeptides lacking amino acid residues on the N-terminal side of hydrophobic amino acids (leu, tyr, phe, val, trp) are poor substrates for endopeptidase 24.11 (EC 3.4.24.11), and peptides lacking a pro residue at the penultimate position at a free carboxyl terminus are poor substrates for carboxypeptidase P (EC 3.4.17). Similar considerations can also be applied to the selection of peptides that are either relatively resistant or relatively susceptible to hydrolysis by cytosolic, renal, hepatic, serum or other peptidases. Such poorly cleaved polypeptide amidates are immunogens or are useful for bonding to proteins in order to prepare immunogens.

Stereoisomers

The compounds of the invention are enriched or resolved optical isomers at any or all asymmetric atoms. For example, the chiral centers apparent from the depictions are provided as the chiral isomers or racemic mixtures. Both racemic and diastereomeric mixtures, as well as the individual optical isomers isolated or synthesized, substantially free of their enantiomeric or diastereomeric partners, are all within the scope of the invention.

One or more of the following enumerated methods are used to prepare the enantiomerically enriched or pure isomers herein. The methods are listed in approximately their order of preference, i.e., one ordinarily should employ stereospecific synthesis from chiral precursors before chromatographic resolution before spontaneous crystallization.

Stereospecific synthesis is described below. Methods of this type conveniently are used when the appropriate chiral starting material is available and reaction steps are chosen do not result in undesired racernization at chiral sites. One advantage of stereospecific synthesis is that it does not produce undesired enantiomers that must be removed from the final product, thereby lowering overall synthetic yield. In general, those skilled in the art would understand what starting materials and reaction conditions should be used to obtain the desired enantiomerically enriched or pure isomers by stereospecific synthesis. If an unexpected racemization occurs in a method thought to be stereospecific then one needs only to use one of the following separation methods to obtain the desired product.

If a suitable stereospecific synthesis cannot be empirically designed or determined with routine experimentation then those skilled in the art would turn to other methods. One method of general utility is chromotographic resolution of enantiomers on chiral chromatography resins. These resins are packed in columns, commonly called Pirkle columns, and are commercially available. The columns contain a chiral stationary phase. The racemate is placed in solution and loaded onto the column, and thereafter separated by HPLC. See for example, Proceedings Chromatographic Society—International Symposium on Chiral Separations, Sep. 3–4, 1987. Examples of chiral columns that could be used to screen for the optimal separation technique would include Diacel Chriacel OD, Regis Pirkle Covalent Dphenylglycine, Regis Pirkle Type 1A, Astec Cyclobond II, Astec Cyclobond III, Serva Chiral D-DL=Daltosil 100, Bakerbond DNBLeu, Surnipax OA-1000, Merck Cellulose Triacetate column, Astec Cyclobond I-Beta, or Regis Pirkle Covalent D-Naphthylalanine. Not all of these columns are likely to be effective with every racemic mixture. However, those skilled in the art understand that a certain amount of routine screening may be required to identify the most effective stationary phase. When using such columns it is desirable to employ embodiments of the compounds of this invention in which the charges are not neutralized, e.g., where acidic functionalities such as carboxyl are not esterified or amidated.

Another method entails converting the enantiomers in the mixture to diastereomers with chiral auxiliaries and then separating the conjugates by ordinary column chromatography. This is a very suitable method, particularly when the embodiment contains free carboxyl, amino or hydroxyl that will form a salt or covalent bond to a chiral auxiliary. Chirally pure amino acids, organic acids or organosulfonic acids are all worthwhile exploring as chiral auxiliaries, all of which are well known in the art. Salts with such auxiliaries can be formed, or they can be covalently (but reversibly) bonded to the functional group. For example, pure D or L amino acids can be used to amidate the carboxyl group of embodiments of this invention and then separated by chromatography.

Enzymatic resolution is another method of potential value. In such methods one prepares covalent derivatives of the enantiomers in the racemic mixture, generally lower alkyl esters (for example of carboxyl), and then exposes the derivative to enzymatic cleavage, generally hydrolysis. For this method to be successful an enzyme must be chosen that is capable of stereospecific cleavage, so it is frequently necessary to routinely screen several enzymes. If esters are to be cleaved, then one selects a group of esterases, phosphatases, and lipases and determines their activity on the derivative. Typical esterases are from liver, pancreas or other animal organs, and include porcine liver esterase.

If the enantiomeric mixture separates from solution or a melt as a conglomerate, i.e., a mixture of enantiomerically-pure crystals, then the crystals can be mechanically separated, thereby producing the enantiomerically enriched preparation. This method, however, is not practical for large scale preparations and is of no value for true racemic compounds.

Asymmetric synthesis is another technique for achieving enantiomeric enrichment. For example, a chiral protecting group is reacted with the group to be protected and the reaction mixture allowed to equilibrate. If the reaction is enantiomerically specific then the product will be enriched in that enantiomer.

Further guidance in the separation of enantiomeric mixtures can be found, by way of example and not limitation, in "Enantiomers, Racemates, and resolutions", Jean Jacques, Andre Collet, and Samuel H. Wilen (Krieger Publishing Company, Malabar, Fla., 1991, ISBN 0-89464-618-4). In particular, Part 2, Resolution of Enantiomer Mixture, pages 217–435; more particularly, section 4, Resolution by Direct Crystallization, pages 217–251, section 5, Formation and Separation of Diastereomers, pages 251–369, section 6, Crystallization-Induced Asymmetric Transformations, pages 369–378, and section 7, Experimental Aspects and Art of Resolutions, pages 378435; still more particularly, section 5.1.4, Resolution of Alcohols, Transformation of Alcohols into Salt-Forming Derivatives, pages 263–266, section 5.2.3, Covalent Derivatives of Alcohols, Thiols, and Phenols, pages 332–335, section 5.1.1, Resolution of Acids, pages 257–259, section 5.1.2, Resolution of Bases, pages 259–260, section 5.1.3, Resolution of Amino Acids, page 261–263, section 5.2.1, Covalent Derivatives of Acids, page 329, section 5.2.2, Covalent derivatives of Amines, pages 330–331, section 5.2.4, Covalent Derivatives of Aldehydes, Ketones, and Sulfoxides, pages 335–339, and section 5.2.7, Chromatographic Behavior of Covalent Diastereomers, pages 348–354, are cited as examples of the skill of the art.

The compounds of the invention can also exist as tautomeric isomers in certain cases. For example, ene-amine tautomers can exist for imidazole, guanidine, amidine, and tetrazole systems and all their possible tautomeric forms are within the scope of the invention.

Exemplary Enumerated Compounds

By way of example and not limitation, embodiment compounds are named below in tabular format (Table 6). Generally, each compound is depicted as a substituted nucleus in which the nucleus is designated by capital letter and each substituent is designated in order by lower case letter or number. Table 1 are a schedule of nuclei which differ principally by the position of ring unsaturation and the nature of ring substituents. Each nucleus is given a alphabetical designation from Table 1, and this designation appears first in each compound name. Similarly, Tables 2, 3, 4, and 5 list the selected $Q_1$, $Q_2$, $Q_3$ and $Q_4$ substituents, again by letter or number designation. Accordingly, each named compound will be depicted by a capital letter designating the nucleus from Table 1, followed by a number designating the $Q_1$ substituent, a lower case letter designating the $Q_2$ substituent, a number designating the $Q_3$ substituent, and a lower case letter or letters designating the $Q_4$ substituent. Thus, the structure below has the name shown.

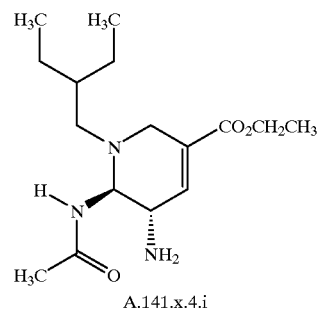

A.141.x.4.i

TABLE 1

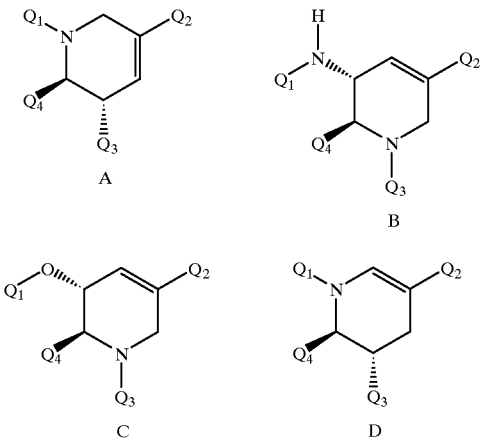

TABLE 1-continued
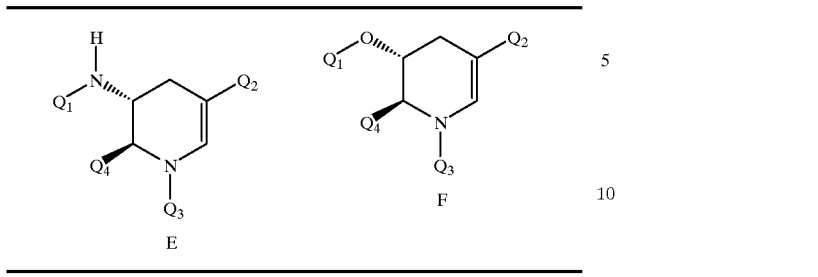
TABLE 2a
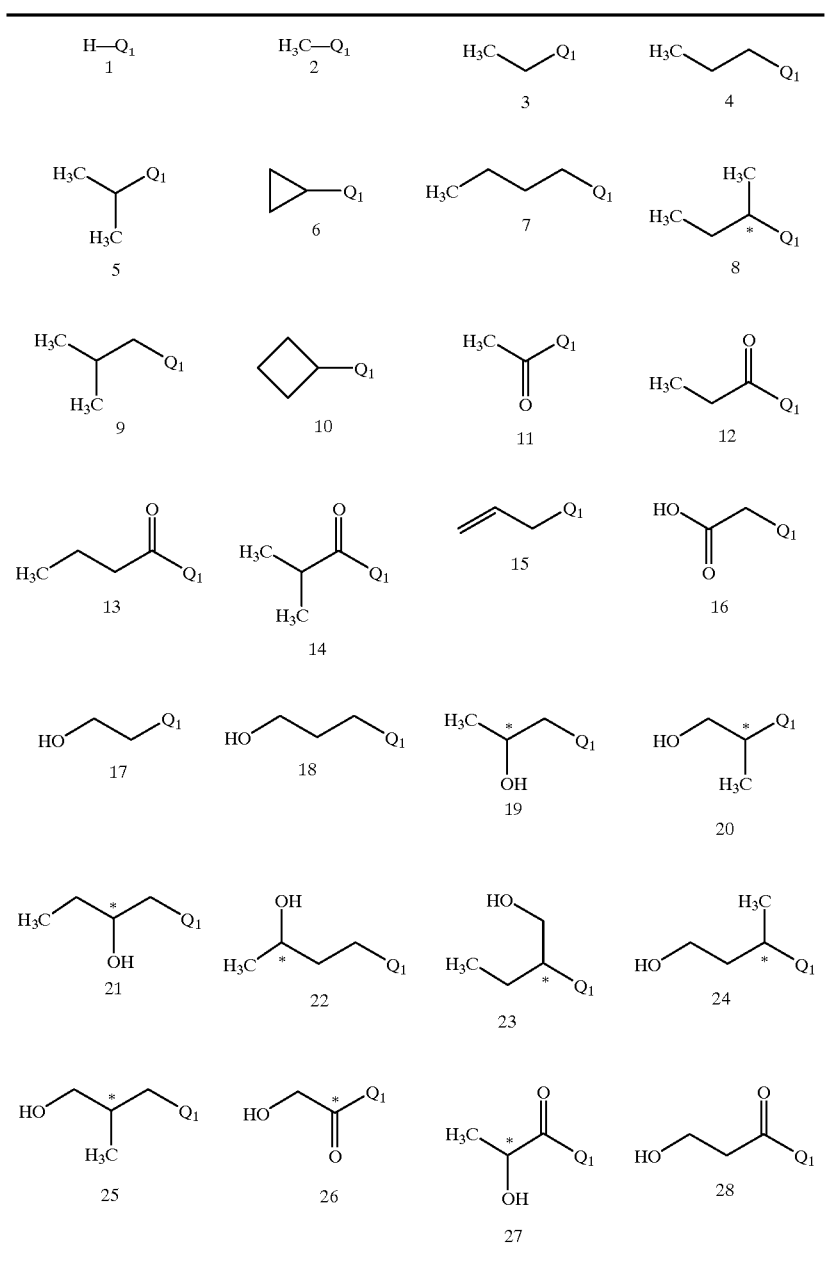

TABLE 2b
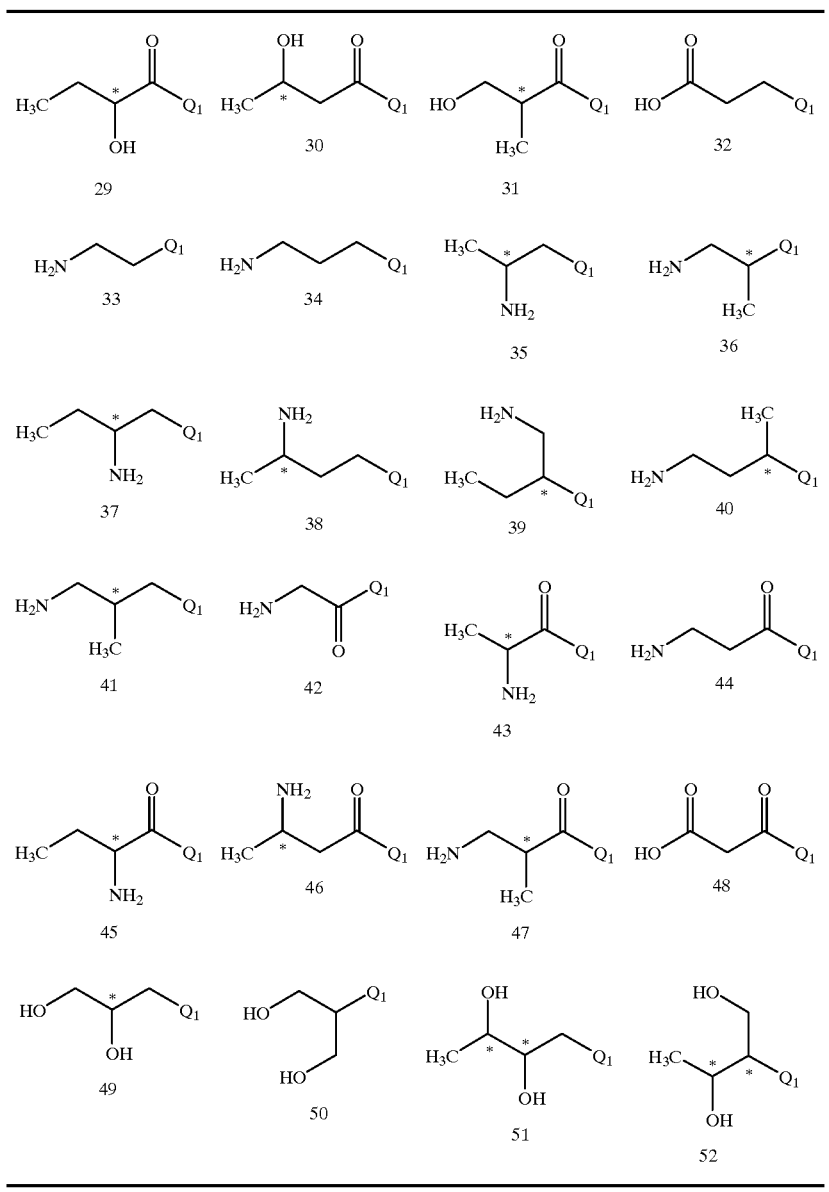
TABLE 2c
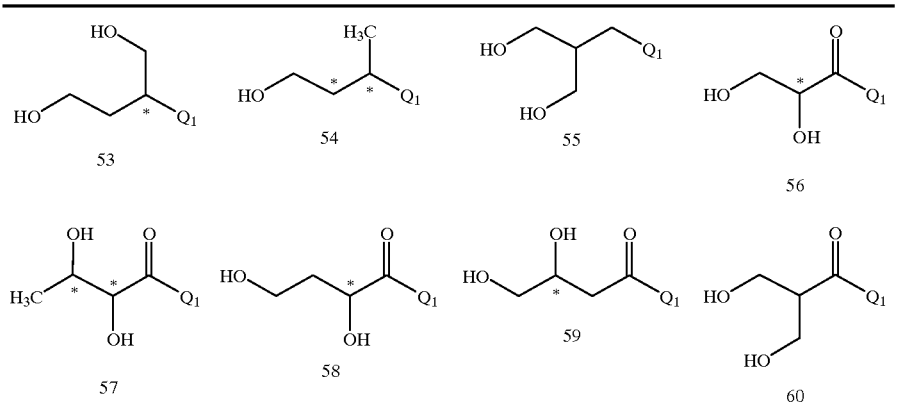

TABLE 2c-continued
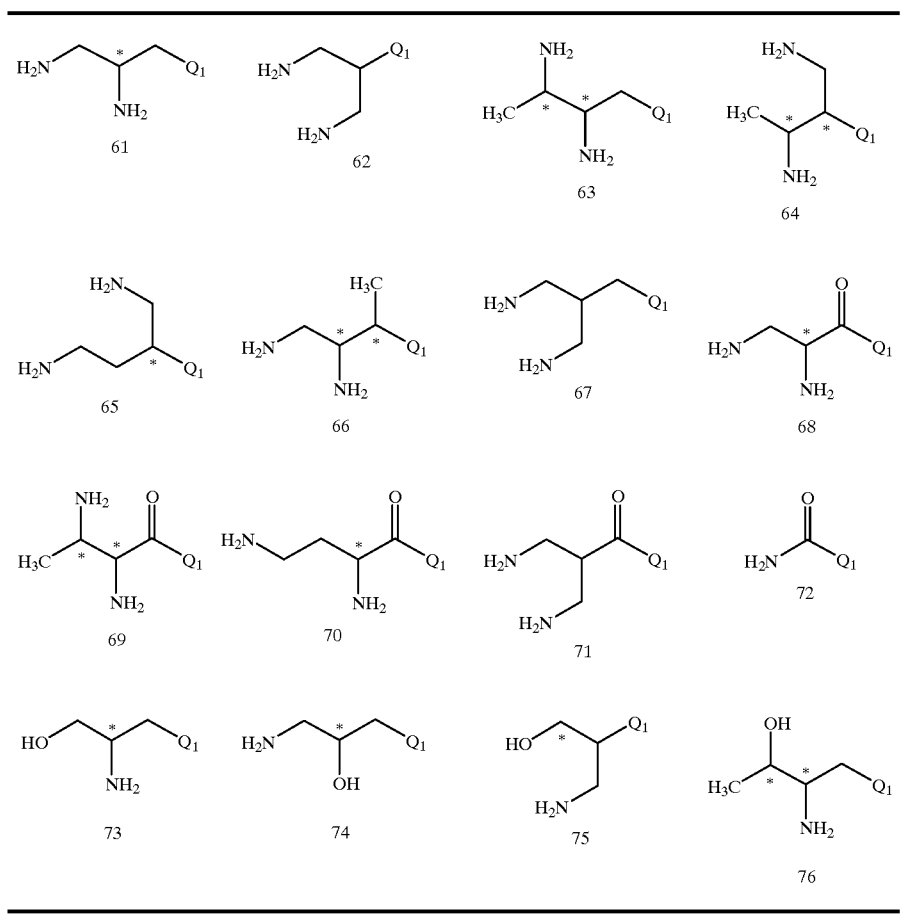
TABLE 2d
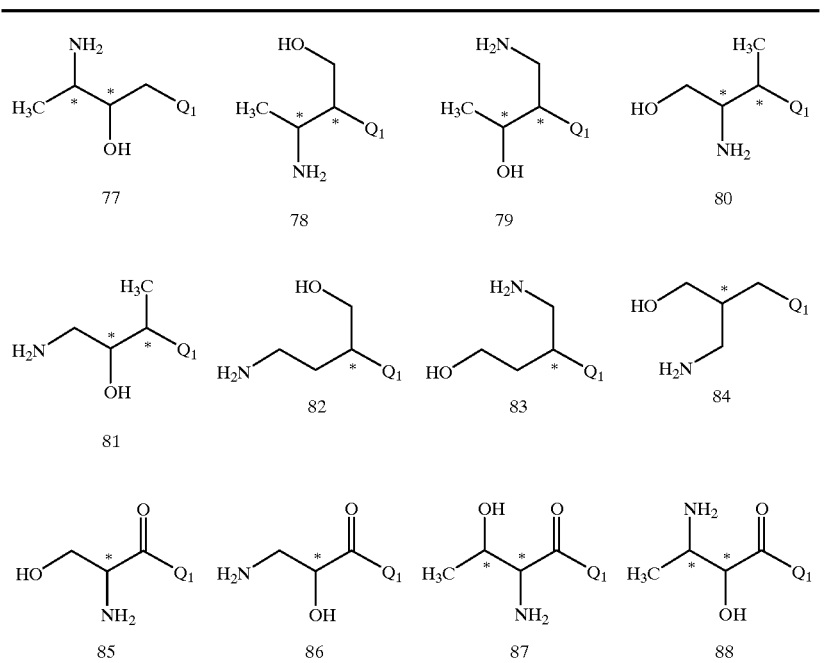

TABLE 2d-continued
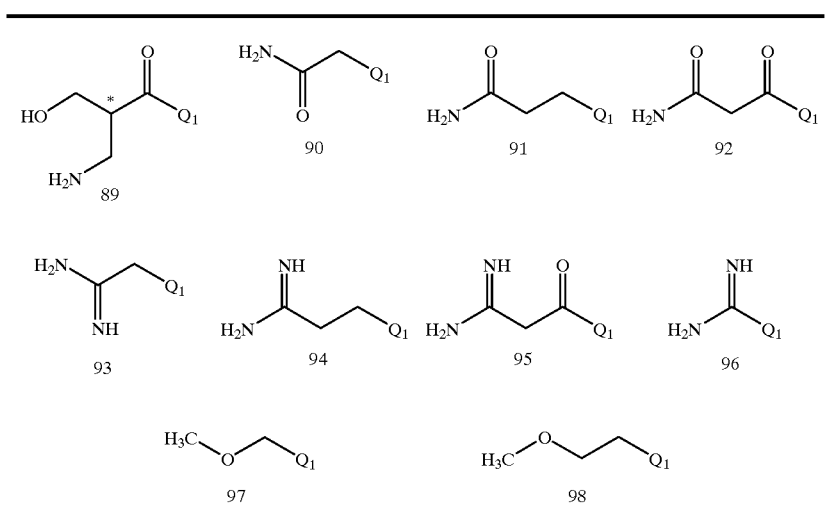
TABLE 2e
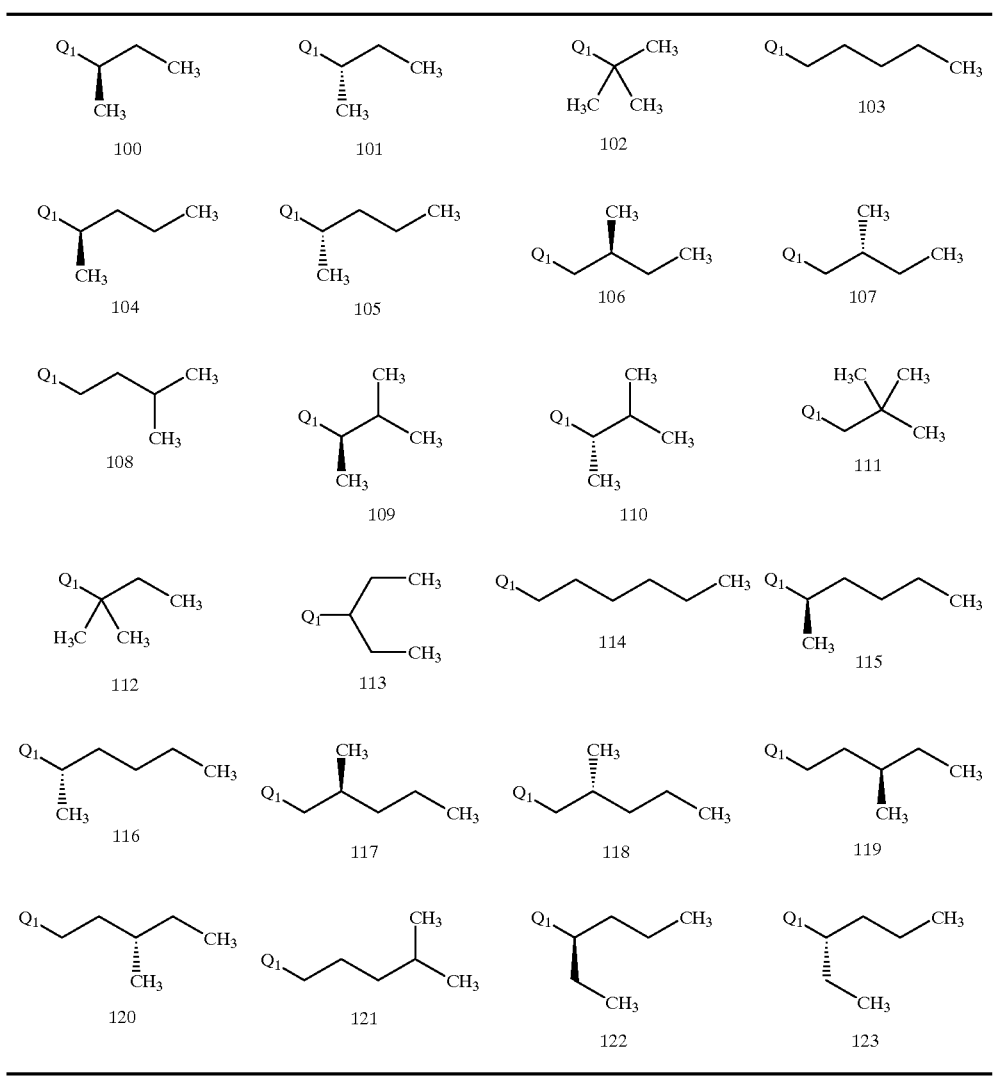

TABLE 2f
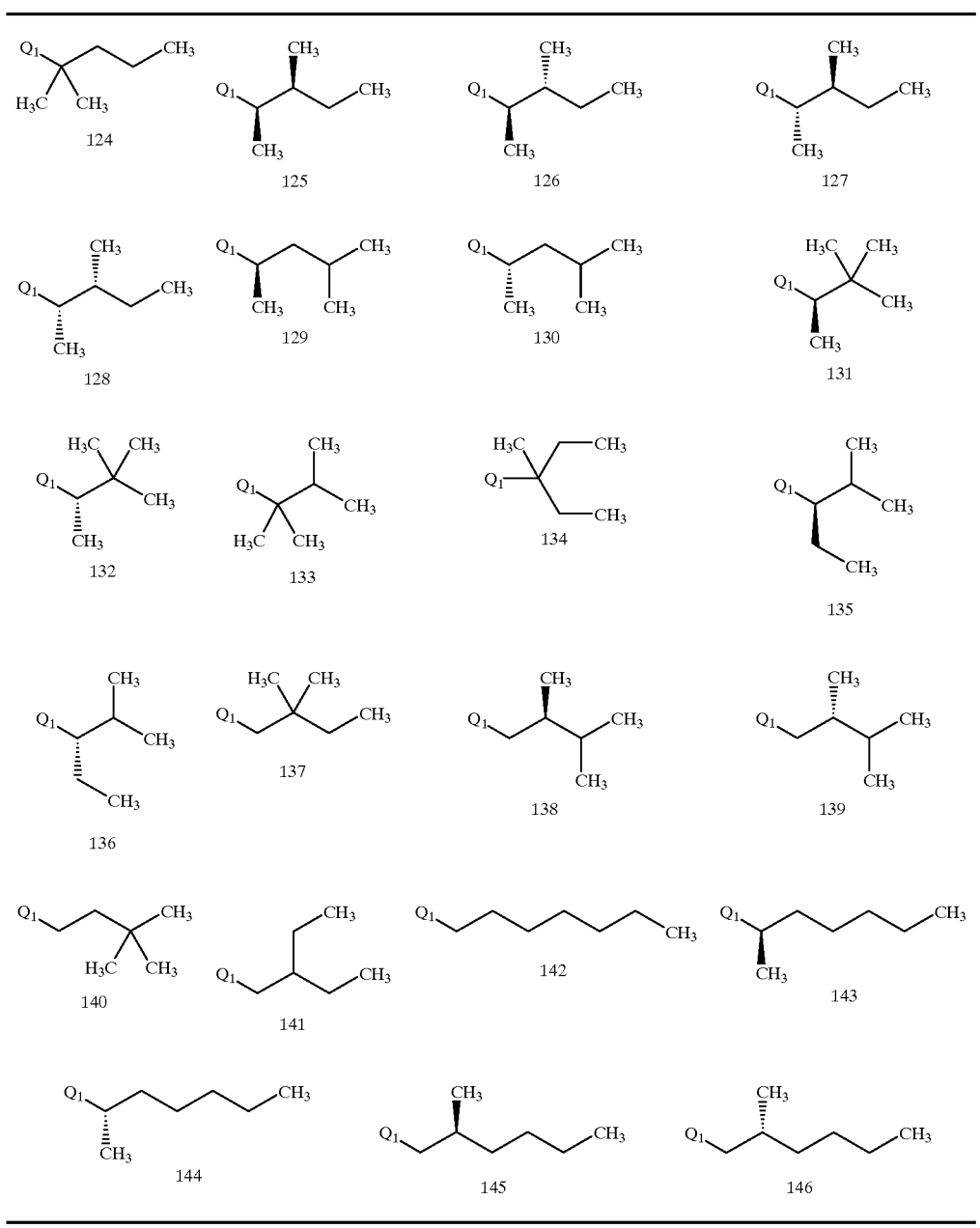
TABLE 2g
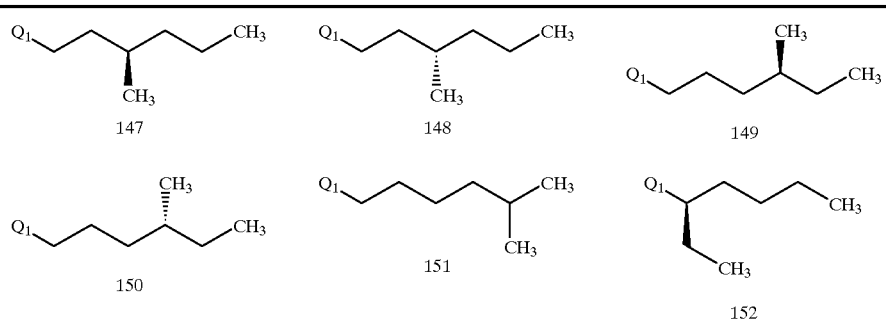

TABLE 2g-continued
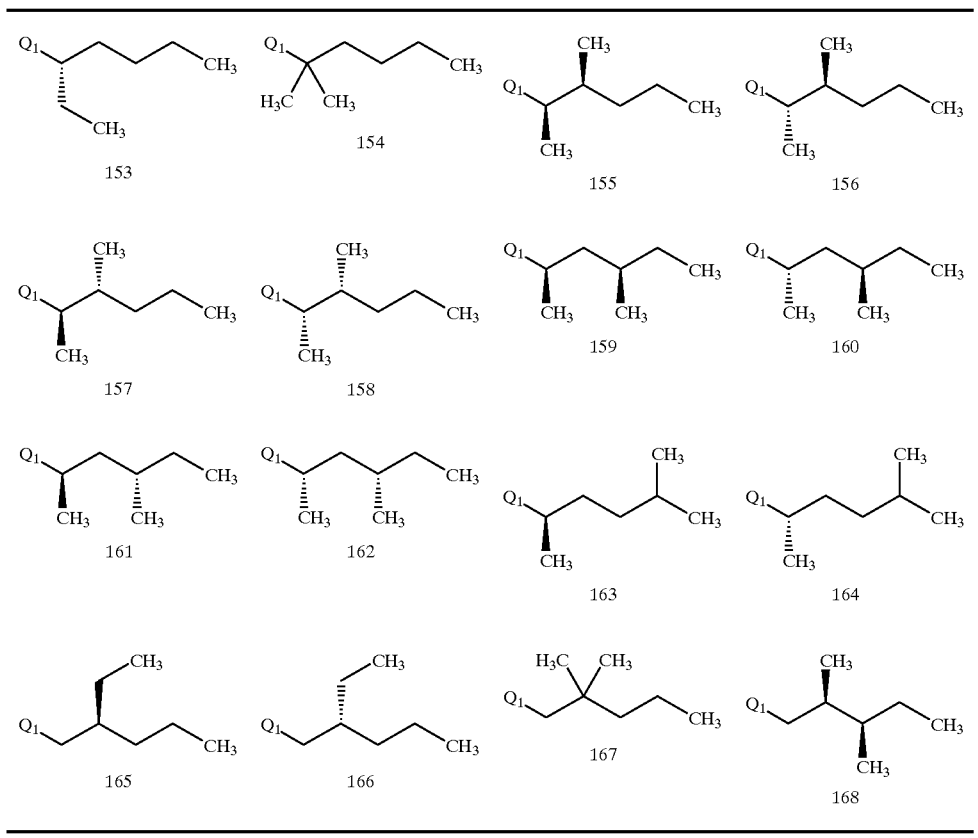
TABLE 2h
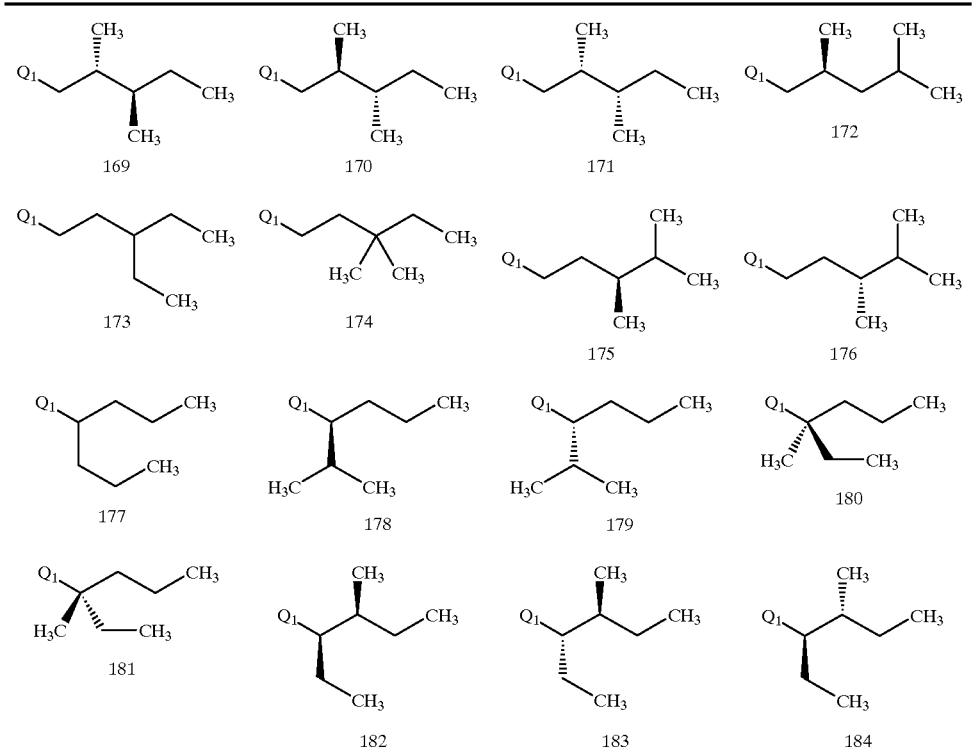

TABLE 2h-continued
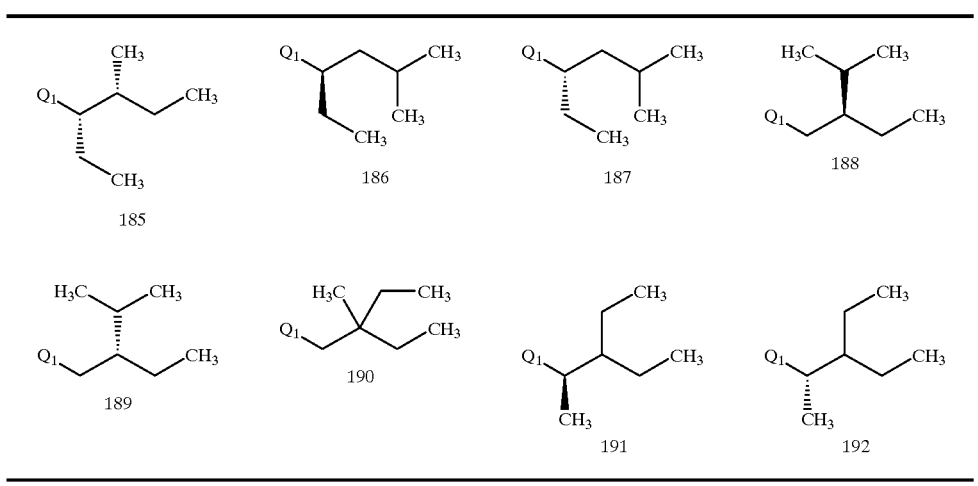
TABLE 2i
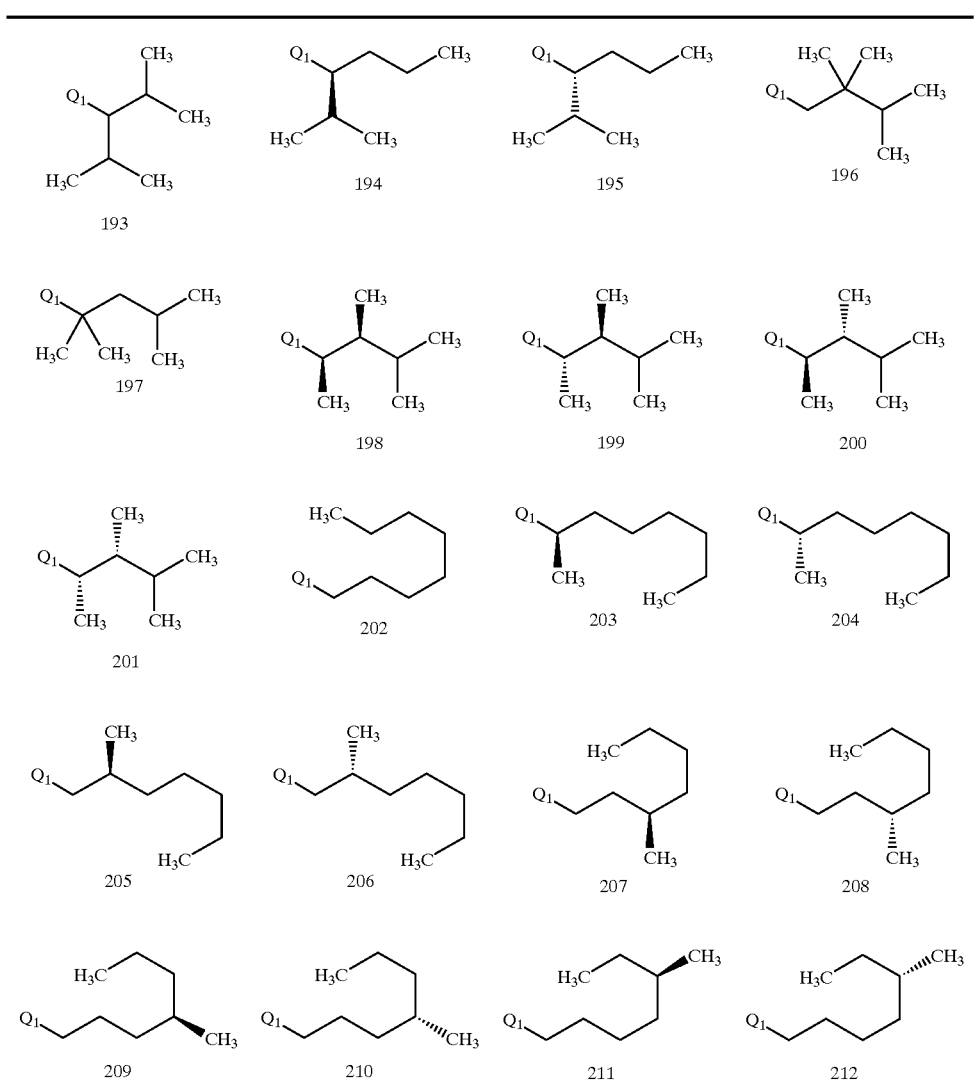

TABLE 2i-continued
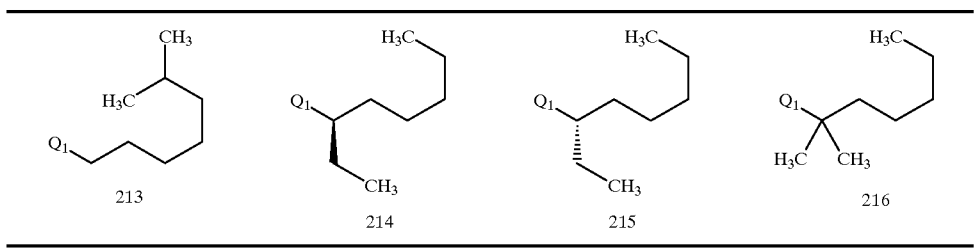
TABLE 2j
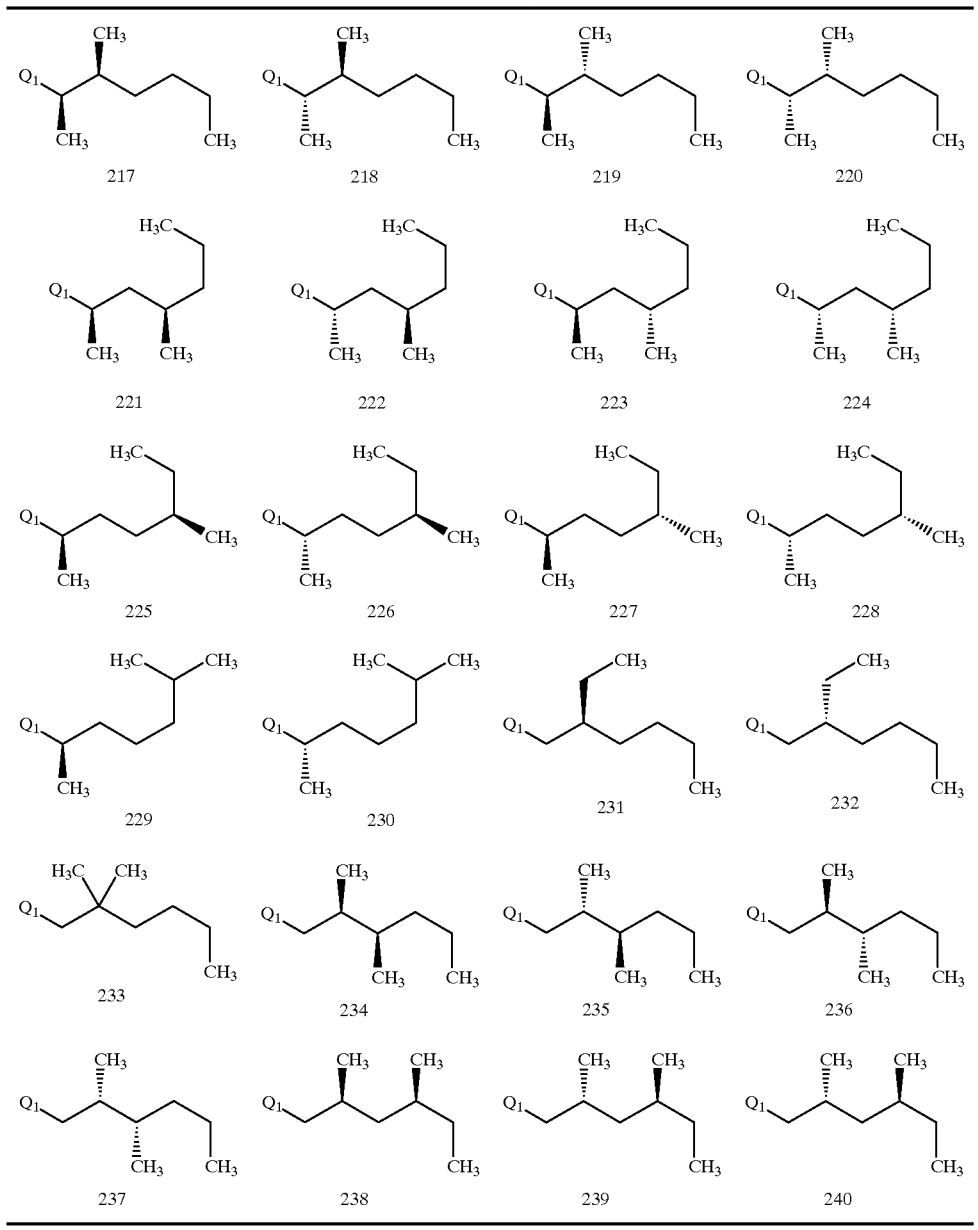

TABLE 2k
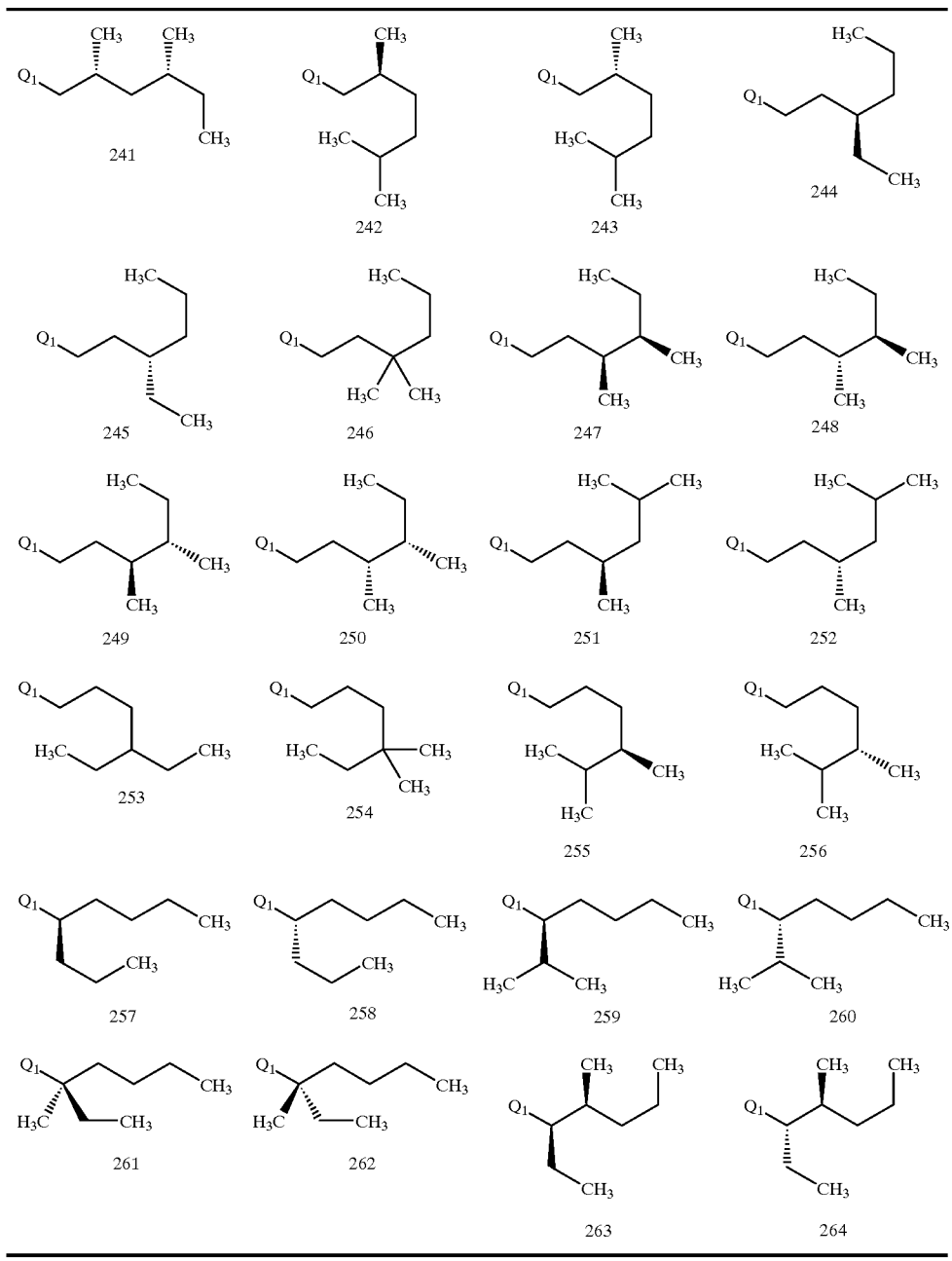
TABLE 2l
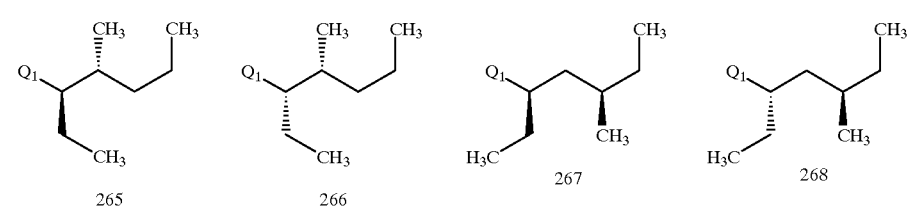

TABLE 2l-continued
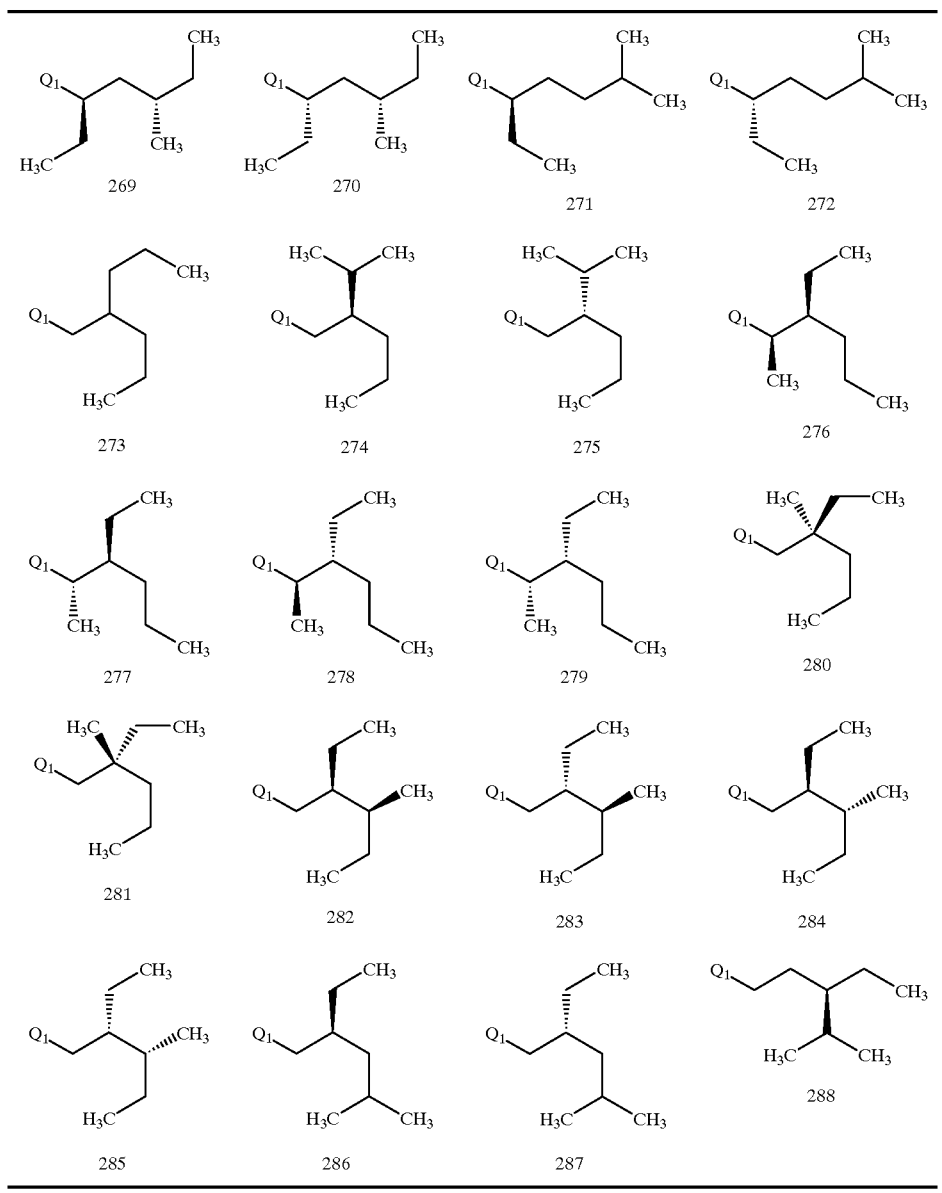
TABLE 2m
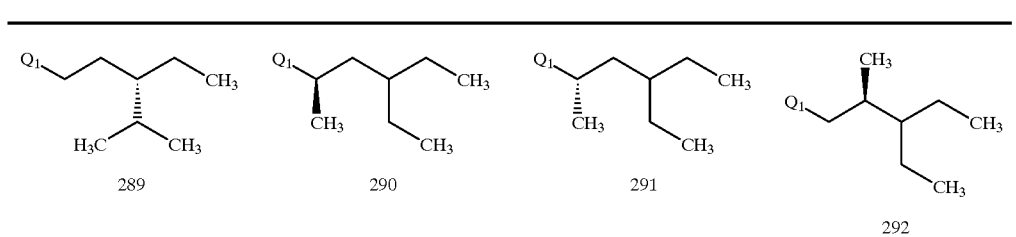

TABLE 2m-continued
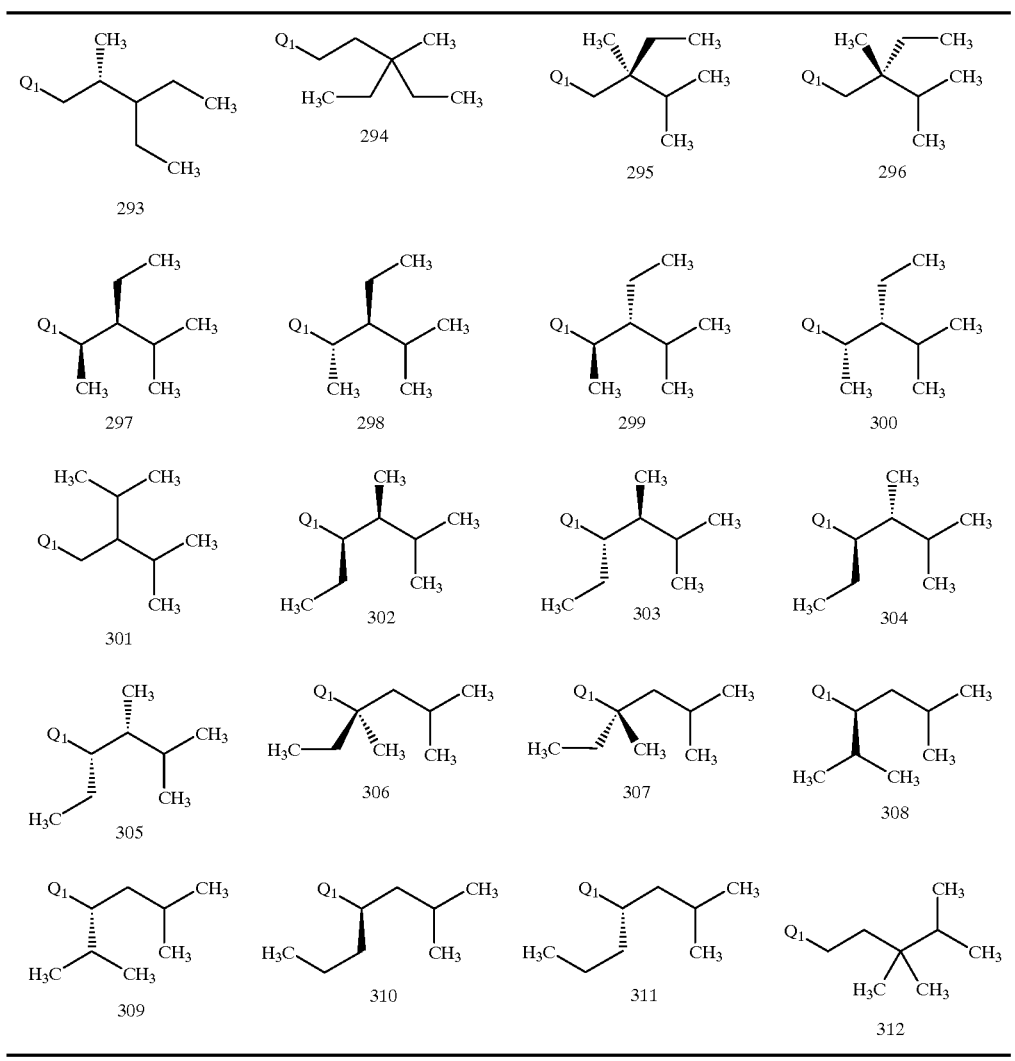
TABLE 2n
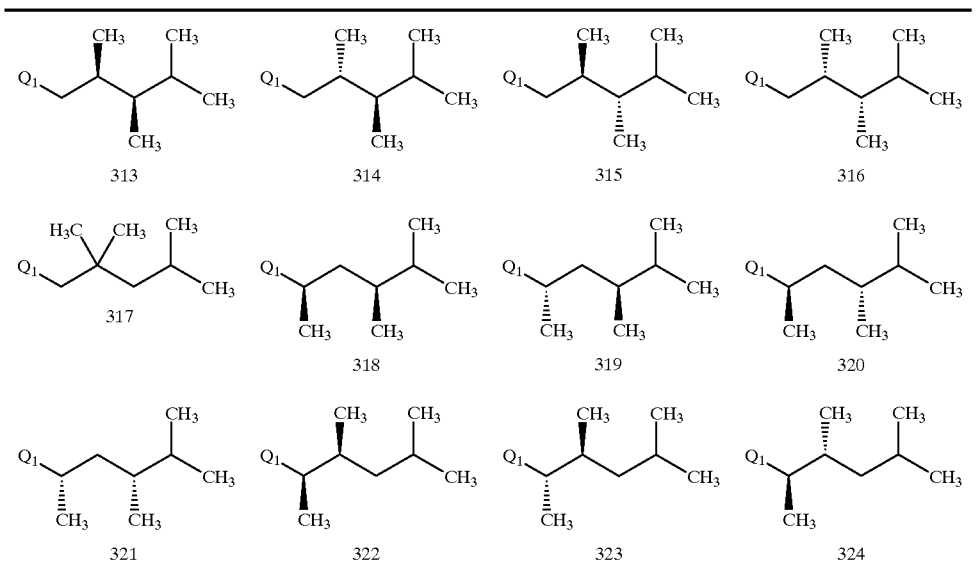

TABLE 2n-continued
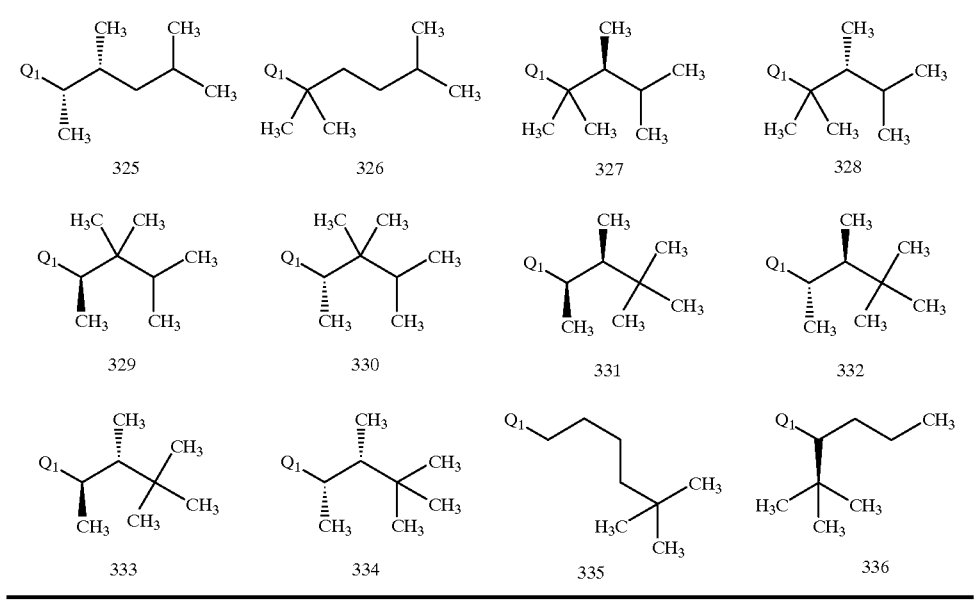
TABLE 2o
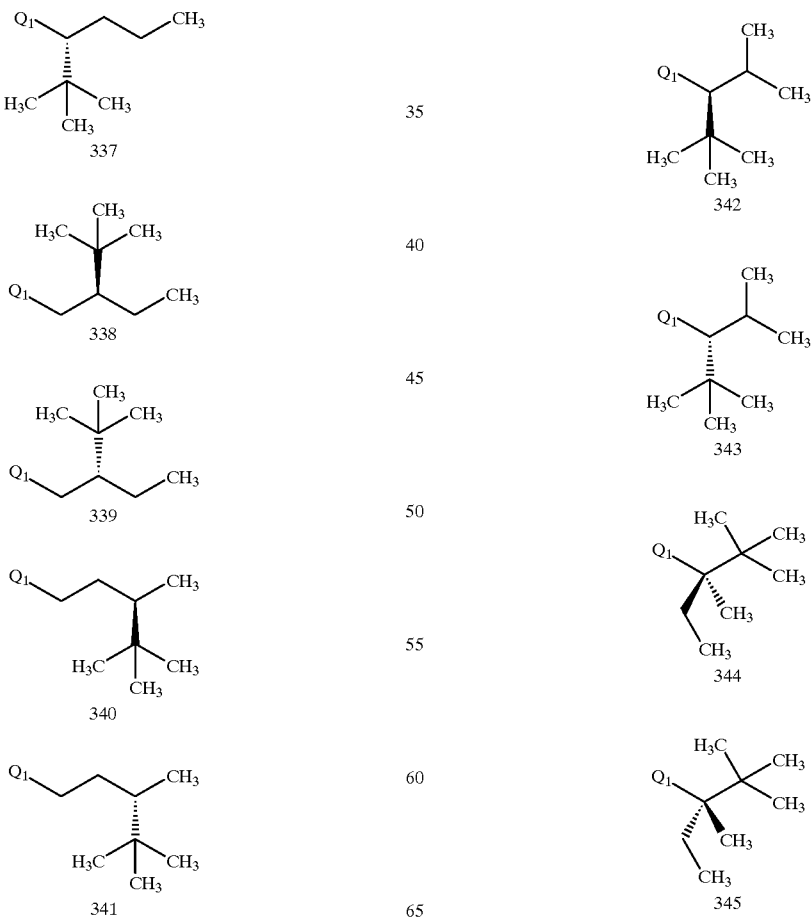

TABLE 2o-continued
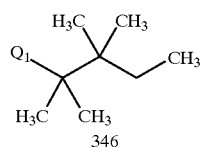
346
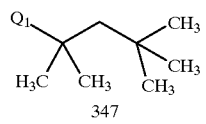
347
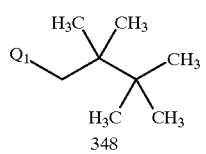
348
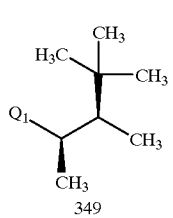
349
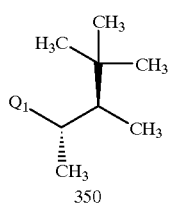
350
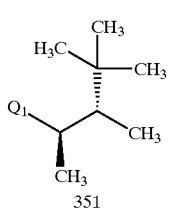
351
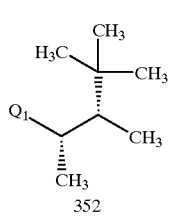
352
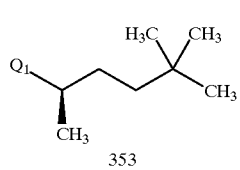
353
TABLE 2o-continued
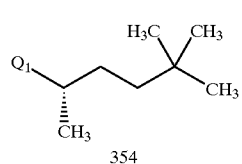
354
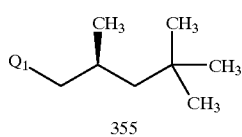
355
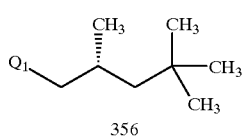
356
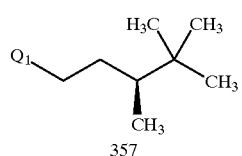
357
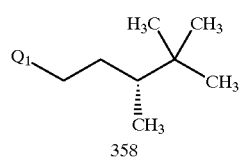
358
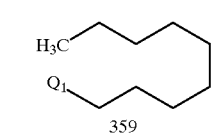
359
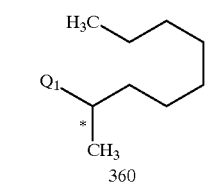
360
TABLE 2p
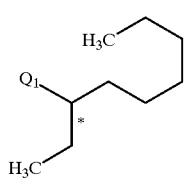
361

TABLE 2p-continued
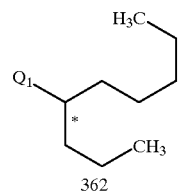
362
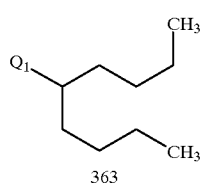
363
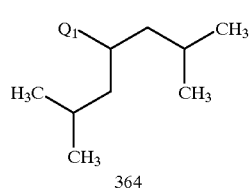
364
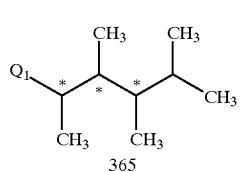
365
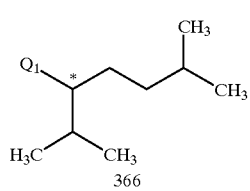
366
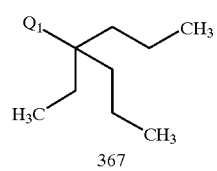
367
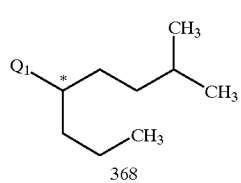
368
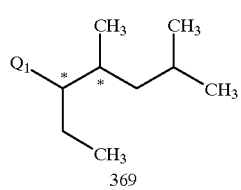
369
TABLE 2p-continued
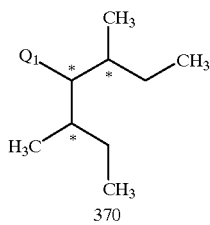
370
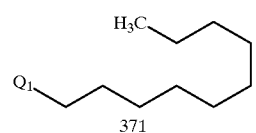
371
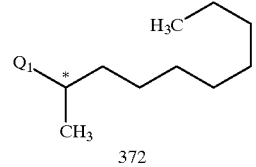
372
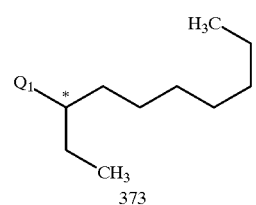
373
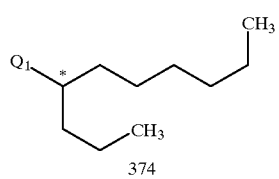
374
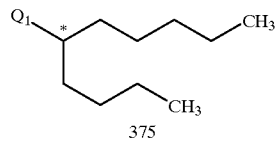
375
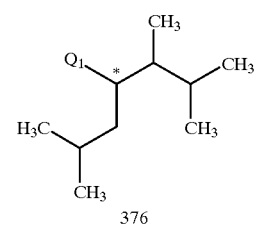
376
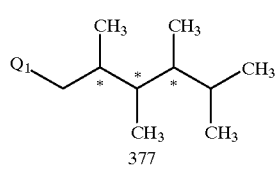
377

TABLE 2p-continued
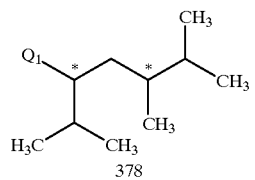
378
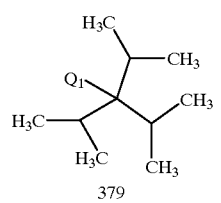
379
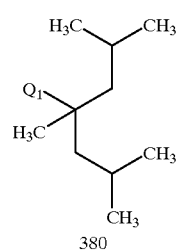
380
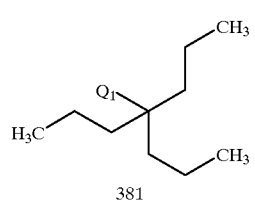
381
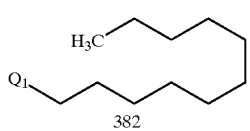
382
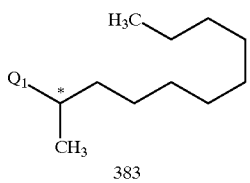
383
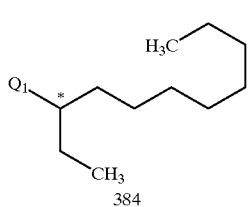
384
TABLE 2q
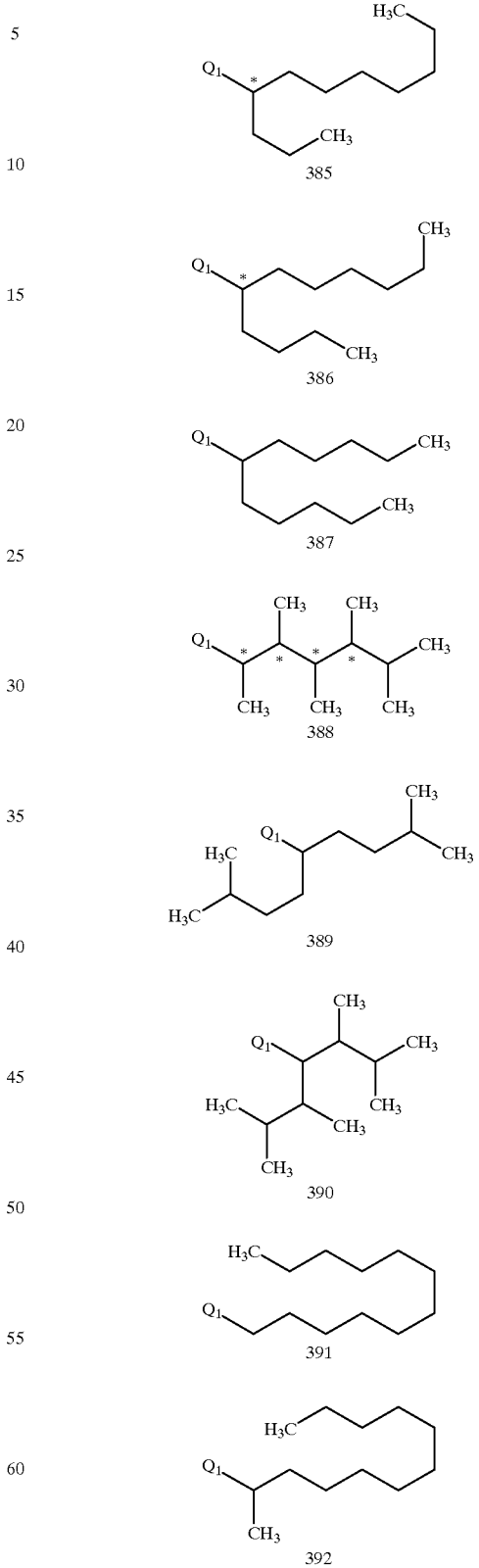

TABLE 2q-continued
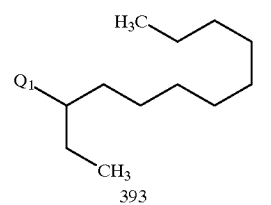
393
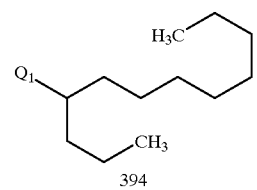
394
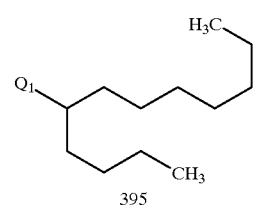
395
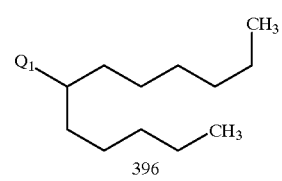
396
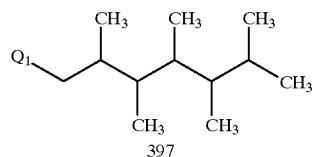
397
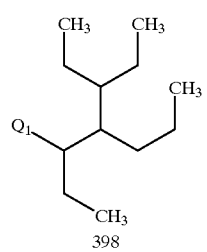
398
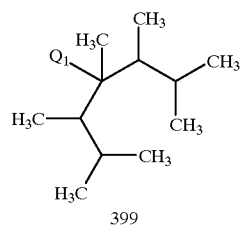
399
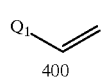
400
TABLE 2q-continued
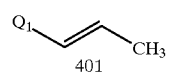
401
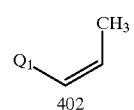
402
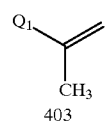
403
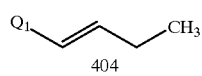
404
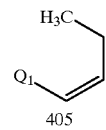
405
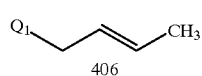
406
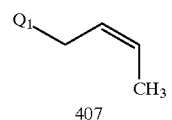
407
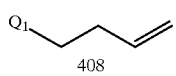
408
TABLE 2r
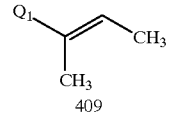
409
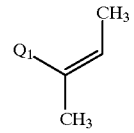
410
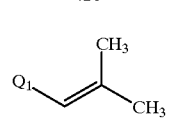
411
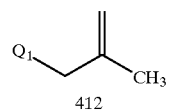
412

TABLE 2r-continued
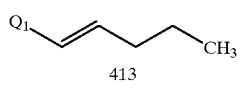
413
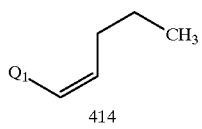
414
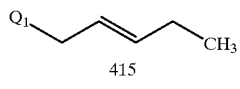
415
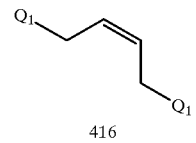
416
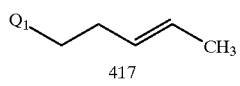
417
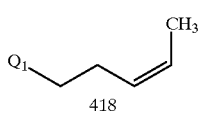
418
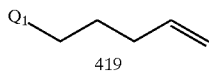
419
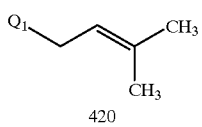
420
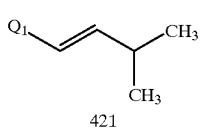
421
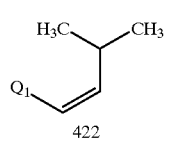
422
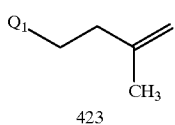
423
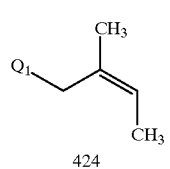
424
TABLE 2r-continued
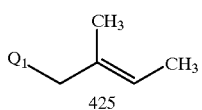
425
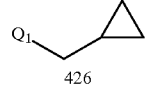
426
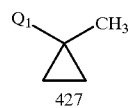
427
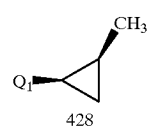
428
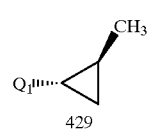
429
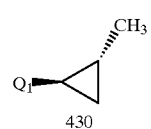
430
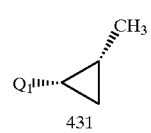
431
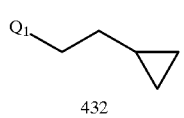
432
TABLE 2s
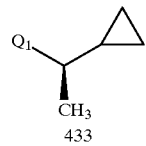
433
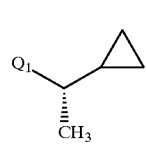
434
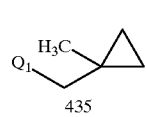
435

TABLE 2s-continued
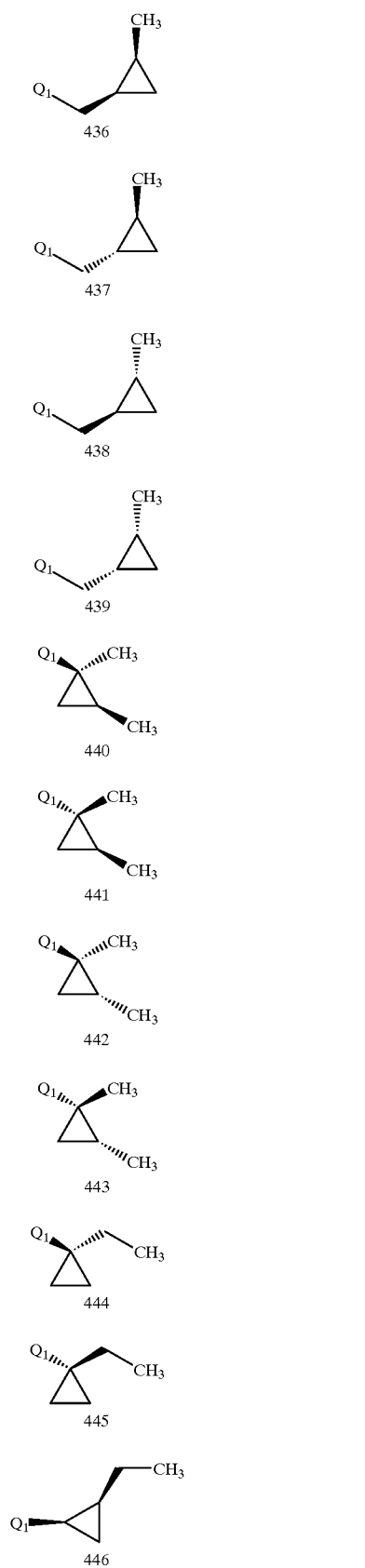
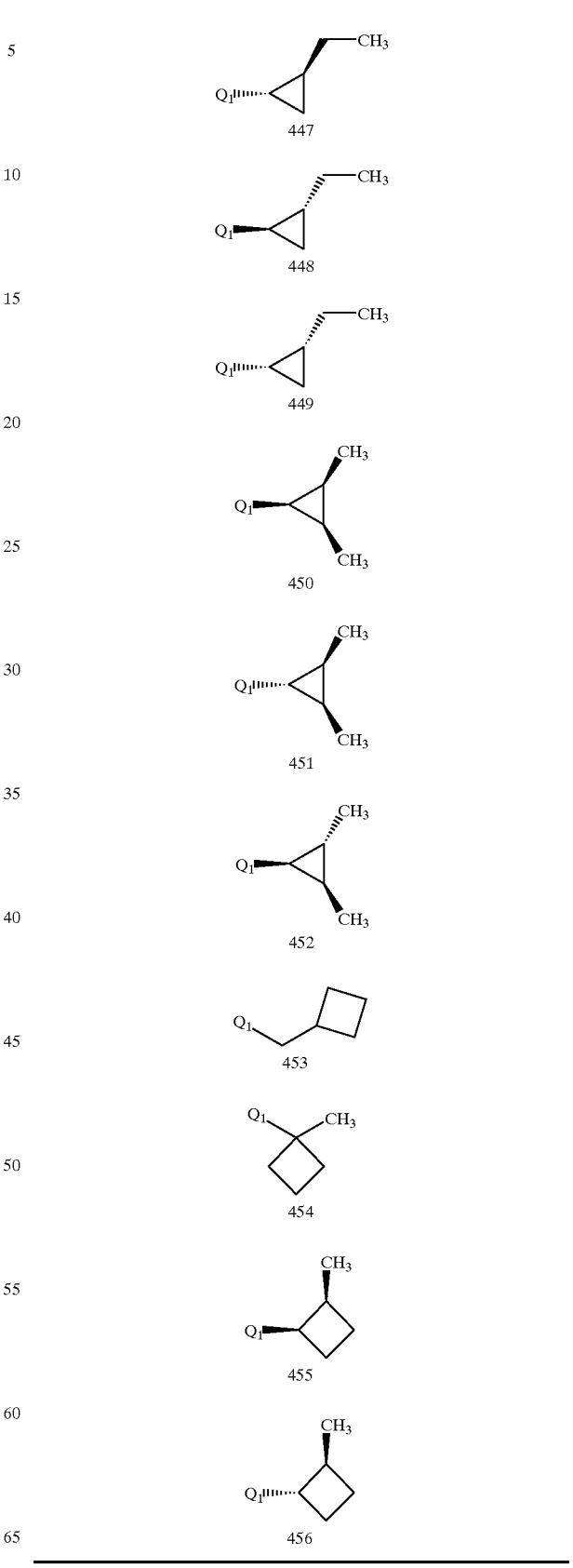

TABLE 2t
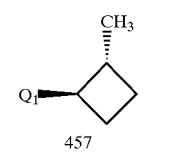
457
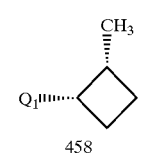
458
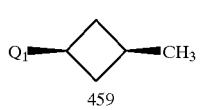
459
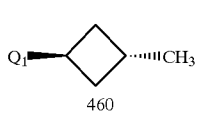
460
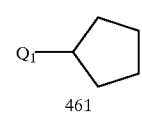
461
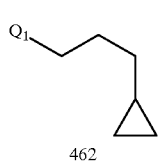
462
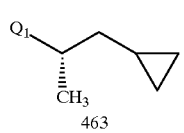
463
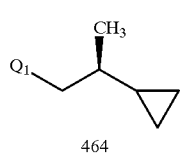
464
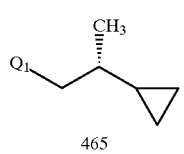
465
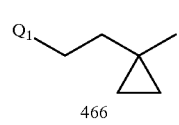
466
467
TABLE 2t-continued
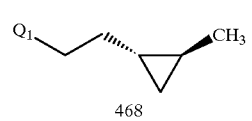
468
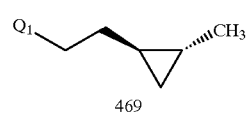
469
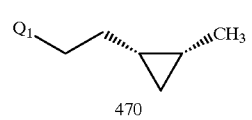
470
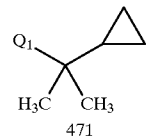
471
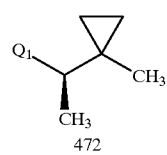
472
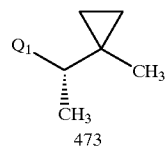
473
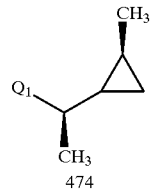
474
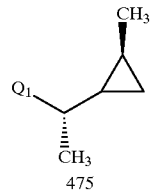
475
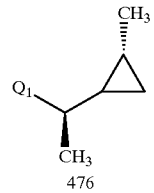
476

TABLE 2t-continued
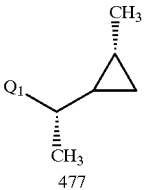
477
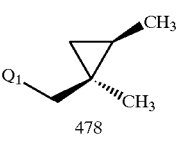
478
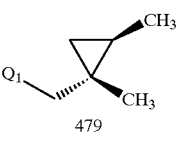
479
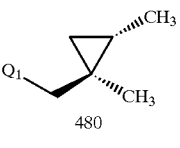
480
TABLE 2u
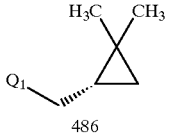
481
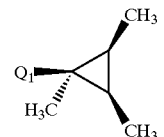
482
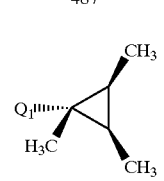
483
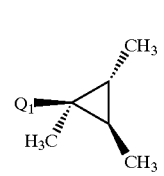
484
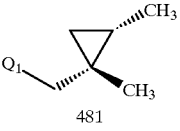
485
TABLE 2u-continued
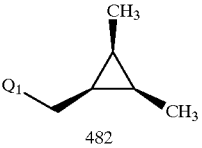
486
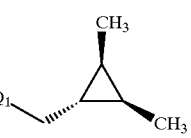
487
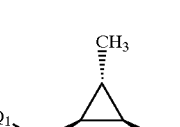
488
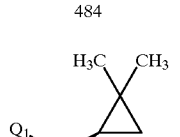
489
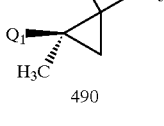
490
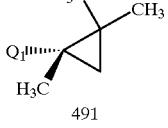
491
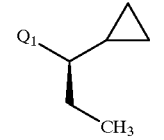
492
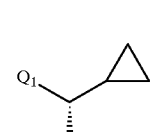
493
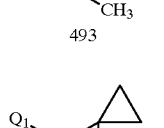
494

TABLE 2u-continued
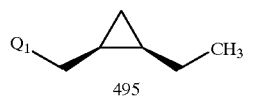
495
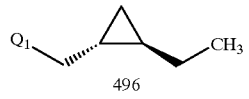
496
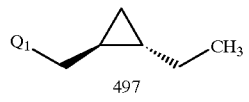
497
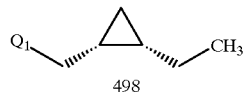
498
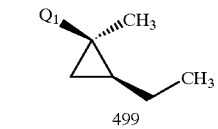
499
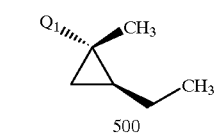
500
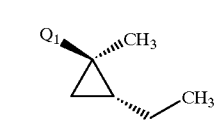
501
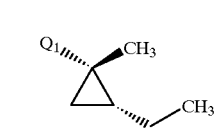
502
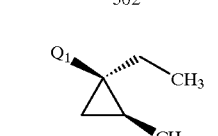
503
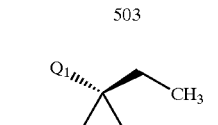
504
TABLE 2v
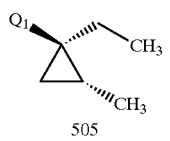
505
TABLE 2v-continued
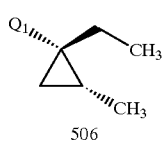
506
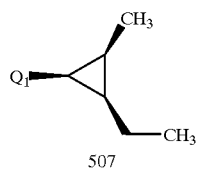
507
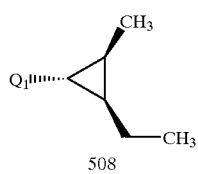
508
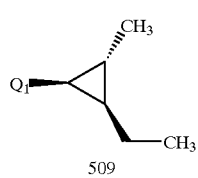
509
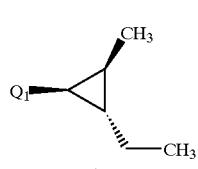
510
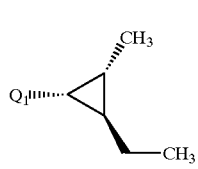
511
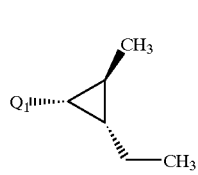
512
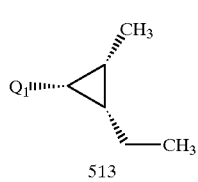
513

TABLE 2v-continued
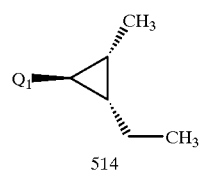
514
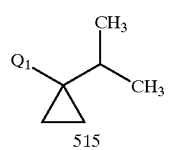
515
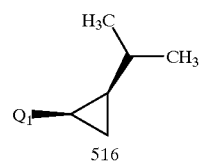
516
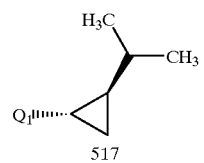
517
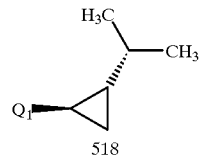
518
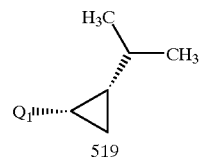
519
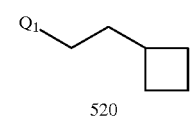
520
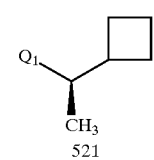
521
TABLE 2v-continued
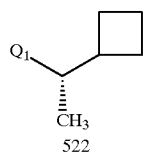
522
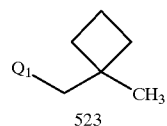
523
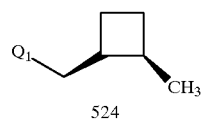
524
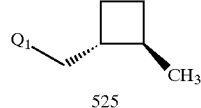
525
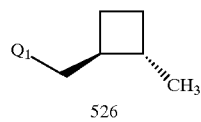
526
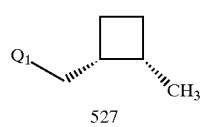
527
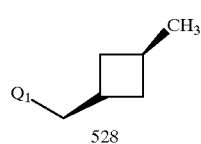
528

TABLE 2w
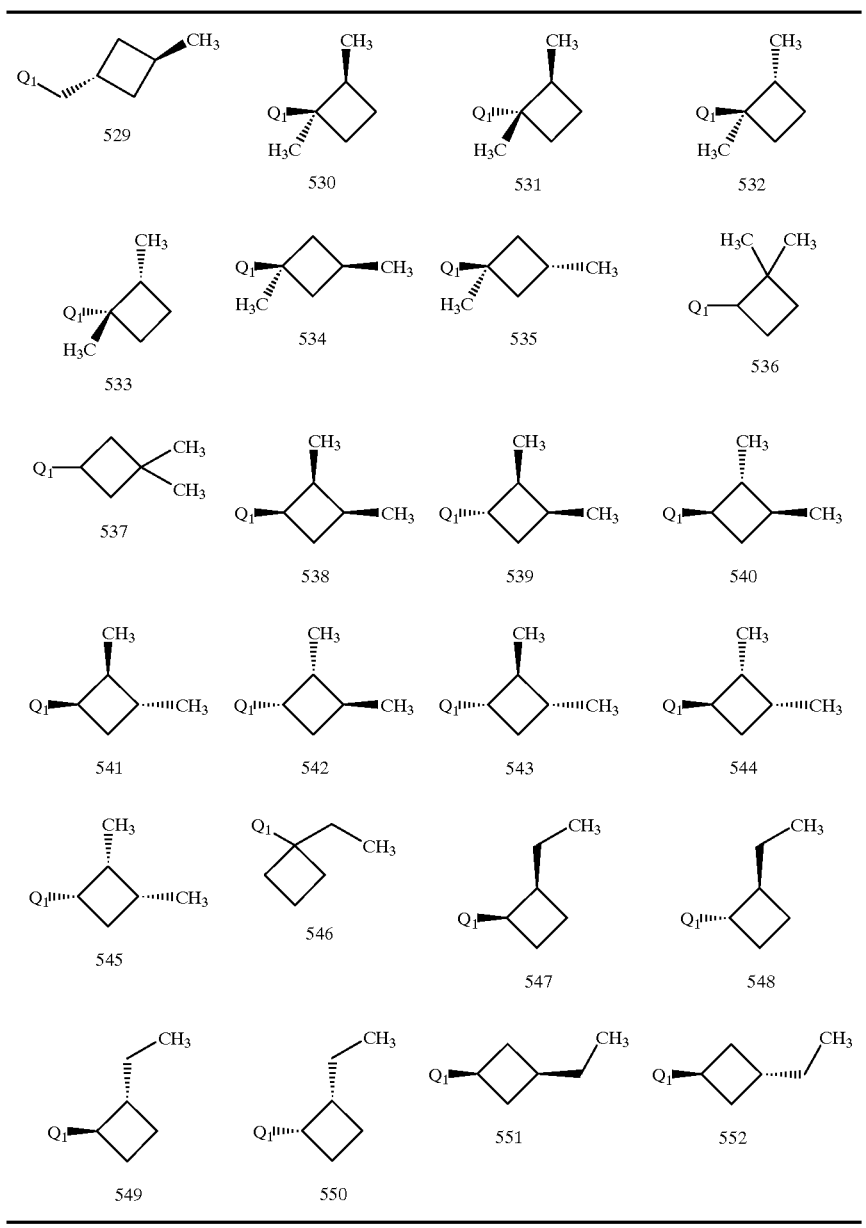
TABLE 2x
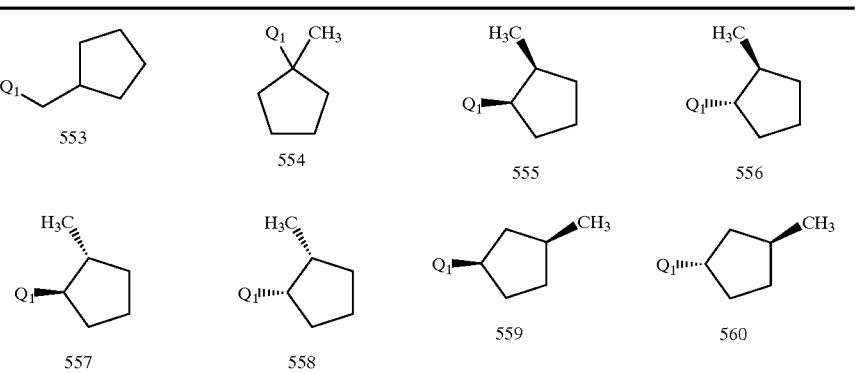

TABLE 2x-continued
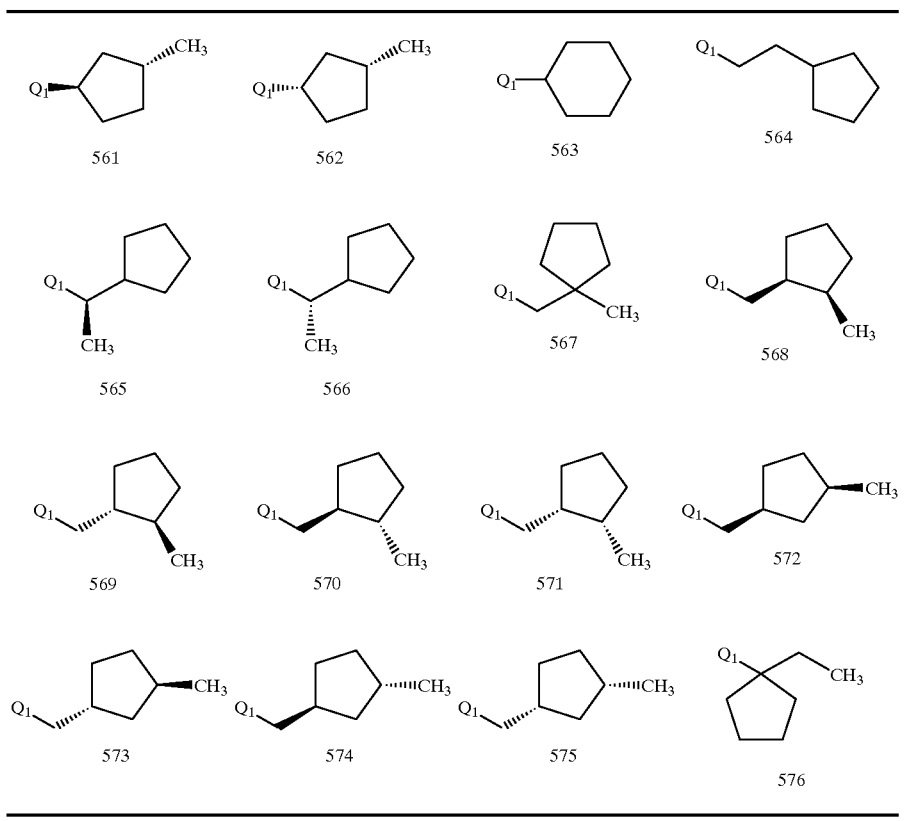
TABLE 2y
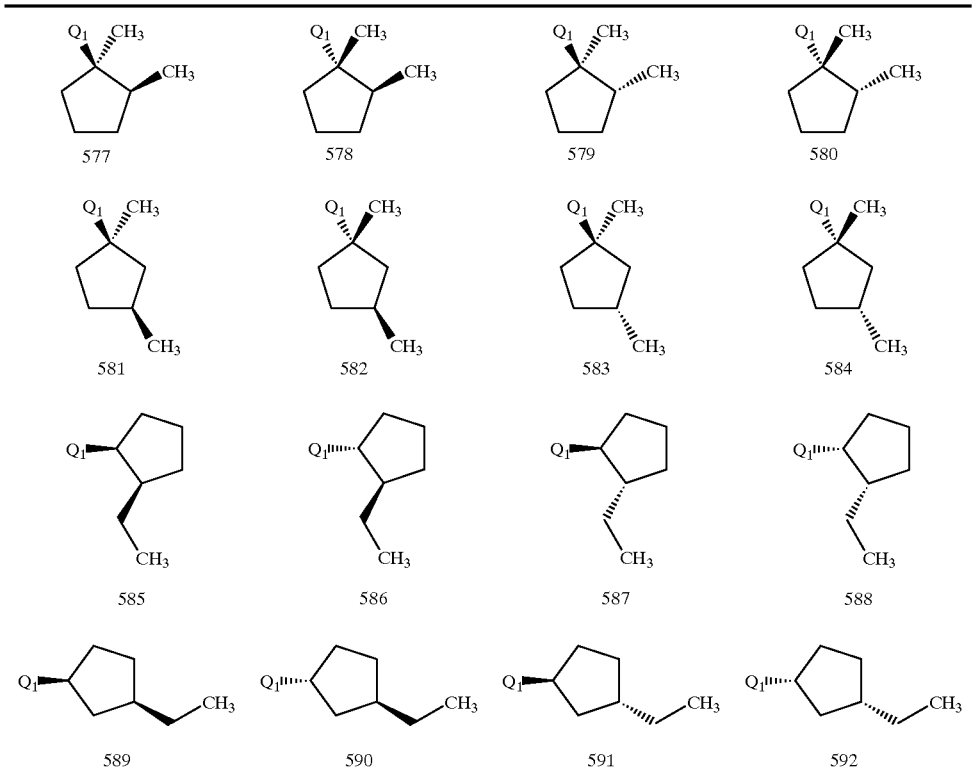

TABLE 2y-continued
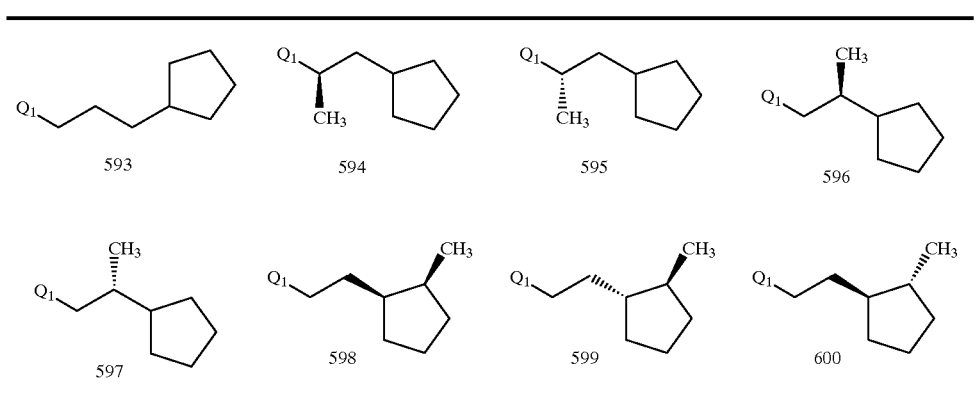
TABLE 2z
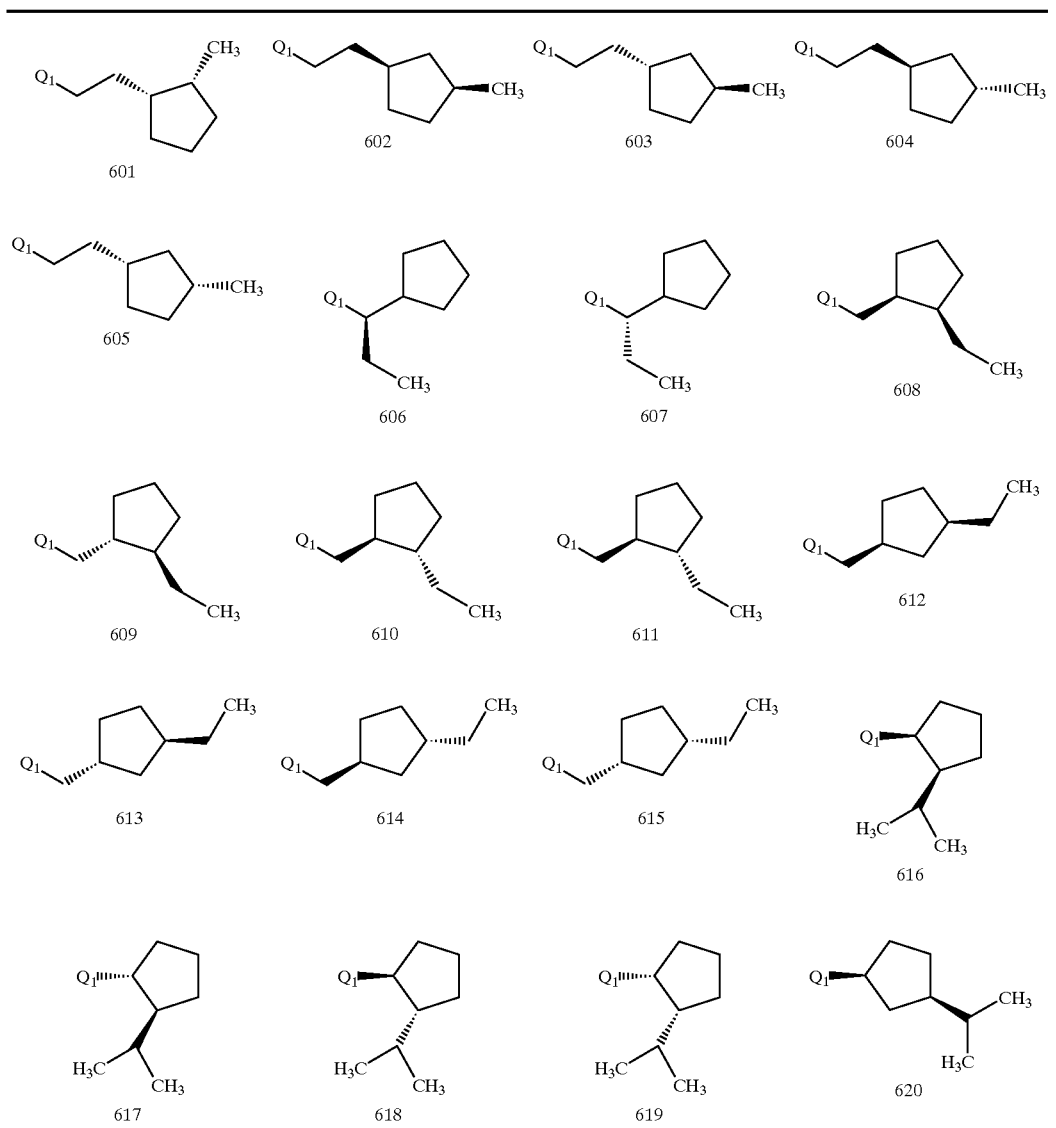

TABLE 2z-continued
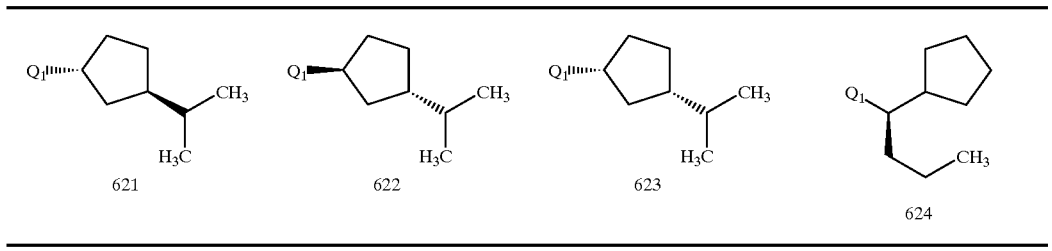
TABLE aa
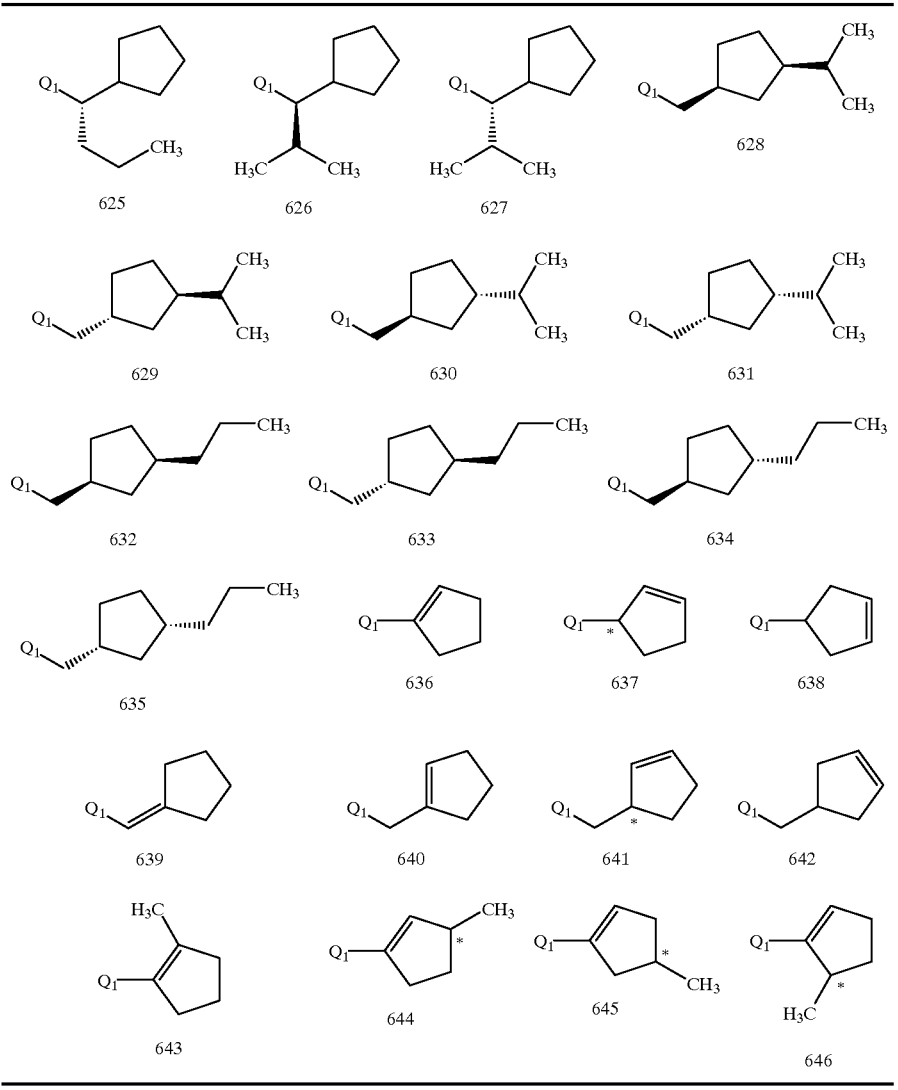
TABLE 2ab
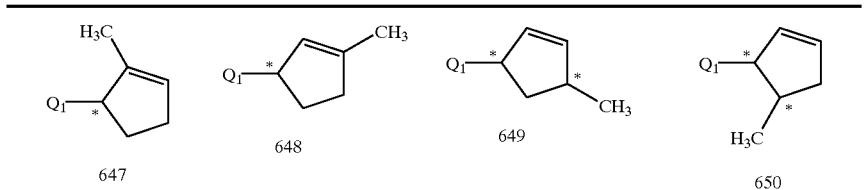

TABLE 2ab-continued
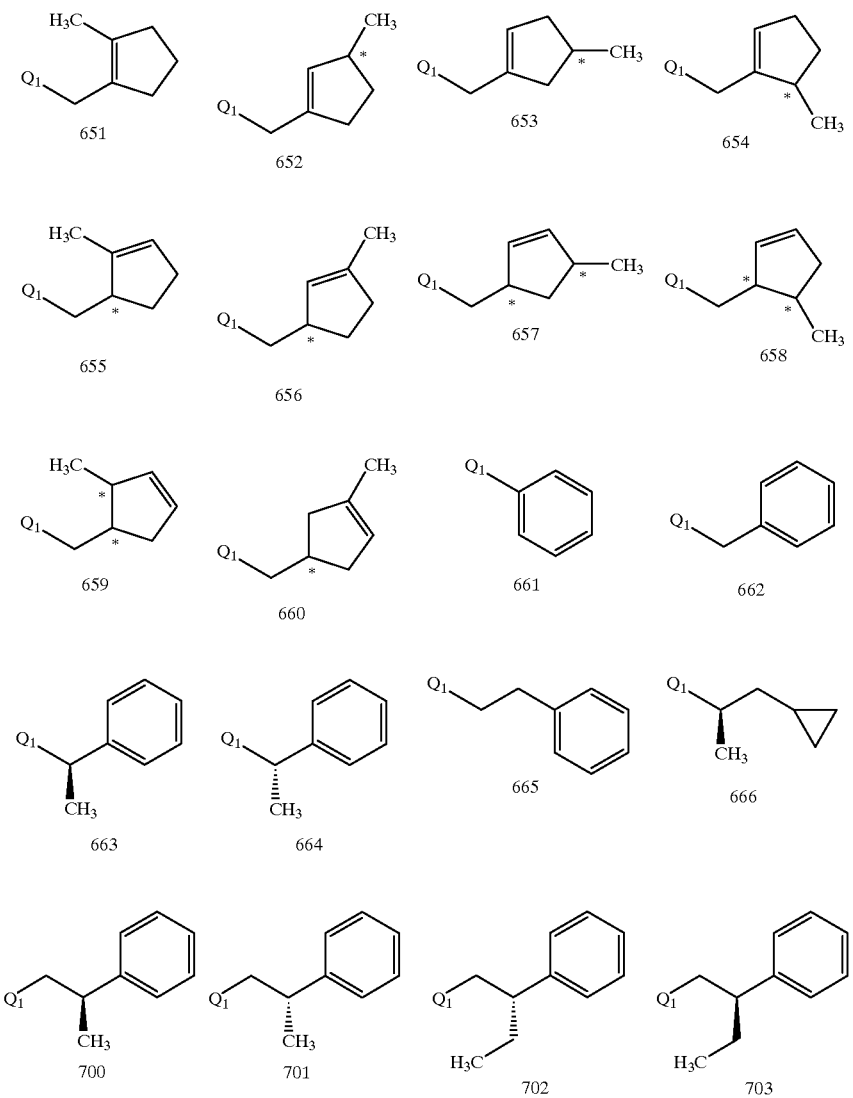
TABLE 2ac
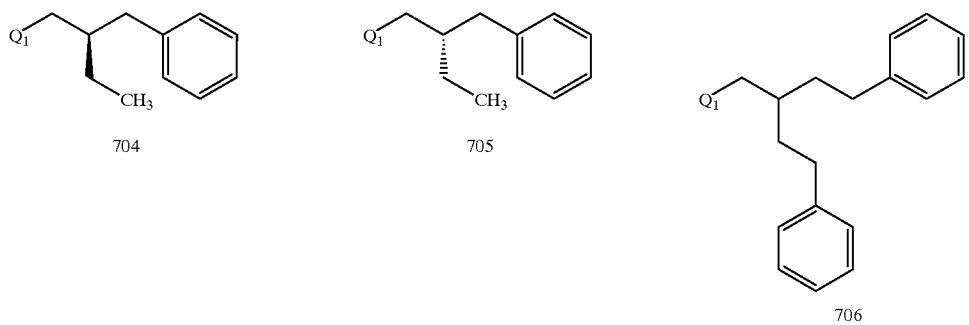

TABLE 2ac-continued
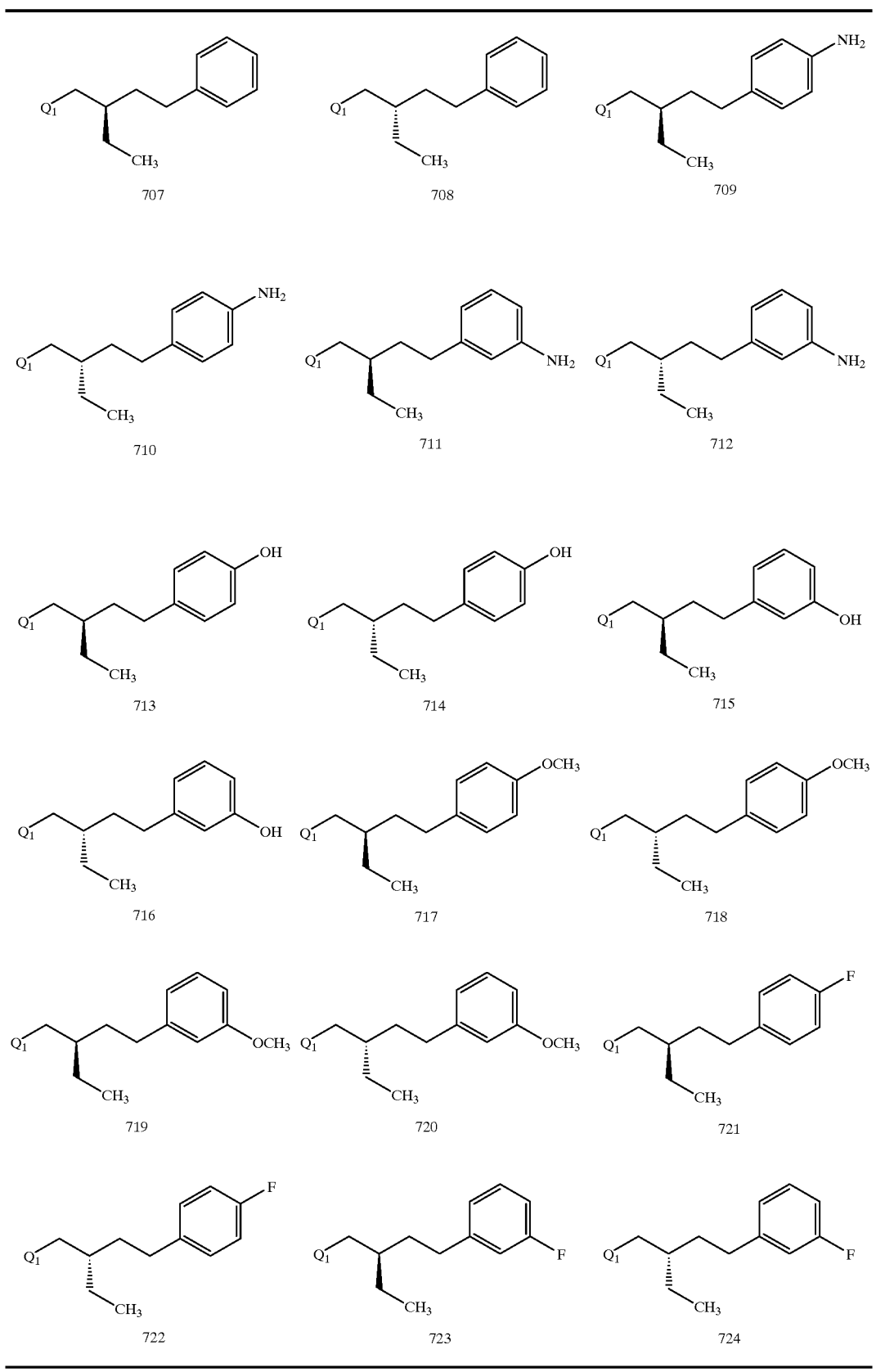

TABLE 3a
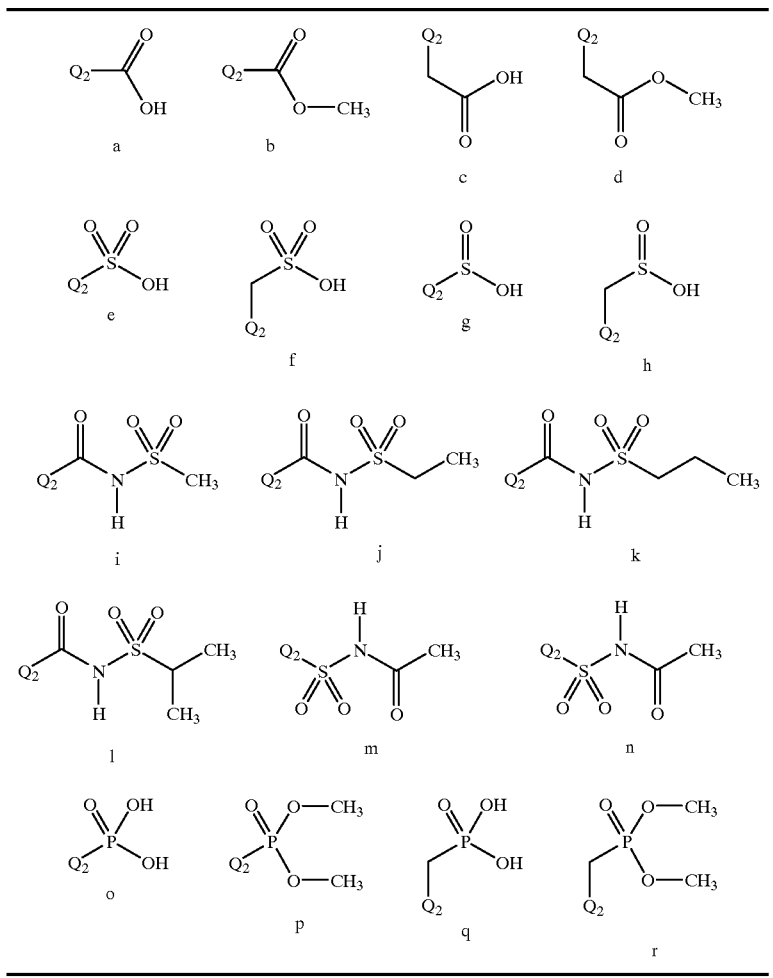
TABLE 3b
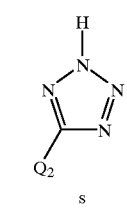
s
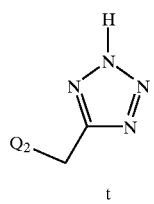
t
TABLE 3b-continued
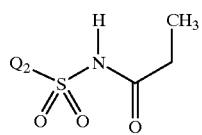
u
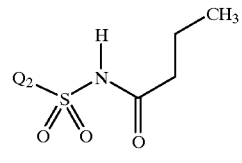
v
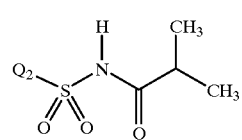
w TABLE 3b-continued
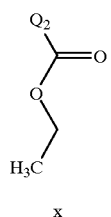
x
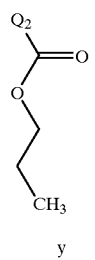
y
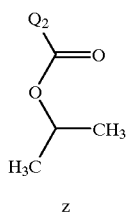
z
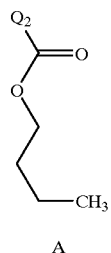
A
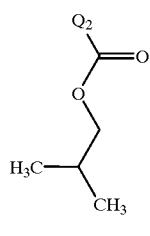
B
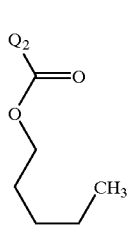
C
TABLE 3b-continued
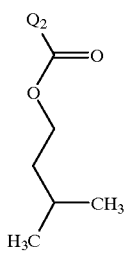
D
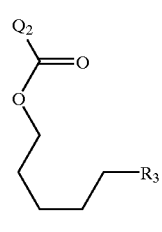
E
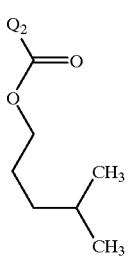
F
TABLE 4a
$Q_3$—OH
1
$Q_3$—$N_3$
2
$Q_3$—$NO_2$
3
$Q_3$—$NH_2$
4
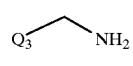
5
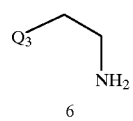
6
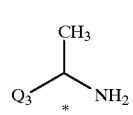
7

TABLE 4a-continued
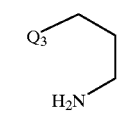
8
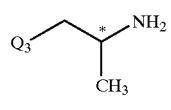
9
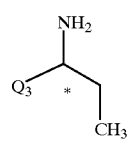
10
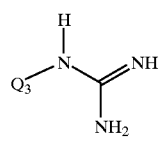
11
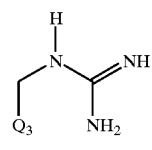
12
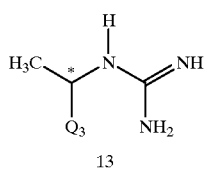
13
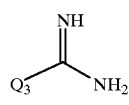
14
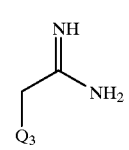
15
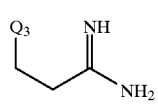
16
TABLE 4a-continued
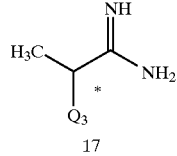
17
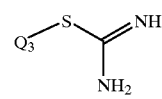
18
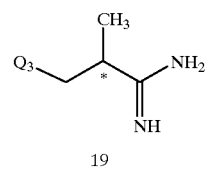
19
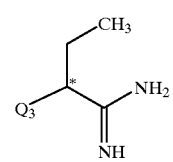
20
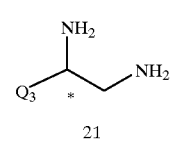
21
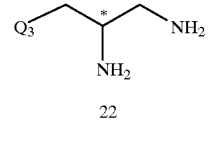
22
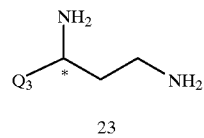
23
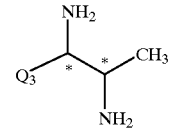
24
TABLE 4b
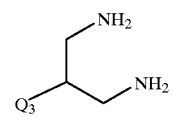
25

TABLE 4b-continued
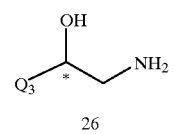
26
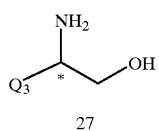
27
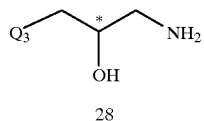
28
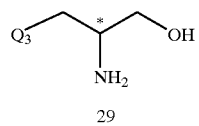
29
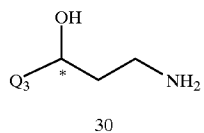
30
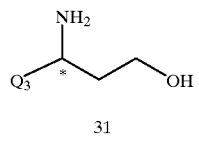
31
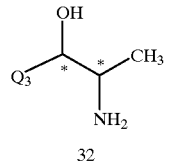
32
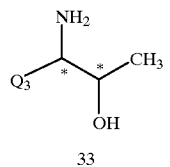
33
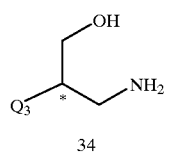
34
35
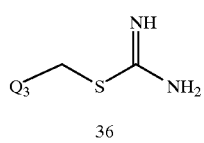
36
TABLE 4b-continued
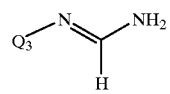
37
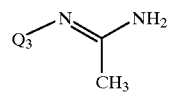
38
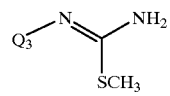
39
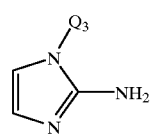
40
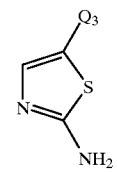
41
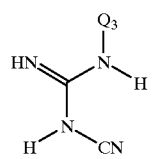
42
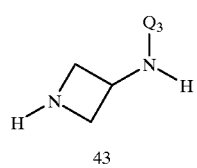
43
TABLE 4c
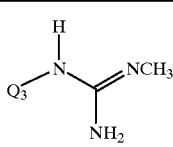
44

TABLE 4c-continued

45: Q₃-N(H)-C(=NH₂)-NCH₂CH₃

46: Q₃-N(H)-CH₃

47: Q₃-N(H)-CH₂CH₃

48: Q₃-N(H)-CH₂CH₂CH₃

49: Q₃-N(H)-CH(CH₃)₂

50: Q₃-N(H)-CH₂CH₂OH

51: Q₃-N(H)-CH₂CH₂NH₂

52: Q₃-N(CH₃)₂

53: Q₃-N(CH₂CH₃)₂

54: Q₃-H

TABLE 5a a: H—Q₄ b: H₃C—Q₄ c: H₃CH₂C—Q₄ d: CH₃CH₂CH₂—Q₄ e: (H₃C)₂CH—Q₄ f: H₃C-C(=O)-Q₄ g: CH₃CH₂-C(=O)-Q₄ h: (CH₃)₂CH-C(=O)-Q₄ i: H₃C-C(=O)-N(H)-Q₄ j: CH₃CH₂-C(=O)-N(H)-Q₄ k: (CH₃)₂CH-O-Q₄

TABLE 5a-continued
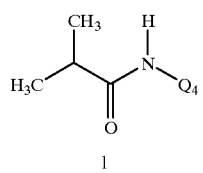
l
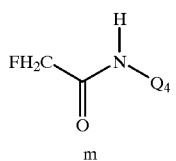
m
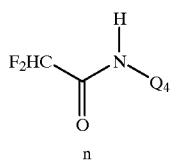
n
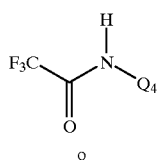
o
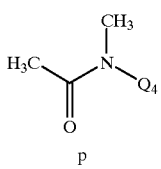
p
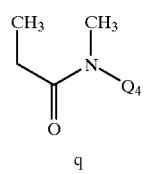
q
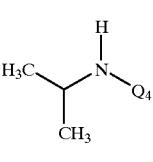
r
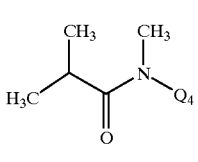
s
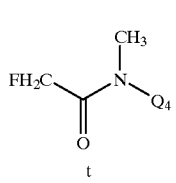
t
TABLE 5a-continued
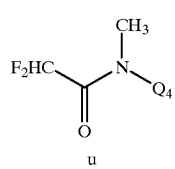
u
TABLE 5b
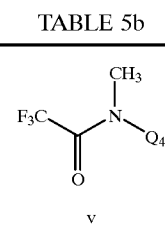
v
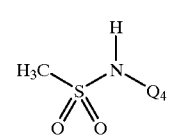
w
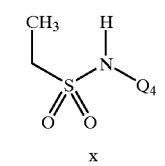
x
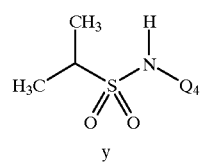
y
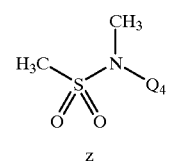
z
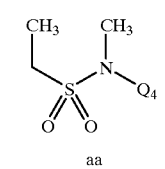
aa
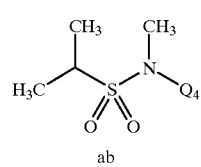
ab

TABLE 5b-continued
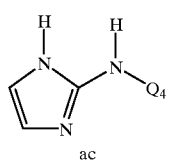
ac
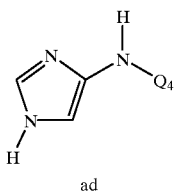
ad
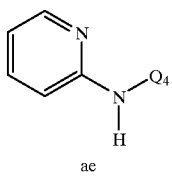
ae
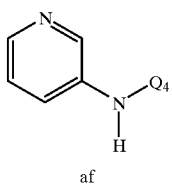
af
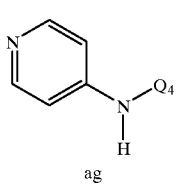
ag
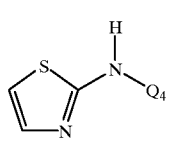
ah
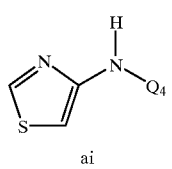
ai
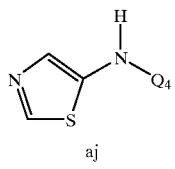
aj
TABLE 5b-continued
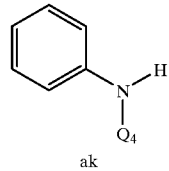
ak
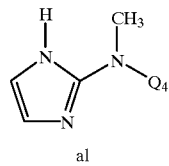
al
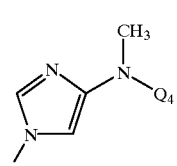
am
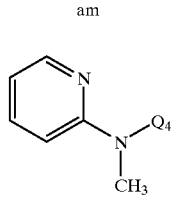
an
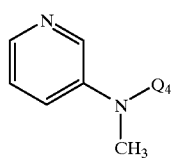
ao
TABLE 5c
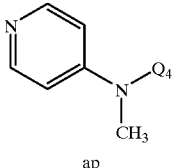
ap
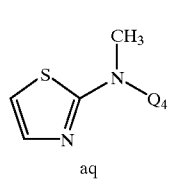
aq
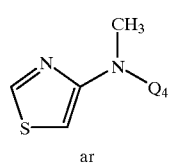
ar TABLE 5c-continued
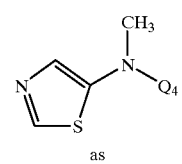
as
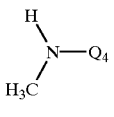
at
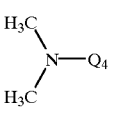
au
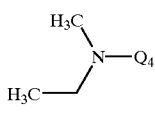
av
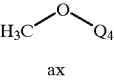
aw
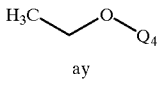
ax
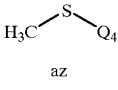
ay
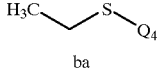
az
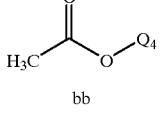
ba
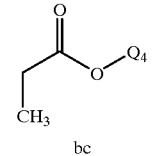
bb
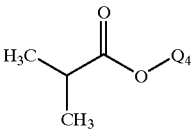
bc
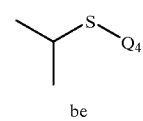
bd
TABLE 5c-continued
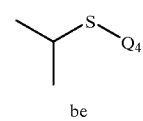
be
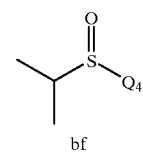
bf
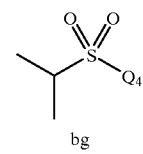
bg
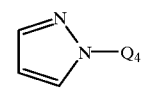
bh
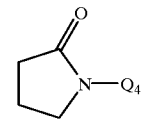
bi
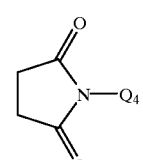
bj
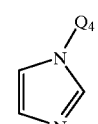
bk

TABLE 6

Exemplary Enumerated Compounds

A.3.a.4.i; A.4.a.4.i; A.7.a.4.i; A.9.a.4.i; A.103.a.4.i; A.106.a.4.i; A.107.a.4.i; A.108.a.4.i;
A.111.a.4.i; A.114.a.4.i; A.117.a.4.i; A.118.a.4.i; A.119.a.4.i; A.120.a.4.i; A.121.a.4.i;
A.137.a.4.i; A.138.a.4.i; A.139.a.4.i; A.140.a.4.i; A.141.a.4.i; A.142.a.4.i; A.145.a.4.i;
A.146.a.4.i; A.147.a.4.i; A.148.a.4.i; A.149.a.4.i; A.150.a.4.i; A.151.a.4.i; A.165.a.4.i;
A.166.a.4.i; A.167.a.4.i; A.168.a.4.i; A.169.a.4.i; A.170.a.4.i; A.171.a.4.i; A.172.a.4.i;
A.173.a.4.i; A.174.a.4.i; A.175.a.4.i; A.176.a.4.i; A.188.a.4.i; A.189.a.4.i; A.190.a.4.i;
A.196.a.4.i; A.202.a.4.i; A.205.a.4.i; A.206.a.4.i; A.207.a.4.i; A.208.a.4.i; A.209.a.4.i;
A.210.a.4.i; A.211.a.4.i; A.212.a.4.i; A.213.a.4.i; A.700.a.4.i; A.701.a.4.i; A.702.a.4.i;
A.703.a.4.i; A.704.a.4.i; A.705.a.4.i; A.706.a.4.i; A.707.a.4.i; A.708.a.4.i; A.709.a.4.i;
A.710.a.4.i; A.711.a.4.i; A.712.a.4.i; A.713.a.4.i; A.714.a.4.i; A.715.a.4.i; A.716.a.4.i;
A.717.a.4.i; A.718.a.4.i; A.719.a.4.i; A.720.a.4.i; A.721.a.4.i; A.722.a.4.i; A.723.a.4.i;
A.724.a.4.i; A.3a.4.o; A.4.a.4.o; A.7.a.4.o; A.9.a.4.o; A.103.a.4.o; A.106.a.4.o;
A.107.a.4.o; A.108.a.4.o; A.111.a.4.o; A.114.a.4.o; A.117.a.4.o; A.118.a.4.o;
A.119.a.4.o; A.120.a.4.o; A.121.a.4.o; A.137.a.4.o; A.138.a.4.o; A.139.a.4.o;
A.140.a.4.o; A.141.a.4.o; A.142.a.4.o; A.145.a.4.o; A.146.a.4.o; A.147.a.4.o;
A.148.a.4.o; A.149.a.4.o; A.150.a.4.o; A.151.a.4.o; A.165.a.4.o; A.166.a.4.o;
A.167.a.4.o; A.168.a.4.o; A.169.a.4.o; A.170.a.4.o; A.171.a.4.o; A.172.a.4.o;
A.173.a.4.o; A.174.a.4.o; A.175.a.4.o; A.176.a.4.o; A.188.a.4.o; A.189.a.4.o;
A.190.a.4.o; A.196.a.4.o; A.202.a.4.o; A.205.a.4.o; A.206.a.4.o; A.207.a.4.o;
A.208.a.4.o; A.209.a.4.o; A.210.a.4.o; A.211.a.4.o; A.212.a.4.o; A.213.a.4.o;
A.700.a.4.o; A.701.a.4.o; A.702.a.4.o; A.703.a.4.o; A.704.a.4.o; A.705.a.4.o;
A.706.a.4.o; A.707.a.4.o; A.708.a.4.o; A.709.a.4.o; A.710.a.4.o; A.711.a.4.o;
A.712.a.4.o; A.713.a.4.o; A.714.a.4.o; A.715.a.4.o; A.716.a.4.o; A.717.a.4.o;
A.718.a.4.o; A.719.a.4.o; A.720.a.4.o; A.721.a.4.o; A.722.a.4.o; A.723.a.4.o;
A.724.a.4.o; A.172.b.4.i; A.173.b.4.i; A.174.b.4.i; A.175.b.4.i; A.176.b.4.i; A.188.b.4.i;
A.189.b.4.i; A.190.b.4.i; A.196.b.4.i; A.202.b.4.i; A.205.b.4.i;p A.206.b.4.i; A.207.b.4.i;
A.208.b.4.i; A.209.b.4.i; A.210.b.4.i; A.211.b.4.i; A.212.b.4.i; A.213.b.4.i; A.700.b.4.i;
A.701.b.4.i; A.702.b.4.i; A.703.b.4.i; A.704.b.4.i; A.705.b.4.i; A.706.b.4.i; A.707.b.4.i;
A.708.b.4.i; A.709.b.4.i; A.710.b.4.i; A.711.b.4.i; A.712.b.4.i; A.713.b.4.i; A.714.b.4.i;
A.715.b.4.i; A.716.b.4.i; A.717.b.4.i; A.718.b.4.i; A.719.b.4.i; A.720.b.4.i; A.721.b.4.i;
A.722.b.4.i; A.723.b.4.i; A.724.b.4.i; A.3.b.3.o; A.4.b.4.o; A.7.b.4.o; A.9.b.4.o;
A.103.b.4.o; A.106.b.4.o; A.107.b.4.o; A.108.b.4.o; A.111.b.4.o; A.114.b.4.o;
A.117.b.4.o; A.118.b.4.o; A.119.b.4.o; A.120.b.4.o; A.121.b.4.o; A.137.b.4.o;
A.138.b.4.o; A.139.b.4.o; A.140.b.4.o; A.141.b.4.o; A.142.b.4.o; A.145.b.4.o;
A.146.b.4.o; A.147.b.4.o; A.148.b.4.o; A.149.b.4.o; A.150.b.4.o; A.151.b.4.o;
A.165.b.4.o; A.166.b.4.o; A.167.b.4.o; A.168.b.4.o; A.169.b.4.o; A.170.b.4.o;
A.171.b.4.o; A.172.b.4.o; A.173.b.4.o; A.174.b.4.o; A.175.b.4.o; A.176.b.4.o;
A.188.b.4.o; A.189.b.4.o; A.190.b.4.o; A.196.b.4.o; A.202.b.4.o; A.205.b.4.o;
A.206.b.4.o; A.207.b.4.o; A.208.b.4.o; A.209.b.4.o; A.210.b.4.o; A.211.b.4.o;
A.212.b.4.o; A.213.b.4.o; A.700.b.4.o; A.701.b.4.o; A.702.b.4.o; A.703.b.4.o;
A.704.b.4.o; A.705.b.4.o; A.706.b.4.o; A.707.b.4.o; A.708.b.4.o; A.709.b.4.o;
A.710.b.4.o; A.711.b.4.o; A.712.b.4.o; A.713.b.4.o; A.714.b.4.o; A.715.b.4.o;
A.716.b.4.o; A.717.b.4.o; A.718.b.4.o; A.719.b.4.o; A.720.b.4.o; A.721.b.4.o;
A.722.b.4.o; A.723.b.4.o; A.724.b.4.o; A.172.x.4.i; A.173.x.4.i; A.174.x.4.i; A.175.x.4.i;
A.176.x.4.i; A.188.x.4.i; A.189.x.4.i; A.190.x.4.i; A.196.x.4.i; A.202.x.4.i; A.205.x.4.i;
A.206.x.4.i; A.207.x.4.i; A.208.x.4.i; A.209.x.4.i; A.210.x.4.i; A.211.x.4.i; A.212.x.4.i;
A.213.x.4.i; A.700.x.4.i; A.701.x.4.i; A.702.x.4.i; A.703.x.4.i; A.704.x.4.i; A.705.x.4.i;
A.706.x.4.i; A.707.x.4.i; A.708.x.4.i; A.709.x.4.i; A.710.x.4.i; A.711.x.4.i; A.712.x.4.i;
A.713.x.4.i; A.714.x.4.i; A.715.x.4.i; A.716.x.4.i; A.717.x.4.i; A.718.x.4.i; A.719.x.4.i;
A.720.x.4.i; A.721.x.4.i; A.722.x.4.i; A.723.x.4.i; A.724.x.4.i; A.3.x.4.o; A.4.x.4.o;
A.7.x.4.o; A.9.x.4.o; A.103.x.4.o; A.106.x.4.o; A.107.x.4.o; A.108.x.4.o; A.111.x.4.o;
A.114.x.4.o; A.117.x.4.o; A.118.x.4.o; A.119.x.4.o; A.120.x.4.o; A.121.x.4.o;
A.137.x.4.o; A.138.x.4.o; A.139.x.4.o; A.140.x.4.o; A.141.x.4.o; A.142.x.4.o;
A.145.x.4.o; A.146.x.4.o; A.147.x.4.o; A.148.x.4.o; A.149.x.4.o; A.150.x.4.o;
A.151.x.4.o; A.165.x.4.o; A.166.x.4.o; A.167.x.4.o; A.168.x.4.o; A.169.x.4.o;
A.170.x.4.o; A.171.x.4.o; A.172.x.4.o; A.173.x.4.o; A.174.x.4.o; A.175.x.4.o;
A.176.x.4.o; A.188.x.4.o; A.189.x.4.o; A.190.x.4.o; A.196.x.4.o; A.202.x.4.o;
A.205.x.4.o; A.206.x.4.o; A.207.x.4.o; A.208.x.4.o; A.209.x.4.o; A.210.x.4.o;
A.211.x.4.o; A.212.x.4.o; A.213.x.4.o; A.700.x.4.o; A.701.x.4.o; A.702.x.4.o;
A.703.x.4.o; A.704.x.4.o; A.705.x.4.o; A.706.x.4.o; A.707.x.4.o; A.708.x.4.o;
A.709.x.4.o; A.710.x.4.o; A.711.x.4.o; A.712.x.4.o; A.713.x.4.o; A.714.x.4.o;
A.715.x.4.o; A.716.x.4.o; A.717.x.4.o; A.718.x.4.o; A.719.x.4.o; A.720.x.4.o;
A.721.x.4.o; A.722.x.4.o; A.723.x.4.o; A.724.x.4.o; A.172.y.4.i; A.173.y.4.i; A.174.y.4.i;
A.175.y.4.i; A.176.y.4.i; A.188.y.4.i; A.189.y.4.i; A.190.y.4.i; A.196.y.4.i; A.202.y.4.i;
A.205.y.4.i; A.206.y.4.i; A.207.y.4.i; A.208.y.4.i; A.209.y.4.i; A.210.y.4.i; A.211.y.4.i;
A.212.y.4.i; A.213.y.4.i; A.700.y.4.i; A.701.y.4.i; A.702.y.4.i; A.703.y.4.i; A.704.y.4.i;
A.705.y.4.i; A.706.y.4.i; A.707.y.4.i; A.708.y.4.i; A.709.y.4.i; A.710.y.4.i; A.711.y.4.i;
A.712.y.4.i; A.713.y.4.i; A.714.y.4.i; A.715.y.4.i; A.716.y.4.i; A.717.y.4.i; A.718.y.4.i;
A.719.y.4.i; A.720.y.4.i; A.721.y.4.i; A.722.y.4.i; A.723.y.4.i; A.724.y.4.i; A.3.y.4.o;
A.4.y.4.o; A.7.y.4.o; A.9.y.4.o; A.103.y.4.o; A.106.y.4.o; A.107.y.4.o; A.108.y.4.o;
A.111.y.4.o; A.114.y.4.o; A.117.y.4.o; A.118.y.4.o; A.119.y.4.o; A.120.y.4.o;
A.121.y.4.o; A.137.y.4.o; A.138.y.4.o; A.139.y.4.o; A.140.y.4.o; A.141.y.4.o;
A.142.y.4.o; A.145.y.4.o; A.146.y.4.o; A.147.y.4.o; A.148.y.4.o; A.149.y.4.o;
A.150.y.4.o; A.151.y.4.o; A.165.y.4.o; A.166.y.4.o; A.167.y.4.o; A.168.y.4.o;
A.169.y.4.o; A.170.y.4.o; A.171.y.4.o; A.172.y.4.o; A.173.y.4.o; A.174.y.4.o;
A.175.y.4.o; A.176.y.4.o; A.188.y.4.o; A.189.y.4.o; A.190.y.4.o; A.196.y.4.o;
A.202.y.4.o; A.205.y.4.o; A.206.y.4.o; A.207.y.4.o; A.208.y.4.o; A.209.y.4.o;

TABLE 6-continued

Exemplary Enumerated Compounds

A.210.y.4.o; A.211.y.4.o; A.212.y.4.o; A.213.y.4.o; A.700.y.4.o; A.701.y.4.o;
A.702.y.4.o; A.703.y.4.o; A.704.y.4.o; A.705.y.4.o; A.706.y.4.o; A.707.y.4.o;
A.708.y.4.o; A.709.y.4.o; A.710.y.4.o; A.711.y.4.o; A.712.y.4.o; A.713.y.4.o;
A.714.y.4.o; A.715.y.4.o; A.716.y.4.o; A.717.y.4.o; A.718.y.4.o; A.719.y.4.o;
A.720.y.4.o; A.721.y.4.o; A.722.y.4.o; A.723.y.4.o; A.724.y.4.o; A.172.z.4.i; A.173.z.4.i;
A.174.z.4.i; A.175.z.4.i; A.176.z.4.i; A.188.z.4.i; A.189.z.4.i; A.190.z.4.i; A.196.z.4.i;
A.202.z.4.i; A.205.z.4.i; A.206.z.4.i; A.207.z.4.i; A.208.z.4.i; A.209.z.4.i; A.210.z.4.i;
A.211.z.4.i; A.212.z.4.i; A.213.z.4.i; A.700.z.4.i; A.701.z.4.i; A.702.z.4.i; A.703.z.4.i;
A.704.z.4.i; A.705.z.4.i; A.706.z.4.i; A.707.z.4.i; A.708.z.4.i; A.709.z.4.i; A.710.z.4.i;
A.711.z.4.i; A.712.z.4.i; A.713.z.4.i; A.714.z.4.i; A.715.z.4.i; A.716.z.4.i; A.717.z.4.i;
A.718.z.4.i; A.719.z.4.i; A.720.z.4.i; A.721.z.4.i; A.722.z.4.i; A.723.z.4.i; A.724.z.4.i;
A.3.z.4.o; A.4.z.4.o; A.7.z.4.o; A.9.z.4.o; A.103.z.4.o; A.106.z.4.o; A.107.z.4.o;
A.108.z.4.o; A.111.z.4.o; A.114.z.4.o; A.117.z.4.o; A.118.z.4.o; A.119.z.4.o;
A.120.z.4.o; A.121.z.4.o; A.137.z.4.o; A.138.z.4.o; A.139.z.4.o; A.140.z.4.o;
A.141.z.4.o; A.142.z.4.o; A.145.z.4.o; A.146.z.4.o; A.147.z.4.o; A.148.z.4.o;
A.149.z.4.o; A.150.z.4.o; A.151.z.4.o; A.165.z.4.o; A.166.z.4.o; A.167.z.4.o;
A.168.z.4.o; A.169.z.4.o; A.170.z.4.o; A.171.z.4.o; A.172.z.4.o; A.173.z.4.o;
A.174.z.4.o; A.175.z.4.o; A.176.z.4.o; A.188.z.4.o; A.189.z.4.o; A.190.z.4.o;
A.196.z.4.o; A.202.z.4.o; A.205.z.4.o; A.206.z.4.o; A.207.z.4.o; A.208.z.4.o;
A.209.z.4.o; A.210.z.4.o; A.211.z.4.o; A.212.z.4.o; A.213.z.4.o; A.700.z.4.o;
A.701.z.4.o; A.702.z.4.o; A.703.z.4.o; A.704.z.4.o; A.705.z.4.o; A.706.z.4.o;
A.707.z.4.o; A.708.z.4.o; A.709.z.4.o; A.710.z.4.o; A.711.z.4.o; A.712.z.4.o;
A.713.z.4.o; A.714.z.4.o; A.715.z.4.o; A.716.z.4.o; A.717.z.4.o; A.718.z.4.o;
A.719.z.4.o; A.720.z.4.o; A.721.z.4.o; A.722.z.4.o; A.723.z.4.o; A.724.z.4.o;
A.172.A.4.i; A.173.A.4.i; A.174.A.4.i; A.175.A.4.i; A.176.A.4.i; A.188.A.4.i;
A.189.A.4.i; A.190.A.4.i; A.196.A.4.i; A.202.A.4.i; A.205.A.4.i; A.206.A.4.i;
A.207.A.4.i; A.208.A.4.i; A.209.A.4.i; A.210.A.4.i; A.211.A.4.i; A.212.A.4.i;
A.213.A.4.i; A.700.A.4.i; A.701.A.4.i; A.702.A.4.i; A.703.A.4.i; A.704.A.4.i;
A.705.A.4.i; A.706.A.4.i; A.707.A.4.i; A.708.A.4.i; A.709.A.4.i; A.710.A.4.i;
A.711.A.4.i; A.712.A.4.i; A.713.A.4.i; A.714.A.4.i; A.715.A.4.i; A.716.A.4.i;
A.717.A.4.i; A.718.A.4.i; A.719.A.4.i; A.720.A.4.i; A.721.A.4.i; A.722.A.4.i;
A.723.A.4.i; A.724.A.4.i; A.3.A.4.o; A.4.A.4.o; A.7.A.4.o; A.9.A.4.o; A.103.A.4.o;
A.106.A.4.o; A.107.A.4.o; A.108.A.4.o; A.111.A.4.o; A.114.A.4.o; A.117.A.4.o;
A.118.A.4.o; A.119.A.4.o; A.120.A.4.o; A.121.A.4.o; A.137.A.4.o; A.138.A.4.o;
A.139.A.4.o; A.140.A.4.o; A.141.A.4.o; A.142.A.4.o; A.145.A.4.o; A.146.A.4.o;
A.147.A.4.o; A.148.A.4.o; A.149.A.4.o; A.150.A.4.o; A.151.A.4.o; A.165.A.4.o;
A.166.A.4.o; A.167.A.4.o; A.168.A.4.o; A.169.A.4.o; A.170.A.4.o; A.171.A.4.o;
A.172.A.4.o; A.173.A.4.o; A.174.A.4.o; A.175.A.4.o; A.176.A.4.o; A.188.A.4.o;
A.189.A.4.o; A.190.A.4.o; A.196.A.4.o; A.202.A.4.o; A.205.A.4.o; A.206.A.4.o;
A.207.A.4.o; A.208.A.4.o; A.209.A.4.o; A.210.A.4.o; A.211.A.4.o; A.212.A.4.o;
A.213.A.4.o; A.700.A.4.o; A.701.A.4.o; A.702.A.4.o; A.703.A.4.o; A.704.A.4.o;
A.705.A.4.o; A.706.A.4.o; A.707.A.4.o; A.708.A.4.o; A.709.A.4.o; A.710.A.4.o;
A.711.A.4.o; A.712.A.4.o; A.713.A.4.o; A.714.A.4.o; A.715.A.4.o; A.716.A.4.o;
A.717.A.4.o; A.718.A.4.o; A.719.A.4.o; A.720.A.4.o; A.721.A.4.o; A.722.A.4.o;
A.723.A.4.o; A.724.A.4.o; A.172.B.4.i; A.173.B.4.i; A.174.B.4.i; A.175.B.4.i; A.176.B.4.i;
A.188.B.4.i; A.189.B.4.i; A.190.B.4.i; A.196.B.4.i; A.202.B.4.i; A.205.B.4.i; A.206.B.4.i;
A.207.B.4.i; A.208.B.4.i; A.209.B.4.i; A.210.B.4.i; A.211.B.4.i; A.212.B.4.i; A.213.B.4.i;
A.700.B.4.i; A.701.B.4.i; A.702.B.4.i; A.703.B.4.i; A.704.B.4.i; A.705.B.4.i; A.706.B.4.i;
A.707.B.4.i; A.708.B.4.i; A.709.B.4.i; A.710.B.4.i; A.711.B.4.i; A.712.B.4.i; A.713.B.4.i;
A.714.B.4.i; A.715.B.4.i; A.716.B.4.i; A.717.B.4.i; A.718.B.4.i; A.719.B.4.i; A.720.B.4.i;
A.721.B.4.i; A.722.B.4.i; A.723.B.4.i; A.724.B.4.i; A.3.B.4.o; A.4.B.4.o; A.7.B.4.o;
A.9.B.4.o; A.103.B.4.o; A.106.B.4.o; A.107.B.4.o; A.108.B.4.o; A.111.B.4.o; A.114.B.4.o;
A.117.B.4.o; A.118.B.4.o; A.119.B.4.o; A.120.B.4.o; A.121.B.4.o; A.137.B.4.o;
A.138.B.4.o; A.139.B.4.o; A.140.B.4.o; A.141.B.4.o; A.142.B.4.o; A.145.B.4.o;
A.146.B.4.o; A.147.B.4.o; A.148.B.4.o; A.149.B.4.o; A.150.B.4.o; A.151.B.4.o;
A.165.B.4.o; A.166.B.4.o; A.167.B.4.o; A.168.B.4.o; A.169.B.4.o; A.170.B.4.o;
A.171.B.4.o; A.172.B.4.o; A.173.B.4.o; A.174.B.4.o; A.175.B.4.o; A.176.B.4.o;
A.188.B.4.o; A.189.B.4.o; A.190.B.4.o; A.196.B.4.o; A.202.B.4.o; A.205.B.4.o;
A.206.B.4.o; A.207.B.4.o; A.208.B.4.o; A.209.B.4.o; A.210.B.4.o; A.211.B.4.o;
A.212.B.4.o; A.213.B.4.o; A.700.B.4.o; A.701.B.4.o; A.702.B.4.o; A.703.B.4.o;
A.704.B.4.o; A.705.B.4.o; A.706.B.4.o; A.707.B.4.o; A.708.B.4.o; A.709.B.4.o;
A.710.B.4.o; A.711.B.4.o; A.712.B.4.o; A.713.B.4.o; A.714.B.4.o; A.715.B,4.o;
A.716.B.4.o; A.717.B.4.o; A.718.B.4.o; A.719.b.4.o; A.720.B.4.o; A.721.B.4.o;
A.722.B.4.o; A.723.B.4.o; A.724.B.4.o; B.3.a.54.i; B.4.a.54.i; B.7.a.54.i; B.9.a.54.i;
B.103.a.54.i; B.106.a.54.i; B.107.a.54.i; B.108.a.54.i; B.111.a.54.i; B.114.a.54.i;
B.117.a.54.i; B.118.a.54.i; B.119.a.54.i; B.120.a.54.i; B.121.a.54.i; B.137.a.54.i;
B.138.a.54.i; B.139.a.54.i; B.140.a.54.i; B.141.a.54.i; B.142.a.54.i; B.145.a.54.i;
B.146.a.54.i; B.147.a.54.i; B.148.a.54.i; B.149.a.54.i; B.150.a.54.i; B.151.a.54.i;
B.165.a.54.i; B.166.a.54.i; B.167.a.54.i; B.168.a.54.i; B.169.a.54.i; B.170.a.54.i;
B.171.a.54.i; B.172.a.54.i; B.173.a.54.i; B.174.a.54.i; B.175.a.54.i; B.176.a.54.i;
B.188.a.54.i; B.189.a.54.i; B.190.a.54.i; B.196.a.54.i; B.202.a.54.i; B.205.a.54.i;
B.206.a.54.i; B.207.a.54.i; B.208.a.54.i; B.209.a.54.i; B.210.a.54.i; B.211.a.54.i;
B.212.a.54.i; B.213.a.54.i; B.700.a.54.i; B.701.a.54.i; B.702.a.54.i; B.703.a.54.i;
B.704.a.54.i; B.705.a.54.i; B.706.a.54.i; B.707.a.54.i; B.708.a.54.i; B.709.a.54.i;
B.710.a.54.i; B.711.a.54.i; B.712.a.54.i; B.713.a.54.i; B.714.a.54.i; B.715.a.54.i;
B.716.a.54.i; B.717.a.54.i; B.718.a.54.i; B.719.a.54.i; B.720.a.54.i; B.721.a.54.i;
B.103.a.54.i; B.106.a.54.i; B.107.a.54.i; B.108.a.54.i; B.11.a.54.i; B.114.a.54.o;

TABLE 6-continued

Exemplary Enumerated Compounds

B.117.a.54.i; B.118.a.54.i; B.119.a.54.i; B.120.a.54.i; B.121.a.54.i; B.137.a.54.o;
B.138.a.54.i; B.139.a.54.i; B.140.a.54.i; B.141.a.54.i; B.142.a.54.i; B.145.a.54.o;
B.146.a.54.i; B.147.a.54.i; B.148.a.54.i; B.149.a.54.i; B.150.a.54.i; B.151.a.54.o;
B.165.a.54.i; B.166.a.54.i; B.167.a.54.i; B.168.a.54.i; B.169.a.54.i; B.170.a.54.o;
B.171.a.54.i; B.172.a.54.i; B.173.a.54.i; B.174.a.54.i; B.175.a.54.i; B.176.a.54.o;
B.188.a.54.i; B.189.a.54.i; B.190.a.54.i; B.196.a.54.i; B.202.a.54.i; B.205.a.54.o;
B.206.a.54.i; B.207.a.54.i; B.208.a.54.i; B.209.a.54.i; B.210.a.54.i; B.211.a.54.o;
B.212.a.54.i; B.213.a.54.i; B.700.a.54.i; B.701.a.54.i; B.702.a.54.i; B.703.a.54.o;
B.704.a.54.i; B.705.a.54.i; B.706.a.54.i; B.707.a.54.i; B.708.a.54.i; B.709.a.54.o;
B.710.a.54.i; B.711.a.54.i; B.712.a.54.i; B.713.a.54.i; B.714.a.54.i; B.715.a.54.o;
B.716.a.54.i; B.717.a.54.i; B.718.a.54.i; B.719.a.54.i; B.720.a.54.i; B.721.a.54.o;
B.722.a.54.i; B.723.a.54.i; B.724.a.54.i; B.172.b.54.i; B.173.b.54.i; B.174.b.54.i;
B.175.b.54.i; B.176.b.54.i; B.188.b.54.i; B.189.b.54.i; B.190.b.54.i; B.196.b.54.i;
B.202.b.54.i; B.205.b.54.i; B.206.b.54.i; B.207.b.54.i; B.208.b.54.i; B.209.b.54.i;
B.210.b.54.i; B.211.b.54.i; B.212.b.54.i; B.213.b.54.i; B.700.b.54.i; B.701.b.54.i;
B.702.b.54.i; B.703.b.54.i; B.704.b.54.i; B.705.b.54.i; B.706.b.54.i; B.707.b.54.i;
B.708.b.54.i; B.709.b.54.i; B.710.b.54.i; B.711.b.54.i; B.712.b.54.i; B.713.b.54.i;
B.714.b.54.i; B.715.b.54.i; B.716.b.54.i; B.717.b.54.i; B.718.b.54.i; B.719.b.54.i;
B.720.b.54.i; B.721.b.54.i; B.722.b.54.i; B.723.b.54.i; B.724.b.54.i; B.3.b.54.o; B.4.b.54.o;
B.7.b.54.o; B.9.b.54.o; B.103.b.54.o; B.106.b.54.o; B.107.b.54.o; B.108.b.54.o;
B.111.b.54.o; B.114.b.54.o; B.117.b.54.o; B.118.b.54.o; B.119.b.54.o; B.120.b.54.o;
B.121.b.54.o; B.137.b.54.o; B.138.b.54.o; B.139.b.54.o; B.140.b.54.o; B.141.b.54.o;
B.142.b.54.o; B.145.b.54.o; B.146.b.54.o; B.147.b.54.o; B.148.b.54.o; B.149.b.54.o;
B.150.b.54.o; B.151.b.54.o; B.165.b.54.o; B.166.b.54.o; B.167.b.54.o; B.168.b.54.o;
B.169.b.54.o; B.170.b.54.o; B.171.b.54.o; B.172.b.54.o; B.173.b.54.o; B.174.b.54.o;
B.175.b.54.o; B.176.b.54.o; B.188.b.54.o; B.189.b.54.o; B.190.b.54.o; B.196.b.54.o;
B.202.b.54.o; B.205.b.54.o; B.206.b.54.o; B.207.b.54.o; B.208.b.54.o; B.209.b.54.o;
B.210.b.54.o; B.211.b.54.o; B.212.b.54.o; B.213.b.54.o; B.700.b.54.o; B.701.b.54.o;
B.702.b.54.o; B.703.b.54.o; B.704.b.54.o; B.705.b.54.o; B.706.b.54.o; B.707.b.54.o;
B.708.b.54.o; B.709.b.54.o; B.710.b.54.o; B.711.b.54.o; B.712.b.54.o; B.713.b.54.o;
B.714.b.54.o; B.715.b.54.o; B.716.b.54.o; B.717.b.54.o; B.718.b.54.o; B.719.b.54.o;
B.720.b.54.o; B.721.b.54.o; B.722.b.54.o; B.723.b.54.o; B.724.b.54.o; B.172.x.54.i;
B.173.x.54.i; B.174.x.54.i; B.175.x.54.i; B.176.x.54.i; B.188.x.54.i; B.189.x.54.i;
B.190.x.54.i; B.196.x.54.i; B.202.x.54.i; B.205.x.54.i; B.206.x.54.i; B.207.x.54.i;
B.208.x.54.i; B.209.x.54.i; B.210.x.54.i; B.211.x.54.i; B.212.x.54.i; B.213.x.54.i;
B.700.x.54.i; B.701.x.54.i; B.702.x.54.i; B.703.x.54.i; B.704.x.54.i; B.705.x.54.i;
B.706.x.54.i; B.707.x.54.i; B.708.x.54.i; B.709.x.54.i; B.710.x.54.i; B.711.x.54.i;
B.712.x.54.i; B.713.x.54.i; B.714.x.54.i; B.715.x.54.i; B.716.x.54.i; B.717.x.54.i;
B.718.x.54.i; B.719.x.54.i; B.720.x.54.i; B.721.x.54.i; B.722.x.54.i; B.723.x.54.i;
B.724.x.54.i; B.3.x.54.o; B.4.x.54.o; B.7.x.54.o; B.9.x.54.0; B.103.x.54.o; B.106.x.54.o;
B.107.x.54.o; B.108.x.54.o; B.111.x.54.o; B.114.x.54.o; B.117.x.54.o; B.118.x.54.o;
B.119.x.54.o; B.120.x.54.o; B.121.x.54.o; B.137.x.54.o; B.138.x.54.o; B.139.x.54.o;
B.140.x.54.o; B.141.x.54.o; B.142.x.54.o; B.145.x.54.o; B.146.x.54.o; B.147.x.54.o;
B.148.x.54.o; B.149.x.54.o; B.150.x.54.o; B.151.x.54.o; B.165.x.54.o; B.166.x.54.o;
B.167.x.54.o; B.168.x.54.o; B.169.x.54.o; B.170.x.54.o; B.171.x.54.o; B.172.x.54.o;
B.173.x.54.o; B.174.x.54.o; B.175.x.54.o; B.176.x.54.o; B.188.x.54.o; B.189.x.54.o;
B.190.x.54.o; B.196.x.54.o; B.202.x.54.o; B.205.x.54.o; B.206.x.54.o; B.207.x.54.o;
B.208.x.54.o; B.209.x.54.o; B.210.x.54.o; B.211.x.54.o; B.212.x.54.o; B.213.x.54.o;
B.700.x.54.o; B.701.x.54.i; B.702.x.54.o; B.703.x.54.o; B.704.x.54.o; B.705.x.54.o;
B.706.x.54.o; B.707.x.54.o; B.708.x.54.o; B.709.x.54.o; B.710.x.54.o; B.711.x.54.o;
B.712.x.54.o; B.713.x.54.o; B.714.x.54.o; B.715.x.54.o; B.716.x.54.o; B.717.x.54.o;
B.718.x.54.o; B.719.x.54.o; B.720.x.54.o; B.721.x.54.o; B.722.x.54.o; B.723.x.54.o;
B.724.x.54.o; B.172.y.54.i; B.173.y.54.i; B.174.y.54.i; B.175.y.54.i; B.176.y.65.i;
B.188.y.54.i; B.189.y.54.i; B.190.y.54.i; B.196.y.54.i; B.202.y.54.i; B.205.y.54.i;
B.206.y.54.i; B.207.y.54.i; B.208.y.54.i; B.209.y.54.i; B.210.y.54.i; B.211.y.54.i;
B.212.y.54.i; B.213.y.54.i; B.700.y.54.i; B.701.y.54.i; B.702.y.54.i; B.703.y.54.i;
B.704.y.54.i; B.705.y.54.i; B.706.y.54.i; B.707.y.54.i; B.708.y.54.i; B.709.y.54.i;
B.710.y.54.i; B.711.y.54.i; B.712.y.54.i; B.713.y.54.i; B.714.y.54.i; B.715.y.54.i;
B.716.y.54.i; B.717.y.54.i; B.718.y.54.i; B.719.y.54.i; B.720.y.54.i; B.721.y.54.i;
B.722.y.54.i; B.723.y.54.i; B.724.y.54.i; B.3.y.54.o; B.4.y.54.o; B.7.y.54.o; B.9.y.54.o;
B.103.y.54.o; B.106.y.54.o; B.107.y.54.o; B.108.y.54.o; B.111.y.54.o; B.114.y.54.o;
B.117.y.54.o; B.118.y.54.o; B.119.y.54.o; B.120.y.54.o; B.121.y.54.o; B.137.y.54.o;
B.138.y.54.o; B.139.y.54.o; B.140.y.54.o; B.141.y.54.o; B.142.y.54.o; B.145.y.54.o;
B.146.y.54.o; B.147.y.54.o; B.148.y.54.o; B.149.y.54.o; B.150.y.54.o; B.151.y.54.o;
B.165.y.54.o; B.166.y.54.o; B.167.y.54.o; B.168.y.54.o; B.169.y.54.o; B.170.y.54.o;
B.171.y.54.o; B.172.y.54.o; B.173.y.54.o; B.174.y.54.o; B.175.y.54.o; B.176.y.54.o;
B.188.y.54.o; B.189.y.54.o; B.190.y.54.o; B.196.y.54.o; B.202.y.54.o; B.205.y.54.o;
B.206.y.54.o; B.207.y.54.o; B.208.y.54.o; B.209.y.54.o; B.210.y.54.o; B.211.y.54.o;
B.212.y.54.o; B.213.y.54.o; B.700.y.54.o; B.701.y.54.o; B.702.y.54.o; B.703.y.54.o;
B.704.y.54.o; B.705.y.54.o; B.706.y.54.o; B.707.y.54.o; B.708.y.54.o; B.709.y.54.o;
B.710.y.54.o; B.711.y.54.o; B.712.y.54.o; B.713.y.54.o; B.714.y.54.o; B.715.y.54.o;
B.716.y.54.o; B.717.y.54.o; B.718.y.54.o; B.719.y.54.o; B.720.y.54.o; B.721.y.54.o;
B.722.y.54.o; B.723.y.54.o; B.724.y.54.o; B.172.z.54.i; B.173.z.54.i; B.174.z.54.i;
B.175.z.54.i; B.176.z.54.i; B.188.z.54.i; B.189.z.54.i; B.190.z.54.i; B.196.z.54.i;
B.202.z.54.i; B.205.z.54.i; B.206.z.54.i; B.207.z.54.i; B.208.z.54.i; B.209.z.54.i;
B.210.z.54.i; B.211.z.54.i; B.212.z.54.i; B.213.z.54.i; B.700.z.54.i; B.701.z.54.i;
B.702.z.54.i; B.703.z.54.i; B.704.z.54.i; B.705.z.54.i; B.706.z.54.i; B.707.z.54.i;

TABLE 6-continued

Exemplary Enumerated Compounds

B.708.z.54.i; B.709.z.54.i; B.710.z.54.i; B.711.z.54.i; B.712.z.54.i; B.713.z.54.i;
B.714.z.54.i; B.715.z.54.i; B.716.z.54.i; B.717.z.54.i; B.718.z.54.i; B.719.z.54.i;
B.720.z.54.i; B.721.z.54.i; B.722.z.54.i; B.723.z.54.i; B.724.b.54.i; B.3.b.54.o; B.4.b.54.o;
B.7.z.54.o; B.9.z.54.o; B.103.z.54.o; B.106.z.54.o; B.107.z.54.o; B.108.z.54.o;
B.111.z.54.o; B.114.z.54.o; B.117.z.54.o; B.118.z.54.o; B.119.z.54.o; B.120.z.54.o;
B.121.z.54.o; B.137.z.54.o; B.138.z.54.o; B.139.z.54.o; B.140.z.54.o; B.141.z.54.o;
B.142.z.54.o; B.145.z.54.o; B.146.z.54.o; B.147.z.54.o; B.148.z.54.o; B.149.z.54.o;
B.150.z.54.o; B.151.z.54.o; B.165.z.54.o; B.166.z.54.o; B.167.z.54.o; B.168.z.54.o;
B.169.z.54.o; B.170.z.54.o; B.171.z.54.o; B.172.z.54.o; B.173.z.54.o; B.174.z.54.o;
B.175.z.54.o; B.176.z.54.o; B.188.z.54.o; B.189.z.54.o; B.190.z.54.o; B.196.z.54.o;
B.202.z.54.o; B.205.z.54.o; B.206.z.54.o; B.207.z.54.o; B.208.z.54.o; B.209.z.54.o;
B.210.z.54.o; B.211.z.54.o; B.212.z.54.o; B.213.z.54.o; B.700.z.54.o; B.701.z.54.o;
B.702.z.54.o; B.703.z.54.o; B.704.z.54.o; B.705.z.54.o; B.706.z.54.o; B.707.z.54.o;
B.708.z.54.o; B.709.z.54.o; B.710.z.54.o; B.711.z.54.o; B.712.z.54.o; B.713.z.54.o;
B.714.z.54.o; B.715.z.54.o; B.716.z.54.o; B.717.z.54.o; B.718.z.54.o; B.719.z.54.o;
B.720.z.54.o; B.721.z.54.o; B.722.z.54.o; B.723.z.54.o; B.724.z.54.o; B.172.A.54.i;
B.173.A.54.i; B.174.A.54.i; B.175.A.54.i; B.176.A.54.i; B.188.A.54.i; B.189.A.54.i;
B.190.A.54.i; B.196.A.54.i; B.202.A.54.i; B.205.A.54.i; B.205.A.54.i; B.206.A.54.i;
B.208.A.54.i; B.209.A.54.i; B.210.A.54.i; B.211.A.54.i; B.212.A.54.i; B.213.A.54.i;
B.700.A.54.i; B.701.A.54.i; B.702.A.54.i; B.703.A.54.i; B.704.A.54.i; B.705.A.54.i;
B.706.A.54.i; B.707.A.54.i; B.708.A.54.i; B.709.A.54.i; B.710.A.54.i; B.711.A.54.i;
B.712.A.54.i; B.713.A.54.i; B.714.A.54.i; B.715.A.54.i; B.716.A.54.i; B.717.A.54.i;
B.718.A.54.i; B.719.A.54.i; B.720.A.54.i; B.721.A.54.i; B.722.A.54.i; B.723.A.54.i;
B.724.A.54.i; B.3.A.54.o; B.4.A.54.o; B.7.A.54.o; B.9.A.54.0; B.103.A.54.o; B.106.A.54.o;
B.107.A.54.o; B.108.A.54.o; B.111.A.54.o; B.114.A.54.o; B.117.A.54.o; B.118.A.54.o;
B.119.A.54.o; B.120.A.54.o; B.121.A.54.o; B.137.A.54.o; B.138.A.54.o; B.139.A.54.o;
B.140.A.54.o; B.141.A.54.o; B.142.A.54.o; B.145.A.54.o; B.146.A.54.o; B.147.A.54.o;
B.148.A.54.o; B.149.A.54.o; B.150.A.54.o; B.151.A.54.o; B.165.A.54.o; B.166.A.54.o;
B.167.A.54.o; B.168.A.54.o; B.169.A.54.o; B.170.A.54.o; B.171.A.54.o; B.172.A.54.o;
B.173.A.54.o; B.174.A.54.o; B.175.A.54.o; B.176.A.54.o; B.188.A.54.o; B.189.A.54.o;
B.190.A.54.o; B.196.A.54.o; B.202.A.54.o; B.205.A.54.o; B.206.A.54.o; B.207.A.54.o;
B.208.A.54.o; B.209.A.54.o; B.210.A.54.o; B.211.A.54.o; B.212.A.54.o; B.213.A.54.o;
B.700.A.54.o; B.701.A.54.o; B.702.A.54.o; B.703.A.54.o; B.704.A.54.o; B.705.A.54.o;
B.706.A.54.o; B.707.A.54.o; B.708.A.54.o; B.709.A.54.o; B.710.A.54.o; B.711.A.54.o;
B.712.A.54.o; B.713.A.54.o; B.714.A.54.o; B.715.A.54.o; B.716.A.54.o; B.717.A.54.o;
B.718.A.54.o; B.719.A.54.o; B.720.A.54.o; B.721.A.54.o; B.722.A.54.o; B.723.A.54.o;
B.724.A.54.o; B.172.B.54.i; B.173.B.54.i; B.174.B.54.i; B.175.B.54.i; B.176.B.65.i;
B.188.B.54.i; B.189.B.54.i; B.190.B.54.i; B.196.B.54.i; B.202.B.54.i; B.205.B.54.i;
B.206.B.54.i; B.207.B.54.i; B.208.B.54.i; B.209.B.54.i; B.210.B.54.i; B.211.B.54.i;
B.212.B.54.i; B.213.B.54.i; B.700.B.54.i; B.701.B.54.i; B.702.B.54.i; B.703.B.54.i;
B.704.B.54.i; B.705.B.54.i; B.706.B.54.i; B.707.B.54.i; b.708.B.54.i; B.709.B.54.i;
B.710.B.54.i; B.711.B.54.i; B.712.B.54.i; B.713.B.54.i; B.714.B.54.i; B.715.B.54.i;
B.716.B.54.i; B.717.B.54.i; B.718.B.54.i; B.719.B.54.i; B.720.B.54.i; B.721.B.54.i;
B.722.B.54.i; B.723.B.54.i; B.724.B.54.i; B.3.B.54.o; B.4.B.54.o; B.7.B.54.o; B.9.B.54.o;
B.103.B.54.o; B.106.B.54.o; B.107.B.54.o; B.108.B.54.o; B.111.B.54.o; B.114.B.54.o;
B.117.B.54.o; B.118.B.54.o; B.119.B.54.o; B.120.B.54.o; B.121.B.54.o; B.137.B.54.o;
B.138.B.54.o; B.139.B.54.o; B.140.B.54.o; B.141.B.54.o; B.142.B.54.o; B.145.B.54.o;
B.146.B.54.o; B.147.B.54.o; B.148.B.54.o; B.149.B.54.o; B.150.B.54.o; B.151.B.54.o;
B.165.B.54.o; B.166.B.54.o; B.167.B.54.o; B.168.B.54.o; B.169.B.54.o; B.170.B.54.o;
B.171.B.54.o; B.172.B.54.o; B.173.B.54.o; B.174.B.54.o; B.175.B.54.o; B.176.B.54.o;
B.188.B.54.o; B.189.B.54.o; B.190.B.54.o; B.196.B.54.o; B.202.B.54.o; B.205.B.54.o;
B.206.B.54.o; B.207.B.54.o; B.208.B.54.o; B.209.B.54.o; B.210.B.54.o; B.211.B.54.o;
B.212.B.54.o; B.213.B.54.o; B.700.B.54.o; B.701.B.54.o; B.702.B.54.o; B.703.B.54.o;
B.704.B.54.o; B.705.B.54.o; B.706.B.54.o; B.707.B.54.o; B.708.B.54.o; B.709.B.54.o;
B.710.B.54.o; B.711.B.54.o; B.712.B.54.o; B.713.B.54.o; B.714.B.54.o; B.715.B.54.o;
B.716.B.54.o; B.717.B.54.o; B.718.B.54.o; B.719.B.54.o; B.720.B.54.o; B.721.B.54.o;
B.722.B.54.o; B.723.B.54.o; B.724.B.54.o; C.3.a.54.i; C.4.a.54.i; C.7.a.54.i; C.9.a.54.i;
C.103.a.54.i; C.106.a.54.i; C.107.a.54.i; C.108.a.54.i; C.111.a.54.i; C.114.a.54.i;
C.117.a.54.i; C.118.a.54.i; C.119.a.54.i; C.120.a.54.i; C.121.a.54.i; C.137.a.54.i;
C.138.a.54.i; C.139.a.54.i; C.140.a.54.i; C.141.a.54.i; C.142.a.54.i; C.145.a.54.i;
C.146.a.54.i; C.147.a.54.i; C.148.a.54.i; C.149.a.54.i; C.150.a.54.i; C.151.a.54.i;
C.165.a.54.i; C.166.a.54.i; C.167.a.54.i; C.168.a.54.i; C.169.a.54.i; C.170.a.54.i;
C.171.a.54.i; C.172.a.54.i; C.173.a.54.i; C.174.a.54.i; C.175.a.54.i; C.176.a.54.i;
C.188.a.54.i; C.189.a.54.i; C.190.a.54.i; C.196.a.54.i; C.202.a.54.i; C.205.a.54.i;
C.206.a.54.i; C.207.a.54.i; C.208.a.54.i; C.209.a.54.i; C.210.a.54.i; C.211.a.54.i;
C.212.a.54.i; C.213.a.54.i; C.700.a.54.i; C.701.a.54.i; C.702.a.54.i; C.703.a.54.i;
C.704.a.54.i; C.705.a.54.i; C.706.a.54.i; C.707.a.54.i; C.708.a.54.i; C.709.a.54.i;
C.710.a.54.i; C.711.a.54.i; C.712.a.54.i; C.713.a.54.i; C.714.a.54.i; C.715.a.54.i;
C.716.a.54.i; C.717.a.54.i; C.718.a.54.i; C.719.a.54.i; C.720.a.54.i; C.721.a.54.i;
C.722.a.54.i; A.723.a.54.i; C.724.a.54.i; C.3.a.54.o; C.4.a.54.o; C.7.a.54.o; C.9.a.54.o;
C.103.z.54.o; C.106.a.54.o; C.107.a.54.o; C.108.a.54.o; C.111.a.54.o; C.114.a.54.o;
C.117.a.54.o; C.118.a.54.o; C.119.a.54.o; C.120.a.54.o; C.121.a.54.o; C.137.a.54.o;
C.138.a.54.o; C.139.a.54.o; C.140.a.54.o; C.141.a.54.o; C.142.a.54.o; C.145.a.54.o;
C.146.a.54.o; C.147.a.54.o; C.148.a.54.o; C.149.a.54.o; C.150.a.54.o; C.151.a.54.o;
C.165.a.54.o; C.166.a.54.o; C.167.a.54.o; C.168.a.54.o; C.169.a.54.o; C.170.a.54.o;
C.171.a.54.o; C.172.a.54.o; C.173.a.54.o; C.174.a.54.o; C.175.a.54.o; C.176.a.54.o;
C.188.a.54.o; C.189.a.54.o; C.190.a.54.o; C.196.a.54.o; C.202.a.54.o; C.205.a.54.o;

TABLE 6-continued

Exemplary Enumerated Compounds

C.206.a.54.o; C.207.a.54.o; C.208.a.54.o; C.209.a.54.o; C.210.a.54.o; C.211.a.54.o;
C.212.a.54.o; C.213.a.54.o; C.700.a.54.o; C.701.a.54.o; C.702.a.54.o; C.703.a.54.o;
C.704.a.54.o; C.705.a.54.o; C.706.a.54.o; C.707.a.54.o; C.708.a.54.o; C.709.a.54.o;
C.710.a.54.o; C.711.a.54.o; C.712.a.54.o; C.713.a.54.o; C.714.a.54.o; C.715.a.54.o;
C.716.a.54.o; C.717.a.54.o; C.718.a.54.o; C.719.a.54.o; C.720.a.54.o; C.721.a.54.o;
C.722.a.54.o; C.723.a.54.o; C.724.a.54.o; C.172.a.54.i; C.173.b.54.i; C.714.b.54.i;
C.175.b.54.i; C.176.b.54.i; C.188.b.54.i; C.189.b.54.i; C.190.b.54.i; C.196.b.54.i;
C.202.b.54.i; C.205.b.54.i; C.206.b.54.i; C.207.b.54.i; C.208.b.54.i; C.209.b.54.i;
C.210.b.54.i; C.211.b.54.i; C.212.b.54.i; C.213.b.54.i; C.700.b.54.i; C.701.b.54.i;
C.702.b.54.i; C.703.b.54.i; C.704.b.54.i; C.705.b.54.i; C.706.b.54.i; C.707.b.54.i;
C.708.b.54.i; C.709.b.54.i; C.710.b.54.i; C.711.b.54.i; C.712.b.54.i; C.713.b.54.i;
C.714.b.54.i; C.715.b.54.i; C.716.b.54.i; C.717.b.54.i; C.718.b.54.i; C.719.b.54.i;
C.720.b.54.i; C.721.b.54.i; C.722.b.54.i; C.723.b.54.i; C.724.b.54.i; C.3.b.54.o; C.4.b.54.o;
C.7.b.54.o; C.9.b.54.o; C.103.b.54.o; C.106.b.54.o; C.107.b.54.o; C.108.b.54.o;
C.111.b.54.o; C.114.b.54.o; C.117.b.54.o; C.118.b.54.o; C.119.b.54.o; C.120.b.54.o;
C.121.b.54.o; C.137.b.54.o; C.138.b.54.o; C.139.b.54.o; C.140.b.54.o; C.141.b.54.o;
C.142.b.54.o; C.145.b.54.o; C.146.b.54.o; C.147.b.54.o; C.148.b.54.o; C.149.b.54.o;
C.150.b.54.o; C.151.b.54.o; C.165.b.54.o; C.166.b.54.o; C.167.b.54.o; C.168.b.54.o;
C.169.b.54.o; C.170.b.54.o; C.171.b.54.o; C.172.b.54.o; C.173.b.54.o; C.174.b.54.o;
C.175.b.54.o; C.176.b.54.o; C.188.b.54.o; C.189.b.54.o; C.190.b.54.o; C.196.b.54.o;
C.202.b.54.o; C.205.b.54.o; C.206.b.54.o; C.207.b.54.o; C.208.b.54.o; C.209.b.54.o;
C.210.b.54.o; C.211.b.54.o; C.212.b.54.o; C.213.b.54.o; C.700.b.54.o; C.701.b.54.o;
C.702.b.54.o; C.703.b.54.o; C.704.b.54.o; C.705.b.54.o; C.706.b.54.o; C.707.b.54.o;
C.708.b.54.o; C.709.b.54.o; C.710.b.54.o; C.711.b.54.o; C.712.b.54.o; C.713.b.54.o;
C.714.b.54.o; C.715.b.54.o; C.716.b.54.o; C.717.b.54.o; C.718.b.54.o; C.719.b.54.o;
C.720.b.54.o; C.721.b.54.o; C.722.b.54.o; C.723.b.54.o; C.724.b.54.o; C.172.x.54.i;
C.173.x.54.i; C.174.x.54.i; C.175.x.54.i; C.176.x.54.i; C.188.x.54.i; C.189.x.54.i;
C.190.x.54.i; C.196.x.54.i; C.202.x.54.i; C.205.x.54.i; C.206.x.54.i; C.207.x.54.i;
C.208.x.54.i; C.209.x.54.i; C.210.x.54.i; C.211.x.54.i; C.212.x.54.i; C.213.x.54.i;
C.700.x.54.i; C.701.x.54.i; C.702.x.54.i; C.703.x.54.i; C.704.x.54.i; C.705.x.54.i;
C.706.x.54.i; C.707.x.54.i; C.708.x.54.i; C.709.x.54.i; C.710.x.54.i; C.711.x.54.i;
C.712.x.54.i; C.713.x.54.i; C.714.x.54.i; C.715.x.54.i; C.716.x.54.i; C.717.x.54.i;
C.718.x.54.i; C.719.x.54.i; C.720.x.54.i; C.721.x.54.i; C.722.x.54.i; C.723.x.54.i;
C.724.x.54.i; C.3.x.54.o; C.4.x.54.o; C.7.x.54.o; C.9.x.54.o; C.103.x.54.o; C.106.x.54.o;
C.107.x.54.o; C.108.x.54.o; C.111.x.54.o; C.114.x.54.o; C.117.x.54.o; C.118.x.54.o;
C.119.x.54.o; C.120.x.54.o; C.121.x.54.o; C.137.x.54.o; C.138.x.54.o; C.139.x.54.o;
C.140.x.54.o; C.141.x.54.o; C.142.x.54.o; C.145.x.54.o; C.146.x.54.o; C.147.x.54.o;
C.148.x.54.o; C.149.x.54.o; C.150.x.54.o; C.151.x.54.o; C.165.x.54.o; C.166.x.54.o;
C.167.x.54.o; C.168.x.54.o; C.169.x.54.o; C.170.x.54.o; C.171.x.54.o; C.172.x.54.o;
C.173.x.54.o; C.174.x.54.o; C.175.x.54.o; C.176.x.54.o; C.188.x.54.o; C.189.x.54.o;
C.190.x.54.o; C.196.x.54.o; C.202.x.54.o; C.205.x.54.o; C.206.x.54.o; C.207.x.54.o;
C.208.x.54.o; C.209.x.54.o; C.210.x.54.o; C.211.x.54.o; C.212.x.54.o; C.213.x.54.o;
C.700.x.54.o; C.701.x.54.o; C.702.x.54.o; C.703.x.54.o; C.704.x.54.o; C.705.x.54.o;
C.706.x.54.o; C.707.x.54.o; C.708.x.54.o; C.709.x.54.o; C.710.x.54.o; C.711.x.54.o;
C.712.x.54.o; C.713.x.54.o; C.714.x.54.o; C.715.x.54.o; C.716.x.54.o; C.717.x.54.o;
C.718.x.54.o; C.719.x.54.o; C.720.x.54.o; C.721.x.54.o; C.722.x.54.o; C.723.x.54.o;
C.724.x.54.o; C.172.y.54.i; C.173.y.54.i; C.174.y.54.i; C.175.y.54.i; C.176.y.54.i;
C.188.y.54.i; C.189.y.54.i; C.190.y.54.i; C.196.y.54.i; C.202.y.54.i; C.205.y.54.i;
C.206.y.54.i; C.297.y.54.i; C.208.y.54.i; C.209.y.54.i; C.210.y.54.i; C.211.y.54.i;
C.212.y.54.i; C.213.y.54.i; C.700.y.54.i; C.701.y.54.i; C.702.y.54.i; C.703.y.54.i;
C.704.y.54.i; C.705.y.54.i; C.706.y.54.i; C.707.y.54.i; C.708.y.54.i; C.709.y.54.i;
C.710.y.54.i; C.711.y.54.i; C.712.y.54.i; C.713.y.54.i; C.714.y.54.i; C.715.y.54.i;
C.716.y.54.i; C.717.y.54.i; C.718.y.54.i; C.719.y.54.i; C.720.y.54.i; C.721.y.54.i;
C.722.y.54.i; C.723.y.54.i; C.724.y.54.i; C.3.y.54.o; C.4.y.54.o; C.7.y.54.o; C.9.y.54.o;
C.103.y.54.o; C.106.y.54.o; C.107.y.54.o; C.108.y.54.o; C.111.y.54.o; C.114.y.54.o;
C.117.y.54.o; C.118.y.54.o; C.119.y.54.o; C.120.y.54.o; C.121.y.54.o; C.137.y.54.o;
C.138.y.54.o; C.139.y.54.o; C.140.y.54.o; C.141.y.54.o; C.142.y.54.o; C.145.y.54.o;
C.146.y.54.o; C.147.y.54.o; C.148.y.54.o; C.149.y.54.o; C.150.y.54.o; C.151.y.54.o;
C.165.y.54.o; C.166.y.54.o; C.167.y.54.o; C.168.y.54.o; C.169.y.54.o; C.170.y.54.o;
C.171.y.54.o; C.172.y.54.o; C.173.y.54.o; C.174.y.54.o; C.175.y.54.o; C.176.y.54.o;
C.188.y.54.o; C.189.y.54.o; C.190.y.54.o; C.196.y.54.o; C.202.y.54.o; C.205.y.54.o;
C.206.y.54.o; C.207.y.54.o; C.208.y.54.o; C.209.y.54.o; C.210.y.54.o; C.211.y.54.o;
C.212.y.54.o; C.213.y.54.o; C.700.y.54.o; C.701.y.54.o; C.702.y.54.o; C.703.y.54.o;
C.704.y.54.o; C.705.y.54.o; C.706.y.54.o; C.707.y.54.o; C.708.y.54.o; C.709.y.54.o;
C.710.y.54.o; C.711.y.54.o; C.712.y.54.o; C.713.y.54.o; C.714.y.54.o; C.715.y.54.o;
C.716.y.54.o; C.717.y.54.o; C.718.y.54.o; C.719.y.54.o; C.720.y.54.o; C.721.y.54.o;
C.722.y.54.o; C.723.y.54.o; C.724.y.54.o; C.172.z.54.i; C.173.z.54.i; C.714.z.54.i;
C.175.z.54.i; C.176.z.54.i; C.188.z.54.i; C.189.z.54.i; C.190.z.54.i; C.196.z.54.i;
C.202.z.54.i; C.205.z.54.i; C.206.z.54.i; C.207.z.54.i; C.208.z.54.i; C.209.z.54.i;
C.210.z.54.i; C.211.z.54.i; C.212.z.54.i; C.213.z.54.i; C.700.z.54.i; C.701.z.54.i;
C.702.z.54.i; C.703.z.54.i; C.704.z.54.i; C.705.z.54.i; C.706.z.54.i; C.707.z.54.i;
C.708.z.54.i; C.709.z.54.i; C.710.z.54.i; C.711.z.54.i; C.712.z.54.i; C.713.z.54.i;
C.714.z.54.i; C.715.z.54.i; C.716.z.54.i; C.717.z.54.i; C.718.z.54.i; C.719.z.54.i;
C.720.z.54.i; C.721.z.54.i; C.722.z.54.i; C.723.z.54.i; C.724.z.54.i; C.3.z.54.o; C.4.z.54.o;
C.7.z.54.o; C.9.z.54.o; C.103.z.54.o; C.106.z.54.o; C.107.z.54.o; C.108.z.54.o;
C.111.z.54.o; C.114.z.54.o; C.117.z.54.o; C.118.z.54.o; C.119.z.54.o; C.120.z.54.o;
C.121.z.54.o; C.137.z.54.o; C.138.z.54.o; C.139.z.54.o; C.140.z.54.o; C.141.z.54.o;

TABLE 6-continued

Exemplary Enumerated Compounds

C.142.z.54.o; C.145.z.54.o; C.146.z.54.o; C.147.z.54.o; C.148.z.54.o; C.149.z.54.o;
C.150.z.54.o; C.151.z.54.o; C.165.z.54.o; C.166.z.54.o; C.167.z.54.o; C.168.z.54.o;
C.169.z.54.o; C.170.z.54.o; C.171.z.54.o; C.172.z.54.o; C.173.z.54.o; C.174.z.54.o;
C.175.z.54.o; C.176.z.54.o; C.188.z.54.o; C.189.z.54.o; C.190.z.54.o; C.196.z.54.o;
C.202.z.54.o; C.205.z.54.o; C.206.z.54.o; C.207.z.54.o; C.208.z.54.o; C.209.z.54.o;
C.210.z.54.o; C.211.z.54.o; C.212.z.54.o; C.213.z.54.o; C.700.z.54.o; C.701.z.54.o;
C.702.z.54.o; C.703.z.54.o; C.704.z.54.o; C.705.z.54.o; C.706.z.54.o; C.707.z.54.o;
C.708.z.54.o; C.709.z.54.o; C.710.z.54.o; C.711.z.54.o; C.712.z.54.o; C.713.z.54.o;
C.714.z.54.o; C.715.z.54.o; C.716.z.54.o; C.717.z.54.o; C.718.z.54.o; C.719.z.54.o;
C.720.z.54.o; C.721.z.54.o; C.722.z.54.o; C.723.z.54.o; C.724.z.54.o; C.172.A.54.i;
C.173.A.54.i; C.174.A.54.i; C.175.A.54.i; C.176.A.54.i; C.188.A.54.i; C.189.A.54.i;
C.190.A.54.i; C.196.A.54.i; C.202.A.54.i; C.205.A.54.i; C.206.A.54.i; C.207.A.54.i;
C.208.A.54.i; C.209.A.54.i; C.210.A.54.i; C.211.A.54.i; C.212.A.54.i; C.213.A.54.i;
C.700.A.54.i; C.701.A.54.i; C.702.A.54.i; C.703.A.54.i; C.704.A.54.i; C.705.A.54.i;
C.706.A.54.i; C.707.A.54.i; C.708.A.54.i; C.709.A.54.i; C.710.A.54.i; C.711.A.54.i;
C.712.A.54.i; C.713.A.54.i; C.714.A.54.i; C.715.A.54.i; C.716.A.54.i; C.717.A.54.i;
C.718.A.54.i; C.719.A.54.i; C.720.A.54.i; C.721.A.54.i; C.722.A.54.i; C.723.A.54.i;
C.724.A.54.i; C.3.A.54.o; C.4.A.54.o; C.7.A.54.o; C.9.A.54.o; C.103.A.54.o;
C.106.A.54.o; C.107.A.54.o; C.108.A.54.o; C.111.A.54.o; C.114.A.54.o; C.117.A.54.o;
C.118.A.54.o; C.119.A.54.o; C.120.A.54.o; C.121.A.54.o; C.137.A.54.o; C.138.A.54.o;
C.139.A.54.o; C.140.A.54.o; C.141.A.54.o; C.142.A.54.o; C.145.A.54.o; C.146.A.54.o;
C.147.A.54.o; C.148.A.54.o; C.149.A.54.o; C.150.A.54.o; C.151.A.54.o; C.165.A.54.o;
C.166.A.54.o; C.167.A.54.o; C.168.A.54.o; C.169.A.54.o; C.170.A.54.o; C.171.A.54.o;
C.172.A.54.o; C.173.A.54.o; C.174.A.54.o; C.175.A.54.o; C.176.A.54.o; C.188.A.54.o;
C.189.A.54.o; C.190.A.54.o; C.196.A.54.o; C.202.A.54.o; C.205.A.54.o; C.206.A.54.o;
C.207.A.54.o; C.208.A.54.o; C.209.A.54.o; C.210.A.54.o; C.211.A.54.o; C.212.A.54.o;
C.213.A.54.o; C.700.A.54.o; C.701.A.54.o; C.702.A.54.o; C.703.A.54.o; C.704.A.54.o;
C.705.A.54.o; C.706.A.54.o; C.707.A.54.o; C.708.A.54.o; C.709.A.54.o; C.710.A.54.o;
C.711.A.54.o; C.712.A.54.o; C.713.A.54.o; C.714.A.54.o; C.715.A.54.o; C.716.A.54.o;
C.717.A.54.o; C.718.A.54.o; C.719.A.54.o; C.720.A.54.o; C.721.A.54.o; C.722.A.54.o;
C.723.A.54.o; C.724.A.54.o; C.172.B.54.i; C.173.B.54.i; C.174.B.54.i; C.175.B.54.i;
C.176.B.54.i; C.188.B.54.i; C.189.B.54.i; C.190.B.54.i; C.196.B.54.i; C.202.B.54.i;
C.205.B.54.i; C.206.B.54.i; C.207.B.54.i; C.208.B.54.i; C.209.B.54.i; C.210.B.54.i;
C.211.B.54.i; C.212.B.54.i; C.213.B.54.i; C.700.B.54.i; C.701.B.54.i; C.702.B.54.i;
C.703.B.54.i; C.704.B.54.i; C.705.B.54.i; C.706.B.54.i; C.707.B.54.i; C.708.B.54.i;
C.709.B.54.i; C.710.B.54.i; C.711.B.54.i; C.712.B.54.i; C.713.B.54.i; C.714.B.54.i;
C.715.B.54.i; C.716.B.54.i; C.717.B.54.i; C.718.B.54.i; C.719.B.54.i; C.720.B.54.i;
C.721.B.54.i; C.722.B.54.i; C.723.B.54.i; C.724.B.54.i; C.3.B.54.o; C.4.B.54.o; C.7.B.54.o;
C.9.B.54.o; C.103.B.54.o; C.106.B.54.o; C.107.B.54.o; C.108.B.54.o; C.111.B.54.o;
C.114.B.54.o; C.117.B.54.o; C.118.B.54.o; C.119.B.54.o; C.120.B.54.o; C.121.B.54.o;
C.137.B.54.o; C.138.B.54.o; C.139.B.54.o; C.140.B.54.o; C.141.B.54.o; C.142.B.54.o;
C.145.B.54.o; C.146.B.54.o; C.147.B.54.o; C.148.B.54.o; C.149.B.54.o; C.150.B.54.o;
C.151.B.54.o; C.165.B.54.o; C.166.B.54.o; C.167.B.54.o; C.168.B.54.o; C.169.B.54.o;
C.170.B.54.o; C.171.B.54.o; C.172.B.54.o; C.173.B.54.o; C.174.B.54.o; C.175.B.54.o;
C.176.B.54.o; C.188.B.54.o; C.189.B.54.o; C.190.B.54.o; C.196.B.54.o; C.202.B.54.o;
C.205.B.54.o; C.206.B.54.o; C.207.B.54.o; C.208.B.54.o; C.209.B.54.o; C.210.B.54.o;
C.211.B.54.o; C.212.B.54.o; C.213.B.54.o; C.700.B.54.o; C.701.B.54.o; C.702.B.54.o;
C.703.B.54.o; C.704.B.54.o; C.705.B.54.o; C.706.B.54.o; C.707.B.54.o; C.708.B.54.o;
C.709.B.54.o; C.710.B.54.o; C.711.B.54.o; C.712.B.54.o; C.713.B.54.o; C.714.B.54.o;
C.715.B.54.o; C.716.B.54.o; C.717.B.54.o; C.718.B.54.o; C.719.B.54.o; C.720.B.54.o;
C.721.B.54.o; C.722.B.54.o; C.723.B.54.o; C.724.B.54.o; D.3.a.4.i; D.4.a.4.i; D.7.a.4.i;
D.9.a.4.i; D.103.a.4.i; D.106.a.4.i; D.107.a.4.i; D.108.a.4.i; D.111.a.4.i; D.114.a.4.i;
D.117.a.4.i; D.118.a.4.i; D.119.a.4.i; D.120.a.4.i; D.121.a.4.i; D.137.a.4.i; D.138.a.4.i;
D.139.a.4.i; D.140.a.4.i; D.141.a.4.i; D.142.a.4.i; D.145.a.4.i; D.146.a.4.i; D.147.a.4.i;
D.148.a.4.i; D.149.a.4.i; D.150.a.4.i; D.151.a.4.i; D.165.a.4.i; D.166.a.4.i; D.167.a.4.i;
D.168.a.4.i; D.169.a.4.i; D.170.a.4.i; D.171.a.4.i; D.172.a.4.i; D.173.a.4.i; D.174.a.4.i;
D.175.a.4.i; D.176.a.4.i; D.188.a.4.i; D.189.a.4.i; D.190.a.4.i; D.196.a.4.i; D.202.a.4.i;
D.205.a.4.i; D.206.a.4.i; D.207.a.4.i; D.208.a.4.i; D.209.a.4.i; D.210.a.4.i; D.211.a.4.i;
D.212.a.4.i; D.213.a.4.i; D.700.a.4.i; D.701.a.4.i; D.702.a.4.i; D.703.a.4.i; D.704.a.4.i;
D.705.a.4.i; D.706.a.4.i; D.707.a.4.i; D.708.a.4.i; D.709.a.4.i; D.710.a.4.i; D.711.a.4.i;
D.712.a.4.i; D.713.a.4.i; D.714.a.4.i; D.715.a.4.i; D.716.a.4.i; D.717.a.4.i; D.718.a.4.i;
D.719.a.4.i; D.720.a.4.i; D.721.a.4.i; D.722.a.4.i; D.723.a.4.i; D.724.a.4.i; D.3.a.4.o;
D.4.a.4.o; D.7.a.4.o; D.9.a.4.o; D.103.a.4.o; D.106.a.4.o; D.107.a.4.o; D.108.a.4.o;
D.111.a.4.o; D.114.a.4.o; D.117.a.4.o; D.118.a.4.o; D.119.a.4.o; D.120.a.4.o;
D.121.a.4.o; D.137.a.4.o; D.138.a.4.o; D.139.a.4.o; D.140.a.4.o; D.141.a.4.o;
D.142.a.4.o; D.145.a.4.o; D.146.a.4.o; D.147.a.4.o; D.148.a.4.o; D.149.a.4.o;
D.150.a.4.o; D.151.a.4.o; D.165.a.4.o; D.166.a.4.o; D.167.a.4.o; D.168.a.4.o;
D.169.a.4.o; D.170.a.4.o; D.171.a.4.o; D.172.a.4.o; D.173.a.4.o; D.174.a.4.o;
D.175.a.4.o; D.176.a.4.o; D.188.a.4.o; D.189.a.4.o; D.190.a.4.o; D.196.a.4.o;
D.202.a.4.o; D.205.a.4.o; D.206.a.4.o; D.207.a.4.o; D.208.a.4.o; D.209.a.4.o;
D.210.a.4.o; D.211.a.4.o; D.212.a.4.o; D.213.a.4.o; D.700.a.4.o; D.701.a.4.o;
D.702.a.4.o; D.703.a.4.o; D.704.a.4.o; D.705.a.4.o; D.706.a.4.o; D.707.a.4.o;
D.708.a.4.o; D.709.a.4.o; D.710.a.4.o; D.711.a.4.o; D.712.a.4.o; D.713.a.4.o;
D.714.a.4.o; D.715.a.4.o; D.716.a.4.o; D.717.a.4.o; D.718.a.4.o; D.719.a.4.o;
D.720.a.4.o; D.721.a.4.o; D.722.a.4.o; D.723.a.4.o; D.724.a.4.o; D.172.b.4.i; D.173.b.4.i;
D.174.b.4.i; D.175.b.4.i; D.176.b.4.i; D.188.b.4.i; D.189.b.4.i; D.190.b.4.i; D.196.b.4.i;
D.202.b.4.i; D.205.b.4.i; D.206.b.4.i; D.207.b.4.i; D.208.b.4.i; D.209.b.4.i; D.210.b.4.i;

TABLE 6-continued

Exemplary Enumerated Compounds

D.211.b.4.i; D.212.b.4.i; D.213.b.4.i; D.700.b.4.i; D.701.b.4.i; D.702.b.4.i; D.703.b.4.i;
D.704.b.4.i; D.705.b.4.i; D.706.b.4.i; D.707.b.4.i; D.708.b.4.i; D.709.b.4.i; D.710.b.4.i;
D.711.b.4.i; D.712.b.4.i; D.713.b.4.i; D.714.b.4.i; D.715.b.4.i; D.716.b.4.i; D.717.b.4.i;
D.718.b.4.i; D.719.b.4.i; D.720.b.4.i; D.721.b.4.i; D.722.b.4.i; D.723.b.4.i; D.724.b.4.i;
D.3.b.4.o; D.4.b.4.o; D.7.b.4.o; D.9.b.4.o; D.103.b.4.o; D.106.b.4.o; D.107.b.4.o;
D.108.b.4.o; D.111.b.4.o; D.114.b.4.o; D.117.b.4.o; D.118.b.4.o; D.119.b.4.o;
D.120.b.4.o; D.121.b.4.o; D.137.b.4.o; D.138.b.4.o; D.139.b.4.o; D.140.b.4.o;
D.141.b.4.o; D.142.b.4.o; D.145.b.4.o; D.146.b.4.o; D.147.b.4.o; D.148.b.4.o;
D.149.b.4.o; D.150.b.4.o; D.151.b.4.o; D.165.b.4.o; D.166.b.4.o; D.167.b.4.o;
D.168.b.4.o; D.169.b.4.o; D.170.b.4.o; D.171.b.4.o; D.172.b.4.o; D.173.b.4.o;
D.174.b.4.o; D.175.b.4.o; D.176.b.4.o; D.188.b.4.o; D.189.b.4.o; D.190.b.4.o;
D.196.b.4.o; D.202.b.4.o; D.205.b.4.o; D.206.b.4.o; D.207.b.4.o; D.208.b.4.o;
D.209.b.4.o; D.210.b.4.o; D.211.b.4.o; D.212.b.4.o; D.213.b.4.o; D.700.b.4.o;
D.701.b.4.o; D.702.b.4.o; D.703.b.4.o; D.704.b.4.o; D.705.b.4.o; D.706.b.4.o;
D.707.b.4.o; D.708.b.4.o; D.709.b.4.o; D.710.b.4.o; D.711.b.4.o; D.712.b.4.o;
D.713.b.4.o; D.714.b.4.o; D.715.b.4.o; D.716.b.4.o; D.717.b.4.o; D.718.b.4.o;
D.719.b.4.o; D.720.b.4.o; D.721.b.4.o; D.722.b.4.o; D.723.b.4.o; D.724.b.4.o; D.172.x.4.i;
D.173.x.4.i; D.174.x.4.i; D.175.x.4.i; D.176.x.4.i; D.188.x.4.i; D.189.x.4.i; D.190.x.4.i;
D.196.x.4.i; D.202.x.4.i; D.205.x.4.i; D.206.x.4.i; D.207.x.4.i; D.208.x.4.i; D.209.x.4.i;
D.210.x.4.i; D.211.x.4.i; D.212.x.4.i; D.213.x.4.i; D.700.x.4.i; D.701.x.4.i; D.702.x.4.i;
D.703.x.4.i; D.704.x.4.i; D.705.x.4.i; D.706.x.4.i; D.707.x.4.i; D.708.x.4.i; D.709.x.4.i;
D.710.x.4.i; D.711.x.4.i; D.712.x.4.i; D.713.x.4.i; D.714.x.4.i; D.715.x.4.i; D.716.x.4.i;
D.717.x.4.i; D.718.x.4.i; D.719.x.4.i; D.720.x.4.i; D.721.x.4.i; D.722.x.4.i; D.723.x.4.i;
D.724.x.4.i; D.3.x.4.o; D.4.x.4.o; D.7.x.4.o; D.9.x.4.o; D.103.x.4.o; D.106.x.4.o;
D.107.x.4.o; D.108.x.4.o; D.111.x.4.o; D.114.x.4.o; D.117.x.4.o; D.118.x.4.o;
D.119.x.4.o; D.120.x.4.o; D.121.x.4.o; D.137.x.4.o; C.138.x.4.o; D.139.x.4.o;
D.140.x.4.o; D.141.x.4.o; D.142.x.4.o; D.145.x.4.o; D.146.x.4.o; D.147.x.4.o;
D.148.x.4.o; D.149.x.4.o; D.150.x.4.o; D.151.x.4.o; D.165.x.4.o; D.166.x.4.o;
D.167.x.4.o; D.168.x.4.o; D.169.x.4.o; D.170.x.4.o; D.171.x.4.o; D.172.x.4.o;
D.173.x.4.o; D.174.x.4.o; D.175.x.4.o; D.176.x.4.o; D.188.x.4.o; D.189.x.4.o;
D.190.x.4.o; D.196.x.4.o; D.202.x.4.o; D.205.x.4.o; D.206.x.4.o; D.207.x.4.o;
D.208.x.4.o; D.209.x.4.o; D.210.x.4.o; D.211.x.4.o; D.212.x.4.o; D.213.x.4.o;
D.700.x.4.o; D.701.x.4.o; D.702.x.4.o; D.703.x.4.o; D.704.x.4.o; D.705.x.4.o;
D.706.x.4.o; D.707.x.4.o; D.708.x.4.o; D.709.x.4.o; D.710.x.4.o; D.711.x.4.o;
D.712.x.4.o; D.713.x.4.o; D.714.x.4.o; D.715.x.4.o; D.716.x.4.o; D.717.x.4.o;
D.718.x.4.o; D.719.x.4.o; D.720.x.4.o; D.721.x.4.o; D.722.x.4.o; D.723.x.4.o;
D.724.x.4.o; D.172.y.4.i; D.173.y.4.i; D.174.y.4.i; D.175.y.4.i; D.176.y.4.i; D.188.y.4.i;
D.189.y.4.i; D.190.y.4.i; D.196.y.4.i; D.202.y.4.i; D.205.y.4.i; D.206.y.4.i; D.207.y.4.i;
D.208.y.4.i; D.209.y.4.i; D.210.y.4.i; D.211.y.4.i; D.212.y.4.i; D.213.y.4.i; D.700.y.4.i;
D.701.y.4.i; D.702.y.4.i; D.703.y.4.i; D.704.y.4.i; D.705.y.4.i; D.706.y.4.i; D.707.y.4.i;
D.708.y.4.i; D.709.y.4.i; D.710.y.4.i; D.711.y.4.i; D.712.y.4.i; D.713.y.4.i; D.714.y.4.i;
D.715.y.4.i; D.716.y.4.i; D.717.y.4.i; D.718.y.4.i; D.719.y.4.i; D.720.y.4.i; D.721.y.4.i;
D.722.y.4.i; D.723.y.4.i; D.724.y.4.i; D.3.y.4.o; D.4.y.4.o; D.7.y.4.o; D.9.y.4.o;
D.103.y.4.o; D.106.y.4.o; D.107.y.4.o; D.108.y.4.o; D.111.y.4.o; D.114.y.4.o;
D.117.y.4.o; D.118.y.4.o; D.119.y.4.o; D.120.y.4.o; D.121.y.4.o; D.137.y.4.o;
D.138.y.4.o; D.139.y.4.o; D.140.y.4.o; D.141.y.4.o; D.142.y.4.o; D.145.y.4.o;
D.146.y.4.o; D.147.y.4.o; D.148.y.4.o; D.149.y.4.o; D.150.y.4.o; D.151.y.4.o;
D.165.y.4.o; D.166.y.4.o; D.167.y.4.o; D.168.y.4.o; D.169.y.4.o; D.170.y.4.o;
D.171.y.4.o; D.172.y.4.o; D.173.y.4.o; D.174.y.4.o; D.175.y.4.o; D.176.y.4.o;
D.188.y.4.o; D.189.y.4.o; D.190.y.4.o; D.196.y.4.o; D.202.y.4.o; D.205.y.4.o;
D.206.y.4.o; D.207.y.4.o; D.208.y.4.o; D.209.y.4.o; D.210.y.4.o; D.211.y.4.o;
D.212.y.4.o; D.213.y.4.o; D.700.y.4.o; D.701.y.4.o; D.702.y.4.o; D.703.y.4.o;
D.704.y.4.o; D.705.y.4.o; D.706.y.4.o; D.707.y.4.o; D.708.y.4.o; D.709.y.4.o;
D.710.y.4.o; D.711.y.4.o; D.712.y.4.o; D.713.y.4.o; D.714.y.4.o; D.715.y.4.o;
D.716.y.4.o; D.717.y.4.o; D.718.y.4.o; D.719.y.4.o; D.720.y.4.o; D.721.y.4.o;
D.722.y.4.o; D.723.y.4.o; D.724.y.4.o; D.172.z.4.i; D.173.z.4.i; D.174.z.4.i; D.175.z.4.i;
D.176.z.4.i; D.188.z.4.i; D.189.z.4.i; D.190.z.4.i; D.196.z.4.i; D.202.z.4.i; D.205.z.4.i;
D.206.z.4.i; D.207.z.4.i; D.208.z.4.i; D.209.z.4.i; D.210.z.4.i; D.211.z.4.i; D.212.z.4.i;
D.213.z.4.i; D.700.z.4.i; D.701.z.4.i; D.702.z.4.i; D.703.z.4.i; D.704.z.4.i; D.705.z.4.i;
D.706.z.4.i; D.707.z.4.i; D.708.z.4.i; D.709.z.4.i; D.710.z.4.i; D.711.z.4.i; D.712.z.4.i;
D.713.z.4.i; D.714.z.4.i; D.715.z.4.i; D.716.z.4.i; D.717.z.4.i; D.718.z.4.i; D.719.z.4.i;
D.720.z.4.i; D.721.z.4.i; D.722.z.4.i; D.723.z.4.i; D.724.z.4.i; D.3.z.4.o; D.4.z.4.o;
D.7.z.4.o; D.9.z.4.o; D.103.z.4.o; D.106.z.4.o; D.107.z.4.o; D.108.z.4.o; D.111.z.4.o;
D.114.z.4.o; D.117.z.4.o; D.118.z.4.o; D.119.z.4.o; D.120.z.4.o; D.121.z.4.o;
D.137.z.4.o; D.138.z.4.o; D.139.z.4.o; D.140.z.4.o; D.141.z.4.o; D.142.z.4.o;
D.145.z.4.o; D.146.z.4.o; D.147.z.4.o; D.148.z.4.o; D.149.z.4.o; D.150.z.4.o;
D.151.z.4.o; D.165.z.4.o; D.166.z.4.o; D.167.z.4.o; D.168.z.4.o; D.169.z.4.o;
D.170.z.4.o; D.171.z.4.o; D.172.z.4.o; D.173.z.4.o; D.174.z.4.o; D.175.z.4.o;
D.176.z.4.o; D.188.z.4.o; D.189.z.4.o; D.190.z.4.o; D.196.z.4.o; D.202.z.4.o;
D.205.z.4.o; D.206.z.4.o; D.207.z.4.o; D.208.z.4.o; D.209.z.4.o; D.210.z.4.o;
D.211.z.4.o; D.212.z.4.o; D.213.z.4.o; D.700.z.4.o; D.701.z.4.o; D.702.z.4.o;
D.703.z.4.o; D.704.z.4.o; D.705.z.4.o; D.706.z.4.o; D.707.z.4.o; D.708.z.4.o;
D.709.z.4.o; D.710.z.4.o; D.711.z.4.o; D.712.z.4.o; D.713.z.4.o; D.714.z.4.o;
D.715.z.4.o; D.716.z.4.o; D.717.z.4.o; D.718.z.4.o; D.719.z.4.o; D.720.z.4.o;
D.721.z.4.o; D.722.z.4.o; D.723.z.4.o; D.724.z.4.o; D.172.A.4.i; D.173.A.4.i;
D.174.A.4.i; D.175.A.4.i; D.176.A.4.i; D.188.A.4.i; D.189.A.4.i; D.190.A.4.i;
D.196.A.4.i; D.202.A.4.i; D.205.A.4.i; D.206.A.4.i; D.207.A.4.i; D.208.A.4.i;

TABLE 6-continued

Exemplary Enumerated Compounds

D.209.A.4.i; D.210.A.4.i; D.211.A.4.i; D.212.A.4.i; D.213.A.4.i; D.700.A.4.i;
D.701.A.4.i; D.702.A.4.i; D.703.A.4.i; D.704.A.4.i; D.705.A.4.i; D.706.A.4.i;
D.707.A.4.i; D.708.A.4.i; D.709.A.4.i; D.710.A.4.i; D.711.A.4.i; D.712.A.4.i;
D.713.A.4.i; D.714.A.4.i; D.715.A.4.i; D.716.A.4.i; D.717.A.4.i; D.718.A.4.i;
D.719.A.4.i; D.720.A.4.i; D.721.A.4.i; D.722.A.4.i; D.723.A.4.i; D.724.A.4.i; D.3.A.4.o;
D.4.A.4.o; D.7.A.4.o; D.9.A.4.o; D.103.A.4.o; D.106.A.4.o; D.107.A.4.o; D.108.A.4.o;
D.111.A.4.o; D.114.A.4.o; D.117.A.4.o; D.118.A.4.o; D.119.A.4.o; D.120.A.4.o;
D.121.A.4.o; D.137.A.4.o; D.138.A.4.o; D.139.A.4.o; D.140.A.4.o; D.141.A.4.o;
D.142.A.4.o; D.145.A.4.o; D.146.A.4.o; D.147.A.4.o; D.148.A.4.o; D.149.A.4.o;
D.150.A.4.o; D.151.A.4.o; D.165.A.4.o; D.166.A.4.o; D.167.A.4.o; D.168.A.4.o;
D.169.A.4.o; D.170.A.4.o; D.171.A.4.o; D.172.A.4.o; D.173.A.4.o; D.174.A.4.o;
D.175.A.4.o; D.176.A.4.o; D.188.A.4.o; D.189.A.4.o; D.190.A.4.o; D.196.A.4.o;
D.202.A.4.o; D.205.A.4.o; D.206.A.4.o; D.207.A.4.o; D.208.A.4.o; D.209.A.4.o;
D.210.A.4.o; D.211.A.4.o; D.212.A.4.o; D.213.A.4.o; D.700.A.4.o; D.701.A.4.o;
D.702.A.4.o; D.703.A.4.o; D.704.A.4.o; D.705.A.4.o; D.706.A.4.o; D.707.A.4.o;
D.708.A.4.o; D.709.A.4.o; D.710.A.4.o; D.711.A.4.o; D.712.A.4.o; D.713.A.4.o;
D.714.A.4.o; D.715.A.4.o; D.716.A.4.o; D.717.A.4.o; D.718.A.4.o; D.719.A.4.o;
D.720.A.4.o; D.721.A.4.o; D.722.A.4.o; D.723.A.4.o; D.724.A.4.o; D.172.B.4.i;
D.173.B.4.i; D.174.B.4.i; D.175.B.4.i; D.176.B.4.i; D.188.B.4.i; D.189.B.4.i; D.190.B.4.i;
D.196.B.4.i; D.202.B.4.i; D.205.B.4.i; D.206.B.4.i; D.207.B.4.i; D.208.B.4.i; D.209.B.4.i;
D.210.B.4.i; D.211.B.4.i; D.212.B.4.i; D.213.B.4.i; D.700.B.4.i; D.701.B.4.i; D.702.B.4.i;
D.703.B.4.i; D.704.B.4.i; D.705.B.4.i; D.706.B.4.i; D.707.B.4.i; D.708.B.4.i; D.709.B.4.i;
D.710.B.4.i; D.711.B.4.i; D.712.B.4.i; D.713.B.4.i; D.714.B.4.i; D.715.B.4.i; D.716.B.4.i;
D.717.B.4.i; D.718.B.4.i; D.719.B.4.i; D.720.B.4.i; D.721.B.4.i; D.722.B.4.i; D.723.B.4.i;
D.724.B.4.i; D.3.B.4.o; D.4.B.4.o; D.7.B.4.o; D.9.B.4.o; D.103.B.4.o; D.106.B.4.o;
D.107.B.4.o; D.108.B.4.o; D.111.B.4.o; D.114.B.4.o; D.117.B.4.o; D.118.B.4.o;
D.119.B.4.o; D.120.B.4.o; D.121.B.4.o; D.137.B.4.o; C.138.B.4.o; D.139.B.4.o;
D.140.B.4.o; D.141.B.4.o; D.142.B.4.o; D.145.B.4.o; D.146.B.4.o; D.147.B.4.o;
D.148.B.4.o; D.149.B.4.o; D.150.B.4.o; D.151.B.4.o; D.165.B.4.o; D.166.B.4.o;
D.167.B.4.o; D.168.B.4.o; D.169.B.4.o; D.170.B.4.o; D.171.B.4.o; D.172.B.4.o;
D.173.B.4.o; D.174.B.4.o; D.175.B.4.o; D.176.B.4.o; D.188.B.4.o; D.189.B.4.o;
D.190.B.4.o; D.196.B.4.o; D.202.B.4.o; D.205.B.4.o; D.206.B.4.o; D.207.B.4.o;
D.208.B.4.o; D.209.B.4.o; D.210.B.4.o; D.211.B.4.o; D.212.B.4.o; D.213.B.4.o;
D.700.B.4.o; D.701.B.4.o; D.702.B.4.o; D.703.B.4.o; D.704.B.4.o; D.705.B.4.o;
D.706.B.4.o; D.707.B.4.o; D.708.B.4.o; D.709.B.4.o; D.710.B.4.o; D.711.B.4.o;
D.712.B.4.o; D.713.B.4.o; D.714.B.4.o; D.715.B.4.o; D.716.B.4.o; D.717.B.4.o;
D.718.B.4.o; D.719.B.4.o; D.720.B.4.o; D.721.B.4.o; D.722.B.4.o; D.723.B.4.o;
D.724.B.4.o; E.3.a.54.i; E.4.a.54.i; E.7.a.54.i; E.9.a.54.i; E.103.a.54.i; E.106.a.54.i;
E.107.a.54.i; E.108.a.54.i; E.111.a.54.i; E.114.a.54.i; E.117.a.54.i; E.118.a.54.i;
E.119.a.54.i; E.120.a.54.i; E.121.a.54.i; E.137.a.54.i; E.138.a.54.i; E.139.a.54.i;
E.140.a.54.i; E.141.a.54.i; E.142.a.54.i; E.145.a.54.i; E.146.a.54.i; E.147.a.54.i;
E.148.a.54.i; E.149.a.54.i; E.150.a.54.i; E.151.a.54.i; E.165.a.54.i; E.166.a.54.i;
E.167.a.54.i; E.168.a.54.i; E.169.a.54.i; E.170.a.54.i; E.171.a.54.i; E.172.a.54.i;
E.173.a.54.i; E.174.a.54.i; E.175.a.54.i; E.176.a.54.i; E.188.a.54.i; E.189.a.54.i;
E.190.a.54.i; E.196.a.54.i; E.202.a.54.i; E.205.a.54.i; E.206.a.54.i; E.207.a.54.i;
E.208.a.54.i; E.209.a.54.i; E.210.a.54.i; E.211.a.54.i; E.212.a.54.i; E.213.a.54.i;
E.700.a.54.i; E.701.a.54.i; E.702.a.54.i; E.703.a.54.i; E.704.a.54.i; E.705.a.54.i;
E.706.a.54.i; E.707.a.54.i; E.708.a.54.i; E.709.a.54.i; E.710.a.54.i; E.711.a.54.i;
E.712.a.54.i; E.713.a.54.i; E.714.a.54.i; E.715.a.54.i; E.716.a.54.i; E.717.a.54.i;
E.718.a.54.i; E.719.a.54.i; E.720.a.54.i; E.721.a.54.i; E.722.a.54.i; E.723.a.54.i;
E.724.a.54.i; E.3.a.54.o; E.4.a.54.o; E.7.a.54.o; E.9.a.54.o; E.103.a.54.o; E.106.a.54.o;
E.107.a.54.o; E.108.a.54.o; E.111.a.54.o; E.114.a.54.o; E.117.a.54.o; E.118.a.54.o;
E.119.a.54.o; E.120.a.54.o; E.121.a.54.o; E.137.a.54.o; E.138.a.54.o; E.139.a.54.o;
E.140.a.54.o; E.141.a.54.o; E.142.a.54.o; E.145.a.54.o; E.146.a.54.o; E.147.a.54.o;
E.148.a.54.o; E.149.a.54.o; E.150.a.54.o; E.151.a.54.o; E.165.a.54.o; E.166.a.54.o;
E.167.a.54.o; E.168.a.54.o; E.169.a.54.o; E.170.a.54.o; E.171.a.54.o; E.172.a.54.o;
E.173.a.54.o; E.174.a.54.o; E.175.a.54.o; E.176.a.54.o; E.188.a.54.o; E.189.a.54.o;
E.190.a.54.o; E.196.a.54.o; E.202.a.54.o; E.205.a.54.o; E.206.a.54.o; E.207.a.54.o;
E.208.a.54.o; E.209.a.54.o; E.210.a.54.o; E.211.a.54.o; E.212.a.54.o; E.213.a.54.o;
E.700.a.54.o; E.701.a.54.o; E.702.a.54.o; E.703.a.54.o; E.704.a.54.o; E.705.a.54.o;
E.706.a.54.o; E.707.a.54.o; E.708.a.54.o; E.709.a.54.o; E.710.a.54.o; E.711.a.54.o;
E.712.a.54.o; E.713.a.54.o; E.714.a.54.o; E.715.a.54.o; E.716.a.54.o; E.717.a.54.o;
E.718.a.54.o; E.719.a.54.o; E.720.a.54.o; E.721.a.54.o; E.722.a.54.o; E.723.a.54.o;
E.724.a.54.o; E.172.z.54.i; E.173.z.54.i; E.174.z.54.i; E.175.z.54.i; E.176.z.54.i;
E.188.b.54.i; E.189.b.54.i; E.190.b.54.i; E.196.b.54.i; E.202.b.54.i; E.205.b.54.i;
E.206.b.54.i; E.207.b.54.i; E.208.b.54.i; E.209.b.54.i; E.210.b.54.i; E.211.b.54.i;
E.212.b.54.i; E.213.b.54.i; E.700.b.54.i; E.701.b.54.i; E.702.b.54.i; E.703.b.54.i;
E.704.b.54.i; E.705.b.54.i; E.706.b.54.i; E.707.b.54.i; E.708.b.54.i; E.709.b.54.i;
E.710.b.54.i; E.711.b.54.i; E.712.b.54.i; E.713.b.54.i; E.714.b.54.i; E.715.b.54.i;
E.716.b.54.i; E.717.b.54.i; E.718.b.54.i; E.719.b.54.i; E.720.b.54.i; E.721.b.54.i;
E.722.b.54.i; E.723.b.54.i; E.724.b.54.i; E.3.b.54.o; E.4.b.54.o; E.7.b.54.o; E.9.b.54.o;
E.103.b.54.o; E.106.b.54.o; E.107.b.54.o; E.108.b.54.o; E.111.b.54.o; E.114.b.54.o:
E.117.b.54.o; E.118.b.54.o; E.119.b.54.o; E.120.b.54.o; E.121.b.54.o; E.137.b.54.o;
E.138.b.54.o; E.139.b.54.o; E.140.b.54.o; E.141.b.54.o; E.142.b.54.o; E.145.b.54.o;
E.146.b.54.o; E.147.b.54.o; E.148.b.54.o; E.149.b.54.o; E.150.b.54.o; E.151.b.54.o;
E.165.b.54.o; E.166.b.54.o; E.167.b.54.o; E.168.b.54.o; E.169.b.54.o; E.170.b.54.o;
E.171.b.54.o; E.172.b.54.o; E.173.b.54.o; E.174.b.54.o; E.175.b.54.o; E.176.b.54.o;

TABLE 6-continued

Exemplary Enumerated Compounds

E.188.b.54.o; E.189.b.54.o; E.190.b.54.o; E.196.b.54.o; E.202.b.54.o; E.205.b.54.o;
E.206.b.54.o; E.207.b.54.o; E.208.b.54.o; E.209.b.54.o; E.210.b.54.o; E.211.b.54.o;
E.212.b.54.o; E.213.b.54.o; E.700.b.54.o; E.701.b.54.o; E.702.b.54.o; E.703.b.54.o;
E.704.b.54.o; E.705.b.54.o; E.706.b.54.o; E.707.b.54.o; E.708.b.54.o; E.709.b.54.o;
E.710.b.54.o; E.711.b.54.o; E.712.b.54.o; E.713.b.54.o; E.714.b.54.o; E.715.b.54.o;
E.716.b.54.o; E.717.b.54.o; E.718.b.54.o; E.719.b.54.o; E.720.b.54.o; E.721.b.54.o;
E.722.b.54.o; E.723.b.54.o; E.724.b.54.o; E.172.b.54.o; E.173.b.54.o; E.174.b.54.o;
E.175.x.54.i; E.176.x.54.i; E.188.x.54.i; E.189.x.54.i; E.190.x.54.i; E,196.x.54.i;
E.202.x.54.i; E.205.x.54.i; E.206.x.54.i; E.207.x.54.i; E.208.x.54.i; E.209.x.54.i;
E.210.x.54.i; E.211.x.54.i; E.212.x.54.i; E.213.x.54.i; E.700.x.54.i; E.701.x.54.i;
E.702.x.54.i; E.703.x.54.i; E.704.x.54.i; E.705.x.54.i; E.706.x.54.i; E.707.x.54.i;
E.708.x.54.i; E.709.x.54.i; E.710.x.54.i; E.711.x.54.i; E.712.x.54.i; E.713.x.54.i;
E.714.x.54.i; E.715.x.54.i; E.716.x.54.i; E.717.x.54.i; E.718.x.54.i; E.719.x.54.i;
E.720.x.54.i; E.721.x.54.i; E.722.x.54.i; E.723.x.54.i; E.724.x.54.i; E.3.x.54.o; E.4.x.54.o;
E.7.x.54.o; E.9.x.54.o; E.103.x.54.o; E.106.x.54.o; E.107.x.54.o; E.108.x.54.o;
E.111.x.54.o; E.114.x.54.o; E.117.x.54.o; E.118.x.54.o; E.119.x.54.o; E.120.x.54.o;
E.121.x.54.o; E.137.x.54.o; E.138.x.54.o; E.139.x.54.o; E.140.x.54.o; E.141.x.54.o;
E.142.x.54.o; E.145.x.54.o; E.146.x.54.o; E.147.x.54.o; E.148.x.54.o; E.149.x.54.o;
E.150.x.54.o; E.151.x.54.o; E.165.x.54.o; E.166.x.54.o; E.167.x.54.o; E.168.x.54.o;
E.169.x.54.o; E.170.x.54.o; E.171.x.54.o; E.172.x.54.o; E.173.x.54.o; E.174.x.54.o;
E.175.x.54.o; E.176.x.54.o; E.188.x.54.o; E.189.x.54.o; E.190.x.54.o; E.196.x.54.o;
E.202.x.54.o; E.205.x.54.o; E.206.x.54.o; E.207.x.54.o; E.208.x.54.o; E.209.x.54.o;
E.210.x.54.o; E.211.x.54.o; E.212.x.54.o; E.213.x.54.o; E.700.x.54.o; E.701.x.54.o;
E.702.x.54.o; E.703.x.54.o; E.704.x.54.o; E.705.x.54.o; E.706.x.54.o; E.707.x.54.o;
E.708.x.54.o; E.709.x.54.o; E.710.x.54.o; E.711.x.54.o; E.712.x.54.o; E.713.x.54.o;
E.714.x.54.o; E.715.x.54.o; E.716.x.54.o; E.717.x.54.o; E.718.x.54.o; E.719.x.54.o;
E.720.x.54.o; E.721.x.54.o; E.722.x.54.o; E.723.x.54.o; E.724.x.54.o; E.172.y.54.i;
E.173.y.54.i; E.174.y.54.i; E.175.y.54.i; E.176.y.54.i; E.188.y.54.i; E.189.y.54.i;
E.190.y.54.i; E.196.y.54.i; E.202.y.54.i; E.205.y.54.i; E.206.y.54.i; E.207.y.54.i;
E.208.y.54.i; E.209.y.54.i; E.210.y.54.i; E.211.y.54.i; E.212.y.54.i; E.213.y.54.i;
E.700.y.54.i; E.701.y.54.i; E.702.y.54.i; E.703.y.54.i; E.704.y.54.i; E.705.y.54.i;
E.706.y.54.i; E.707.y.54.i; E.708.y.54.i; E.709.y.54.i; E.710.y.54.i; E.711.y.54.i;
E.712.y.54.i; E.713.y.54.i; E.714.y.54.i; E.715.y.54.i; E.716.y.54.i; E.717.y.54.i;
E.718.y.54.i; E.719.y.54.i; E.720.y.54.i; E.721.y.54.i; E.722.y.54.i; E.723.y.54.i;
E.724.y.54.i; E.3.y.54.o; E.4.y.54.o; E.7.y.54.o; E.9.y.54.o; E.103.y.54.o; E.106.y.54.o;
E.107.y.54.o; E.108.y.54.o; E.111.y.54.o; E.114.y.54.o; E.117.y.54.o; E.118.y.54.o;
E.119.y.54.o; E.120.y.54.o; E.121.y.54.o; E.137.y.54.o; E.138.y.54.o; E.139.y.54.o;
E.140.y.54.o; E.141.y.54.o; E.142.y.54.o; E.145.y.54.o; E.146.y.54.o; E.147.y.54.o;
E.148.y.54.o; E.149.y.54.o; E.150.y.54.o; E.151.y.54.o; E.165.y.54.o; E.166.y.54.o;
E.167.y.54.o; E.168.y.54.o; E.169.y.54.o; E.170.y.54.o; E.171.y.54.o; E.172.y.54.o;
E.173.y.54.o; E.174.y.54.o; E.175.y.54.o; E.176.y.54.o; E.188.y.54.o; E.189.y.54.o;
E.190.y.54.o; E.196.y.54.o; E.202.y.54.o; E.205.y.54.o; E.206.y.54.o; E.207.y.54.o;
E.208.y.54.o; E.209.y.54.o; E.210.y.54.o; E.211.y.54.o; E.212.y.54.o; E.213.y.54.o;
E.700.y.54.o; E.701.y.54.o; E.702.y.54.o; E.703.y.54.o; E.704.y.54.o; E.705.y.54.o;
E.706.y.54.o; E.707.y.54.o; E.708.y.54.o; E.709.y.54.o; E.710.y.54.o; E.711.y.54.o;
E.712.y.54.o; E.713.y.54.o; E.714.y.54.o; E.715.y.54.o; E.716.y.54.o; E.717.y.54.o;
E.718.y.54.o; E.719.y.54.o; E.720.y.54.o; E.721.y.54.o; E.722.y.54.o; E.723.y.54.o;
E.724.y.54.o; E.172.z.54.i; E.173.z.54.i; E.174.z.54.i; E.175.z.54.i; E.176.z.54.i;
E.188.z.54.i; E.189.z.54.i; E.190.z.54.i; E.196.z.54.i; E.202.z.54.i; E.205.z.54.i;
E.206.z.54.i; E.207.z.54.i; E.208.z.54.i; E.209.z.54.i; E.210.z.54.i; E.211.z.54.i;
E.212.z.54.i; E.213.z.54.i; E.700.z.54.i; E.701.z.54.i; E.702.z.54.i; E.703.z.54.i;
E.704.z.54.i; E.705.z.54.i; E.706.z.54.i; E.707.z.54.i; E.708.z.54.i; E.709.z.54.i;
E.710.z.54.i; E.711.z.54.i; E.712.z.54.i; E.713.z.54.i; E.714.z.54.i; E.715.z.54.i;
E.716.z.54.i; E.717.z.54.i; E.718.z.54.i; E.719.z.54.i; E.720.z.54.i; E.721.z.54.i;
E.722.z.54.i; E.723.z.54.i; E.724.z.54.i; E.3.z.54.o; E.4.z.54.o; E.7.z.54.o; E.9.z.54.o;
E.103.z.54.o; E.106.z.54.o; E.107.z.54.o; E.108.z.54.o; E.111.z.54.o; E.114.z.54.o;
E.117.z.54.o; E.118.z.54.o; E.119.z.54.o; E.120.z.54.o; E.121.z.54.o; E.137.z.54.o;
E.138.z.54.o; E.139.z.54.o; E.140.z.54.o; E.141.z.54.o; E.142.z.54.o; E.145.z.54.o;
E.146.z.54.o; E.147.z.54.o; E.148.z.54.o; E.149.z.54.o; E.150.z.54.o; E.151.z.54.o;
E.165.z.54.o; E.166.z.54.o; E.167.z.54.o; E.168.z.54.o; E.169.z.54.o; E.170.z.54.o;
E.171.z.54.o; E.172.z.54.o; E.173.z.54.o; E.174.z.54.o; E.175.z.54.o; E.176.z.54.o:
E.188.z.54.o; E.189.z.54.o; E.190.z.54.o; E.196.z.54.o; E.202.z.54.o; E.205.z.54.o;
E.206.z.54.o; E.207.z.54.o; E.208.z.54.o; E.209.z.54.o; E.210.z.54.o; E.211.z.54.o;
E.212.z.54.o; E.213.z.54.o; E.700.z.54.o; E.701.z.54.o; E.702.z.54.o; E.703.z.54.o;
E.704.z.54.o; E.705.z.54.o; E.706.z.54.o; E.707.z.54.o; E.708.z.54.o; E.709.z.54.o;
E.710.z.54.o; E.711.z.54.o; E.712.z.54.o; E.713.z.54.o; E.714.z.54.o; E.715.z.54.o;
E.716.z.54.o; E.717.z.54.o; E.718.z.54.o; E.719.z.54.o; E.720.z.54.o; E.721.z.54.o;
E.722.z.54.o; E.723.z.54.o; E.724.z.54.o; E.172.A.54.i; E.173.A.54.i; E.174.A.54.i;
E.175.A.54.i; E.176.A.54.i; E.188.A.54.i; E.189.A.54.i; E.190.A.54.i; E,196.A.54.i;
E.202.A.54.i; E.205.A.54.i; E.206.A.54.i; E.207.A.54.i; E.208.A.54.i; E.209.A.54.i;
E.210.A.54.i; E.211.A.54.i; E.212.A.54.i; E.213.A.54.i; E.700.A.54.i; E.701.A.54.i;
E.702.A.54.i; E.703.A.54.i; E.704.A.54.i; E.705.A.54.i; E.706.A.54.i; E.707.A.54.i;
E.708.A.54.i; E.709.A.54.i; E.710.A.54.i; E.711.A.54.i; E.712.A.54.i; E.713.A.54.i;
E.714.A.54.i; E.715.A.54.i; E.716.A.54.i; E.717.A.54.i; E.718.A.54.i; E.719.A.54.i;
E.720.A.54.i; E.721.A.54.i; E.722.A.54.i; E.723.A.54.i; E.724.A.54.i; E.3.A.54.o;
E.4.A.54.o; E.7.A.54.o; E.9.A.54.o; E.103.A.54.o; E.106.A.54.o; E.107.A.54.o;
E.108.A.54.o; E.111.A.54.o; E.114.A.54.o; E.117.A.54.o; E.118.A.54.o; E.119.A.54.o;

TABLE 6-continued

Exemplary Enumerated Compounds

E.120.A.54.o; E.121.A.54.o; E.137.A.54.o; E.138.A.54.o; E.139.A.54.o; E.140.A.54.o;
E.141.A.54.o; E.142.A.54.o; E.145.A.54.o; E.146.A.54.o; E.147.A.54.o; E.148.A.54.o;
E.149.A.54.o; E.150.A.54.o; E.151.A.54.o; E.165.A.54.o; E.166.A.54.o; E.167.A.54.o;
E.168.A.54.o; E.169.A.54.o; E.170.A.54 o; E.171.A.54.o; E.172.A.54.o; E.173.A.54.o;
E.174.A.54.o; E.175.A.54.o; E.176.A.54.o; E.188.A.54.o; E.189.A.54.o; E.190.A.54.o;
E.196.A.54.o; E.202.A.54.o; E.205.A.54.o; E.206.A.54.o; E.207.A.54.o; E.208.A.54.o;
E.209.A.54.o; E.210.A.54.o; E.211.A.54.o; E.212.A.54.o; E.213.A.54.o; E.700.A.54.o;
E.701.A.54.o; E.702.A.54.o; E.703.A.54.o; E.704.A.54.o; E.705.A.54.o; E.706.A.54.o;
E.707.A.54.o; E.708.A.54.o; E.709.A.54.o; E.710.A.54.o; E.711.A.54.o; E.712.A.54.o;
E.713.A.54.o; E.714.A.54.o; E.715.A.54.o; E.716.A.54.o; E.717.A.54.o; E.718.A.54.o;
E.719.A.54.o; E.720.A.54.o; E.721.A.54.o; E.722.A.54.o; E.723.A.54.o; E.724.A.54.o;
E.172.B.54.i; E.173.B.54.i; E.174.B.54.i; E.175.B.54.i; E.176.B.54.i; E.188.B.54.i;
E.189.B.54.i; E.190.B.54.i; E.196.B.54.i; E.202.B.54.i; E.205.B.54.i; E.206.B.54.i;
E.207.B.54.i; E.208.B.54.i; E.209.B.54.i; E.210.B.54.i; E.211.B.54.i; E.212.B.54.i;
E.213.B.54.i; E.700.B.54.i; E.701.B.54.i; E.702.B.54.i; E.703.B.54.i; E.704.B.54.i;
E.705.B.54.i; E.706.B.54.i; E.707.B.54.i; E.708.B.54.i; E.709.B.54.i; E.710.B.54.i;
E.711.B.54.i; E.712.B.54.i; E.713.B.54.i; E.714.B.54.i; E.715.B.54.i; E.716.B.54.i;
E.717.B.54.i; E.718.B.54.i; E.719.B.54.i; E.720.B.54.i; E.721.B.54.i; E.722.B.54.i;
E.723.B.54.i; E.724.B.54.i; E.3.B.54.o; E.4.B.54.o; E.7.B.54.o; E.9.B.54.o; E.103.B.54.o;
E.106.B.54.o; E.107.B.54.o; E.108.B.54.o; E.111.B.54.o; E.114.B.54.o; E.117.B.54.o;
E.118.B.4.o; E.119.B.54.o; E.120.B.54.o; E.121.B.54.o; E.137.B.54.o; E.138.B.54.o;
E.139.B.54.o; E.140.B.54.o; E.141.B.54.o; E.142.B.54.o; E.145.B.54.o; E.146.B.54.o;
E.147.B.54.o; E.148.B.54.o; E.149.B.54.o; E.150.B.54.o; E.151.B.54.o; E.165.B.54.o;
E.166.B.54.o; E.167.B.54.o; E.168.B.54.o; E.169.B.54.o; E.170.B.54.o; E.171.B.54.o;
E.172.B.54.o; E.173.B.54.o; E.174.B.54.o; E.175.B.54.o; E.176.B.54.o; E.188.B.54.o;
E.189.B.54.o; E.190.B.54.o; E.196.B.54.o; E.202.B.54.o; E.205.B.54.o; E.206.B.54.o;
E.207.B.54.o; E.208.B.54.o; E.209.B.54.o; E.210.B.54.o; E.211.B.54.o; E.212.B.54.o;
E.213.B.54.o; E.700.B.54.o; E.701.B.54.o; E.702.B.54.o; E.703.B.54.o; E.704.B.54.o;
E.705.B.54.o; E.706.B.54.o; E.707.B.54.o; E.708.B.54.o; E.709.B.54.o; E.710.B.54.o;
E.711.B.54.o; E.712.B.54.o; E.713.B.54.o; E.714.B.54.o; E.715.B.54.o; E.716.B.54.o;
E.717.B.54.o; E.718.B.54.o; E.719.B.54.o; E.720.B.54.o; E.721.B.54.o; E.722.B.54.o;
E.723.B.54.o; E.724.B.54.o; F.3.a.54.o; F.4.a.54.i; F.7.a.54.i; F.9.a.54.i; F.103.a.54.i;
F.106.a.54.i; F.107.a.54.i; F.108.a.54.i; F.111.a.54.i; F.114.a.54.i; F.117.a.54.i;
F.118.a.54.i; F.119.a.54.i; F.120.a.54.i; F.121.a.54.i; F.137.a.54.i; F.138.a.54.i;
F.139.a.54.i; F.140.a.54.i; F.141.a.54.i; F.142.a.54.i; F.145.a.54.i; F.146.a.54.i;
F.147.a.54.i; F.148.a.54.i; F.149.a.54.i; F.150.a.54.i; F.151.a.54.i; F.165.a.54.i;
F.166.a.54.i; F.167.a.54.i; F.168.a.54.i; F.169.a.54.i; F.170.a.54.i; F.171.a.54.i;
F.172.a.54.i; F.173.a.54.i; F.174.a.54.i; F.175.a.54.i; F.176.a.54.i; F.188.a.54.i;
F.189.a.54.i; F.190.a.54.i; F.196.a.54.i; F.202.a.54.i; F.205.a.54.i; F.206.a.54.i;
F.207.a.54.i; F.208.a.54.i; F.209.a.54.i; F.210.a.54.i; F.211.a.54.i; F.212.a.54.i;
F.213.a.54.i; F.700.a.54.i; F.701.a.54.i; F.702.a.54.i; F.703.a.54.i; F.704.a.54.i;
F.705.a.54.i; F.706.a.54.i; F.707.a.54.i; F.708.a.54.i; F.709.a.54.i; F.710.a.54.i;
F.711.a.54.i; F.712.a.54.i; F.713.a.54.i; F.714.a.54.i; F.715.a.54.i; F.716.a.54.i;
F.717.a.54.i; F.718.a.54.i; F.719.a.54.i; F.720.a.54.i; F.721.a.54.i; F.722.a.54.i;
F.106.a.54.o; F.107.a.54.o; F.108.a.54.o; F.111.a.54.o; F.114.a.54.o; F.117.a.54.o;
F.118.a.54.o; F.119.a.54.o; F.120.a.54.o; F.121.a.54.o; F.137.a.54.o; F.138.a.54.o;
F.139.a.54.o; F.140.a.54.o; F.141.a.54.o; F.142.a.54.o; F.145.a.54.o; F.146.a.54.o;
F.147.a.54.o; F.148.a.54.o; F.149.a.54.o; F.150.a.54.o; F.151.a.54.o; F.165.a.54.o;
F.166.a.54.o; F.167.a.54.o; F.168.a.54.o; F.169.a.54.o; F.170.a.54.o; F.171.a.54.o;
F.172.a.54.o; F.173.a.54.o; F.174.a.54.o; F.175.a.54.o; F.176.a.54.o; F.188.a.54.o;
F.189.a.54.o; F.190.a.54.o; F.196.a.54.o; F.202.a.54.o; F.205.a.54.o; F.206.a.54.o;
F.207.a.54.o; F.208.a.54.o; F.209.a.54.o; F.210.a.54.o; F.211.a.54.o; F.212.a.54.o;
F.213.a.54.o; F.700.a.54.o; F.701.a.54.o; F.702.a.54.o; F.703.a.54.o; F.704.a.54.o;
F.705.a.54.o; F.706.a.54.o; F.707.a.54.o; F.708.a.54.o; F.709.a.54.o; F.710.a.54.o;
F.711.a.54.o; F.712.a.54.o; F.713.a.54.o; F.714.a.54.o; F.715.a.54.o; F.716.a.54.o;
F.717.a.54.o; F.718.a.54.o; F.719.a.54.o; F.720.a.54.o; F.721.a.54.o; F.722.a.54.o;
F.723.a.54.o; F.724.a.54.o; F.172.b.54.i; F.173.b.54.i; F.174.b.54.i; F.174.b.54.i;
F.176.b.54.i; F.188.b.54.i; F.189.b.54.i; F.190.b.54.i; F.196.b.54.i; F.202.b.54.i;
F.205.b.54.i; F.206.b.54.i; F.207.b.54.i; F.208.b.54.i; F.209.b.54.i; F.210.b.54.i;
F.211.b.54.i; F.212.b.54.i; F.213.b.54.i; F.700.b.54.i; F.701.b.54.i; F.702.b.54.i;
F.703.b.54.i; F.704.b.54.i; F.705.b.54.i; F.706.b.54.i; F.707.b.54.i; F.708.b.54.i;
F.709.b.54.i; F.710.b.54.i; F.711.b.54.i; F.712.b.54.i; F.713.b.54.i; F.714.b.54.i;
F.715.b.54.i; F.716.b.54.i; F.717.b.54.i; F.718.b.54.i; F.719.b.54.i; F.720.b.54.i;
F.721.b.54.i; F.722.b.54.i; F.723.b.54.i; F.724.b.54.i; F.3.b.54.o; F.4.b.54.o; F.7.b.54.o;
F.9.b.54.o; F.103.b.54.o; F.106.b.54.o; F.107.b.54.o; F.108.b.54.o; F.111.b.54.o;
F.114.b.54.o; F.117.b.54.o; F.118.b.54.o; F.119.b.54.o; F.120.b.54.o; F.121.b.54.o;
F.137.b.54.o; F.138.b.54.o; F.139.b.54.o; F.140.b.54.o; F.141.b.54.o; F.142.b.54.o;
F.145.b.54.o; F.146.b.54.o; F.147.b.54.o; F.148.b.54.o; F.149.b.54.o; F.150.b.54.o;
F.151.b.54.o; F.165.b.54.o; F.166.b.54.o; F.167.b.54.o; F.168.b.54.o; F.169.b.54.o;
F.170.b.54.o; F.171.b.54.o; F.172.b.54.o; F.173.b.54.o; F.174.b.54.o; F.175.b.54.o;
F.176.b.54.o; F.188.b.54.o; F.189.b.54.o; F.190.b.54.o; F.196.b.54.o; F.202.b.54.o;
F.205.b.54.o; F.206.b.54.o; F.207.b.54.o; F.208.b.54.o; F.209.b.54.o; F.210.b.54.o;
F.211.b.54.o; F.212.b.54.o; F.213.b.54.o; F.700.b.54.o; F.701.b.54.o; F.702.b.54.o;
F.703.b.54.o; F.704.b.54.o; F.705.b.54.o; F.706.b.54.o; F.707.b.54.o; F.708.b.54.o;
F.709.b.54.o; F.710.b.54.o; F.711.b.54.o; F.712.b.54.o; F.713.b.54.o; F.714.b.54.o;
F.715.b.54.o; F.716.b.54.o; F.717.b.54.o; F.718.b.54.o; F.719.b.54.o; F.720.b.54.o;
F.721.b.54.o; F.722.b.54.o; F.723.b.54.o; F.724.b.54.o; F.172.x.54.i; F.173.x.54.i;

TABLE 6-continued

Exemplary Enumerated Compounds

F.174.x.54.i; F.175.x.54.i; F.176.x.54.i; F.188.x.54.i; F.189.x.54.i; F.190.x.54.i;
F.196.x.54.i; F.202.x.54.i; F.205.x.54.i; F.206.x.54.i; F.207.x.54.i; F.208.x.54.i;
F.209.x.54.i; F.210.x.54.i; F.211.x.54.i; F.212.x.54.i; F.213.x.54.i; F.700.x.54.i;
F.701.x.54.i; F.702.x.54.i; F.703.x.54.i; F.704.x.54.i; F.705.x.54.i; F.706.x.54.i;
F.707.x.54.i; F.708.x.54.i; F.709.x.54.i; F.710.x.54.i; F.711.x.54.i; F.712.x.54.i;
F.713.x.54.i; F.714.x.54.i; F.715.x.54.i; F.716.x.54.i; F.717.x.54.i; F.718.x.54.i;
F.719.x.54.i; F.720.x.54.i; F.721.x.54.i; F.722.x.54.i; F.723.x.54.i; F.724.x.54.i; F.3.x.54.o;
F.4.x.54.o; F.7.x.54.o; F.9.x.54.o; F.103.x.54.o; F.106.x.54.o; F.107.x.54.o; F.108.x.54.o;
F.111.x.54.o; F.114.x.54.o; F.117.x.54.o; F.118.x.54.o; F.119.x.54.o; F.120.x.54.o;
F.121.x.54.o; F.137.x.54.o; F.138.x.54.o; F.139.x.54.o; F.140.x.54.o; F.141.x.54.o;
F.142.x.54.o; F.145.x.54.o; F.146.x.54.o; F.147.x.54.o; F.148.x.54.o; F.149.x.54.o;
F.150.x.54.o; F.151.x.54.o; F.165.x.54.o; F.166.x.54.o; F.167.x.54.o; F.168.x.54.o;
F.169.x.54.o; F.170.x.54.o; F.171.x.54.o; F.172.x.54.o; F.173.x.54.o; F.174.x.54.o;
F.175.x.54.o; F.176.x.54.o; F.188.x.54.o; F.189.x.54.o; F.190.x.54.o; F.196.x.54.o;
F.202.x.54.o; F.205.x.54.o; F.206.x.54.o; F.207.x.54.o; F.208.x.54.o; F.209.x.54.o;
F.210.x.54.o; F.211.x.54.o; F.212.x.54.o; F.213.x.54.o; F.700.x.54.o; F.701.x.54.o;
F.702.x.54.o; F.703.x.54.o; F.704.x.54.o; F.705.x.54.o; F.706.x.54.o; F.707.x.54.o;
F.708.x.54.o; F.709.x.54.o; F.710.x.54.o; F.711.x.54.o; F.712.x.54.o; F.713.x.54.o;
F.714.x.54.o; F.715.x.54.o; F.716.x.54.o; F.717.x.54.o; F.718.x.54.o; F.719.x.54.o;
F.720.x.54.o; F.721.x.54.o; F.722.x.54.o; F.723.x.54.o; F.724.x.54.o; F.172.y.54.i;
F.173.y.54.i; F.174.y.54.i; F.175.y.54.i; F.176.y.54.i; F.188.y.54.i; F.189.y.54.i;
F.190.y.54.i; F.196.y.54.i; F.202.y.54.i; F.205.y.54.i; F.206.y.54.i; F.207.y.54.i;
F.208.y.54.i; F.209.y.54.i; F.210.y.54.i; F.211.y.54.i; F.212.y.54.i; F.213.y.54.i;
F.700.y.54.i; F.701.y.54.i; F.702.y.54.i; F.703.y.54.i; F.704.y.54.i; F.705.y.54.i;
F.706.y.54.i; F.707.y.54.i; F.708.y.54.i; F.709.y.54.i; F.710.y.54.i; F.711.y.54.i;
F.712.y.54.i; F.713.y.54.i; F.714.y.54.i; F.715.y.54.i; F.716.y.54.i; F.717.y.54.i;
F.718.y.54.i; F.719.y.54.i; F.720.y.54.i; F.721.y.54.i; F.722.y.54.i; F.723.y.54.i;
F.724.y.54.i; F..3.y.54.o; F.4.y.54.o; F.7.y.54.o; F.9.y.54.o; F.103.y.54.o; F.106.y.54.o;
F.107.y.54.o; F.108.y.54.o; F.111.y.54.o; F.114.y.54.o; F.117.y.54.o; F.118.y.54.o;
F.119.y.54.o; F.120.y.54.o; F.121.y.54.o; F.137.y.54.o; F.138.y.54.o; F.139.y.54.o;
F.140.y.54.o; F.141.y.54.o; F.142.y.54.o; F.145.y.54.o; F.146.y.54.o; F.147.y.54.o;
F.148.y.54.o; F.149.y.54.o; F.150.y.54.o; F.151.y.54.o; F.165.y.54.o; F.166.y.54.o;
F.167.y.54.o; F.168.y.54.o; F.169.y.54.o; F.170.y.54.o; F.171.y.54.o; F.172.y.54.o;
F.173.y.54.o; F.174.y.54.o; F.175.y.54.o; F.176.y.54.o; F.188.y.54.o; F.189.y.54.o;
F.190.y.54.o; F.196.y.54.o; F.202.y.54.o; F.205.y.54.o; F.206.y.54.o; F.207.y.54.o;
F.208.y.54.o; F.209.y.54.o; F.210.y.54.o; F.211.y.54.o; F.212.y.54.o; F.213.y.54.o;
F.700.y.54.o; F.701.y.54.o; F.702.y.54.o; F.703.y.54.o; F.704.y.54.o; F.705.y.54.o;
F.706.y.54.o; F.707.y.54.o; F.708.y.54.o; F.709.y.54.o; F.710.y.54.o; F.711.y.54.o;
F.712.y.54.o; F.713.y.54.o; F.714.y.54.o; F.715.y.54.o; F.716.y.54.o; F.717.y.54.o;
F.718.y.54.o; F.719.y.54.o; F.720.y.54.o; F.721.y.54.o; F.722.y.54.o; F.723.y.54.o;
F.724.y.54.o; F.172.z.54.i; F.173.z.54.i; F.174.z.54.i; F.175.z.54.i; F.176.z.54.i;
F.188.z.54.i; F.189.z.54.i; F.190.z.54.i; F.196.z.54.i; F.202.z.54.i; F.205.z.54.i;
F.206.z.54.i; F.207.z.54.i; F.208.z.54.i; F.209.z.54.i; F.210.z.54.i; F.211.z.54.i;
F.212.z.54.i; F.213.z.54.i; F.700.z.54.i; F.701.z.54.i; F.702.z.54.i; F.703.z.54.i;
F.704.z.54.i; F.705.z.54.i; F.706.z.54.i; F.707.z.54.i; F.708.z.54.i; F.709.z.54.i;
F.710.z.54.i; F.711.z.54.i; F.712.z.54.i; F.713.z.54.i; F.714.z.54.i; F.715.z.54.i;
F.716.z.54.i; F.717.z.54.i; F.718.z.54.i; F.719.z.54.i; F.720.z.54.i; F.721.z.54.i;
F.722.z.54.i; F.723.z.54.i; F.724.z.54.i; F.3.z.54.o; F.4.z.54.o; F.7.z.54.o; F.9.z.54.o;
F.103.z.54.o; F.106.z.54.o; F.107.z.54.o; F.108.z.54.o; F.11.z.54.o; F.114.z.54.o;
F.117.z.54.o; F.118.z.54.o; F.119.z.54.o; F.120.z.54.o; F.121.z.54.o; F.137.z.54.o;
F.138.z.54.o; F.139.z.54.o; F.140.z.54.o; F.141.z.54.o; F.142.z.54.o; F.145.z.54.o;
F.146.z.54.o; F.147.z.54.o; F.148.z.54.o; F.149.z.54.o; F.150.z.54.o; F.151.z.54.o;
F.165.z.54.o; F.166.z.54.o; F.167.z.54.o; F.168.z.54.o; F.169.z.54.o; F.170.z.54.o;
F.171.z.54.o; F.172.z.54.o; F.173.z.54.o; F.174.z.54.o; F.175.z.54.o; F.176.z.54.o;
F.188.z.54.o; F.189.z.54.o; F.190.z.54.o; F.196.z.54.o; F.202.z.54.o; F.205.z.54.o;
F.206.z.54.o; F.207.z.54.o; F.208.z.54.o; F.209.z.54.o; F.210.z.54.o; F.211.z.54.o;
F.212.z.54.o; F.213.z.54.o; F.700.z.54.o; F.701.z.54.o; F.702.z.54.o; F.703.z.54.o;
F.704.z.54.o; F.705.z.54.o; F.706.z.54.o; F.707.z.54.o; F.708.z.54.o; F.709.z.54.o;
F.710.z.54.o; F.711.z.54.o; F.712.z.54.o; F.713.z.54.o; F.714.z.54.o; F.715.z.54.o;
F.716.z.54.o; F.717.z.54.o; F.718.z.54.o; F.719.z.54.o; F.720.z.54.o; F.721.z.54.o;
F.722.z.54.o; F.723.z.54.o; F.724.z.54.o; F.172.A.54.i; F.173.A.54.i; F.174.A.54.i;
F.175.A.54.i; F.176.A.54.i; F.188.A.54.i; F.189.A.54.i; F.190.A.54.i; F.196.A.54.i;
F.202.A.54.i; F.205.A.54.i; F.206.A.54.i; F.207.A.54.i; F.208.A.54.i; F.209.A.54.i;
F.210.A.54.i; F.211.A.54.i; F.212.A.54.i; F.213.A.54.i; F.700.A.54.i; F.701.A.54.i;
F.702.A.54.i; F.703.A.54.i; F.704.A.54.i; F.705.A.54.i; F.706.A.54.i; F.707.A.54.i;
F.708.A.54.i; F.709.A.54.i; F.710.A.54.i; F.711.A.54.i; F.712.A.54.i; F.713.A.54.i;
F.714.A.54.i; F.715.A.54.i; F.716.A.54.i; F.717.A.54.i; F.718.A.54.i; F.719.A.54.i;
F.720.A.54.i; F.721.A.54.i; F.722.A.54.i; F.723.A.54.i; F.724.A.54.i; F.3.A.54.o
F.4.A.54.o; F.7.A.54.o; F.9.A.54.o; F.103.A.54.o; F.106.A.54.o; F.107.A.54.o;
F.108.A.54.o; F.111.A.54.o; F.114.A.54.o; F.117.A.54.o; F.118.A.54.o; F.119.A.54.o;
F.120.A.54.o; F.121.A.54.o; F.137.A.54.o; F.138.A.54.o; F.139.A.54.o; F.140.A.54.o;
F.141.A.54.o; F.142.A.54.o; F.145.A.54.o; F.146.A.54.o; F.147.A.54.o; F.148.A.54.o;
F.149.A.54.o; F.150.A.54.o; F.151.A.54.o; F.165.A.54.o; F.166.A.54.o; F.167.A.54.o;
F.168.A.54.o; F.169.A.54.o; F.170.A.54.o; F.171.A.54.o; F.172.A.54.o; F.173.A.54.o;
F.174.A.54.o; F.175.A.54.o; F.176.A.54.o; F.188.A.54.o; F.189.A.54.o; F.190.A.54.o;
F.196.A.54.o; F.202.A.54.o; F.205.A.54.o; F.206.A.54.o; F.207.A.54.o; F.208.A.54.o;
F.209.A.54.o; F.210.A.54.o; F.211.A.54.o; F.212.A.54.o; F.213.A.54.o; F.700.A.54.o;

TABLE 6-continued

Exemplary Enumerated Compounds

F.701.A.54.o; F.702.A.54.o; F.703.A.54.o; F.704.A.54.o; F.705.A.54.o; F.706.A.54.o;
F.707.A.54.o; F.708.A.54.o; F.709.A.54.o; F.710.A.54.o; F.711.A.54.o; F.712.A.54.o;
F.713.A.54.o; F.714.A.54.o; F.715.A.54.o; F.716.A.54.o; F.717.A.54.o; F.718.A.54.o;
F.719.A.54.o; F.720.A.54.o; F.721.A.54.o; F.722.A.54.o; F.723.A.54.o; F.724.A.54.o;
F.172.B.54.i; F.173.B.54.i; F.174.B.54.i; F.175.B.54.i; F.176.B.54.i; F.188.B.54.i;
F.189.B.54.i; F.190.B.54.i; F.196.B.54.i; F.202.B.54.i; F.205.B.54.i; F.206.B.54.i;
F.207.B.54.i; F.208.B.54.i; F.209.B.54.i; F.210.B.54.i; F.211.B.54.i; F.212.B.54.i;
F.213.B.54.i; F.700.B.54.i; F.701.B.54.i; F.702.B.54.i; F.703.B.54.i; F.704.B.54.i;
F.705.B.54.i; F.706.B.54.i; F.707.B.54.i; F.708.B.54.i; F.709.B.54.i; F.710.B.54.i;
F.711.B.54.i; F.712.B.54.i; F.713.B.54.i; F.714.B.54.i; F.715.B.54.i; F.716.B.54.i;
F.717.B.54.i; F.718.B.54.i; F.719.B.54.i; F.720.B.54.i; F.721.B.54.i; F.722.B.54.i;
F.723.B.54.i; F.724.B.54.i; F.3.B.54.o; F.4.B.54.o; F.7.B.54.o; F.9.B.54.o; F.103.B.54.o;
F.106.B.54.o; F.107.B.54.o; F.108.B.54.o; F.111.B.54.o; F.114.B.54.o; F.117.B.54.o;
F.118.B.54.o; F.119.B.54.o; F.120.B.54.o; F.121.B.54.o; F.137.B.54.o; F.138.B.54.o;
F.139.B.54.o; F.140.B.54.o; F.141.B.54.o; F.142.B.54.o; F.145.B.54.o; F.146.B.54.o;
F.147.B.54.o; F.148.B.54.o; F.149.B.54.o; F.150.B.54.o; F.151.B.54.o; F.165.B.54.o;
F.166.B.54.o; F.167.B.54.o; F.168.B.54.o; F.169.B.54.o; F.170.B.54.o; F.171.B.54.o;
F.172.B.54.o; F.173.B.54.o; F.174.B.54.o; F.175.B.54.o; F.176.B.54.o; F.188.B.54.o;
F.189.B.54.o; F.190.B.54.o; F.196.B.54.o; F.202.B.54.o; F.205.B.54.o; F.206.B.54.o;
F.207.B.54.o; F.208.B.54.o; F.209.B.54.o; F.210.B.54.o; F.211.B.54.o; F.212.B.54.o;
F.213.B.54.o; F.700.B.54.o; F.701.B.54.o; F.702.B.54.o; F.703.B.54.o; F.704.B.54.o;
F.705.B.54.o; F.706.B.54.o; F.707.B.54.o; F.708.B.54.o; F.709.B.54.o; F.710.B.54.o;
F.711.B.54.o; F.712.B.54.o; F.713.B.54.o; F.714.B.54.o; F.715.B.54.o; F.716.B.54.o;
F.717.B.54.o; F.718.B.54.o; F.719.B.54.o; F.720.B.54.o; F.721.B.54.o; F.722.B.54.o;
F.723.B.54.o; F.724.B.54.o.

Salts and Hydrates

The compositions of this invention optionally comprise salts of the compounds herein, especially pharmaceutically acceptable non-toxic salts containing, for example, $Na^+$, $Li^+$, $K^+$, $Ca^{++}$ and $Mg^{++}$. Such salts may include those derived by combination of appropriate cations such as alkali and alkaline earth metal ions or ammonium and quaternary amino ions with an acid anion moiety, typically the $W_1$ group carboxylic acid. Monovalent salts are preferred if a water soluble salt is desired.

Metal salts typically are prepared by reacting the metal hydroxide with a compound of this invention. Examples of metal salts which are prepared in this way are salts containing $Li^+$, $Na^+$, and $K^+$. A less soluble metal salt can be precipitated from the solution of a more soluble salt by addition of the suitable metal compound.

In addition, salts may be formed from acid addition of certain organic and inorganic acids, e.g., HCl, HBr, $H_2SO_4$, $H_3PO_4$, or organic sulfonic acids, to basic centers, typically amines of group $G_1$, or to acidic groups such as $E_1$. Finally, it is to be understood that the compositions herein comprise compounds of the invention in their un-ionized, as well as zwitterionic form, and combinations with stoiochimetric amounts of water as in hydrates.

Also included within the scope of this invention are the salts of the parental compounds with one or more amino acids. Any of the amino acids described above are suitable, especially the naturally-occurring amino acids found as protein components, although the amino acid typically is one bearing a side chain with a basic or acidic group, e.g., lysine, arginine or glutamic acid, or a neutral group such as glycine, serine, threonine, alanine, isoleucine, or leucine.

Methods of Inhibition of Neuraminidase

Another aspect of the invention relates to methods of inhibiting the activity of neuraminidase comprising the step of treating a sample suspected of containing neuraminidase with a compound of the invention.

Compositions of the invention act as inhibitors of neuraminidase, as intermediates for such inhibitors or have other utilities as described below. The inhibitors will bind to locations on the surface or in a cavity of neuraminidase having a geometry unique to neuraminidase. Compositions binding neuraminidase may bind with varying degrees of reversibility. Those compounds binding substantially irreversibly are ideal candidates for use in this method of the invention. In a typical embodiment the compositions bind neuraminidase with a binding coefficient of less than $10^{-4}M$, more typically less than $10^{-6}M$, still more typically $10^{-8}M$. Once labeled, the substantially irreversibly binding compositions are useful as probes for the detection of neuraminidase. Accordingly, the invention relates to methods of detecting neuraminidase in a sample suspected of containing neuraminidase comprising the steps of: treating a sample suspected of containing neuraminidase with a composition comprising a compound of the invention bound to a label; and observing the effect of the sample on the activity of the label. Suitable labels are well known in the diagnostics field and include stable free radicals, fluorophores, radioisotopes, enzymes, chemiluminescent groups and chromogens. The compounds herein are labeled in conventional fashion using functional groups such as hydroxyl or amino.

Within the context of the invention samples suspected of containing neuraminidase include natural or man-made materials such as living organisms; tissue or cell cultures; biological samples such as biological material samples (blood, serum, urine, cerebrospinal fluid, tears, sputum, saliva, tissue samples, and the like); laboratory samples; food, water, or air samples; bioproduct samples such as extracts of cells, particularly recombinant cells synthesizing a desired glycoprotein and the like. Typically the sample will be suspected of containing an organism which produces neuraminidase, frequently a pathogenic organism such as a virus. Samples can be contained in any medium including water and organic solvent/water mixtures. Samples include living organisms such as humans, and man made materials such as cell cultures.

The treating step of the invention comprises adding the composition of the invention to the sample or it comprises adding a precursor of the composition to the sample. The addition step comprises any method of administration as described above.

If desired, the activity of neuraminidase after application of the composition can be observed by any method including direct and indirect methods of detecting neuraminidase activity. Quantitative, qualitative, and semiquantitative methods of determining neuraminidase activity are all contemplated. Typically one of the screening methods described above are applied, however, any other method such as observation of the physiological properties of a living organism are also applicable.

Organisms that contain neuraminidase include bacteria (Vibrio cholerae, Clostridium perfringens, Streptococcus pneumoniae, and Arthrobacter sialophilus) and viruses (especially orthomyxoviruses or paramyxoviruses such as influenza virus A and B, parainfluenza virus, mumps virus, Newcastle disease virus, fowl plague virus, and sendai virus). Inhibition of neuraminidase activity obtained from or found within any of these organisms is within the objects of this invention. The virology of influenza viruses is described in "Fundamental Virology" (Raven Press, New York, 1986), Chapter 24. The compounds of this invention are useful in the i treatment or prophylaxis of such infections in animals, e.g. duck, rodents, or swine, or in man.

However, in screening compounds capable of inhibiting influenza viruses it should be kept in mind that the results of enzyme assays may not correlate with cell culture assays, as shown Table 1 of Chandler et al., supra. Thus, a plaque reduction assay should be the primary screening tool.

Screens for Neuraminidase Inhibitors

Some of the compounds of the invention will be selective for particular organisms such as bacterial verses viral neuraminidases or neuraminidase from influenza verses parainfluenza. These compositions are identified by routine screening.

Compositions of the invention are screened for inhibitory activity against neuraminidase by any of the conventional techniques for evaluating enzyme activity. Within the context of the invention, typically compositions are first screened for inhibition of neuraminidase in vitro and compositions showing inhibitory activity are then screened for activity in vivo. Compositions having in vitro Ki (inhibitory constants) of less then about $5\times10^{-6}$ M, typically less than about $1\times10^{-7}$ M and preferably less than about $5\times10^{-8}$ M are preferred for in vivo use.

Useful in vitro screens have been described in detail and will not be elaborated here. However, von Itzstein, M. et al. "Nature", 363(6428):418–423 (1993), in particular page 420, column 2, full paragraph 3, to page 421, column 2, first partial paragraph, describes a suitable in vitro assay of Potier, M. et al. "Analyt. Biochem.", 94:287–296 (1979), as modified by Chong, A. K. J. et al. "Biochem. Biophys. Acta", 1077:65–71 (1991); and Colman, P. M. et al. International Publication No. WO 92/06691 (Int. App. No. PCT/AU90/00501, publication date Apr. 30, 1992) page 34, line 13, to page 35, line 16, describes another useful in vitro screen.

In vivo screens have also been described in detail, see von Itzstein, M. et al. op. cit., in particular page 421, column 2, first full paragraph, to page 423, column 2, first partial paragraph, and Colman, P. M. et al. op. cit. page 36, lines 1–38, describe suitable in vivo screens.

In screening assays used herein, compositions having $IC_{50}$ values greater than 1 $\mu M$ (micromolar) are considered as being inactive against influenza neuraminidase.

Pharmaceutical Formulations and Routes of Administration

The compounds of this invention are formulated with conventional carriers and excipients, which will be selected in accord with ordinary practice. Tablets will contain excipients, glidants, fillers, binders and the like. Aqueous formulations are prepared in sterile form, and when intended for delivery by other than oral administration generally will be isotonic. All formulations will optionally contain excipients such as those set forth in the "Handbook of Pharmaceutical Excipients" (1986). Excipients include ascorbic acid and other antioxidants, chelating agents such as EDTA, carbohydrates such as dextrin, hydroxyalkylcellulose, hydroxyalkylmethylcellulose, stearic acid and the like. The pH of the formulations ranges from about 3 to about 11, but is ordinarily about 7 to 10.

One or more compounds of the invention (herein referred to as the active ingredients) are administered by any route appropriate to the condition to be treated. Suitable routes include oral, rectal, nasal, topical (including buccal and sublingual), vaginal and parenteral (including subcutaneous, intramuscular, intravenous, intradermal, intrathecal and epidural), and the like. It will be appreciated that the preferred route may vary with for example the condition of the recipient. An advantage of the compounds of this invention is that they are orally bioavailable and can be dosed orally; it is not necessary to administer them by intrapulmonary or intranasal routes.

While it is possible for the active ingredients to be administered alone it may be preferable to present them as pharmaceutical formulations. The formulations, both for veterinary and for human use, of the invention comprise at least one active ingredient, as above defined, together with one or more acceptable carriers therefor and optionally other therapeutic ingredients. The carrier(s) must be "acceptable" in the sense of being compatible with the other ingredients of the formulation and physiologically innocuous to the recipient thereof.

The formulations include those suitable for the foregoing administration routes. The formulations may conveniently be presented in unit dosage form and may be prepared by any of the methods well known in the art of pharmacy. Techniques and formulations generally are found in Remington's Pharmaceutical Sciences (Mack Publishing Co., Easton, Pa.). Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of the invention suitable for oral administration are prepared as discrete units such as capsules, cachets or tablets each containing a predetermined amount of the active ingredient; as a powder or granules; as solution or a suspension in an aqueous liquid or a non-aqueous liquid; or as an oil-in-water liquid emulsion or a water-in-oil liquid emulsion. The active ingredient may also be presented as a bolus, electuary or paste.

A tablet is made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom. In one embodiment acid hydrolysis of the medicament is obviated by use of an enteric coating.

For infections of the eye or other external tissues e.g. mouth and skin, the formulations are preferably applied as a topical ointment or cream containing the active ingredient (s) in an amount of, for example, 0.075 to 20% w/w (including active ingredient(s) in a range between 0.1% and 20% in increments of 0.1% w/w such as 0.6% w/w, 0.7% w/w, etc.), preferably 0.2 to 15% w/w and most preferably 0.5 to 10% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include, for example, at least 30% w/w of a polyhydric alcohol, i.e. an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulphoxide and related analogs.

The oily phase of the emulsions of this invention may be constituted from known ingredients in a known manner. While the phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations.

Emulgents and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

The choice of suitable oils or fats for the formulation is based on achieving the desired cosmetic properties. The cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils are used.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of 0.5 to 20%, advantageously 0.5 to 10% particularly about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 microns (including particle sizes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis of influenza A or B infections as described below.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations are presented in unit-dose or multi-dose containers, for example sealed ampoules and vials, and may be stored in a freeze-dried (lyophilized) condition requiring only the addition of the sterile liquid carrier, for example water for injection, immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

It should be understood that in addition to the ingredients particularly mentioned above the formulations of this invention may include other agents conventional in the art having regard to the type of formulation in ari question, for example those suitable for oral administration may include flavoring agents.

The invention further provides veterinary compositions comprising at least one active ingredient as above defined together with a veterinary carrier therefor.

Veterinary carriers are materials useful for the purpose of administering the composition and may be solid, liquid or gaseous materials which are otherwise inert or acceptable in the veterinary art and are compatible with the active ingredient. These veterinary compositions may be administered orally, parenterally or by any other desired route.

Compounds of the invention are used to provide controlled release pharmaceutical formulations containing as active ingredient one or more compounds of the invention ("controlled release formulations") in which the release of the active ingredient are controlled and regulated to allow less frequency dosing or to improve the pharmacokinetic or toxicity profile of a given active ingredient.

Effective dose of active ingredient depends at least on the nature of the condition being treated, toxicity, whether the compound is being used prophylactically (lower doses) or against an active influenza infection, the method of delivery, and the pharmaceutical formulation, and will be determined by the clinician using conventional dose escalation studies. It can be expected to be from about 0.0001 to about 100 mg/kg body weight per day. Typically, from about 0.01 to about 10 mg/kg body weight per day. More typically, from about 0.01 to about 5 mg/kg body weight per day. More typically, from about 0.05 to about 0.5 mg/kg body weight per day. For example, for inhalation the daily candidate dose for an adult human of approximately 70 kg body weight will range from 1 mg to 1000 mg, preferably between 5 mg and 500 mg, and may take the form of single or multiple doses.

Active ingredients of the invention are also used in combination with other active ingredients. Such combinations are selected based on the condition to be treated, cross-reactivities of ingredients and pharmaco-properties of the combination. For example, when treating viral infections of the respiratory system, in particular influenza infection, the compositions of the invention are combined with anti-virals (such as amantidine, rimantadine and ribavirin), mucolytics, expectorants, bronchialdilators, antibiotics, antipyretics, or analgesics. Ordinarily, antibiotics, antipyretics, and analgesics are administered together with the compounds of this invention.

Enteric Protection

Another embodiment of the present invention is directed toward enteric protected forms of the compounds of the invention. As used herein the term "enteric protection" means protecting a compound of the invention in order to avoid exposing a portion of the gastrointestinal tract, typically the upper gastrointestinal tract, in particular the stomach and esophagus, to the compound of this invention. In this way gastric mucosal tissue is protected against rates of exposure to a compound of the invention which produce adverse effects such as nausea; and, alternatively, a compound of the invention is protected from conditions present in one or more portions of the gastrointestinal tract, typically the upper gastrointestinal tract.

By way of example and not limitation, such enterically protected forms include enteric coated vehicles, such as enteric coated tablets, enteric coated granules, enteric coated beads, enteric coated particles, enteric coated microparticles, and enteric coated capsules. In preferred embodiments, a compound of the invention is placed in a suitable vehicle such as a tablet, granule or capsule, and the vehicle is coated with a pharmaceutically acceptable enteric coating. In alternative preferred embodiments, a compound of the invention is prepared as enterically protected granules, particles, microparticles, spheres, microspheres, or colloids, and the enteric protected granules, particles, microparticles, spheres, microspheres, or colloids, are prepared as pharmaceutically acceptable dosage forms such as tablets, granules, capsules, or suspensions.

One aspect of the invention is directed to enteric-coated dosage forms of the compounds of the invention to effect delivery to the intestine of a human or other mammal, preferably to the small intestine, of a pharmaceutical composition comprised of a therapeutically effective amount of about 0.1–1000 mg of an active ingredient and optional pharmaceutically acceptable excipients.

The term "vehicle" as used herein includes pharmaceutically acceptable dose vehicles. Many vehicles are well known in the art cited herein such as tablet, coated tablet, capsule, hard capsule, soft gelatin capsule, particle, microparticle, sphere, microsphere, colloid, microencapsulationed, sustained release, semisolid, suppository or granule vehicles.

The term "pharmaceutically-acceptable excipients" as used herein includes any physiologically inert, pharmacologically inactive material known to one skilled in the art, which is compatible with the physical and chemical characteristics of the particular compound of the invention selected for use. These excipients are described elsewhere herein. The excipients may, but need not, provide enteric protection.

The term "unit dose" is used herein in the conventional sense to mean a single application or administration of the compound of this invention to the subject being treated in an amount as stated below. It should be understood that a therapeutic or prophylactic dosage can be given in one unit dose, or alternatively, in multiples of two or more of such dose units with the total adding up to the desired amount of compound for a given time period.

In general, the oral unit dosage form compositions of this invention, preferably employ from about 1 to about 1000 milligrams (mg), typically, about 10 to 500 mg, more typically from about 50 to about 300 mg, more typically yet, 75 mg of the compound for each unit dose. The actual amount will vary depending upon the active compound selected.

In typical embodiments, an enteric protectant is applied to the vehicle containing the compound, or to the compound without vehicle, the protectant prevents nausea inducing exposure, contact or rates of exposure of the mouth, esophagus or stomach with the compound, but which releases the compound for absorption when the dosage form passes into the proximal portion of the lower gastrointestinal tract, or in some embodiments, substantially only in the colon.

The relative proportions of the protectant and compound of the invention are varied to achieve optimum absorption depending on the compound selected. The minimum or maximum amount of enteric protectant by weight percent is not critical. Typically, enteric protected embodiments contain less than about 50% enteric coating by weight. More typically about 1% to about 25%, still more typically, about 1% to about 15%, more typically yet, about 1% to about 10% (all by weight).

Related Art:

A number of monographs describe enteric protection and related technology. Such monographs include: "Theory and Practice of Industrial Pharmacy," 3rd ed. Lea & Febiger, Philadelphia, 1986 (ISBN 0-8121-0977-5); Lehmann, K.; "Practical Course in Laquer Coating,", Eudragit, 1989; Lieberman; Lachman, L.; Schwartz, "Pharmaceutical Dosage Forms: Tablets", 1990, Dekker (ISBN: 0-8247-8289-5); Lee, Ping I. Editor Good, William R. Editor, "Controlled-Release Technology: Pharmaceutical Applications", ACS Symposium Ser.Vol. 348 (ISBN: 0-608-03871-7); Wilson, Billie E., Shannon, Margaret T., "Dosage Calculation: A Simplified Approach", 1996, Appleton & Lange (ISBN: 0-8385-9297-X); Lieberman, Herbert A. Editor Rieger, Martin M., "Pharmaceutical Dosage Forms—Disperse Systems", 1996, Dekker (ISBN: 0-8247-9387-0); "Basic Tests for Pharmaceutical Dosage Forms", 1995, World Health (ISBN: 92-4-154418-X); Karsa, D. R., Editor; Stephenson, R. A., Editor, "Excipients & Delivery Systems for Pharmaceutical Formulations: Proceedings of the "Formulate '94" British Association for Chemical Specialties Symposium", 1995, CRC Pr (ISBN: 0-85404-715-8); Ansel, Howard C.; Popovich, Nicholas G.; Allen, Lloyd V., "Pharmaceutical Dosage Forms & Drug Delivery Systems, 6th ed.", 1994, Williams & Wilkins (ISBN: 0-683-01930-9); "The Sourcebook for Innovative Drug Delivery: Manufacturers of Devices & Pharmaceuticals, Suppliers of Products & Services, Sources of Information", 1987, Canon Cornns (ISBN: 0-9618649-0-7); Chiellini, E., Editor; Giusti, G., Editor; Migliaresi, C., Editor; Nicolais, L., Editor, "Polymers in Medicine II: Biomedical & Pharmaceutical Applications", 1986, Plenum (ISBN: 0-306-42390-1); "Pharmaceutical Aerosol: A Drug Delivery System in Transition", 1994, Technomic (ISBN: 0-87762-971-4); Avid; Lieberman, L.; Lachman, "Pharmaceutical Dosage Forms: Parenteral Medication, 2nd Expanded; Revised ed.", 1992, Dekker (ISBN: 0-8247-9020-0); Laffer, U., Editor; Bachmann, I., Editor; Metzger, U., Editor, "Implantable Drug Delivery Systems", 1991, S Karger (ISBN: 3-8055-5434-6); Borchardt, Ronald T., Editor; Repta, Arnold J., Editor; Stella, Valentino J., Editor, "Directed Drug Delivery: A Multidisciplinary Approach", 1985, Humana (ISBN: 0-89603-089-X); Anderson, James M., Editor, "Advances in Drug Delivery Systems 5: Proceedings of the Fifth International Symposium on Recent Advances in Drug Delivery Systems, Salt Lake City, UT, U. S. A., Feb. 25–28, 1991", Elsevier (ISBN: 0-444-88664-8); Turco, Salvatore J.; King, Robert E., "Sterile Dosage Forms: Their Preparation & Clinical Application", 1987, Williams & Wilkins (ISBN: 0-8121-1067-6); Tomlinson, E., Editor; Davis, S. S., Editor, "Site—Specific Drug Delivery: Cell Biology, Medical & Pharmaceutical Aspects", 1986, Wiley (ISBN: 0-471-91236-0); Hess, H., Editor, "Pharmaceutical Dosage Forms & Their Use", 1986, Hogrefe & Huber Pubs (ISBN: 3-456-81422-4); Avis; Lieberman; Lachman, "Pharmaceutical Dosage Forms, Vol. 2", 1986, Dekker (ISBN: 0-8247-7085-4); Carstensen, Jens T., "Pharmaceutics of Solids & Solid Dosage Forms", 1977, Wiley (ISBN: 0-471-13726-X); Robinson, Joseph R., Editor, "Ophthalmic Drug Delivery Systems", 1980, Am Pharm Assn (ISBN: 0-917330-32-3); Ansel, Howard C., "Introduction to Pharmaceutical Dosage Forms, 4th ed.", 1985, Williams & Wilkins (ISBN: 0-8121-0956-2); "High Tech Drug Delivery Systems", 1984, Intl Res Dev (ISBN: 0-88694-622-0); Swarbrick, James, "Current Concepts in Pharmaceutical Sciences: Dosage Form Design & Bioavailability", 1985, Lea & Febiger (ISBN: 0-318-79917-0); Sprowls, Joseph B., Editor, "Prescription Pharmacy: Dosage Formulation & Pharmaceutical Adjuncts, 2nd ed.", 1970, Lippincott (ISBN: 0-397-52050-6); and Polderman, J., Editor, "Formulation & Preparation of Dosage Forms: Proceedings of the 37th International Congress of Pharmaceutical Sciences of F.I.P., The Hague, Netherlands, September, 1977", Elsevier (ISBN: 0-444-80033-6).

Specific Embodiments:

In another embodiment, the inventive composition is in the form of an enteric coated tablet dosage form. In this embodiment, the formulation is formed into a hard tablet by conventional means and the tablet is coated with the enteric coating in accordance with conventional techniques.

In a preferred embodiment, the inventive compound is in the form of an enteric coated powder dosage form. In this embodiment, the formulation is filled into a hard or soft-shell capsule or their equivalent and the capsule is coated with the enteric coating in accordance with conventional techniques.

In one embodiment the inventive composition is in the form of a liquid suspension of enteric coated particles of a compound of the invention. In this embodiment, a suspension of the inhibitor in a liquid is filled into a hard or soft-shell capsule or their equivalent and the capsule is coated with the enteric coating in accordance with conventional techniques.

As alternatives to the foregoing embodiments the capsule or other dosage container is itself constructed of an enteric protection reagent or component, or otherwise is integral to the container.

In another embodiment enteric protectants are used to administer a compound of the invention to the colon. The delivery system is a tablet comprised of three layers: 1) a core containing the active compound of the invention; 2) a non-swelling, erodible polymer layer surrounding the core (with the combination of core and erodible polymer layer being referred to as the "dual matrix tablet"); and 3) an enteric coating applied to the dual matrix tablet. The composition and function of the components of such a colon targeted delivery system are further described in U.S. Pat. No. 5,482,718, which is incorporated herein by reference in its entirety at this location, in particular column 2, line 29, to column 4, line 12, are incorporated herein with specificity.

Another embodiment of the invention is directed toward enteric protected emulsion, suspension, tablet, coated tablet, hard capsule, soft gelatin capsule, microencapsulation, sustained release, liquid, semisolid, suppositories and aerosol dosage forms of the compounds of the invention. "Theory and Practice of Industrial Pharmacy," 3rd ed. Lea & Febiger, Philadelphia, 1986 (ISBN 0-8121-0977-5), describes each of these standard dosage forms in detail at the following locations: emulsion and suspension dosage forms (pp. 100–122), tablets (pp. 293–345), coated tablet (pp. 346–373), hard capsules (pp. 374–397), soft gelatin capsules (pp. 398–411), microencapsulation (pp. 412–430), sustained release dosage forms (pp. 430–456), liquids (pp. 457–478), pharmaceutical suspensions (pp. 479–501), emulsions (pp. 502–533), semisolids (pp. 534–563), suppositories (pp. 564–587), and pharmaceutical aerosols (pp. 589–618).

Alternative embodiments include enteric protected sustained release, controlled release, particulate, microencapsulated, multiparticulate, microparticulate, colloidal, nasal, inhalation, oral mucosal, colonic, dermal, transdermal, ocular, topical, and veterinary dosage forms of the compounds of the invention. Each of these dosage form technologies is described in detail in "Drugs and the Pharmaceutical Sciences", Edited by James Swarbrick, Marcel Dekker, New York.

Materials:

Conventional enteric protectant polymers or mixtures of polymers for use herein include insoluble at a pH below about 5.5, i.e., that which is generally found in the stomach, but are soluble at pH about 5.5 or above, i.e., that present in the small intestine and the large intestine. The effectiveness of particular enteric protectant materials can be measured using known USP procedures.

Exemplary enteric protectant polymers employable in this embodiment include cellulose acetate phthalate, methyl acrylate-methacrylic acid copolymers, cellulose acetate succinate, hydroxypropylmethylcellulose phthalate, polyvinyl acetate phthalate, and methyl methacrylate-methacrylic acid copolymers. Another example is an anionic carboxylic copolymers based on methacrylic acid and methacrylate, commercially available as Eudragit(r). Typical examples include cellulose acetate phthalate ("CAP"), cellulose acetate trimellitate, hydroxypropyl methylcellulose phthalate ("HPMCP"), hydroxypropyl methylcellulose phthalate succinate, polyvinyl acetate phthalate ("PVAP"), methacrylic acid, and methacrylic acid esters. More typically the protectant is selected from, PVAP and/or HPMCP, particularly PVAP. PVAP is known under the trademark Sureteric (r), manufactured by Colorcon, Inc.

The enteric protectant materials may be applied to the vehicle with or without conventional plasticizers, such as acetylated mono glycerides, propylene glycol, glycerol, glyceryl triacetate, polyethylene glycol, triethyl citrate, tributyl citrate, diethyl phthalate, or dibutyl phthalate using methods known to those skilled in the art.

Exemplary Embodiments of Enteric Protection:

Embodiment 1

Enteric Protected A.141.x.4.i Capsules

In this exemplary embodiment, compound A.141.x.4.i, phosphate salt form, 100 mg/capsule, is mixed with Croscarmellose Sodium (2.6 mg/capsule) in a size 4 white opaque hard gelatin capsule shells (capsule composition: gelatin NF, titanium dioxide USP) and the capsule is enterically coated.

The following enteric coating formulations are applied to the capsule by rocedures known to those in the art.

| Ingredients | % w/w |
| --- | --- |
| Preparation A: | |
| Hydroxypropyl methylcellulose phthalate ("HPMCP") | 5.0 |
| Triacetin | 0.5 |
| Alcohol USP | 7.9 |
| Water | 15.5 |
| Preparation B: | |
| HPMCP | 10.0 |
| Titanium dioxide | 0.2 |
| Dimethyl polysiloxane | 0.05 |
| Triethyl citrate | 1.0 |
| Alcohol USP | 72.75 |
| Water | 16.00 |
| Preparation C: | |
| Cellulose acetate phthalate ("CAP") | 8.5 |
| Diethyl phthalate | 1.5 |
| Titanium dioxide | 0.2 |
| Acetone | 44.9 |
| Denatured alcohol | 44.9 |
| Preparation D: | |
| Polyvinyl acetate phthalate ("PVAP") | 5.0 |
| Acetylated glycerides | 0.8 |
| Methylene chloride | 47.1 |
| Denatured alcohol | 47.1 |
| Preparation E: | |
| Methacrylic acid or methacrylic acid ester (Eudragit (r) S or L, manufactured by Rohm Pharma, GMBH, Wetterstadt, West Germany) | 8.0 |
| Acetone | 46.0 |
| Anhydrous alcohol | 46.0 |
| Plasticizer | q.s. |

Typically the enteric polymer (with or without plasticizer) is dissolved in the solvents described under each formulation to form a suspension/solution. Optionally, an opacifer such as titanium dioxide is added. The vehicle is sprayed with the coating suspension/solution in a suitable vessel under conditions such that an enterically-protected coating is laid down on the vehicle without dissolving or disrupting the vehicle. Approximately 1–50%, typically 1–15%, more typically, 5–10% by weight of the finished coated vehicle of the enteric polymer coating will be useful for adequate enteric protection.

Embodiment 2

Enteric Protected Tablet

In another exemplary embodiment a core tablet is encased within an enteric coating. Optionally, a subcoating is used.

Core Tablets:

Core tablets of the present invention may be formed by combining (a) the active ingredient with pharmaceutically-acceptable excipients in a mixture including for example: a diluent, a binder, a disintegrant, and optionally one or more ingredients selected from a group consisting of: compression aids, flavors, flavor enhancers, sweeteners, dyes, pigments, buffer systems, and preservatives; (b) lubricating the mixture with a lubricant; and (c) compressing the resultant lubricated mixture into a desired tablet form using various tableting techniques available to those skilled in the art. The term "tablet" as used herein is intended to encompass compressed or formed pharmaceutical dosage formulations of all shapes and sizes.

Typical diluents employable in this embodiment include lactose or microcrystalline cellulose.

Typical binders employable in this embodiment include, but are not limited to, povidone. Povidone is available under the trade name "Avicel" from ISP Corporation.

The disintegrant may be one of several modified starches, or modified cellulose polymers. Typically, croscarmellose sodium is used. Croscarmellose sodium NF Type A is commercially available under the trade name "Ac-di-sol".

Typical lubricants include magnesium stearate, stearic acid, hydrogenated vegetable oil or talc.

Flavoring agents include those described in Remington's Pharmaceutical Sciences, 18th Edition, Mack Publishing Company, 1990, pp. 1288–1300.

Typical sweeteners include saccharin, Aspartame, or edible mono- or disaccharides such as glucose or sucrose.

Dyes and pigments include those described in the Handbook of Pharmaceutical Excipients, pp. 81–90, 1986 by the American Pharmaceutical Association & the Pharmaceutical Society of Great Britain.

Typical preservatives include methyl paraben, propyl paraben, cetylpyridinium chloride, and the salts thereof, sorbic acid and the salts thereof, thimerosal, or benzalkonium chloride.

Enteric Coating:

Eudragit L-30-D(r), a methacrylic acid copolymer, manufactured by Rohm Pharma GmbH, Weiterstadt, West Germany, is a suitable enteric polymer. Eudragit L-30-D(r) has a ratio of free carboxyl groups to ester groups of approximately 1:1 and is freely soluble at pH 5.5 and above. In general, the greater the percentage of Eudragit L-30-D(r) contained in the enteric coating, the more proximal the release of active in the lower gastrointestinal tract. The location in the lower gastrointestinal tract at which the coating releases the compound can be manipulated by one skilled in the art through control of the composition and thickness of the applied enteric coating.

Typically a plasticizer, such as those set forth above, is included. Other additives such as talc or silica may be used as detackifiers to improve the coating process.

Subcoating:

Optionally a stability enhancing subcoat on the core tablet is used to minimize interaction between the compound of this invention and the enteric coating. This also permits utilization of a single 10–300 micron thick enteric film without affecting product stability. This subcoat inhibits migration of active ingredient from the core tablet into the enteric coating, thus improving shelf life and product stability, but the subcoat rapidly dissolves in intestinal fluid once the exterior enteric coating has been breached.

Typical subcoating polymers employable in this embodiment include hydroxypropyl methylcellulose, hydroxypropyl cellulose, hydroxypropyl ethylcellulose, or polyvinylpyrrolidone.

Metabolites of the Compounds of the Invention

Also falling within the scope of this invention are the in vivo metabolic products of the compounds described herein, to the extent such products are novel and unobvious over the prior art. Such products may result for example from the oxidation, reduction, hydrolysis, amidation, esterification and the like of the administered compound, primarily due to enzymatic processes. Accordingly, the invention includes novel and unobvious compounds produced by a process comprising contacting a compound of this invention with a mammal for a period of time sufficient to yield a metabolic product thereof. Such products typically are identified by preparing a radiolabelled (e.g. $C^{14}$ or $H^3$) compound of the invention, administering it parenterally in a detectable dose (e.g. greater than about 0.5 mg/kg) to an animal such as rat, mouse, guinea pig, monkey, or to man, allowing sufficient time for metabolism to occur (typically about 30 seconds to hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g. by MS or NMR analysis. In general, analysis of metabolites is done in the same way as conventional drug metabolism studies well-known to those skilled in the art. The conversion products, so long as they are not otherwise found in vivo, are useful in diagnostic assays for therapeutic dosing of the compounds of the invention even if they possess no neuraminidase inhibitory activity of their own.

Additional Uses for the Compounds of This Invention

The compounds of this invention, or the biologically active substances produced from these compounds by hydrolysis or metabolism in vivo, are used as immunogens or for conjugation to proteins, whereby they serve as components of immunogenic compositions to prepare antibodies capable of binding specifically to the protein, to the compounds or to their metabolic products which retain immunologically recognized epitopes (sites of antibody binding). The immunogenic compositions therefore are useful as intermediates in the preparation of antibodies for use in diagnostic, quality control, or the like, methods or in assays for the compounds or their novel metabolic products. The compounds are useful for raising antibodies against otherwise non-immunogenic polypeptides, in that the compounds serve as haptenic sites stimulating an immune response that cross-reacts with the urmodified conjugated protein.

The hydrolysis products of interest include products of the hydrolysis of the protected acidic and basic groups discussed above. As noted above, the acidic or basic amides comprising immunogenic polypeptides such as albumin or keyhole limpet hemocyanin generally are useful as immunogens.

The metabolic products described above may retain a substantial degree of immunological cross reactivity with the compounds of the invention. Thus, the antibodies of this invention will be capable of binding to the unprotected compounds of the invention without binding to the protected compounds; alternatively the metabolic products, will be capable of binding to the protected compounds and/or the metabolitic products without binding to the protected compounds of the invention, or will be capable of binding specifically to any one or all three. The antibodies desirably will not substantially cross-react with naturally-occurring materials. Substantial cross-reactivity is reactivity under specific assay conditions for specific analytes sufficient to interfere with the assay results.

The immunogens of this invention contain the compound of this invention presenting the desired epitope in association with an immunogenic substance. Within the context of the invention such association means covalent bonding to form an immunogenic conjugate (when applicable) or a mixture of non-covalently bonded materials, or a combination of the above. Immunogenic substances include adjuvants such as Freund's adjuvant, immunogenic proteins such as viral, bacterial, yeast, plant and animal polypeptides, in particular keyhole limpet hemocyanin, serum albumin, bovine thyroglobulin or soybean trypsin inhibitor, and immunogenic polysaccharides. Typically, the compound having the structure of the desired epitope is covalently conjugated to an immunogenic polypeptide or polysaccharide by the use of a polyfunctional (ordinarily bifunctional) cross-linking agent. Methods for the manufacture of hapten immunogens are conventional per se, and any of the methods used heretofore for conjugating haptens to immunogenic polypeptides or the like are suitably employed here as well, taking into account the functional groups on the precursors or hydrolytic products which are available for cross-linking and the likelihood of producing antibodies specific to the epitope in question as opposed to the immunogenic substance.

Typically the polypeptide is conjugated to a site on the compound of the a invention distant from the epitope to be recognized.

The conjugates are prepared in conventional fashion. For example, the cross-linking agents N-hydroxysuccinimide, succinic anhydride or alkN=C=Nalk are useful in preparing the conjugates of this invention. The conjugates comprise a compound of the invention attached by a bond or a linking group of 1–100, typically, 1–25, more typically 1–10 carbon atoms to the immunogenic substance. The conjugates are separated from starting materials and by products using chromatography or the like, and then are sterile filtered and vialed for storage.

The compounds of this invention are cross-linked for example through any one or more of the following groups: a hydroxyl group of $W_6$; a carboxyl group of $E_1$; a carbon atom of $W_6$, $E_1$, $G_1$, or $T_1$, in substitution of H; and an amine group of $G_1$. Included within such compounds are amides of polypeptides where the polypeptide serves as an above-described $R_{6c}$ or $R_{6b}$ groups.

Animals are typically immunized against the immunogenic conjugates or derivatives and antisera or monoclonal antibodies prepared in conventional fashion.

The compounds of the invention are useful for maintaining the structural integrity of glycoproteins in recombinant cell culture, i.e., they are added to fermentations in which glycoproteins are being produced for recovery so as to inhibit neuraminidase-catalyzed cleavage of the desired glycoproteins. This is of particular value in the recombinant synthesis of proteins in heterologous host cells that may disadvantageously degrade the carbohydrate portion of the protein being synthesized.

The compounds of the invention are polyfunctional. As such they represent a unique class of monomers for the synthesis of polymers. By way of example and not limitation, the polymers prepared from the compounds of this invention include polyamides and polyesters.

The present compounds are used as monomers to provide access to polymers having unique pendent functionalities. The compounds of this invention are useful in homopolymers, or as comonomers with monomers which do not fall within the scope of the invention. Homopolymers of the compounds of this invention will have utility as cation exchange agents (polyesters or polyamides) in the preparation of molecular sieves (polyamides), textiles, fibers, films, formed articles and the like where the acid functionality $E_1$ is esterified to a hydroxyl group in $W_6$, for example, whereby the pendant basic group $G_1$ is capable of binding acidic functionalities such as are found in polypeptides whose purification is desired. Polyamides are prepared by cross-linking $E_1$ and $G_1$, with $W_6$ and the adjacent portion of the ring remaining free to function as a hydrophilic or hydrophobic affinity group, depending up the selection of the $W_6$ group. The preparation of these polymers from the compounds of the invention is conventional per se.

The compounds of the invention are also useful as a unique class of polyfunctional surfactants. Particularly when $W_6$ does not contain a hydrophilic substituent and is, for example, alkyl or alkoxy, the compounds have the properties of bi-functional surfactants. As such they have useful surfactant, surface coating, emulsion modifying, rheology modifying and surface wetting properties.

As polyfunctional compounds with defined geometry and carrying simultaneously polar and non-polar moieties, the compounds of the invention are useful as a unique class of phase transfer agents. By way of example and not limitation, the compounds of the invention are useful in phase transfer catalysis and liquid/liquid ion extraction (LIX).

The compounds of the invention optionally contain asymmetric carbon atoms in groups $W_6$, $E_1$, $G_1$, and $T_1$. As such, they are a unique class of chiral auxiliaries for use in the synthesis or resolution of other optically active materials. For example, a racemic mixture of carboxylic acids can be resolved into its component enantiomers by: 1) forming a mixture of diastereomeric esters or amides with a compound of the invention wherein $W_6$ is an asymmetric hydroxyalkane or amino alkane group; 2) separating the diastereomers; and 3) hydrolyzing the ester structure. Racemic alcohols are separated by ester formation with an acid group of $E_1$. Further, such a method can be used to resolve the compounds of the invention themselves if optically active acids or alcohols are used instead of racemic starting materials.

The compounds of this invention are useful as linkers or spacers in preparing affinity absorption matrices, immobilized enzymes for process control, or immunoassay reagents. The compounds herein contain a multiplicity of functional groups that are suitable as sites for cross-linking desired substances. For example, it is conventional to link affinity reagents such as hormones, peptides, antibodies, drugs, and the like to insoluble substrates. These insolublized reagents are employed in known fashion to absorb binding partners for the affinity reagents from manufactured preparations, diagnostic samples and other impure mixtures. Similarly, immobilized enzymes are used to perform catalytic conversions with facile recovery of enzyme. Bifunctional compounds are commonly used to link analytes to detectable groups in preparing diagnostic reagents.

Many functional groups in the compounds of this invention are suitable for use in cross-linking. For example, the carboxylic or phosphonic acid of group $E_1$ is used to form esters with alcohols or amides with amines of the reagent to be cross-linked. The $G_1$ sites substituted with OH, $NHR_1$, SH, azido (which is reduced to amino if desired before cross-linking), CN, $NO_2$, amino, guanidino, halo and the like are suitable sites. Suitable protection of reactive groups will be used where necessary while assembling the cross-linked reagent to prevent polymerization of the bifunctional compound of this invention. In general, the compounds here are used by linking them through carboxylic or phosphonic acid to the hydroxyl or amino groups of the first linked partner, then covalently bonded to the other binding partner through a $T_1$ or $G_1$ group. For example a first binding partner such as a steroid hormone is esterified to the carboxylic acid of a compound of this invention and then this conjugate is crossinked through a $G_1$ hydroxyl to cyanogen bromide activated Sepaharose, whereby immobilized steroid is obtained. Other chemistries for conjugation are well known. See for example Maggio, "Enzyme-Immunoassay" (CRC, 1988, pp 71–135) and references cited therein.

As noted above, the therapeutically useful compounds of this invention in which the $W_1$, or $G_1$ carboxyl, hydroxyl or amino groups are protected are useful as oral or sustained release forms. In these uses the protecting group is removed in vivo, e.g., hydrolyzed or oxidized, so as to yield the free carboxyl, amino or hydroxyl. Suitable esters or amides for this utility are selected based on the substrate specificity of esterases and/or carboxypeptidases expected to be found within cells where precursor hydrolysis a is desired. To the extent that the specificity of these enzymes is unknown, one will screen a plurality of the compounds of this invention until the desired substrate specificity is found. This will be apparent from the appearance of free compound or of antiviral activity. One generally selects amides or esters of the invention compound that are (i) not hydrolyzed or hydrolyzed comparatively slowly in the upper gut, (ii) gut and cell permeable and (iii) hydrolyzed in the cell cytoplasm and/or systemic circulation. Screening assays preferably use cells from particular tissues that are susceptible to influenza infection, e.g. the mucous membranes of the bronchopulmonary tract. Assays known in the art are suitable for determining in vivo bioavailability including intestinal lumen stability, cell permeation, liver homogenate stability and plasma stability assays. However, even if the ester, amide or other protected derivatives are not converted in vivo to the free carboxyl, amino or hydroxyl groups, they remain useful as chemical intermediates.

Exemplary Methods of Making the Compounds of the Invention

The invention also relates to methods of making the compositions of the invention. The compositions are prepared by any of the applicable techniques of organic synthesis. Many such techniques are well known in the art. However, many of the known techniques are elaborated in "Compendium of Organic Synthetic Methods" cohn Wiley & Sons, New York), Vol. 1, Ian T. Harrison and Shuyen Harrison, 1971; Vol. 2, Ian T. Harrison and Shuyen Harrison, 1974; Vol. 3, Louis S. Hegedus and Leroy Wade, 1977; Vol. 4, Leroy G. Wade, Jr., 1980; Vol. 5, Leroy G. Wade, Jr., 1984; and Vol. 6, Michael B. Smith; as well as March, J., "Advanced Organic Chemistry, Third Edition", (John Wiley & Sons, New York, 1985), "Comprehensive Organic Synthesis. Selectivity, Strategy & Efficiency in Modern Organic Chemistry. In 9 Volumes", Barry M. Trost, Editor-in-Chief (Pergamon Press, New York, 1993 printing).

A number of exemplary methods for the preparation of the compositions of the invention are provided below. These methods are intended to illustrate the nature of such preparations are not intended to limit the scope of applicable methods.

Generally, the reaction conditions such as temperature, reaction time, solvents, workup procedures, and the like, will be those common in the art for the particular reaction to be performed. The cited reference material, together with material cited therein, contains detailed descriptions of such conditions. Typically the temperatures will be −100° C. to 200° C., solvents will be aprotic or protic, and reaction times will be 10 seconds to 10 days. Workup typically consists of quenching any unreacted reagents followed by partition between a water/organic layer system (extraction) and separating the layer containing the product.

Oxidation and reduction reactions are typically carried out at temperatures near room temperature (about 20° C.), although for metal hydride reductions frequently the temperature is reduced to 0° C. to −100° C., solvents are typically aprotic for reductions and may be either protic or aprotic for oxidations. Reaction times are adjusted to achieve desired conversions.

Condensation reactions are typically carried out at temperatures near room temperature, although for non-equilibrating, kinetically controlled condensations reduced temperatures (0° C. to −100° C.) are also common. Solvents can be either protic (common in equilibrating reactions) or aprotic (common in kinetically controlled reactions).

Standard synthetic techniques such as azeotropic removal of reaction by-products and use of anhydrous reaction conditions (e.g. inert gas environments) are common in the art and will be applied when applicable.

Exemplary methods of preparing the compounds of the invention are shown in the Schemes below.

General aspects of these exemplary methods are described below. Each of the products of the following processes is optionally separated, isolated, and/or purified prior to its use in subsequent processes.

The terms "treated", "treating", "treatment", and the like, mean contacting, mixing, reacting, allowing to react, bringing into contact, and other terms common in the art for indicating that one or more chemical entities is treated in such a manner as to convert it to one or more other chemical entities. This means that "treating compound one with compound two" is synonymous with "allowing compound one to react with compound two", "contacting compound one with compound two", "reacting compound one with compound two", and other expressions common in the art of organic synthesis for reasonably indicating that compound one was "treated", "reacted", "allowed to react", etc., with compound two.

"Treating" indicates the reasonable and usual manner in which organic chemicals are allowed to react. Normal concentrations (0.1M to 10M, typically 0.1M to 1M), temperatures (−100° C. to 250° C., typically −78° C. to 150° C., more typically −78° C. to 100° C., still more typically 0° C. to 100° C.), reaction vessels (typically glass, plastic, metal), solvents, pressures, atmospheres (typically air for oxygen and water insensitive reactions or nitrogen or argon for oxygen or water sensitive), etc., are intended unless otherwise indicated. The knowledge of similar reactions known in the art of organic synthesis are used in selecting the conditions and apparatus for "treating" in a given process. In particular, one of ordinary skill in the art of organic synthesis selects conditions and apparatus reasonably expected to successfully carry out the chemical reactions of the described processes based on the knowledge in the art.

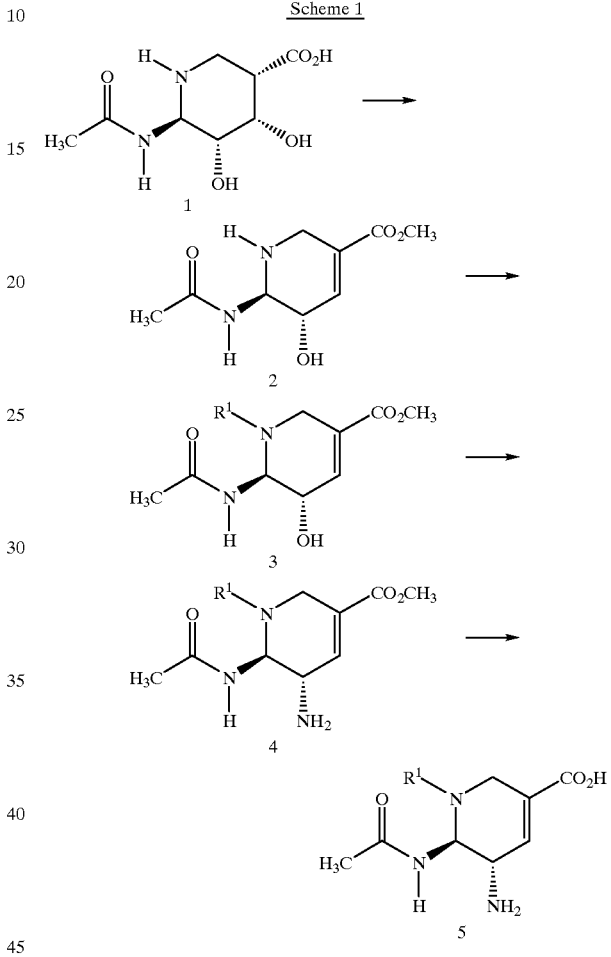

Scheme 1

In one embodiment, compounds of the invention are prepared as depicted in Scheme 1. Siastatin B (1) from natural materials (Umezawa, H. et al. "J. Antibiotics", 27:963–969 (1974) or ribose (Nishimura, Y. et al. "J. Am. Chem. Soc.", 110:7249–7250, 1988); and "Bull. Chem. Soc. Jpn.", 65:978–986, 1992) is available in either enantiomer. Conversion to compound 2 is accomplished by known methods (Nishimura, Y. et al. "J. Antibiotics", 46(2) :300–309, 1993). Reductive alkylation to form 3 is accomplished by known methods (Nishimura, Y. et al. "J. Antibiotics", 45(10):1662–1668, 1992). Conversion of the alcohol 3 to the amine 4 is accomplished by the methods of Zbiral, E. et al. "Liebigs Ann. Chem.", 129–134 (1991); and von Itzstein, M. et al. "Carbohydrate Res.", 244:181–185 (1993) Deprotection provides compound 5.

By way of example and not limitation, compounds 5 wherein $R^1$ is ethyl (Et, —$CH_2CH_3$), 1-propyl (n-Pr, n-propyl, —$CH_2CH_2CH_3$), 1-butyl (n-Bu, n-butyl, —$CH_2CH_2CH_2CH_3$), 2-methyl-1-propyl (i-Bu, i-butyl, —$CH_2CH(CH_3)_2$), 1-pentyl (n-pentyl, —$CH_2CH_2CH_2CH_2CH_3$), 3-methyl-1-butyl (—$CH_2CH_2CH$ ($CH_3$)$_2$), 2-methyl-1-butyl (—$CH_2CH(CH_3)CH_2CH_3$), 1-hexyl (—$CH_2CH_2CH_2CH_2CH_2CH_3$), 2-ethyl-1-butyl (—$CH_2CH(CH_2CH_3)_2$), 2-ethyl phenyl-1-butyl (—$CH_2CH(CH_2CH_3)(CH_2CH_2Ph)$)), or 2-(2-phenylethyl)-4-phenyl-1-butyl (—$CH_2CH(CH_2CH_2Ph)_2$) are prepared by the method of Scheme 1.

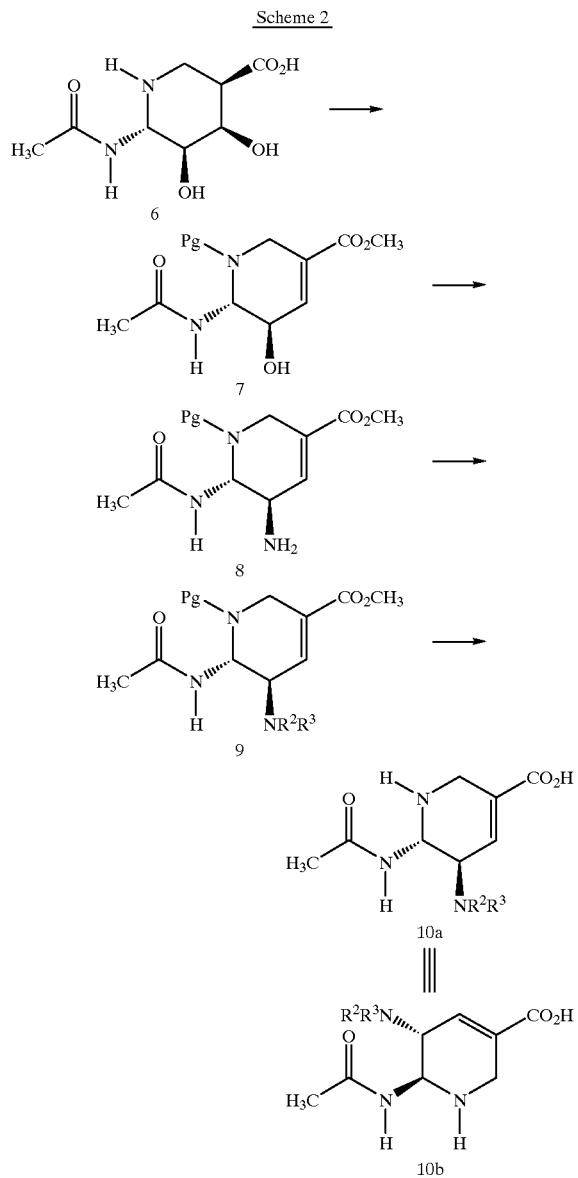

In another embodiment, compounds of the invention are prepared as depicted in Scheme 2. The enantiomer of Siastatin B (6) is prepared from ribose (Nishimura, Y. et al., "J. Am. Chem. Soc.", 110:7249–7250, 1988); and "Bull. Chem. Soc. Jpn.", 65:978–986, 1992). Conversion to protected compound 7 is accomplished by known methods (e.g. Pg is Boc, Nishimura, Y. et al. "J. Antibiotics", 46(2):300–309, 1993). Conversion of the alcohol 7 to the amine 8 is accomplished by the methods of Zbiral, E. et al. "Liebigs Ann. Chem.", 129–134, 1991; and von Itzstein, M. et al. "Carbohydrate Res.", 244:181–185, 1993. Reductive alkylation to form 9 is accomplished by known methods (Nishimura, Y. et al. "J. Antibiotics", 45(10):1662–1668, 1992). Deprotection provides compound 10a. Compound 10a is compound 10b By way of example and not limitation, compounds 10b wherein $R^2$ is H and $R^3$ is ethyl (Et, —$CH_2CH_3$), 1-propyl (n-Pr, n-propyl, —$CH_2CH_2CH_3$), 1-butyl (n-Bu, n-butyl, —$CH_2CH_2CH_2CH_3$), 2-methyl-1-propyl (i-Bu, i-butyl, —$CH_2CH(CH_3)_2$), 1-pentyl (n-pentyl, —$CH_2CH_2CH_2CH_2CH_3$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-ethyl-1-butyl ($CH_2CH(CH_2CH_3)_2$), 2-ethyl-phenyl-1-butyl (—$CH_2CH(CH_2CH_3)(CH_2CH_2Ph)$)), or 2-(2-phenylethyl)-4-phenyl-1-butyl (—$CH_2CH(CH_2CH_2Ph)_2$) are prepared by the method of Scheme 2.

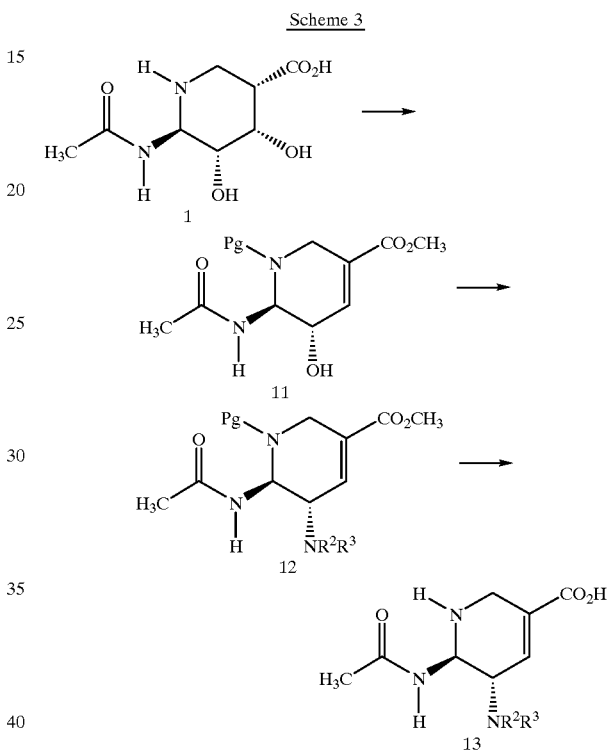

In another embodiment, compounds of the invention are prepared as depicted in Scheme 3. Siastatin B (1) from natural materials (Umezawa, H. et al., "J. Antibiotics", 27:963–969, 1994) or ribose (Nishimura, Y. et al., "J. Am. Chem. Soc.", 110:7249–7250, 1988); and "Bull. Chem. Soc. Jpn.", 65:978–986, 1992) is available in either enantiomer. Conversion to protected compound 11 is accomplished by known methods (e.g. Pg is Boc, Nishimura, Y. et al., "J. Antibiotics", 46(2):300–309, 1993). Conversion of the alcohol 11 to the amine is accomplished by the methods of Zbiral, E. et al., "Liebigs Ann. Chem.", 129–134, 1991); and von Itzstein, M. et al., "Carbohydrate Res.", 244:181–185, 1993 and reductive alkylation to form 12 is accomplished by known methods (Nishimura, Y. et al. "J. Antibiotics", 45(10): 1662–1668, 1992). Deprotection provides compound 13.

By way of example and not limitation, compounds 13 wherein $R^2$ is H and $R^3$ is ethyl (Et, —$CH_2CH_3$), 1-propyl (n-Pr, n-propyl, —$CH_2CH_2CH_3$), 1-butyl (n-Bu, n-butyl, —$CH_2CH_2CH_2CH_3$), 2-methyl-1-propyl (i-Bu, i-butyl, —$CH_2CH(CH_3)_2$), 1-pentyl (n-pentyl, —$CH_2CH_2CH_2CH_2CH_3$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-ethyl-1-butyl (—$CH_2CH(CH_2CH_3)_2$), 2-ethyl-4-phenyl-1-butyl (—CH₂CH(CH₂CH₃)(CH₂CH₂Ph)), or 2-(2-phenylethyl)-4-phenyl-1-butyl (—CH₂CH(CH₂CH₂Ph)₂) are prepared by the method of Scheme 3.
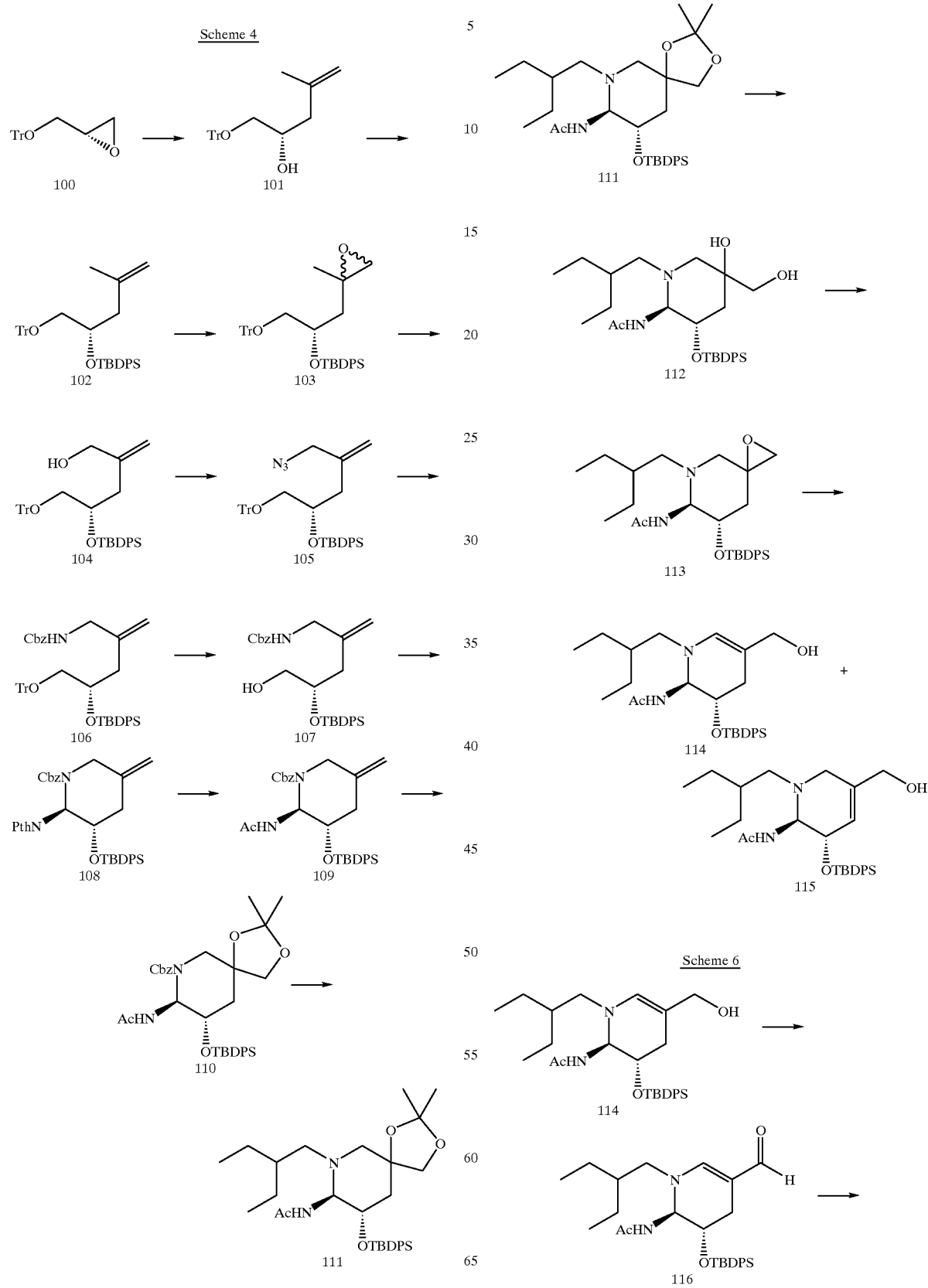

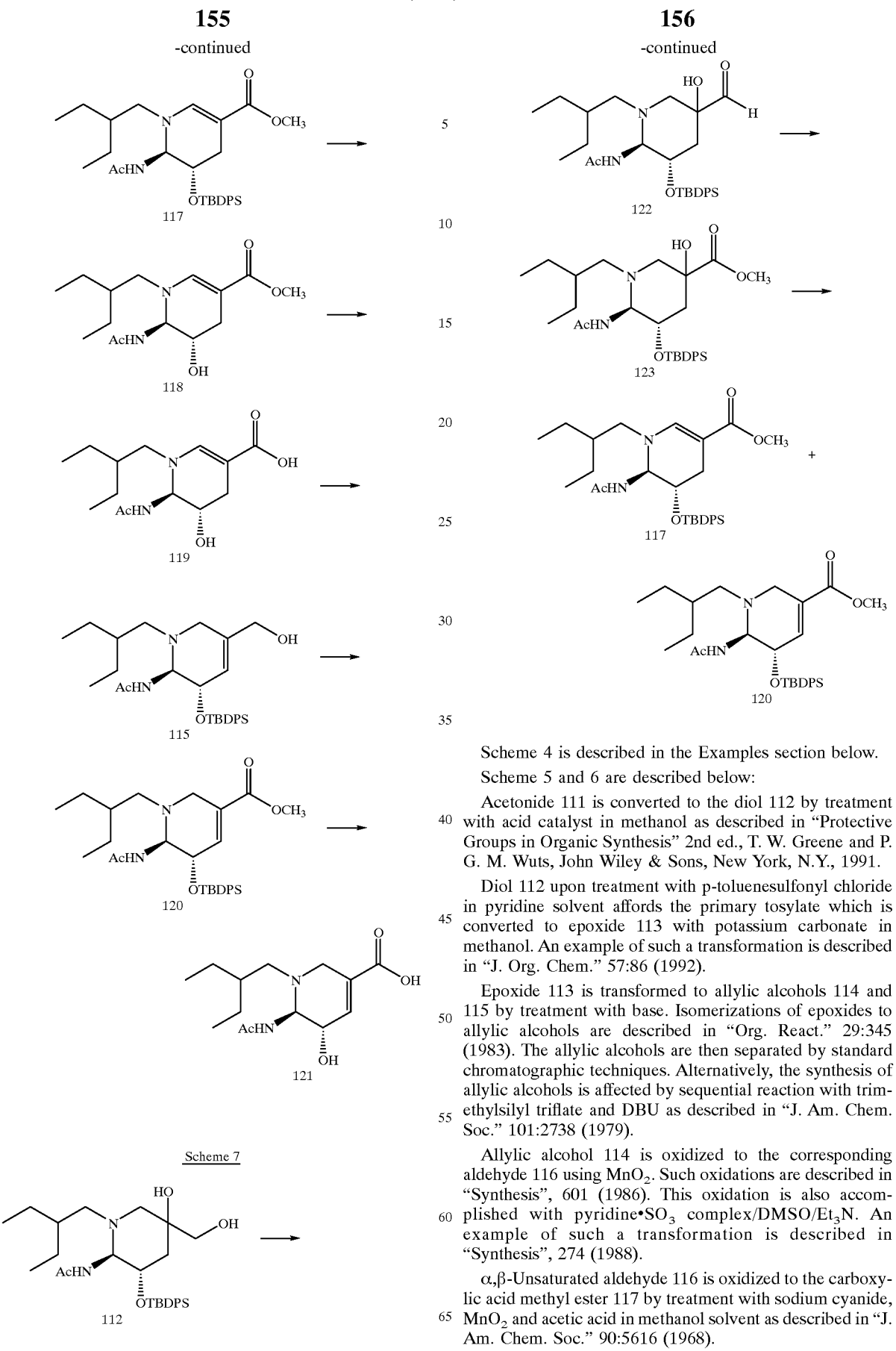

Scheme 4 is described in the Examples section below.

Scheme 5 and 6 are described below:

Acetonide 111 is converted to the diol 112 by treatment with acid catalyst in methanol as described in "Protective Groups in Organic Synthesis" 2nd ed., T. W. Greene and P. G. M. Wuts, John Wiley & Sons, New York, N.Y., 1991.

Diol 112 upon treatment with p-toluenesulfonyl chloride in pyridine solvent affords the primary tosylate which is converted to epoxide 113 with potassium carbonate in methanol. An example of such a transformation is described in "J. Org. Chem." 57:86 (1992).

Epoxide 113 is transformed to allylic alcohols 114 and 115 by treatment with base. Isomerizations of epoxides to allylic alcohols are described in "Org. React." 29:345 (1983). The allylic alcohols are then separated by standard chromatographic techniques. Alternatively, the synthesis of allylic alcohols is affected by sequential reaction with trimethylsilyl triflate and DBU as described in "J. Am. Chem. Soc." 101:2738 (1979).

Allylic alcohol 114 is oxidized to the corresponding aldehyde 116 using $MnO_2$. Such oxidations are described in "Synthesis", 601 (1986). This oxidation is also accomplished with pyridine•$SO_3$ complex/DMSO/$Et_3N$. An example of such a transformation is described in "Synthesis", 274 (1988).

α,β-Unsaturated aldehyde 116 is oxidized to the carboxylic acid methyl ester 117 by treatment with sodium cyanide, $MnO_2$ and acetic acid in methanol solvent as described in "J. Am. Chem. Soc." 90:5616 (1968).

Deprotection of silyl ether 117 to alcohol 118 is carried out using tetrabutylammonium fluoride. Hydrolysis of the methyl ester to carboxylic acid 119 is conducted with potassium hydroxide. Both of these deprotection methods are described in "Protective Groups in Organic Synthesis" 2nd ed., T. W. Greene and P. G. M. Wuts, John Wiley & Sons, New York, N.Y., 1991.

In a similar fashion as described for 114, allylic alcohol 115 is converted to carboxylic acid 121.

Diol 112 is oxidized with pyridine•$SO_3$ complex/DMSO/ $Et_3N$ to afford α-hydroxyaldehyde 122 as described in "J. Chem. Soc. Chem. Commun." 18: 2197 (1994). The same reference describes the oxidation of an α-hydroxyaldehyde to the corresponding α-hydroxycarboxylic acid using $NaClO_2$/$NaH_2PO_4$/2-methyl-2-butene. Treatment of the carboxylic acid with diazomethane affords carboxylic ester 123. Such an esterification of a carboxylic acid is described in "Tetrahedron Lett." 1397 (1973).

α-Hydroxyester 123 is dehydrated to a mixture unsaturated esters 117 and 120 with $SOCl_2$ and pyridine. Example of a similar reaction is described in "J. Org. Chem." 60:2753 (1995).

Hydroxyesters 117 and 120 are deprotected to 119 and 121 respectively using conditions previously described.

Modification of the exemplary starting materials to form different $E_1$ groups has been described in detail and will not be elaborated here. See Fleet, G. W. J. et al., "J. Chem. Soc. Perkin Trans. I", 905–908 (1984), Fleet, G. W. J. et al., "J. Chem. Soc., Chem. Commun.", 849–850 (1983), Yee, Ying K. et al., "J. Med. Chem.", 33:2437–2451 (1990); Olson, R. E. et al., "Bioorganic & Medicinal Chemistry Letters", 4(18):2229–2234 (1994); Santella, J. B. III et al., "Bioorganic & Medicinal Chemistry Letters", 4(18):2235–2240 (1994); Judd, D. B. et al., "J. Med. Chem.", 37:3108–3120 (1994) and De Lombaert, S. et al., "Bioorganic & Medicinal Chemistry Letters", 5(2):151–154 (1994).

The $E_1$ sulfur analogs of the carboxylic acid compounds of the invention are prepared by any of the standard techniques. By way of example and not limitation, the carboxylic acids are reduced to the alcohols by standard methods. The alcohols are converted to halides or sulfonic acid esters by standard methods and the resulting compounds are reacted with NaSH to produce the sulfide product. Such reactions are described in Patai, "The Chemistry of the Thiol Group" (John Wiley, New York, 1974), pt. 2, and in particular pages 721–735.

Modifications of each of the above schemes leads to various analogs of the specific exemplary materials produced above. The above cited citations describing suitable methods of organic synthesis are applicable to such modifications.

In each of the above exemplary schemes it may be advantageous to separate reaction products from one another and/or from starting materials. The desired products of each step or series of steps is separated and/or purified (hereinafter separated) to the desired degree of homogeneity by the techniques common in the art. Typically such separations involve multiphase extraction, crystallization from a solvent or solvent mixture, distillation, sublimation, or chromatography. Chromatography can involve any number of methods including, for example, size exclusion or ion exchange chromatography, high, medium, or low pressure liquid chromatography, small scale and preparative thin or thick layer chromatography, as well as techniques of small scale thin layer and flash chromatography.

Another class of separation methods involves treatment of a mixture with a reagent selected to bind to or render otherwise separable a desired product, unreacted starting material, reaction by product, or the like. Such reagents include adsorbents or absorbents such as activated carbon, molecular sieves, ion exchange media, or the like. Alternatively, the reagents can be acids in the case of a basic material, bases in the case of an acidic material, binding reagents such as antibodies, binding proteins, selective chelators such as crown ethers, liquid/liquid ion extraction reagents (LIX), or the like.

Selection of appropriate methods of separation depends on the nature of the materials involved. For example, boiling point, and molecular weight in distillation and sublimation, presence or absence of polar functional groups in chromatography, stability of materials in acidic and basic media in multiphase extraction, and the like. One skilled in the art will apply techniques most likely to achieve the desired separation.

EXAMPLES

The following Examples refer to the Schemes.

Example 1

Alcohol 101

To magnesium turnings (0.90 g, 37.2 mmol) in THF (50 mL) was added several drops of 1,2-dibromoethane as initiator followed by the addition of 2-bromopropene (4.5 g, 37.2 mmol) over a period of 1 h. Additional 2-bromopropene (0.68 g, 5.6 mmol) was added and stirred for 1.5 h. To a slurry of CuI (0.7 g, 3.7 mmol) in THF (30 mL) at −30° C. was added via cannula the grignard reagent over 15 min and was stirred an additional 20 min at −30° C. A solution of epoxide 100 (9.4 g, 29.8 mmol) in THF (40 mL) was then added to the grignard/CuI mixture and was stirred at −30° C. for 1 h. The reaction was quenched at 0° C. with saturated $NH_4Cl$ (100 mL) followed by the addition of 1N $NH_4OH$ to dissolve precipitated solids. Brine was added and the product was extracted into ether. The organic phase was washed with brine, dried ($MgSO_4$), filtered and solvent was evaporated to afford alcohol 101 (11.8 g) which was suitable for further transformations: $^1$H NMR ($CDCl_3$) δ 7.51–7.27 (m, 15H), 4.84 (s, 1H), 4.77 (d, 1H, J=0.9), 3.97 (m, 1H), 3.20 (m, 2H), 2.30 (m, 1H), 2.21 (d, 2H, J=6.6), 1.76 (s, 3H).

Example 2

Silyl Ether 102

To a solution of alcohol 101 (1.77 g, 4.9 mmol) and imidazole (1.5 g, 22 mmol) in DMF (5 mL) was added tert-butyldiphenylsilyl chloride (2.0 g, 7.4 mmol). After stirring for 1 h at room temperature the reaction mixture was diluted with water and extracted with several portions of ether. The combined organic extracts were washed with water and brine and were dried ($MgSO_4$), filtered and evaporated. The residue was chromatographed on silica gel (20/1-hexane/ethyl acetate) to afford silyl ether 102 (2.85 g, 97%) as an oil: $^1$H NMR ($CDCl_3$) δ 7.73–7.65 (m, 4H), 7.49–7.20 (m, 21H), 4.56 (s, 1H), 4.50 (s, 1H), 4.02–3.98 (m, 1H), 3.11 (m, 2H), 2.45 (dd, 1H, J=7.5, 13.5), 2.10 (dd, 1H, J=5.4, 13.5), 1.35 (s, 3H), 1.09 (s, 9H).

Example 3

Epoxide 103

To a solution of 102 (44.3 g, 74.2 mmol) in $CH_2Cl_2$ (600 mL) at 0° C. was added $NaHCO_3$ (31 g, 371 mmol) and MCPBA (32 g, 50–60% MCPBA w/w). After stirring for 1 h at 0° C., water (100 mL) was added and the mixture was stirred for 1 h more. After evaporation of the CH$_2$Cl$_2$, the reaction was diluted with water and extracted with ether. The organic phase was washed with cold 0.5 M sodium thiosulfate, saturated NaHCO$_3$, brine and was dried (MgSO$_4$), filtered and evaporated. The residue was chromatographed on silica gel (2/1-CH$_2$Cl$_2$/hexane) to afford epoxide 103 (35.2 g) as a 1.5:1 mixture of diastereomers.

Example 4

Allylic Alcohol 104

To a solution of lithium diethylamide (generated from 11.5 mL diethylamine and 52 mL of 2.1 M butyl lithium in hexane) in ether (400 mL) at 0° C. was added epoxide 103 (33.5 g) in ether (150 mL). The reaction was allowed to warm to room temperature and was stirred for 17 h. The reaction was cooled to 0° C. and was poured into ice-water mixture (500 mL). The organic phase was washed with water, brine, and was dried (MgSO$_4$), filtered and evaporated. The crude product was chromatographed on silica gel (3/1-hexane/ethyl acetate) to afford allylic alcohol 104 (15.4 g, 46%) as an oil: $^1$H NMR (CDCl$_3$) δ 7.75–7.65 (m, 4H), 7.53–7.22 (m, 21H), 4.90 (m, 1H), 4.71 (s, 1H), 4.03 (m, 1H), 3.73 (d, 2H, J=5.1), 3.16 (d, 2H, J=5.1), 2.53 (dd, 1H, J=6.9, 13.8), 2.25 (dd, 1H, J=5.1, 13.8), 1.54 (br t, 1H, J=6), 1.12 (s, 9H).

Example 5

Allylic Azide 105

To a solution of alcohol 104 (13.1 g, 21.4 mmol) in CH$_2$Cl$_2$ (100 mL) at 0° C. was added triethylamine (7.45 mL, 53.5 mmol) followed by methanesulfonyl chloride (1.82 g, 23.5 mmol). After 30 min at 0° C. cold water was added and CH$_2$Cl$_2$ was evaporated and the residue was partitioned between ether and water. The organic phase was washed with water, brine, and was dried (MgSO$_4$), filtered, and evaporated. The crude mesylate was dissolved in DMF (100 mL), sodium azide (2.8 g, 42.8 mmol) was added and the mixture was stirred at room temperature for 30 min. Volatiles were evaporated and the residue was partitioned between ether and water. The organic phase was washed with water, brine and was dried (MgSO$_4$), filtered and evaporated. The crude product was chromatographed on silica gel (10/1-hexane/ethyl acetate) to afford allylic azide 105 (11.9 g, 87%) as an oil: $^1$H NMR (CDCl$_3$) δ 7.71–7.60 (m, 4H), 7.51–7.21 (m, 21H), 4.89 (d, 1H, J=1.5), 4.78 (s, 1H), 3.97 (m, 1H), 3.36 (s, 2H), 3.10 (d, 2H, J=5.1), 2.56 (dd, 1H, J=6.3, 13.8), 2.20 (dd, 1H, J=5.1, 13.8), 1.08 (s, 9H).

Example 6

Carbamate 106

To a solution of azide 105 (9.3 g, 14.6 mmol) in CH$_3$CN (100 mL) and water (5 mL) at 0° C. was added trimethylphosphine (2.3 mL, 22 mmol). After stirring for 2 h at 0° C. the reaction was warmed to room temperature and was stirred for 18 h. To the solution was added potassium carbonate (4.0 g, 29.6 mmol) and water (20 mL) followed by addition of benzyl chloroformate (3.1 mL, 95% purity, ~21 mmol). The reaction was stirred for 1.5 h and solvent was evaporated. Water was added and the organics were extracted into ether. The combined organic extracts were washed with brine, dried (MgSO$_4$), filtered, and evaporated. The residue was chromatographed on silica gel (3/1-hexane ethyl acetate) to afford carbamate 106 (10.6 g, 97%) as a thick oil: $^1$H NMR (CDCl$_3$) δ 7.72–7.60 (m, 4H), 7.51–7.20 (m, 26H), 5.08 (br s, 2H), 4.76 (s, 1H), 4.66 (s, 1H), 4.50 (m, 1H), 3.99 (m, 1H), 3.45 (dd, 1H, J=5.7, 16), 3.33 (dd, 1H, J=5.7, 16), 3.12 (d, 2H), 2.48 (dd, 1H, J=6.6, 13.8), 2.16 (dd, 1H, J=6, 13.8), 1.08 (s, 9H).

Example 7

Alcohol 107

To a solution of 106 (10.6 g, 14.2 mmol) in CH$_2$Cl$_2$ (20 mL) and methanol (20 mL) at 0° C. was added formic acid (25 mL). The solution was stirred at 0° C. for 2.5 h and was then poured into saturated NaHCO$_3$ (600 mL) with stirring. The aqueous phase was saturated with NaCl and extracted with ethyl acetate. The combined organic extracts were dried (MgSO$_4$), filtered, and evaporated. The crude residue was chromatographed on silica gel (2/1-hexane ethyl acetate) to afford alcohol 107 (5.9 g, 83%) as an oil: $^1$H NMR (CDCl$_3$) δ 7.73–7.68 (m, 4H), 7.50–7.34 (m, 11H), 5.09 (s, 2H), 4.92 (d, 1H, J=1.2), 4.79 (s, 1H), 4.68 (m, 1H), 3.92 (m, 1H), 3.60–3.39 (m, 4H), 2.36 (dd, 1H, J=8.4, 13.5), 2.15 (dd, 1H J=4.8, 13.5), 1.94 (br t, 1H) 1.10 (s, 9H).

Example 8

Phthalimide Adduct 108

To a solution of DMSO (0.76 mL, 10.8 mmol) in CH$_2$Cl$_2$ (4 mL) at −78° C. was added oxalyl chloride (0.39 mL, 4.5 mmol). After stirring for 5 min a solution of alcohol 107 (2.19 g, 4.3 mmol) in CH$_2$Cl$_2$ (5 mL) was added, stirred 25 min, Triethylamine (3 mL, 21.5 mmol) was added, the reaction was stirred at −78° C. for 30 min and was warmed to room temperature. After 1 h the reaction was diluted with ether, filtered, and evaporated. The residue was dissolved in ethyl acetate, washed with water, brine and the organic phase was dried (MgSO$_4$), filtered, and evaporated. To a solution of the residue in DMF (20 mL) was added Ph$_3$P (2.2 g, 8.3 mmol) and phthalimide (1.22 g, 8.3 mmol) and the solution was cooled to 0° C. at which time diethylazodicarboxylate (1.3 mL, 8.3 mmol) was added. The reaction was stirred at 0° C. for 1 h and was warmed to room temperature stirring for 3.5 h. Water was added to quench excess diethylazodicarboxylate and DMF was evaporated. The residue was chromatographed on silica gel (2% ethyl acetate in CH$_2$Cl$_2$). Rechromatography of the mixed fractions (1% ethyl acetate in CH$_2$Cl$_2$) afforded phthalimide adduct 108 (1.95 g, 72%) as a foam. $^1$H NMR (CDCl$_3$) δ 7.83–7.08 (m, 19H), 5.98 (br d, 1H, J=6.9), 5.22 (d, 1H, J=12.3), 4.97 (d, 1H, J=12.3), 4.88 (s, 1H), 4.71 (s, 1H), 4.60–4.52 (m, 2H), 4.20 (br d, 1H, J=16.2), 2.54 (dd, 1H, J=4, 15.6), 2.41–2.33 (m, 1H), 0.98 (s, 9H).

Example 9

Acetamide 109

A solution of 108 (4.2 g, 6.7 mmol) in MeOH (100 mL) was treated with hydrazine monohydrate (1.6 mL, 33 mmol) at 40° C. for 5 h. Solvent was evaporated and the residue was suspended in ethyl acetate and the solid residue was removed by filtration. Evaporation of the filtrate gave a residue which was dissolved in pyridine (30 mL), and cooled to 0° C. Acetic anhydride (6.9 mL, 73 mmol) was added and the reaction was warmed to room temperature stirring for 2 h. After evaporation of the volatiles the residue was dissolved in ethyl acetate and washed with water and brine. The organic phase was dried (MgSO$_4$), filtered, evaporated and chromatographed on silica gel (1/1 hexane-ethyl acetate) to afford 2.7 g of purified product. Precipitation from ether/hexane gave acetamide 109 (1.89 g, 52%) as a white solid. $^1$H NMR (CD$_3$OD) δ 7.69–7.62 (m, 4H), 7.45–7.32 (m, 11H), 6.23 (d, 1H, J=2.4), 5.22 (br d, 1H), 5.04 (br s, 2H), 4.76 (s, 1H), 4.56 (d, 1H, J=14.4), 4.03 (br s, 1H), 3.73 (br d, 1H), 2.43 (br d, 1H), 2.10 (br d, 1H), 1.93 (s, 3H), 1.02 (s, 9H)

Example 10

Acetonide 110

To a solution of 109 (478 mg, 0.88 mmol) in acetone (3 mL) was added 4-methylmorpholine N-oxide (291 mg, 2.5 mmol) and 0.04M OsO$_4$ solution in water (1 mL). The reaction was stirred for 16 h at room temperature, cooled to 0° C. and was treated with 10 sodium thiosulfate solution (10 mL). The mixture was diluted with brine and extracted with ethyl acetate. The combined organic extracts were dried (MgSO$_4$), filtered, evaporated and the residue was dissolved in ethyl acetate and filtered through a pad of silica gel. Evaporation of the filtrate gave a residue which was dissolved in acetone (10 mL) and was treated with dimethoxypropane (5 mL) and a catalytic amount of p-toluenesulfonic acid. After stirring for 15 min at room temperature saturated NaHCO$_3$ was added and solvents were evaporated. The product was extracted into ethyl acetate and the combined organic extracts were dried (MgSO$_4$), filtered, and evaporated. The residue chromatographed on silica gel (1/1 hexane-ethyl acetate) to afford acetonide 110 (465 mg, 85%) as a white solid. $^1$H NMR (CD$_3$OD) δ 7.62 (br s, 4H), 7.51–7.23 (m, 11H), 6.05 (br s, 1H), 5.20 (br d, 1H), 5.05 (br d, 1H), 4.11 (m, 3H), 3.71 (br s, 1H), 2.85 (br d, 1H), 2.04 (m, 1H), 1.91 (s, 3H), 1.62 (m, 1H), 1.41 (s, 3H), 1.18 (br s, 3H), 1.04 (s, 9H).

Example 11

N-alkyl Derivative 111

A solution of 110 (465 mg, 0.75 mmol) was treated with 10% Pd/C (90 mg) and was stirred under hydrogen (balloon) for 4 h. The catalyst was removed by filtration (celite) and the filtrate was evaporated to afford a residue which was used directly. To a solution of the amine (324 mg, 0.67 mmol) in methanol (4 mL) was added 2-ethylbutyraldehyde (0.83 mL, 67 mmol) and the solution was cooled to 0° C. To this solution was added 1.34 mL of NaCNBH$_3$/ZnCl$_2$ reagent prepared from NaCNBH$_3$ (314 mg, 5 mmol) and ZnCl$_2$ (340 mg, 2.5 mmol) in methanol (10 mL). The reaction was stirred at 0° C. for 40 min and was evaporated. The residue was partitioned between ether and 0.1N NaOH. The organic phase was dried (MgSO$_4$), filtered and evaporated. The residue was chromatographed on silica gel (2/1-hexane/ethyl acetate) to afford N-alkyl derivative 111 (212 mg, 56%) as a white solid. An analytical sample was recrystallized from hexane as thin needles: mp 136–138° C.; $^1$H NMR (CDCl$_3$) δ 7.76–7.66 (m, 4H), 7.507.36 (m, 6H), 5.58 (d, 1H, J=9), 4.84 (dd, 1H, J=2.7, 9), 4.26 (d, 1H, J=9), 4.01 (d, 1H, J=3.3), 3.74 (d, 1H, J=8.7), 2.61 (d, 1H, J=11.7), 2.37 (dd, 1H, J=6, 12.3), 2.30 (d, 1H, J=12), 2.20 (dd, 1H, J=5.7, 12.6), 1.92 (s, 3H), 1.69 (dd, 1H, J=3.3, 14.1), 1.54–1.28 (m, 9H), 1.17 (s, 3H), 1.13 (s, 9H), 0.96–0.82 (m, 6H).

All literature and patent citations above are hereby expressly incorporated by reference at the locations of their citation. Specifically cited sections or pages of the above cited works are incorporated by reference with specificity. The invention has been described in detail sufficient to allow one of ordinary skill in the art to make and use the subject matter of the following claims. It is apparent that certain modifications of the methods and compositions of the following claims can be made within the scope and spirit of the invention.

What is claimed is:

1. A compound of formula (XX) or (XXa):

(XX)

(XXa)

wherein $A_3$ is N, N(O) or N(S);

$Z_3$ is H, $W_6$, $G_1$ or $R_{3a}$;

$E_1$ is —(CR$_1$R$_1$)$_{m1}$W$_1$;

$G_1$ is —(CR$_1$R$_1$)$_{m1}$W$_2$;

$G_2$ is $G_1$;

$T_1$ is —NR$_1$W$_3$;

$J_1$ is $R_1$, Br, Cl, F, I, CN, NO$_2$ or N$_3$;

$J_2$ and $J_{2a}$ are H or $R_1$;

$J_3$ is $J_1$ if $X_1$ is a bond; and $J_3$ is $J_2$ if $X_1$ is —O—, —N(H)—, —N(W$_6$)—, —N(OH)—, —N(OW$_6$)—, —N(NH$_2$)—, —N(N(H)(W$_6$))—, —N(N(W$_6$)$_2$)—, —N(H)N(W$_6$)—, —S—, —SO—, or —SO$_2$—;

$R_1$ is independently H or alkyl of 1 to 12 carbon atoms;

$R_2$ is independently $R_3$ or $R_4$ wherein each $R_4$ is independently substituted with 0 to 3 $R_3$ groups;

$R_3$ is independently F, Cl, Br, I, —CN, N$_3$, —NO$_2$, —OR$_{6a}$, —OR$_1$, —N(R$^1$)$_2$, —N(R$_1$)(R$_{6b}$), —N(R$_{6b}$)$_2$, —SR$_1$, —SR$_{6a}$, —S(O)R$_1$, —S(O)$_2$R$_1$, —S(O)OR$_1$, —S(O)OR$_{6a}$, —S(O)$_2$OR$_1$, —S(O)$_2$OR$_{6a}$, —C(O)OR$_1$, —C(O)R$_{6c}$, —C(O)OR$_{6a}$, —OC(O)R$_1$, —N(R$_1$)(C(O)R$_1$), —N(R$_{6b}$)(C(O)R$_1$), —N(R$_1$)(C(O)OR$_1$), —N(R$_{6b}$)(C(O)OR$_1$), —C(O)N(R$_1$)$_2$, —C(O)N(R$_{6b}$)(R$_1$), —C(O)N(R$_{6b}$)$_2$, —C(NR$_1$)(N(R$_1$)$_2$, —C(N(R$_{6b}$))(N(R$_1$)$_2$), —C(N(R$_1$))(N(R$_1$)(R$_{6b}$)), —C(N(R$_{6b}$))(N(R$_1$)(R$_{6b}$)), —C(N(R$_1$))(N(R$_{6b}$)$_2$), —C(N(R$_{6b}$))(N(R$_{6b}$)$_2$), —N(R$_1$)C(N(R$_1$))(N(R$_1$)$_2$), —N(R$_1$)C(N(R$_1$))(N(R$_1$)(R$_{6b}$)), —N(R$_1$)C(N(R$_{6b}$))(N(R$_1$)$_2$), —N(R$_{6b}$)C(N(R$_1$))(N(R$_1$)$_2$), —N(R$_{6b}$)C(N(R$_{6b}$))(N(R$_1$)$_2$), —N(R$_{6b}$)C(N(R$_1$))(N(R$_1$)(R$_{6b}$)), —N(R$_1$)C(N(R$_{6b}$))(N(R$_1$)(R$_{6b}$)), —N(R$_1$)C(N(R$_1$))(N(R$_{6b}$)$_2$), —N(R$_{6b}$)C(N(R$_{6b}$))(N(R$_1$)(R$_{6b}$)), —N(R$_{6b}$)C(N(R$_1$))(N(R$_{6b}$)$_2$), —N(R$_1$)C(N(R$_{6b}$))(N(R$_{6b}$)$_2$), —N(R$_{6b}$)C(N(R$_{6b}$))(N(R$_{6b}$)$_2$), =O, =S, =N(R$_1$), =N(R$_{6b}$) or W$_5$;

$R_{3a}$ is independently —CN, N$_3$, —NO, —NO$_2$, —OR$_{6a}$, —OR$_1$, —N(R$_1$)$_2$, —N(R$_1$)(R$_{6b}$), —N(R$_{6b}$)$_2$, —SR$_1$, —$SR_{6a}$, —$S(O)R_1$, —$S(O)_2R_1$, —$S(O)OR_1$, —$S(O)OR_{6a}$, —$S(O)_2OR_1$, —$S(O)_2OR_{6a}$, —$C(O)OR_1$, —$C(O)R_{6c}$, —$C(O)OR_{6a}$, —$OC(O)R_1$, —$N(R_1)(C(O)R_1)$, —$N(R_{6b})(C(O)R_1)$, —$N(R_1)(C(O)OR_1)$, —$N(R_{6b})(C(O)OR_1)$, —$C(O)N(R_1)_2$, —$C(O)N(R_{6b})(R_1)$, —$C(O)N(R_{6b})_2$, —$C(NR_1)(N(R_1)_2)$, —$C(N(R_{6b}))(N(R_1)_2)$, —$C(N(R_1))(N(R_1)(R_{6b}))$, —$C(N(R_{6b}))(N(R_1)(R_{6b}))$, —$C(N(R_1))(N(R_{6b})_2)$, —$C(N(R_{6b}))(N(R_{6b})_2)$, —$N(R_1)C(N(R_1))(N(R_1)_2)$, —$N(R_1)C(N(R_1))(N(R_1)(R_{6b}))$, —$N(R_1)C(N(R_{6b}))(N(R_1)_2)$, —$N(R_{6b})C(N(R_1))(N(R_1)_2)$, —$N(R_{6b})C(N(R_{6b}))(N(R_1)_2)$, —$N(R_{6b})C(N(R_1))(N(R_1)(R_{6b}))$, —$N(R_1)C(N(R_1))(N(R_{6b})_2)$, —$N(R_{6b})C(N(R_{6b}))(N(R_1)(R_{6b}))$, —$N(R_{6b})C(N(R_1))(N(R_{6b})_2)$, —$N(R_1)C(N(R_{6b}))(N(R_{6b})_2)$ or —$N(R_{6b})C(N(R_{6b}))(N(R_{6b})_2)$;

$R_4$ is independently alkyl of 1 to 12 carbon atoms, alkenyl of 2 to 12 carbon atoms, or alkynyl of 2 to 12 carbon atoms;

$R_5$ is independently $R_4$ wherein each $R_4$ is substituted with 0 to 3 $R_3$ groups;

$R_{5a}$ is independently alkylene of 1 to 12 carbon atoms, alkenylene of 2 to 12 carbon atoms, or alkynylene of 2–12 carbon atoms any one of which alkylene, alkenylene or alkynylene is substituted with 0–3 $R_3$ groups;

$R_{6a}$ is independently H or an ether- or ester-forming group;

$R_{6b}$ is independently H, a protecting group for amino or the residue of a carboxyl-containing compound;

$R_{6c}$ is independently H or the residue of an amino-containing compound;

$W_1$ is COOH;

$W_2$ is $NH_2$;

$W_3$ is $W_4$ or $W_5$;

$W_4$ is $R_5$ or —$C(O)R_5$, —$C(O)W_5$, —$SO_2R_5$, or —$SO_2W_5$;

$W_5$ is carbocycle or heterocycle wherein $W_5$ is independently substituted with 0 to 3 $R_2$ groups;

$W_6$ is —$R_5$, —$W_5$, —$R_{5a}W_5$, —$C(O)OR_{6a}$, —$C(O)R_{6c}$, —$C(O)N(R_{6b})_2$, —$C(NR_{6b})(N(R_{6b})_2)$, —$C(NR_{6b})(N(H)(R_{6b}))$, —$C(N(H)(N(R_{6b})_2)$, —$C(S)N(R_{6b})_2$, or —$C(O)R_2$;

$X_1$ is a bond, —O—, —N(H)—, —$N(W_6)$—, —N(OH)—, —$N(OW_6)$—, —$N(NH_2)$—, —$N(N(H)(W_6))$—, —$N(N(W_6)_2)$—, —$N(H)N(W_6)$—, —S—, —SO—, or —$SO_2$—; and each $m_1$ is 0 provided, however, that compounds of formula (XX) are excluded wherein $A_3$ is N, each $J_1$, $J_2$, $J_{2a}$ and $J_3$ is H and $T_1$ is —N(H)(Ac) and:

$E_1$ is —$CO_2H$ or —$CO_2CH_3$,
$G_2$ is —OBoc, and
$Z_3$ is Boc;
$E_1$ is —$CO_2H$ or —$CO_2CH_3$,
$G_2$ is —OH, and
$Z_3$ is H;
$E_1$ is —$CO_2H$, —$CO_2CH_3$ or —$CO_2Bn$
$G_2$ is —OH, and
$Z_3$ is Boc;
$E_1$ is —$CONH_2$,
$G_2$ is —OH, and
$Z_3$ is Boc or H;

$E_1$ is —$CO_2H$ or —$CO_2CH_3$,
$G_2$ is OH, and
$Z_3$ is Bn; or
$E_1$ is —$CO_2H$ or —$CO_2CH_3$,
$G_2$ is —OH, and
$Z_3$ is —$CH_2CH(OH)CH_2(OH)$;

wherein Bn is benzyl and Boc is —$CO_2C(CH_3)_3$; further excluded are compounds of the formula: (VII) or (VIII):

(VII)

(VIII)

wherein
$E_1$ is —$(CR_1R_1)_{m1}W_1$;
$G_1$ is $N_3$, —CN, —OH, —$OR_{6a}$, —$NO_2$, or —$(CR_1R_1)_{m1}W_2$;
$T_1$ is —$NR_1W_3$, a heterocycle, or is taken together with $G_1$ to form a group having the structure $U_1$ is —$X_1W_6$;
$J_1$ and $J_{1a}$ are independently $R_1$, Br, Cl, F, I, CN, $NO_2$ or $N_3$;
$J_2$ and $J_{2a}$ are independently H or $R_1$;
$R_1$ is independently H or alkyl of 1 to 12 carbon atoms;
$R_2$ is independently $R_3$ or $R_4$ wherein each $R_4$ is independently substituted with 0 to 3 $R_3$ groups;
$R_3$ is independently F, Cl, Br, I, —CN, $N_3$, —$NO_2$, —$OR_{6a}$, —$OR_1$, —$N(R_1)_2$, —$N(R_1)(R_{6b})$, —$N(R_{6b})_2$, —$SR_1$, —$SR_{6a}$, —$S(O)R_1$, —$S(O)_2R_1$, —$S(O)OR_1$, —$S(O)OR_{6a}$, —$S(O)_2OR_1$, —$S(O)_2OR_{6a}$, —$C(O)OR_1$, —$C(O)R_{6c}$, —$C(O)OR_{6a}$, —$OC(O)R_1$, —$N(R_1)(C(O)R_1)$, —$N(R_{6b})(C(O)R_1)$, —$N(R_1)(C(O)OR_1)$, —$N(R_{6b})(C(O)OR_1)$, —$C(O)N(R_1)_2$, —$C(O)N(R_{6b})(R_1)$, —$C(O)N(R_{6b})_2$, —$C(NR_1)(N(R_1)_2)$, —$C(N(R_{6b}))(N(R_1)_2)$, —$C(N(R_1))(N(R_1)(R_{6b}))$, —$C(N(R_{6b}))(N(R_1)(R_{6b}))$, —$C(N(R_1))(N(R_{6b})_2)$, —$C(N(R_{6b}))(N(R_{6b})_2)$, —$N(R_1)C(N(R_1))(N(R_1)_2)$, —$N(R_1)C(N(R_1))(N(R_1)(R_{6b}))$, —$N(R_1)C(N(R_{6b}))(N(R_1)_2)$, —$N(R_{6b})C(N(R_1))(N(R_1)_2)$, —$N(R_{6b})C(N(R_{6b}))(N(R_1)_2)$, —$N(R_1)C(N(R_{6b}))(N(R_1)(R_{6b}))$, —$N(R_1)C(N(R_1))(N(R_{6b})_2)$, —$N(R_{6b})C(N(R_{6b}))(N(R_1)(R_{6b}))$, —$N(R_{6b})C(N(R_1))(N(R_{6b})_2)$, —$N(R_1)C(N(R_{6b}))(N(R_{6b})_2)$, —$N(R_{6b})C(N(R_{6b}))(N(R_{6b})_2)$, =O, =S, =$N(R_1)$ or =$N(R_{6b})$;

$R_4$ is independently alkyl of 1 to 12 carbon atoms, alkenyl of 2 to 12 carbon atoms, or alkynyl of 2 to 12 carbon atoms;

$R_5$ is independently $R_4$ wherein each $R_4$ is substituted with 0 to 3 $R_3$ groups;

$R_{5a}$ is independently alkylene of 1 to 12 carbon atoms, alkenylene of 2 to 12 carbon atoms, or alkynylene of 2–12 carbon atoms any one of which alkylene, alkenylene or alkynylene is substituted with 0–3 $R_3$ groups;

$R_{6a}$ is independently H or an ether- or ester-forming group;

$R_{6b}$ is independently H, a protecting group for amino or the residue of a carboxyl-containing compound;

$R_{6c}$ is independently H or the residue of an amino-containing compound;

$W_1$ is a group comprising an acidic hydrogen, a protected acidic group, or an $R_{6c}$ amide of the group comprising an acidic hydrogen;

$W_2$ is a group comprising a basic heteroatom or a protected basic heteroatom, or an $R_{6b}$ amide of the basic heteroatom;

$W_3$ is $W_4$ or $W_5$;

$W_4$ is $R_5$ or —C(O)$R_5$, —C(O)$W_5$, —SO$_2 R_5$, or —SO$_2 W_5$;

$W_5$ is carbocycle or heterocycle wherein $W_5$ is independently substituted with 0 to 3 $R_2$ groups;

$W_6$ is —$R_5$, —$W_5$, —$R_{5a}W_5$, —C(O)O$R_{6a}$, —C(O)$R_{6c}$, —C(O)N($R_{6b}$)$_2$, —C(N$R_{6b}$)(N($R_{6b}$)$_2$), —C(N$R_{6b}$)(N(H)($R_{6b}$)), —C(N(H)(N($R_{6b}$)$_2$), —C(S)N($R_{6b}$)$_2$, or —C(O)$R_2$;

$X_1$ is a bond, —O—, —N(H)—, —N($W_6$)—, —S—, —SO—, or —SO$_2$—; and each $m_1$ is independently an integer from 0 to 2; and the salts, solvates, resolved enantiomers and purified diastereomers thereof.

2. The compound of claim 1 wherein $E_1$ is $W_1$.

\* \* \* \* \*